US006958352B2

(12) United States Patent
Pei et al.

(10) Patent No.: US 6,958,352 B2
(45) Date of Patent: Oct. 25, 2005

(54) COMPOUNDS FOR INHIBITING INSULIN SECRETION AND METHODS RELATED THERETO

(75) Inventors: Yazhong Pei, San Diego, CA (US); Soumitra S. Ghosh, San Diego, CA (US); Ian William James, Clayton (AU)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/364,292

(22) Filed: Feb. 10, 2003

(65) Prior Publication Data

US 2004/0044049 A1 Mar. 4, 2004

Related U.S. Application Data

(60) Provisional application No. 60/355,389, filed on Feb. 8, 2002.

(51) Int. Cl.[7] .................... C07D 211/06; A61K 31/445

(52) U.S. Cl. .................... 514/327; 514/330; 514/364; 514/617; 546/217; 546/225; 548/134; 564/161; 564/180

(58) Field of Search .................... 564/161, 180; 514/617, 327, 330, 364; 546/217, 225; 548/134

(56) References Cited

FOREIGN PATENT DOCUMENTS

| | | | |
|---|---|---|---|
| EP | 467435 | * 6/1991 | ......... C07C/323/25 |
| WO | WO 87/07891 | * 12/1987 | ......... C07D/233/64 |
| WO | WO 00/71511 | 11/2000 | |
| WO | WO 02/24204 A2 | 3/2002 | |

OTHER PUBLICATIONS

Baron and Thayer, "CGP37157 Modulates Mitochondrial $Ca^{2+}$ Homeostasis in Cultured Rat Dorsal Root Ganglion Neurons," *Eur. J. Pharmacol. 340*(2–3):295–300, Dec. 11, 1997.

Chiesi et al., "Structural Dependency of the Inhibitory Action of Benzodiazepines and Related Compounds on the Mitochondrial $Na^+$–$Ca^{2+}$ Exchanger," *Biochem. Pharmacol. 37*(22):4399–4403, Nov. 15, 1988.

Cox and Matlib, "Modulation of Intramitochondrial Free $Ca^{2+}$ Concentration by Antagonists of $Na^+$–$Ca^{2+}$ Exchange," *Trends Pharmacol. Sci. 14*(11):408–413, Nov. 1993.

Cox et al., "Selectivity of Inhibition of $Na^+$–$Ca^{2+}$ Exchange of Heart Mitochondria by Benzothiazepine CGP–37157," *Cardiovasc. Pharmacol. 21*(4):595–599, Apr. 1993.

Crompton and Andreeva, "On the Involvement of a Mitochondrial Pore in Reperfusion Injury," *Basic Res. Cardiol. 88*(5):513–523, 1993.

Gunter and Gunter, "Transport of Calcium by Mitochondria," *J. Bioenerg. Biomembr. 26*(5):471–485, Oct. 1994.

Kennedy et al., "Glucose–Stimulated Insulin Secretion Correlates With Changes in Mitochondrial and Cytosolic $Ca^{2+}$ in Aequorin–Expressing INS–1 Cells," *J. Clin. Invest. 98*(11):2524–2538, Dec. 1, 1996.

Maechler et al., "Mitochondrial Activation Directly Triggers the Exocytosis of Insulin in Permeabilized Pancreatic β–cells," *EMBO J. 16*(13):3833–3841, Jul. 1, 1997.

Magnus et al., "Model of β–cell Mitochondrial Calcium Handling and Electrical Activity. II. Mitochondrial Variables," *Am. J. Physiol. 274*(4pt1):C1174–C1184, Apr. 1998.

Matlib et al., "A Specific Inhibitory Action of Certain Benzothiazepines and Benzodiazepines on the Sodium–Calcium Exchange Process of Heart and Brain Mitochondria," *Eur. J. Pharmacol. 89*(3–4):327–328, May 6, 1983.

Matlib et al., "Selective Effects of Diltiazem, a Benzothiazepine Calcium Channel Blocker, and Diazepam, and other Benzodiazepines on the $Na^+/Ca^{2+}$ Exchange Carrier System of Heart and Brain Mitochondria," *Life Sci. 32*(25):2837–2842, Jun. 20, 1983.

Matlib, "Action of Bepridil, a New Calcium Channel Blocker on Oxidative Phosphorylation, Oligomycin–Sensitive Adenosine Triphosphatase Activity, Swelling, $Ca^{++}$ Uptake and $Na^+$–Induced $Ca^{++}$ Release Processes of Rabbit Heart Mitochondria in Vitro," *J. Pharmacol. Exp. Ther. 233*(2):376–381, May 1985.

Newgard et al., "Metabolic Coupling Factors in Pancreatic β–cell Signal Transduction," *Ann. Rev. Biochem. 64*:689–719, 1995.

Rutter et al., "Regulation of $NAD^+$–Linked Isocitrate Dehydrogenase and 2–Oxoglutarate Dehydrogenase by $Ca^{2+}$ Ions Within Toluene–Permeabilized Rat Heart Mitochondria. Interactions With Regulation by Adenine Nucleotides and $NADH/NAD^+$ Ratios," *Biochem. J. 252*(1):181–189, May 15, 1988.

Rutter et al., "Stimulated $Ca^{2+}$ Influx Raises Mitochondrial Free $Ca^{2+}$ to Supramicromolar Levels in a Pancreatic β–Cell Line. Possible Role in Glucose and Agonist–Induced Insulin Secretion," *J. Biol. Chem. 268*(30):22385–22390, Oct. 25, 1993.

(Continued)

*Primary Examiner*—Zinna Northington Davis
(74) *Attorney, Agent, or Firm*—Jennifer L. Fox

(57) ABSTRACT

Compounds, compositions and methods for altering insulin secretion, particularly in the context of treatment of subjects having, or suspected of being at risk for having, diabetes mellitus. The compounds have the following structure (I):

(I)

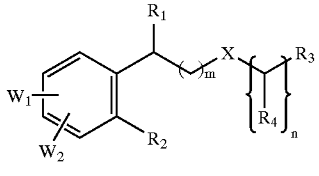

including stereoisomers, prodrugs and pharmaceutically acceptable salts thereof, wherein $W_1$, $W_2$, X, $R_1$, $R_2$, $R_3$, $R_4$, m and n are defined herein.

15 Claims, 3 Drawing Sheets

OTHER PUBLICATIONS

White et al., "Mitochondria Accumulate $Ca^{2+}$ Following Intense Glutamate Stimulation of Cultured Rat Forebrain Neurones," *J. Physiol. 498*(Pt 1):31–47, Jan. 1, 1997.

Zoratti et al., "Electrophysiology of the Inner Mitochondrial Membrane," *J. Bioenerget. Biomembr. 26*(5):543–553, Oct. 1994.

Klosa, J. "Synthese Von Benzothiazepinonen, Einer Neuen Koerperklasse Synthesis of Benzothiazepinones, a New Class of Compounds," *Journal Fuer Praktische Chemie 3*(1/2):5–18, 1967.

Pei, Y. et al., "Efficient Syntheses of Benzothiazepines as Antagonists for the Mitochondrial Sodium–Calcium Exchanger: Potential Therapeutics for Type II Diabetes," *Journal of Organic Chemistry 68*(1):92–103, Nov. 2002.

* cited by examiner

COMPOUNDS FOR INHIBITING INSULIN SECRETION AND METHODS RELATED THERETO

CROSS-REFERENCE TO RELATED APPLICATION

This application claims the benefit of U.S. Provisional Patent Application No. 60/355,389 filed Feb. 8, 2002, where this provisional application is incorporated herein by reference in its entirety.

TECHNICAL FIELD

The invention generally relates to compounds that alter insulin secretion, as well as to composition and methods related thereto.

BACKGROUND OF THE INVENTION

Type 2 diabetes mellitus, or "late onset" diabetes, is a common, degenerative disease affecting 5 to 10 percent of the population in developed countries. The propensity for developing type 2 diabetes mellitus ("type 2 DM") is reportedly maternally inherited, suggesting a mitochondrial genetic involvement. (Alcolado, J. C. and Alcolado, R., *Br. Med. J.* 302:1178–1180 (1991); Reny, S. L., *International J. Epidem.* 23:886–890 (1994)). Diabetes is a heterogeneous disorder with a strong genetic component; monozygotic twins are highly concordant and there is a high incidence of the disease among first degree relatives of affected individuals.

At the cellular level, the pathologic phenotype that may be characteristic of the presence of, or risk for predisposition to, late onset diabetes mellitus includes the presence of one or more indicators of altered mitochondrial respiratory function, for example impaired insulin secretion, decreased ATP synthesis and increased levels of reactive oxygen species. Studies have shown that type 2 DM may be preceded by or associated with certain related disorders. For example, it is estimated that forty million individuals in the U.S. suffer from impaired glucose tolerance (IGT). Following a glucose load, circulating glucose concentrations in IGT patients rise to higher levels, and return to baseline levels more slowly, than in unaffected individuals. A small percentage of IGT individuals (5–10%) progress to non-insulin dependent diabetes (NIDDM) each year. This form of diabetes mellitus, type 2 DM, is associated with decreased release of insulin by pancreatic beta cells and a decreased end-organ response to insulin. Other symptoms of diabetes mellitus and conditions that precede or are associated with diabetes mellitus include obesity, vascular pathologies, peripheral and sensory neuropathies and blindness.

Glucose-mediated insulin secretion from the pancreatic beta cell is triggered by a complex sequence of intracellular events. Glucose is taken up by the beta cell via GLUT-2 glucose transporters; it is subsequently phosphorylated by glucokinase to glucose-6-phosphate, which enters the glycolytic pathway. The reducing equivalents (NADH) and substrate (pyruvate) produced through glycolysis enter the mitochondria and fuel increased respiration and oxidative phosphorylation. The consequent rise in cellular ATP levels triggers closure of the $K^+$-ATP channels at the plasma membrane, depolarizing the membrane and permitting influx of calcium. Calcium appears to have two main roles: stimulating release of insulin from the cells (e.g., Kennedy et al., 1996 *J. Clin. Invest.* 98:2524; Maechler et al., 1997

*EMBO J.* 16:3833), and acting as a "feed-forward" regulator of mitochondrial ATP production (e.g., Cox and Matlib, 1993 *Trends Pharmacol. Sci.* 14:408). The latter is accomplished by mitochondrial uptake of calcium through the mitochondrial calcium uniporter (e.g., Newgard et al., 1995 *Ann. Rev. Biochem.* 64:689; Magnus et al., 1998 *Am. J. Physiol.* 274:C1174–C1184). The rise in mitochondrial calcium stimulates respiration and oxidative phosphorylation through stimulation of calcium-sensitive dehydrogenase (Rutter et al., 1988 *Biochem. J.* 252:181; Rutter et al., 1993 *J. Biol. Chem.* 268:22385). However, the rise in mitochondrial calcium is transient, since calcium returns to the cytoplasm through regulated calcium efflux channels, for instance a mitochondrial calcium antiporter such as the mitochondrial calcium/sodium antiporter (MCA) also known as the mitochondrial sodium/calcium exchanger (mNCE; see, e.g., Newgard 1995; Magnus 1998; for a general review of mitochondrial membrane transporters, see, e.g., Zonatti et al., 1994 *J. Bioenergetics Biomembr.* 26:543 and references cited therein). The use of MCA inhibitors has been contemplated for their potential effects on cardiac function (e.g., Cox and Matlib, 1993 *Trends Pharmacol. Sci.* 14:408–413), but such use has not been suggested for certain other indications such as diabetes. Thus, for example, while elevated intramitochondrial calcium concentration has been correlated with insulin secretion and oxidative ATP synthesis, as noted above (e.g., Kennedy et al., 1996 *J. Clin. Invest.* 98:2524; Maechler et al., 1997 *EMBO J.* 16:3833; Cox and Matlib, 1993 *Trends Pharmacol. Sci.* 14:408), no inducer-effector relationship between oxidative ATP synthesis and insulin secretion has been universally accepted (see, e.g., Newgard, 1995 *Ann. Rev. Biochem.* 64:689). Moreover, currently available inhibitors of the MCA are regarded as either not specific for the MCA, or useful only at extremely high concentrations, precluding their apparent suitability for pharmaceutical compositions (Cox and Matlib, 1993 *Trends Pharmacol. Sci.* 14:408–413).

Current pharmacological therapies for type 2 DM include injected insulin, and oral agents that are designed to lower blood glucose levels. Currently available oral agents include: (i) the sulfonylureas, which act by enhancing the sensitivity of the pancreatic beta cell to glucose, thereby increasing insulin secretion in response to a given glucose load; (ii) the biguamides, which improve glucose disposal rates and inhibit hepatic glucose output; (iii) the thiazolidinediones, which improve peripheral insulin sensitivity through interaction with nuclear peroxisome proliferator-activated receptors (PPAR, see, e.g., Spiegelman, 1998 *Diabetes* 47:507–514; Schoonjans et al., 1997 *Curr Opin. Lipidol.* 8:159–166; Staels et al., 1997 *Biochimie* 79:95–99); (iv) repaglinide, which enhances insulin secretion through interaction with ATP-dependent potassium channels; and (v) acarbose, which decreases intestinal absorption of carbohydrates. Although currently available drugs for treating type 2 diabetes, such as the sulfonylureas, improve insulin secretion, both basal and insulin stimulated insulin secretion are enhanced by such compounds. Consequently, undesirable chronic hyperinsulinemia, hypoglycemia and/or excessive weight gain may result following treatment with such drugs (Cobb et al., 1998 *Ann. Rep. Med. Chem.* 33:213–222; Krentz et al., 1994 *Drug Safety* 11:223–241).

None of the current pharmacological therapies corrects the underlying biochemical defect in type 2 DM. Neither do any of these currently available treatments improve all of the physiological abnormalities in type 2 DM such as impaired insulin secretion, insulin resistance and/or excessive hepatic glucose output. In addition, treatment failures are common with these agents, such that multi-drug therapy is frequently necessary.

Mitochondria are organelles that are the main energy source in cells of higher organisms. These organelles provide direct and indirect biochemical regulation of a wide array of cellular respiratory, oxidative and metabolic processes, including metabolic energy production, aerobic respiration and intracellular calcium regulation. For example, mitochondria are the site of electron transport chain (ETC) activity, which drives oxidative phosphorylation to produce metabolic energy in the form of adenosine triphosphate (ATP), and which also underlies a central mitochondrial role in intracellular calcium homeostasis. These processes require the maintenance of a mitochondrial membrane electrochemical potential, and defects in such membrane potential can result in a variety of disorders.

Mitochondria contain an outer mitochondrial membrane that serves as an interface between the organelle and the cytosol, a highly folded inner mitochondrial membrane that appears to form attachments to the outer membrane at multiple sites, and an intermembrane space between the two mitochondrial membranes. The subcompartment within the inner mitochondrial membrane is commonly referred to as the mitochondrial matrix (for review, see, e.g., Ermster et al., *J. Cell Biol.* 91:227s, 1981). While the outer membrane is freely permeable to ionic and non-ionic solutes having molecular weights less than about ten kilodaltons, the inner mitochondrial membrane exhibits selective and regulated permeability for many small molecules, including certain cations, and is impermeable to large (greater than about 10 kD) molecules.

Four of the five multisubunit protein complexes (Complexes I, III, IV and V) that mediate ETC activity are localized to the inner mitochondrial membrane. The remaining ETC complex (Complex II) is situated in the matrix. In at least three distinct chemical reactions known to take place within the ETC, protons are moved from the mitochondrial matrix, across the inner membrane, to the intermembrane space. This disequilibrium of charged species creates an electrochemical membrane potential of approximately 220 mV referred to as the "proton motive force" (PMF). The PMF, which is often represented by the notation Δp, corresponds to the sum of the electric potential (ΔΨm) and the pH differential (ΔpH) across the inner membrane according to the equation $$\Delta p = \Delta\Psi m - Z\Delta pH$$

wherein Z stands for −2.303 RT/F. The value of Z is −59 at 25° C. when Δp and ΔΨm are expressed in mV and ΔpH is expressed in pH units (see, e.g., Emster et al., *J. Cell Biol.* 91:227s, 1981, and references cited therein).

ΔΨm provides the energy for phosphorylation of adenosine diphosphate (ADP) to yield ATP by ETC Complex V, a process that is coupled stoichiometrically with transport of a proton into the matrix. ΔΨm is also the driving force for the influx of cytosolic $Ca^{2+}$ into the mitochondrion. Normal alterations of intramitochondrial $Ca^{2+}$ are associated with normal metabolic regulation (Dykens, 1998 in *Mitochondria & Free Radicals in Neurodegenerative Diseases*, Beal, Howell and Bodis-Wollner, Eds., Wiley-Liss, New York, pp. 29–55; Radi et al., 1998 in *Mitochondria & Free Radicals in Neurodegenerative Diseases*, Beal, Howell and Bodis-Wollner, Eds., Wiley-Liss, New York, pp. 57–89; Gunter and Pfeiffer, 1991, *Am. J. Physiol.* 27: C755; Gunter et al., *Am. J. Physiol.* 267:313, 1994). For example, fluctuating levels of mitochondrial free $Ca^{2+}$ may be responsible for regulating oxidative metabolism in response to increased ATP utilization, via allosteric regulation of enzymes (reviewed by Crompton and Andreeva, *Basic Res. Cardiol.* 88:513–523, 1993), and the glycerophosphate shuttle (Gunter and Gunter, *J. Bioenerg. Biomembr.* 26:471, 1994).

Normal mitochondrial function includes regulation of cytosolic free calcium levels by sequestration of excess $Ca^{2+}$ within the mitochondrial matrix, including transiently elevated cytosolic free calcium that results from physiologic biological signal transduction. Depending on cell type, cytosolic $Ca^{2+}$ concentration is typically 50–100 nM. In normally functioning cells, when $Ca^{2+}$ levels reach 200–300 nM, mitochondria begin to accumulate $Ca^{2+}$ as a function of the equilibrium between influx via a $Ca^{2+}$ uniporter in the inner mitochondrial membrane and $Ca^{2+}$ efflux via both $Na^+$ dependent and $Na^+$ independent calcium carriers, including notably the MCA. The low affinity of this rapid uniporter mechanism suggests that the primary uniporter function may be to lower cytosolic $Ca^{2+}$ in response to elevation of cytosolic free calcium levels, which may result from calcium influx across the plasma membrane that occurs as part of a biological signal transduction mechanism (Gunter and Gunter, *J. Bioenerg. Biomembr.* 26:471, 1994; Gunter et al., *Am. J. Physiol.* 267:313, 1994). In certain instances, for example in pancreatic beta cells, physiologic rises in cytoplasmic calcium occur in response to glucose (or other secretagogues) and lead to calcium uptake by mitochondria, stimulating increased ATP synthesis. Similarly, the primary calcium antiporter (e.g., MCA) function may be to lower mitochondrial $Ca^{2+}$ concentrations in response to mitochondrial $Ca^{2+}$ influxes, such as may result from glucose stimulation of a glucose-sensitive cell, and which produce transient increases in oxidative ATP synthesis. Thus, mitochdndrially regulated calcium cycling between, inter alia, cytosolic and mitochondrial compartments may provide an opportunity for manipulation of intracellular ATP levels (e.g., Cox and Matlib, 1993 *Trends Pharmacol. Sci.* 14:408–413; Matlib et al., 1983 *Eur. J. Pharmacol.* 89:327; Matlib 1985 *J. Pharmacol. Exp. Therap.* 233:376; Matlib et al. 1983 *Life Sci.* 32:2837).

In view of the significance of mitochondrial regulation of intracellular calcium and the relationship of this mitochondrial activity to diabetes, which includes any of a wide range of disease states characterized by inappropriate and sustained hyperglycemia, there is clearly a need for agents to control mitochondrial calcium homeostasis. To provide improved therapies for diabetes, agents that alter mitochondrial calcium cycling between intramitochondrial and extramitochondrial subcellular compartments would be beneficial. Further, there is a need for improved therapeutics that are targeted to correct biochemical and/or metabolic defects responsible for, or associated with, type 2 DM, regardless of whether such a defect underlying altered mitochondrial function may have mitochondrial or extramitochondrial origins.

Accordingly, there is a need in the art agents that modulate mitochondrial calcium/sodium antiporter function and are thus useful for treating diabetes, type 2 DM, by enhancing insulin secretion. There is also a need for pharmaceutical compositions containing such agents, as well as for methods relating to use thereof. The present invention fulfills these needs, and provides further related advantages.

SUMMARY OF THE INVENTION

In brief, this invention is generally directed to compounds that enhance insulin secretion, and thus are useful for the treatment of diabetes mellitus. Thus, in one embodiment, methods are disclosed for treating diabetes mellitus by administration a compound to a subject having or suspected of being at risk for having diabetes mellitus, wherein the compound has the following general structure (I):

(I)

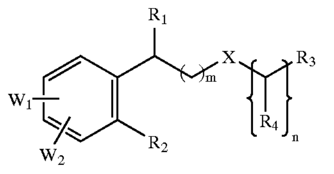

including stereoisomers, prodrugs and pharmaceutically acceptable salts thereof, wherein $W_1$, $W_2$, X, $R_1$, $R_2$, $R_3$, $R_4$, m and n are defined herein.

In one aspect of this embodiment, the diabetes mellitus is type 2 diabetes mellitus or maturity onset diabetes of the young. In another aspect, the compounds enhance insulin secretion, such as insulin secretion that is stimulated by glucose. In other aspects, the compounds enhances insulin secretion that is stimulated by a supraphysiological glucose concentration, and does not enhance insulin secretion in the presence of a physiological glucose concentration. In further aspects, the methods may further comprise administering to the subject one or more agents that lowers circulating glucose concentration in the subject, such as insulin, an insulin secretagogue, an insulin sensitizer, an inhibitor of hepatic glucose output and/or an agent that impairs glucose absorption.

In other embodiments, pharmaceutical compositions are disclosed that contain one or more compounds having structure (I) in combination with one or more pharmaceutically acceptable carriers, as well as novel compounds within structure (I).

These and other aspects of the present invention will become apparent upon reference to the following detailed description and attached drawings. All references disclosed herein are hereby incorporated by reference in their entireties as if each was incorporated individually.

DETAILED DESCRIPTION OF THE INVENTION

Figure 1:
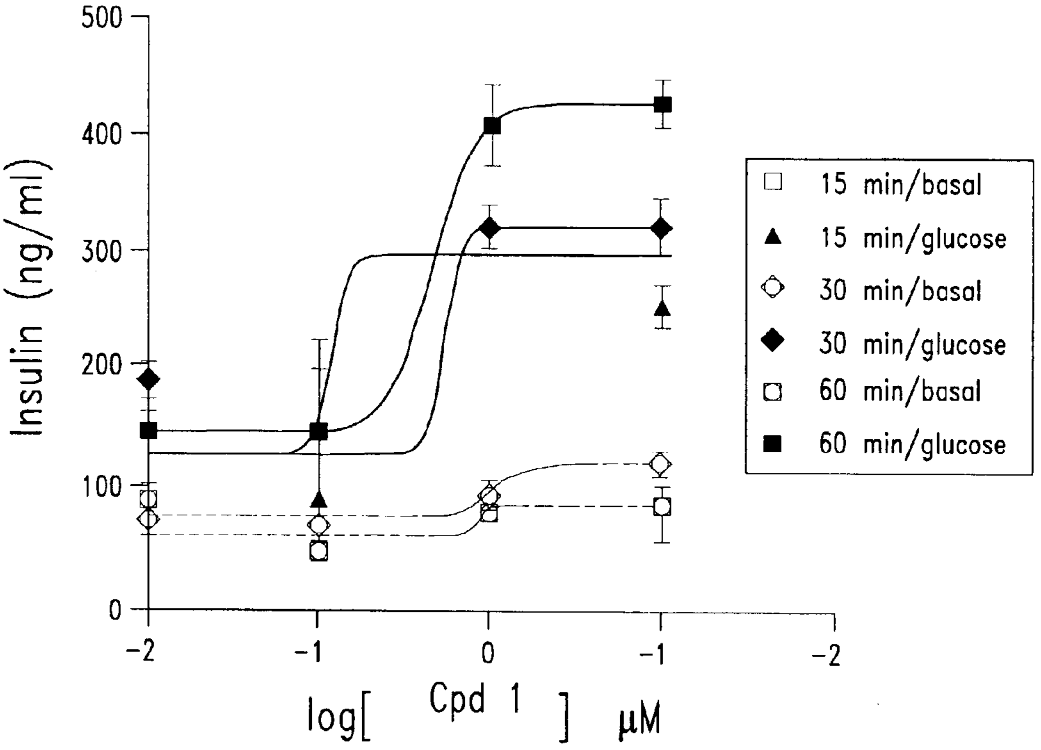
FIGS. 1 and 2 show enhanced glucose stimulated insulin secretion by INS-1 cells (FIG. 1) and on rat pancreatic islet cells (FIG. 2) when exposed to CPG37157, a known potent inhibitor of MCA, in the presence of basal or supraphysiological glucose.

This invention is generally directed to compounds that enhance insulin secretion, and thus are useful for the treatment of diabetes mellitus. Thus, in one embodiment, methods are disclosed for treating diabetes mellitus by administration a compound to a subject having or suspected of being at risk for having diabetes mellitus, wherein the compounds has the following general structure (I):

(I)

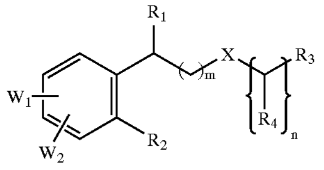

or a stereoisomers, prodrug or pharmaceutically acceptable salt thereof, wherein X is —$S(O)_q$—, —O—, —N(R)— or —C(R)(R')—;

m is 0 or 1;

n is 0, 1 or 2;

q is 0, 1 or 2;

$W_1$ and $W_2$ each represent an optional substituent, wherein $W_1$ and $W_2$ are the same or different and independently halogen, nitro, or lower alkyl;

R and R' are the same or different and independently alkyl, substituted alkyl, aryl, substituted aryl, arylalkyl or substituted arylalkyl, or R and R' taken together with the carbon atom to which they are bonded form a carbocycle, substituted carbocycle, heterocycle or substituted heterocycle;

$R_1$ is alkyl, substituted alkyl, aryl, substituted aryl, arylalkyl, substituted arylalkyl, heteroaryl or substituted heteroaryl;

$R_2$ is hydrogen, nitro, —$OR_{2a}$, —C(═O)$NR_{2b}R_{2c}$, —$CH_2NR_{2b}R_{2c}$, —$CH_2OR_{2a}$, —$NR_{2b}R_{2c}$, —NHC(═O)$R_{2a}$, —NHC(═O)$NR_{2b}R_2$, or —NHC(═NH)$NR_{2b}R_{2c}$;

$R_{2a}$ is hydrogen, alkyl, substituted alkyl, arylalkyl, or substituted arylalkyl;

$R_{2b}$ and $R_{2c}$ are the same or different and independently hydrogen, alkyl, substituted alkyl, —$SO_2R_4$, —C(═NH)$NH_2$ or —C(═O)$R_{2d}$ where $R_{2d}$ is amino, alkyl, substituted alkyl, aryl or substituted aryl;

$R_3$ is hydroxy, alkyl, substituted alkyl, aryl, substituted aryl, arylalkyl, substituted arylalkyl, heterocycle, substituted heterocycle, heterocyclealkyl, substituted heterocyclealkyl, —C(—O)N($R_{3a}$)($R_{3b}$), —NHC(═O)N($R_{3a}$)($R_{3b}$), —NHC(S)N($R_{3a}$)($R_{3b}$), —C(═O)$OR_{3c}$, —C(—O)$R_{3c}$, —NHC(═O)$R_{3d}$ or —$NHSO_2R_{3d}$;

$R_{3a}$ and $R_{3b}$ are the same or different and independently hydrogen, alkyl, substituted alkyl, aryl, substituted aryl, arylalkyl or substituted arylalkyl, or $R_{3a}$ and $R_{3b}$ taken together with the nitrogen atom to which they are attached form a heterocycle or substituted heterocycle;

$R_{3c}$ is hydrogen, alkyl, substituted alkyl, aryl, substituted aryl, arylalkyl, substituted arylalkyl, heteroaryl, substituted heteroaryl, heteroarylalkyl or substituted heteroarylalkyl;

$R_{3d}$ is alkyl, substituted alkyl, aryl, substituted aryl, arylalkyl, substituted arylalkyl, heteroaryl, substituted heteroaryl, heteroarylalkyl or substituted heteroarylalkyl; and $R_4$ is, at each occurrence, the same or different and independently hydrogen, alkyl, substituted alkyl, aryl, substituted aryl, arylalkyl or substituted arylalkyl.

As used herein, the terms used above have the following meaning:

"Alkyl" means a straight chain or branched, saturated or unsaturated, cyclic or non-cyclic hydrocarbon having from 1 to 10 carbon atoms, while "lower alkyl" has the same meaning but only has from 1 to 0.6 carbon atoms. Representative saturated straight chain alkyls include methyl, ethyl, n-propyl, n-butyl, n-pentyl, n-hexyl, and the like;

while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propyridyl, 1-butynyl, 2-butynyl, 1-pentynyl, 2-pentynyl, 3-methyl-1butynyl, and the like. Representative saturated cyclic alkyls include cyclopropyl, cyclobutyl, cyclopentyl, cyclohexyl, —$CH_2$cyclohexyl and the like; while unsaturated cyclic alkyls include cyclopentenyl, cyclohexenyl, —$CH_2$cyclohexenyl and the like. Cycloalkyls are also referred to herein as "carbocyclic" rings systems, and include bi- and tri-cyclic ring systems having from 8 to 14 carbon atoms such as a cycloalkyl (such as cyclopentane or cyclohexane) fused to one or more aromatic (such as phenyl) or non-aromatic (such as cyclohexane) carbocyclic rings.

"Halogen" means fluorine, chlorine, bromine or iodine.

"Oxo" means a carbonyl group (i.e., =O).

"Mono- or di-alkylamino represents an amino substituted with one alkyl or with two alkyls, respectively.

"Alkanediyl" means a divalent alkyl from which two hydrogen atoms are taken from the same carbon atom or from different carbon atoms, such as —$CH_2$—$CH_2CH_2$—, —$CH_2CH_2CH_2$—, —$CH(CH_3)CH_2$—, and the like.

"Aryl" means an aromatic carbocyclic moiety such as phenyl or naphthyl.

"Arylalkyl" means an alkyl having at least one alkyl hydrogen atom replaced with an aryl moiety, such as benzyl, —$(CH_2)_2$phenyl, —$(CH_2)_3$phenyl, —CH$(phenyl)_2$, and the like.

"Heteroaryl" means an aromatic heterocycle ring of 5 to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$ pyridinyl, —$CH_2$pyrimidinyl, and the like.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —$CH_2$morpholinyl, and the like.

The term "substituted" as used herein means any of the above groups (i.e., alkyl, aryl, arylalkyl, heteroaryl, heteroarylalkyl, heterocycle and heterocyclealkyl) wherein at least one hydrogen atom is replaced with a substituent (also referenced herein as "Q"). In the case of an oxo substituent ("=O") two hydrogen atoms are replaced. Substituents include halogen, hydroxy, oxo, alkyl, substituted alkyl (such as haloalkyl, mono- or di-substituted aminoalkyl, alkyloxyalkyl, and the like), aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —$NR_aR_b$, —$NR_aC(=O)R_b$, —$NR_cC(=O)NR_aR_b$, $NR_aC(=O)OR_b$, —$NR_aSO_2R_b$, —$OR_a$, —$C(=O)R_a$, —$C(=O)OR_a$, —$C(=O)NR_aR_b$, —$OC(=O)R_a$, —$OC(=O)OR_a$, —$OC(=O)NR_aR_b$, —$NR_aSO_2R_b$, —$CONR_a$(alkanediyl)$OR_b$, —$CONR_c$(alkanediyl-O)$_{1-6}$(alkanediyl)$NR_aR_b$, or a radical of the formula —Y-Z-$R_a$ where Y is alkanediyl, substituted alkanediyl or a direct bond, Z is —O—, —S—, —S(=O)—, —$S(=O)_2$—, —$N(R_b)$—, —C(=O)—, —C(=O)O—, —OC(=O)—, —$N(R_b)C(=O)$—, —$C(=O)N(R_b)$— or a direct bond, wherein $R_a$, $R_b$ and $R_c$ are the same or different and independently hydrogen, amino, alkyl, substituted alkyl (including halogenated alkyl), aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl, or wherein $R_a$ and $R_b$ taken together with the nitrogen atom to which they are attached form a heterocycle or substituted heterocycle.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The compounds of the present invention may generally be utilized as the free acid or base. Alternatively, the compounds of this invention may be used in the form of acid or based addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Based addition salts include the ammonium ion, as well as other suitable cations. Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structure (I) may have chiral centers and may occur as racemates, racemic mixtures and as individual enantiomers or diastereomers. All such isomeric forms are included within the present invention, including mixtures thereof Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The compounds of structure (I), as well as the more specific embodiments discussed below, may be made by techniques knows to those skilled in the field of organic chemistry, and as more specifically exemplified in the Examples.

In one embodiment, X is —S(O)$_q$— and the compounds have the following structure (II):

(II)

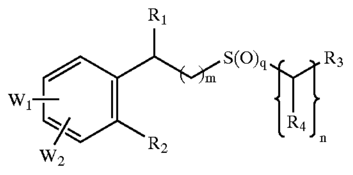

In one aspect of this embodiment, q is 2, 1 or 0 and the compounds have the following structure (II-1), (II-2) or (II-3), respectively:

(II-1)

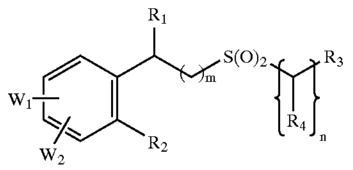

(II-2)

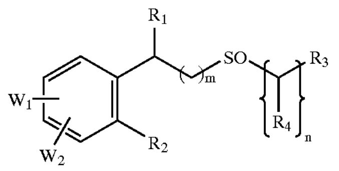

(II-3)

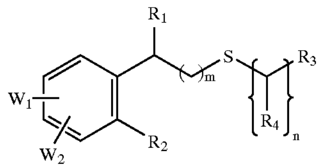

In another embodiment, X is —O— and the compounds have the following structure (III):

(III)

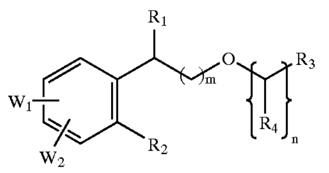

In a further embodiment, X is —N(R)— and the compounds have the following structure (IV):

(IV)

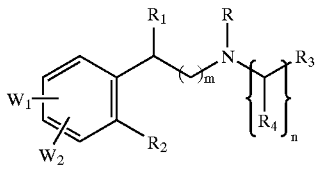

In yet another embodiment, X is —C(R)(R')— and the compounds have the following structure (V):

(V)

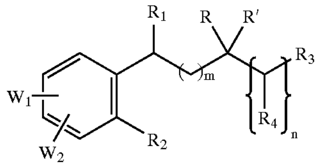

Depending upon the choice of m in structure (I), the compound have the following structure (I-1) when m is 0 and structure (I-2) when m is 1:

(I-1)

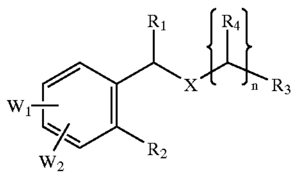

(I-2)

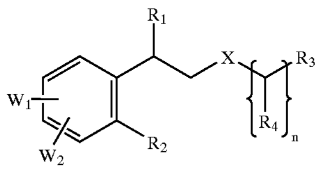

Depending upon the choice of n, compounds of this invention have the following structure (I-3) when n is 0, structure (I-4) when n is 1, and structure (I-5) when n is 2:

(I-3)

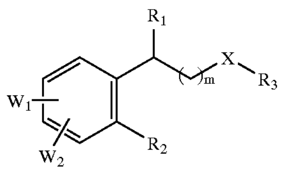

(I-4)

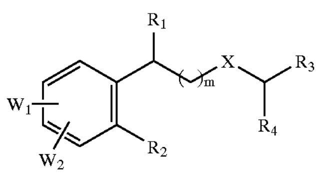

-continued (I-5)

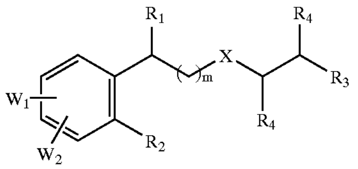

Depending upon the choice of the $R_2$ group, compounds have the following structure (I-6) when $R_2$ is hydrogen, structure (I-7) when $R_2$ is $—OR_{2a}$, structure (I-8) when $R_2$ is $—C(=O)NR_{2b}R_{2a}$, structure (I-9) when $R_2$ is $—CH_2NR_{2b}R_{2a}$, structure (I-10) when $R_2$ is $—CH_2OR_{2a}$, structure (I-11) when $R_2$ is $—NR_{2b}R_{2c}$, structure (I-12) when $R_2$ is $—NHC(=O)R_{2a}$, structure (I-13) when $R_2$ is $—NHC(=O)NR_{2b}R_{2c}$, and structure (I-14) when $R_2$ is $—NHC(—NH)NR_{2b}R_{2c}$:

(I-6)

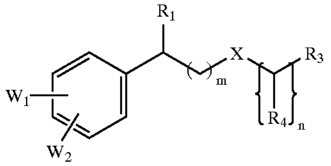

(I-7)

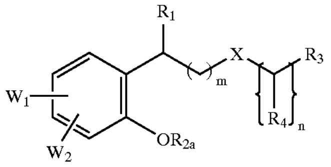

(I-8)

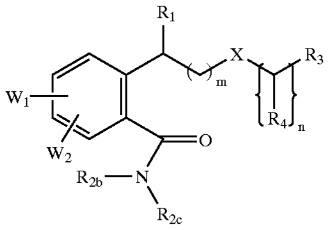

(I-9)

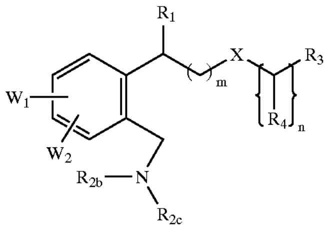

(I-10)

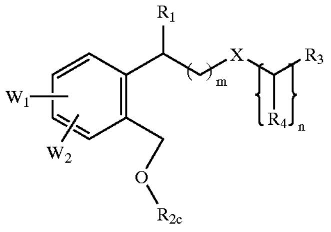

-continued (I-11)

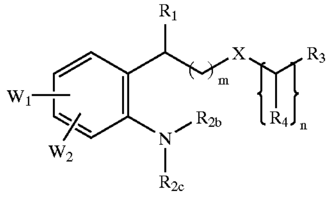

(I-12)

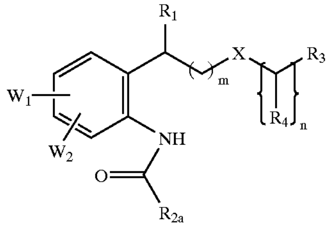

(I-13)

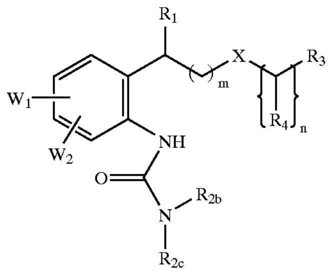

(I-14)

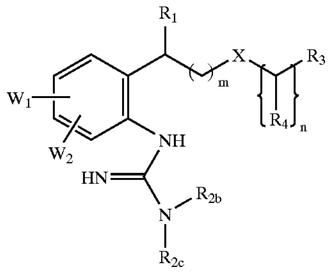

In one embodiment, $R_1$ is aryl or substituted aryl and the compounds have the following structure (VI):

(VI)

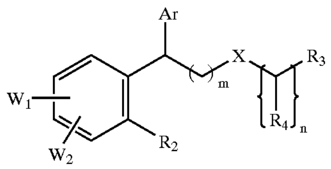

wherein Ar represents aryl or substituted aryl as defined herein.

In a more specific aspect of structure (VI), $W_1$ is present at the 5-position, $W_2$ is not present, and the compounds have the following structure (VII):

(VII)

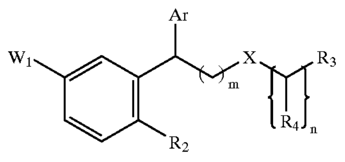

In a particular embodiment of structure (VII), $W_1$ is halogen, such as chloro, bromo or fluoro, and more particularly chloro.

In more specific embodiments of structure (VII), X is $S(O)_q$ where q is 0, $R_2$ is —$NR_{2a}R_{2d}$, n is 1 and m is 0 or 1, and the compounds have the following structure (VII-1) or (VII-2), respectively:

(VII-1)

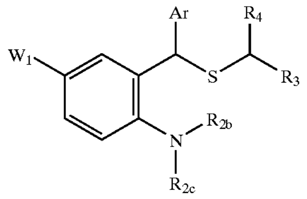

(VII-2)

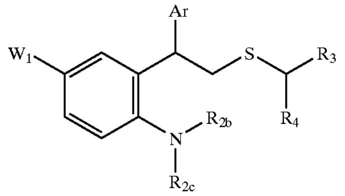

In other more specific embodiments of structure (VII), X is $S(O)_q$ where q is 0, $R_2$ is —$NR_{2a}R_{2c}$, n is 2 and m is 0 or 1, and the compounds have the following structure (VII-3) or (VII-4), respectively:

(VII-3)

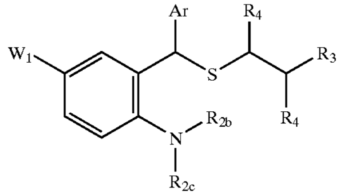

(VII-4)

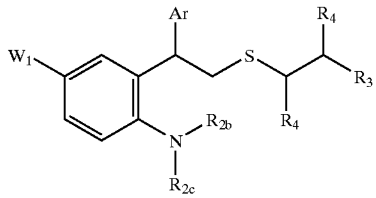

In another embodiment, $R_1$ is alkyl or substituted alkyl and the compounds have the following structure (VIII):

(VIII)

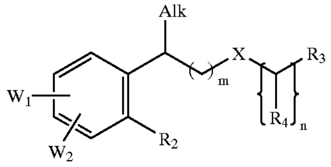

wherein Alk represents alkyl or substituted alkyl as defined herein.

In a more specific aspect of structure (VIII), $W_1$ is present at the 5-position, $W_2$ is not present, and the compounds have the following structure (IX):

(IX)

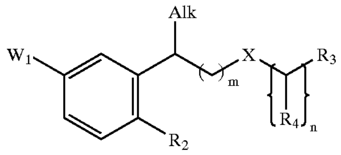

In a particular embodiment of structure (IX), $W_1$ is halogen, such as chloro, bromo or fluoro, and more particularly chloro.

In more specific embodiments of structure (IX), X is $S(O)_q$ where q is 0, $R_2$ is —$NR_{2a}R_{2b}$, n is 1and m is 0 or 1, and the compounds have the following structure (IX-1) or (IX-2), respectively:

(IX-1)

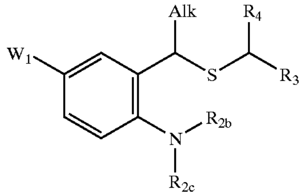

(IX-2)

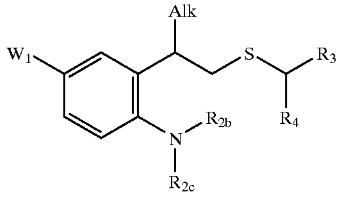

In more specific embodiments of structure (IX), X is $S(O)_q$ where q is 0, $R_2$ is —$NR_{2a}R_{2c}$, n is 2 and m is 0 or 1, and the compounds have the following structure (IX-3) or (IX-4), respectively:

(IX-3)

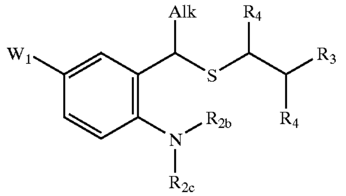

-continued (IX-4)

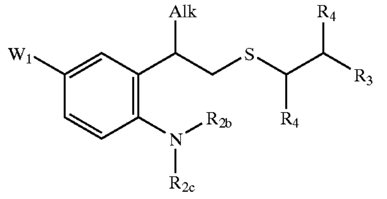

In other specific embodiments, X is $S(O)_q$, $R_3$ is $—C(=O)N(R_{3a})(R_{3b})$, $—C(—O)OR_{3c}$, $—C(=O)R_{3c}$, heterocycle or substituted heterocycle, $—NHC(=O)N(R_{3a})(R_{3b})$, $—NHC(=S)N(R_{3a})(R_{3b})$, $—NHC(=O)R_{3d}$ or $—NHSO_2R_{3d}$, $R_4$ is hydrogen, and the compounds have the following structures (X) through (XVII), respectively:

(X)

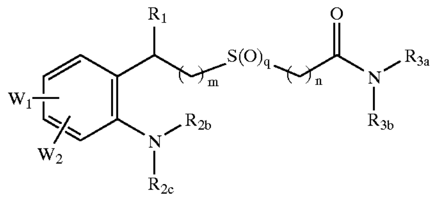

(XI)

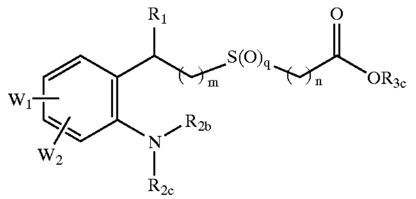

(XII)

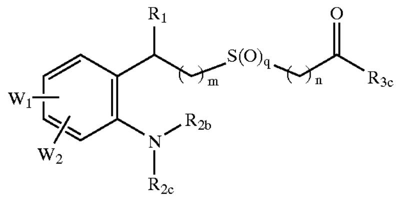

(XIII)

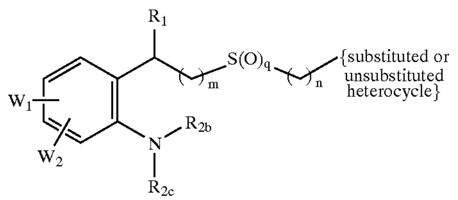

(XIV)

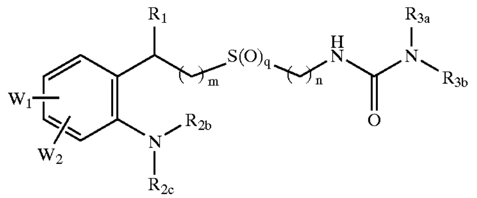

-continued (XV)

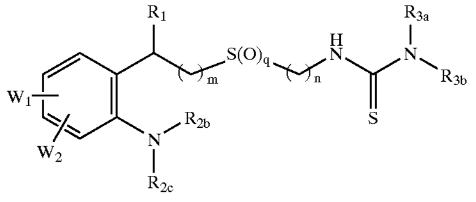

(XVI)

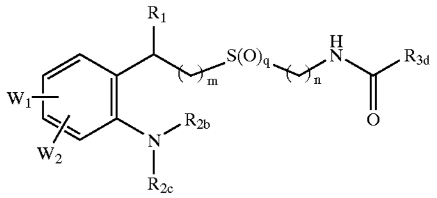

(XVII)

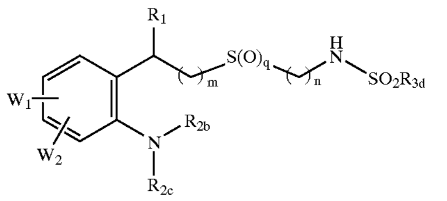

Although not intending to be limited by the following theory, it is believed that compounds of structure (I) are selective inhibitors of the mitochondrial calcium/sodium antiporter (MCA). As described in greater detail herein, such compounds substantially enhance insulin secretion. In one aspect, the compounds enhance insulin secretion that is stimulated by supraphysiological glucose concentrations (e.g., glucose stimulated insulin secretion), but does not substantially enhance insulin secretion under conditions where normal physiological glucose concentrations are present (e.g., basal insulin secretion). In this aspect of the invention, the compounds selectively interfere with MCA and/or other mitochondrial calcium efflux mechanisms in a manner that preferentially enhances glucose stimulated insulin secretion relative to basal insulin secretion, and thus are particularly useful for treatment of diabetes.

More specifically, it is believed that the compounds of structure (I) maintain increased and sustained intramitochondrial calcium concentrations, thereby driving oxidative phosphorylation and the consequent elevation of intracellular ATP concentration. Such elevated ATP concentrations promote enhanced insulin secretion and effect the desirable result of providing sufficient insulin to lower supraphysiological circulating glucose concentrations and preferably return them to concentrations at or near normal levels.

In certain aspects, there is provided a method for treating diabetes comprising administering to a subject a therapeutically effective amount of a compound of structure (I), and further comprising administering an agent that lowers circulating glucose concentrations. While current agents for treating type 2 DM may lower blood glucose levels without correcting underlying biochemical defects in this disease, it is desirable in certain instances to combine a compound of structure (I) with an existing hypoglycemic agent. For example, an agent of the sulfonylurea class or of the more recently developed non-sulfonylurea class of agents that close the potassium/ATP channel may be combined with a compound of structure (I). As other non-limiting examples, agents that supply substrates for mitochondrial metabolism (e.g., KCl, α-ketoisocaproic acid or leucine), insulin sensitizers (e.g., thiazolidinediones), inhibitors of hepatic glucose output (e.g., metformin) or glucose uptake blockers (e.g., acarbose) may also be employed.

An "agent that lowers circulating glucose concentrations" includes any hypoglycemic agent as known in the art and provided herein, including anti-diabetic agents such as sulfonylurea compounds and non-sulfonylurea compounds, and may further include a biguamide, a thiazolidinedione, repaglinide, acarbose, metformin or other hypoglycemic compositions (e.g., 6LP-1 and its analogs, DPP-IV inhibitors, α-ketoisocaproic acid, leucine or analogs of other amino acids).

A "biological sample" may comprise any tissue or cell preparation as described herein and a "biological sample containing a mitochondrial calcium/sodium antiporter polypeptide" comprises any tissue or cell preparation in which an expressed MCA polypeptide or other mitochondrial molecular component as provided herein that mediates $Ca^{2+}$ efflux from a mitochondrion is thought to be present. Biological samples (including those containing a MCA polypeptide) may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid or cytoplasmic hybrid "cybrid" cell lines, differentiated or differentiatable cell lines, transformed cell lines and the like. A biological sample may, for example, be derived from a recombinant cell line or from a transgenic animal.

In certain preferred embodiments the subject or biological source is a human known to have, or suspected of being at risk for having, diabetes mellitus. In certain further preferred embodiments the diabetes mellitus is type 2 diabetes mellitus, and in certain other further preferred embodiments the diabetes mellitus is maturity onset diabetes of the young (MODY). Well known criteria have been established for determining a presence of, or risk for having diabetes mellitus (e.g., type 2 diabetes mellitus, MODY) as described herein and as known in the art, and these may be found, for example, in *Clinical Practice Recommendations* 2000 (2000 *Diabetes Care* 23: supplement 1) or elsewhere (see, e.g., www.diabetes.org/, the website of the American Diabetes Association). Among these recognized physiological parameters that relate to diabetes, those familiar with the art will appreciate that a variety of methodologies have been established for the determination of glucose and insulin concentrations in the circulation. For example, methods for quantifying insulin in a biological sample as provided herein (e.g., a blood, serum or plasma sample) may include a radioimmunoassay (RIA) using an antibody that specifically binds to insulin. Variations on RIA such as enzyme linked immunosorbent assays and immunoprecipitation analysis, and other assays for the presence of insulin or proinsulin in a biological sample are readily apparent to those familiar with the art, and may further include assays that measure insulin secretion by cells in the presence or absence of secretagogues such as glucose, KCl, amino acids, sulfonylureas, forskolin, glyceraldehyde, succinate or other agents that may increase or decrease insulin or proinsulin in a cell conditioned medium. Such methods may also be used to quantify the amount of insulin produced by or released from an insulin-secreting cell.

Because it is well recognized by those familiar with the art that there may be large quantitative variations in circulating glucose and insulin levels among individual subjects (see, e.g., *Clinical Practice Recommendations* 2000, 2000 *Diabetes Care* 23 (suppl. 1), and references cited therein), the present invention contemplates in preferred embodiments a method for treating diabetes with a pharmaceutical composition comprising a compound of structure (I) that selectively impairs MCA activity as provided herein, wherein the compound does not substantially enhance insulin secretion at physiological glucose concentration (i.e., under fasting or basal metabolic conditions) and wherein the compound substantially enhances insulin secretion at supraphysiological glucose concentration (i.e., under non-fasting conditions or conditions of glucose stimulation). Although certain preferred embodiments of the present invention relate to compositions and methods for treating diabetes in humans, the invention need not be so limited. In particular, those having ordinary skill in the art will readily appreciate that diabetes, including any disease state characterized by inappropriate and/or sustained periods of hyperglycemia such as type 2 DM or other diabetes mellitus, may be a condition that is present in a number of non-human animals (e.g., Ford, 1995 *Veterin. Clinics of N. Amer.: Small Animal Practice* 25(3):599–615). Accordingly, compositions and methods provided herein as may be useful for the treatment of these and other manifestations of diabetes in non-human animals are within the scope and spirit of the present invention.

Normal or fasting physiological glucose concentration thus refers to the concentration of glucose in the circulation of a subject under normal conditions (e.g., fasting basal conditions), which are distinct from transient supraphysiological, non-fasting or otherwise temporarily elevated glucose concentrations that are achieved under non-normal conditions such as after feeding or other conditions of glucose stimulation. For example by way of illustration and not limitation, depending on a variety of factors such as the physiological status, diet, activity level, health and/or genetic constitution of a subject, or the like, metabolic homeostatic mechanisms (including insulin secretion) typically operate to maintain a relatively narrow range of circulating glucose concentrations under fasting conditions that are significantly lower than circulating glucose concentrations that are reached following feeding or other glucose stimulation. Such elevated glucose concentrations, which typically are not sustained over time, reflect a departure from the normal or fasting state sought to be maintained by the homeostatic mechanisms, and are referred to herein as supraphysiological glucose concentrations. Accordingly, and as a further non-limiting example, many normal individuals may maintain a fasting or physiological circulating glucose concentration at or around approximately 40–80 mg/dl and generally less than about 10 mg/dl, which may be generally less than 126 mg/dl in an individual characterized as having "impaired fasting glucose", and which may be generally greater than 126 mg/dl in an individual characterized as diabetic (see, e.g., Gavin et al., 2000 *Diabetes Care* 23 (suppl. 1):S4–S19 and references cited therein) such that a glucose concentration induced by feeding or other type of glucose stimulation that is greater than such a fasting or physiological glucose concentration in a statistically significant manner may be regarded as a supraphysiological glucose concentration. Similarly, there may be large variations among individuals with regard to circulating insulin concentrations and the degree to which an agent that impairs MCA activity according to the invention effects elevated insulin concentrations.

Therefore, the present invention contemplates "enhanced" insulin secretion to refer to an insulin concentration that is, in a statistically significant manner, detectably increased by an MCA activity-impairing agent to a greater degree following supraphysiological glucose stimulation than is the degree (if any) to which the MCA activity-impairing agent increases the detectable insulin concentration under fasting or physiological conditions. Accordingly, in preferred embodiments, the compound that selectively impairs an MCA activity enhances insulin secretion that is stimulated by a supraphysiological glucose concentration and does not enhance insulin secretion in the presence of a fasting glucose concentration.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise. Throughout this application various publications are referenced within parentheses. The disclosures of these publications in their entireties are hereby incorporated by reference in this application.

Reference to particular buffers, media, reagents, cells, culture conditions and the like, or to some subclass of the same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

According to certain embodiments of the present invention a "therapeutically effective amount" of a compound of structure (I) that impairs a MCA activity and/or a compound that lowers circulating glucose concentration may be administered. The person having ordinary skill in the art can readily and without undue experimentation determine what is a therapeutically effective amount as provided herein. Thus, for example and as described elsewhere herein, in the context of diabetes, and more specifically in the context of monitoring efficacy of diabetes therapy, periodic determination of circulating blood glucose concentrations may be routinely performed in order to determine whether a subject's blood glucose has attained a normal, physiological level. (see, e.g., Gavin et al., 2000 *Diabetes Care* 23 (suppl. 1):S4–S19 and references cited therein) Optionally or additionally, according to certain contemplated embodiments it may be desirable to monitor blood insulin and/or glycated hemoglobin levels, which as described herein may be performed according to any of a number of routine and well established methodologies.

Those having ordinary skill in the art are readily able to compare ATP production by an ATP biosynthetic pathway in the presence and absence of a candidate ATP biosynthesis factor. Routine determination of ATP production may be accomplished using any known method for quantitative ATP detection, for example by way of illustration and not limitation, by differential extraction from a sample optionally including chromatographic isolation; by spectrophotometry; by quantification of labeled ATP recovered from a sample contacted with a suitable form of a detectably labeled ATP precursor molecule such as, for example, $^{32}P$; by quantification of an enzyme activity associated with ATP synthesis or degradation; or by other techniques that are known in the art. Accordingly, in certain embodiments of the present invention, the amount of ATP in a biological sample or the production of ATP (including the rate of ATP production) in a biological sample may be an indicator of altered mitochondrial function. In one embodiment, for instance, ATP may be quantified by measuring luminescence of luciferase catalyzed oxidation of D-luciferin, an ATP dependent process.

As described herein, a compound that selectively impairs MCA activity may in certain preferred embodiments interfere with transmembrane transport of calcium cations, whereby such activity may be determined by detecting calcium. A variety of calcium indicators are known in the art and are suitable for generating a detectable signal in solution or as an intracellular signal, for example, a signal that is proportional to the level of calcium in the cytosol, including but not limited to fluorescent indicators such as fura-2 (McCormack et al., 1989 *Biochim. Biophys. Acta* 973:420); mag-fura-2; BTC (U.S. Pat. No. 5,501,980); fluo-3, fluo-4, fluo-5F and fluo-5N (U.S. Pat. No. 5,049,673); fura-4F, fura-5F, fura-6F, and fura-FF; rhod-2 and rhod-5F; Calcium Green 5N™; benzothiaza-1 and benzothiaza-2; and others, which are available from Molecular Probes, Inc., Eugene, Oreg. (see also, e.g. *Calcium Signaling Protocols—Meths. In Mol. Biol.*—Vol. 114, Lambert, D. (ed.), Humana Press, 1999).

Calcium Green 5N™ is a particularly preferred calcium indicator molecule for use according to the present invention. Depending, however, on the particular assay conditions to be used, a person having ordinary skill in the art can select a suitable calcium indicator from those described above or from other calcium indicators, according to the teachings herein and based on known properties (e.g., solubility, stability, etc.) of such indicators. For example by way of illustration and not limitation, whether a cell permeant or cell impermeant indicator is needed (e.g., whether a sample comprises a permeabilized cell), affinity of the indicator for calcium (e.g., dynamic working range of calcium concentrations within a sample as provided herein) and/or fluorescence spectral properties such as a calcium-dependent fluorescence excitation shift, may all be factors in the selection of a suitable calcium indicator. Calcium-Green-5N™ (potassium salt) is commercially available (Molecular Probes, Eugene, Oreg.; C-3737). Calcium-Green-5N™ is a low affinity $Ca^{2+}$ indicator (as is, for example, Oregon Green 488 BAPTA-5N). Low affinity indicators are preferred because of the $Ca^{2+}$ concentrations used in the assays. High affinity dyes require a lower $Ca^{2+}$ concentration and therefore a lower number of cells, and thus a lower number of mitochondria, would be required than the number used in the assays.

Other calcium-sensitive detectable reagents that can be used in the assay of the invention include Calcein, Calcein Blue, Calcium-Green-1, Calcium-Green-2, Calcium-Green-$C_{18}$, Calcium Orange, Calcium-Orange-5N, Calcium Crimson, Fluo-3, Fluo-3 AM ester, Fluo-4, Fura-2, Fura-2FF, Fura Red, Fura-$C_{18}$, Indo-1, Bis-Fura-2, Mag-Fura-2, Mag-Fura-5, Mag-Indo-1, Magnesium Green, Quin-2, Quin-2 AM (acetoxymethyl) ester, Methoxyquin MF, Methoxyquin MF AM ester, Rhod-2, Rhod-2 AM ester, Texas Red-Calcium Green, Oregon Green 488 BAPTA-1, Oregon Green 488 BAPTA-2, BTC, BTC AM ester, (all from Molecular probes, OR), and aequorin. As noted above, in certain preferred embodiments intramitochondrial calcium concentrations are directly determined using mitochondrially targeted aequorin.

In the practice of the methods of this invention, compounds of structure (I) are typically administered to a patient in the form of a pharmaceutically acceptable composition, which comprises one or more compounds of structure (I) in combination with one or more pharmaceutically acceptable carrier(s). A "pharmaceutically acceptable carrier" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions that contain one or more compounds as provided herein may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrastemal, intracavernous, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, which is the route of administration in preferred embodiments, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more compounds of structure (I), one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of a compound as provided herein such that a suitable dosage will be obtained. Typically, this amount is at least 0.01 wt % of the compound in the composition. When intended for oral administration, this amount may be varied to be between 0.1 and about 70% of the weight of the composition. Preferred oral compositions contain between about 4% and about 50% of the compound(s). Preferred compositions and preparations are prepared so that a parenteral dosage unit contains between 0.01 to 1% by weight of the compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of from about 0.1 to about 10% w/v (weight per unit volume).

The composition may be intended for rectal administration, in the form, e.g., of a suppository that will melt in the rectum and release the drug. The composition for rectal administration may contain an oleaginous base as a suitable nonirritating excipient. Such bases include, without limitation, lanolin, cocoa butter and polyethylene glycol. In the methods of the invention, the agent(s) that alter mitochondrial function identified as described herein may be administered through use of insert(s), bead(s), timed-release formulation(s), patch(es) or fast-release formulation(s).

It will be evident to those of ordinary skill in the art that the optimal dosage of the compound(s) may depend on the weight and physical condition of the patient; on the severity and longevity of the physical condition being treated; on the particular form of the active ingredient, the manner of administration and the composition employed. The use of the minimum dosage that is sufficient to provide effective therapy is usually preferred. Patients may generally be monitored for therapeutic or prophylactic effectiveness using assays suitable for the condition being treated or prevented, which will be familiar to those having ordinary skill in the art and which, as noted above, will typically involve determination of whether circulating insulin and/or glucose concentrations fall within acceptable parameters according to well-known techniques. Suitable dose sizes will vary with the size, condition and metabolism of the patient, but will typically range from about 10 mL to about 500 mL for 10–60 kg individual. It is to be understood that according to certain embodiments the compound may be membrane permeable, preferably permeable through the plasma membrane and/or through mitochondrial outer and/or inner membranes. According to certain other embodiments, the use of the compound as disclosed herein in a chemotherapeutic composition can involve such an agent being bound to another compound, for example, a monoclonal or polyclonal antibody, a protein or a liposome, which assist the delivery of said compound.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The following Examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

EXAMPLE 1

SCHEME 1
GENERAL SYNTHESIS OF 2-AMINO-BENZHYDROL ANALOGS AS INTERMEDIATES (ROUTE A)

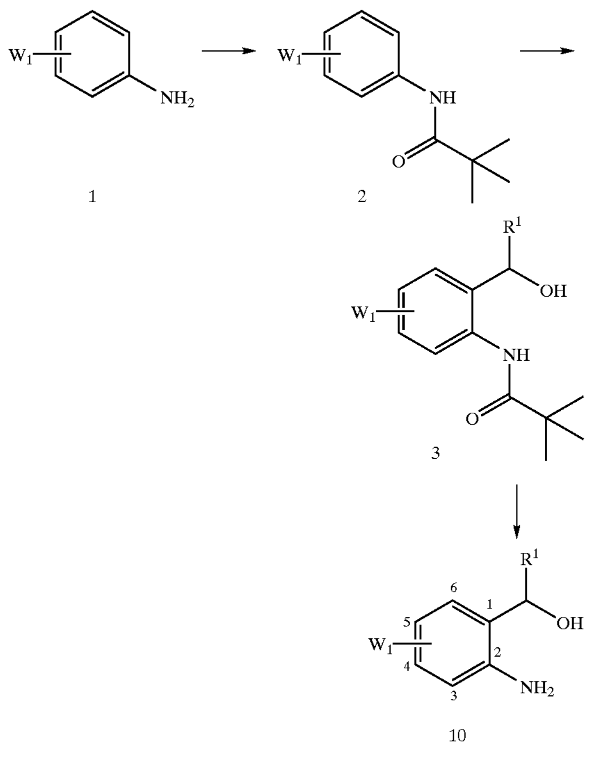

1 2 3 10

Synthesis of 4-chloro-1',1',1'-trimethylacetanilide (2a)

To a solution of 4-chloroaniline (1a) (20 g, 0.157 mole) in DCM (400 ml) at 0° C. was added DIEA (54.7 ml, 0.314 mol) and pivaloyl chloride (23.2 ml, 0.188 mol). The mixture was stirred for 2 hours and washed with water (500 ml×2), 10% $NaHCO_3$ (aq.) (500 ml×2), water (500 ml×2) and dried over $Na_2SO_4$. The crude product was recrystalized from ethyl acetate to give the title compound 2a as a white solid (23 g, 69% yield).

Synthesis of 3a ($W_1$=5-Cl, $R_1$=4-pyridyl)

To a solution of the 4-chloro-1',1',1'-trimethylacetanilide (2a) (509 mg, 2.4 mmol) in THF (10 ml) under an atmosphere of nitrogen cooled to −78° C. was added n-butyllithium (2.5 ml, 2.4 M solution in diethyl ether, 6 mmol) over 5 min. The reaction was left to warm up to 0° C. and kept at this temperature for 2 hrs. Pyridine-4-carboxaldehyde (515 mg, 4.8 mmol) dissolved in THF (2 ml) was added and the reaction was left to slowly warm to room temperature over 1 hr. The reaction was quenched with 1M HCl (10 ml) and then extracted with ethyl acetate (3×50 ml). The combined organic phase was dried over sodium sulfate, filtered and the solvent removed in vacuum. The oily residue was passed through a plug of silica gel (5 g) using ethyl acetate as eluent. The material was recrystallized from ethyl acetate to yield compound 3a as white crystals (585 mg, 76% yield). clogP=3.23; $R_f$ (petroleum ether:ethyl acetate (1:1)=0.31; HPLC (214 nm) $t_R$=8.20 (98.12%) min; $^1H$ NMR (400 MHz, $CDCl_3$) δ 1.04 (s, 9H), 5.74 (s, 1H), 7.07 (d, J=2.4 Hz, 1H), 7.24–7.30 (m, 4H), 8.10 (d, J=8.8 Hz, 1H), 8.34 (d, J=5.7 Hz, 2H), 9.08 (s, 1H); 13C NMR (100 MHz, $CDCl_3$) δ 27.2, 39.5, 73.9, 121.4, 124.4, 128.8, 129.0, 132.5, 135.9, 149.0, 151.2, 177.1; ESMS m/z 319.3 $[M+H]^+$, 637.3 $[2M+H]^+$; LC/MS $t_R$=5.22 (319.1 $[M+H]^+$, 637.1 $[2M+H]^+$) min.

Synthesis of 10a ($W_1$=5-Cl, $R_1$=4-pyridyl)

A solution of the amide 3a (266 mg, 0.83 mmol) was dissolved in 3 M HCl solution (9 ml) and was heated at reflux for 4.5 hrs. After this time the reaction was diluted with water (20 ml) and brought to basic pH using 10M NaOH (4 ml). The aqueous solution was extracted with dichloromethane (3×50 ml). The combined organic phase was dried over sodium sulfate, filtered and the solvent removed in vacuum to yield compound 10a as an off white solid (189 mg, 96% yield) which was analytically pure and was used without further characterization. clogP=1.31; $R_f$ (ethyl acetate)=0.36; ESMS m/z 235.1 $[M+H]^+$; LC/MS $t_R$=3.90 (235.0 $[M+H]^+$, 469.2 $[2M+H]^+$) min.

Using similar procedures as outlined in 2 and 3, the following benzhydrol derivatives were prepared:

10b ($W_1$=5-Cl, $R_1$=2,6-dimethylphenyl) was synthesized from 2a and 2,6-methylbenzaldehyde. Compound 10b was obtained as thick oil (285 mg, 44% yield). clogP=5.54; $R_f$ (petroleum ether:ethyl acetate (1:1)=0.41; HPLC (214 nm) $t_R$=9.42 (84.35%) min; $^1H$ NMR (400 MHz, $CDCl_3$) δ 1.21 (s, 9H), 2.18 (s, 6H), 6.23 (s, 1H), 6.51 (d, J=2.4 Hz, 1H), 6.99–7.01 (m, 2H), 7.11 (s, 1H), 7.13 (dd, J=2.4, 8.8 Hz, 1H), 8.04 (d, J=8.8 Hz, 2H), 9.67 (s, 1H); 13C NMR (100 MHz, $CDCl_3$) δ 20.9, 27.5, 39.8, 71.0, 123.4, 127.0, 128.0, 128.2, 128.4, 128.5, 129.6, 130.9, 136.1, 136.6, 137.1, 177.4; ESMS m/z 328.4 $[M-OH]^+$, 346.5 $[M+H]^+$; LC/MS $t_R$-9.74 (328.1 $[M-OH]^+$, 346.3 $[M+H]^+$, 691.4 $[2M+H]^+$) min.

10c ($W_1$=5-Cl, $R_1$=3-methyl-2-thiophenyl) was synthesized from 2a and 3-methyl-2-thiophene carboxaldehyde. Compound 10c was used immediately in the subsequent step.

EXAMPLE 2

SCHEME 2
GENERAL SYNTHESIS OF 2-AMINO-BENZHYDROL ANALOGS AS INTERMEDIATES (ROUTE B)

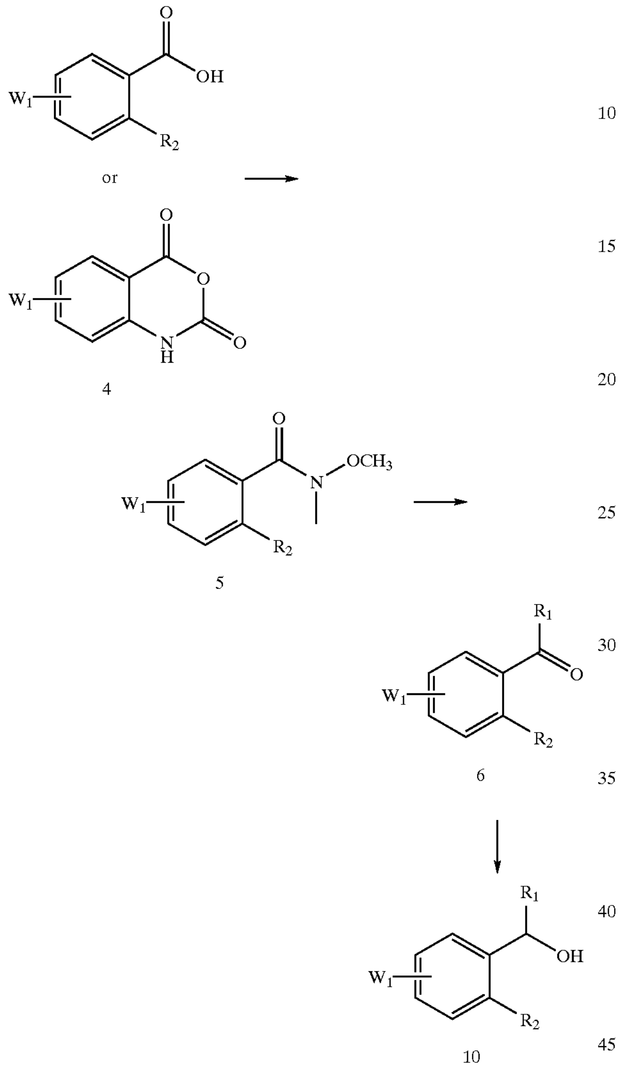

or

4

5

6

10

Synthesis of 5a ($W_1$=5-Cl, $R_2$=$NH_2$)

To a solution of N,O-dimethylhydroxylamine hydrochloride (2.0 g, 20 mmol) dissolved in 90% ethanol (40 ml) was added triethylamine (2.5 ml, 20 mmol). The reaction was left stirring for 10 min and 5-chloroisatoic anhydride (3 g, 15.2 mmol) was added to the above solution in small portions. The reaction was heated to reflux for 1 h, after which time it was poured into a 1:1 ice/saturated sodium bicarbonate solution (50 ml). The ethanol was removed under reduced pressure and the resulting aqueous solution was extracted with ethyl acetate (3×50 ml). The combined organic phase was dried over magnesium sulfate, filtered and the solvent removed in vacuum to yield a colorless oil. This material was further purified by flash chromatography on silica gel (150 g) using petroleum ether:ethyl acetate 2:1 then 1:1 as eluent, to provide the desired compound 5a as a slightly off white solid (2.61 g, 70% yield)); $R_f$ (petroleum ether:ethyl acetate (2:1)=0.42; HPLC (214 nm) $t_R$=5.50 (94.6%) min; $^1$H NMR (400 MHz, $CDCl_3$) δ 3.34 (s, 3H), 3.59 (s, 3H), 4.66 (brs, 2H), 6.30 (dd, J=3.3, 8.6 Hz, 1H), 7.13 (dd, J=2.5, 8.6 Hz, 1H), 7.36 (d, J=2.5 Hz, 1H); LC/MS $t_R$=5.44 (215.1 $[M+H]^+$, 429.3 $[2M+H]^+$, 643.4 $[3M+H]^+$) min.

In the case of starting with benzoic acid derivatives, the transformation of 4 to 5 was carried out in the presence of EDC and DIEA.

Synthesis of 6a ($W_1$=5-Cl, $R_1$=3,5-dimethylphenyl, $R_2$=$NH_2$)

To a solution of 3,5-dimethyliodobenzene (1.59 g, 6.85 mmol) dissolved in THF (10 ml) under an atmosphere of nitrogen cooled to −78° C. was added n-butyllithium (2.76 ml, 2.4 M solution in diethyl ether, 1 equivalent based on the arylhalide). The reaction was left for 20 min after which time the amide 5a (350 mg) dissolved in tetrahydrofuran (2.5 ml) was added dropwise. The reaction was left stirring for a further 20 min. The reaction was then quenched with the addition of 1M hydrochloric acid solution (5 ml) warmed to room temperature and diluted with ethyl acetate (80 ml). The layers separated and the organic phase was washed with water (1×20 ml), brine (1×20 ml), dried over sodium sulfate, filtered and the solvent removed in vacuum. The material was frozen in 1:1 water/acetonitrile mixture and lyophilized to remove any volatile material. Compound 6a was obtained as a brown crystalline solid (450 mg), which was analytically pure and used in the next step without further purification. clogP=3.25; $R_f$ (petroleum ether:ethyl acetate (5:1)=0.66; $^1$H NMR (400 MHz, $CDCl_3$) δ 2.37 (s, 6H), 6.00 (brs, 2H), 6.68 (d, J=8.8 Hz, 1H), 7.21–7.26 (m, 4H), 7.41 (d, J=2.4 Hz, 1H); ESMS m/z 260.0 $[M+H]^+$; LC/MS $t_R$=10.83 (259.9 $[M+H]^+$) min.

Synthesis of 6ad ($W_1$=5-$CH_3$, $R_1$=2-methylphenyl, $R_2$=OH)

Compound 6ac ($W_1$=5-$CH_3$, $R_1$=2-methylphenyl, $R_2$=—$OCH_3$) (0.094 g, 0.42 mmol) was dissolved in anhydrous $CH_2Cl_2$ (3 ml) and cooled to 0° C. Boron tribromide (0.180 ml, 1.87 mmol, 4.5 eq.) was added to cool solution dropwise. The color of the solution changed from medium yellow to dark yellow-brown. The reaction was stirred at 0° C. for 1 hr. The progress of the reaction was monitored by TLC (ethyl acetate:petroleum ether=1:14). Water was added and the reaction solution partitioned between water and $CH_2Cl_2$. The aqueous layer was back-extracted with $CH_2Cl_2$, then the combined organic fractions washed with brine, dried ($Na_2SO_4$) then evaporated under reduced pressure to give a dark orange oil (0.11 g), which was purified using flash chromatography on silica (5 g) using 1:20 diethyl ether:petroleum ether to give the target compound 6ad (0.06 g). $R_f$ (1:5 diethyl ether:petrol)=0.56. HPLC (214 nm) $t_R$=10.03 min (96% overloaded).

Synthesis of 10d ($W_1$=5-Cl, $R_1$=3,5-dimethylphenyl, $R_2$=$NH_2$)

To the starting ketone 6a (250 mg, 0.96 mmol) dissolved in THF (5 ml) under an atmosphere of nitrogen cooled to 0° C. was added lithium aluminum hydride (0.5 ml, 1.0M solution in diethyl ether). Analysis by TLC indicated the reaction was complete, saturated sodium bicarbonate (20 ml) was carefully added and the resultant solution was extracted with ethyl acetate (3×50 ml). The combined organic phase was dried over sodium sulfate, filtered and the solvent removed in vacuum to yield 10d as a brown oil which was used immediately in the next step.

Using similar procedures as outlined above, the following benzhydrol derivatives are prepared:

10e ($W_1$=5-Cl, $R_1$=1-methyl-2-imidazolyl, $R_2$=$NH_2$).

10f ($W_1$=5-Cl, $R_1$=2-benzothiazolyl, $R_2$=$NH_2$).

10g ($W_1$=5-Cl, $R_1$=2-thiophenyl, $R_2$=$NH_2$).

10h ($W_1$=5-Cl, $R_1$=1-methyl-2-pyrrolyl, $R_2$=$NH_2$).

10i ($W_1$=5-Cl, $R_1$=3-methylphenyl, $R_2$=$NH_2$).

10j ($W_1$=5-Cl, $R_1$=4-methylphenyl, $R_2$=$NH_2$).
10k ($W_1$=5-Cl, $R_1$=2,3-dimethylphenyl, $R_2$=$NH_2$).
10l ($W_1$=5-Cl, $R_1$=3,4-dimethylphenyl, $R_2$=$NH_2$).
10m ($W_1$=5-Cl, $R_1$=2,5-dimethylphenyl, $R_2$=$NH_2$).
10n ($W_1$=3,5-dichloro, $R_1$=2-methylphenyl, $R_2$=$NH_2$).
10o ($W_1$=3,5-dibromo, $R_1$=2-methylphenyl, $R_2$=$NH_2$).
10u ($W_1$=5-Cl, $R_1$=2-thiazolyl, $R_2$=$NH_2$)
10v ($W_1$=H, $R_1$=2,4-dimethylphenyl, $R_2$=$NH_2$)
10w ($W_1$=5-Cl, $R_1$=2,4-dimethylphenyl, $R_2$=$NH_2$)

fully added and the resultant solution was extracted with ethyl acetate (3x50 ml). The combined organic phase was dried over sodium sulfate, filtered and the solvent removed in vacuum to yield 10z ($W_1$=5-Cl, $R_1$=t-butyl, $R_2$=$NH_2$) as a brown oil which was used immediately in the next step.

EXAMPLE 3

SCHEME 3
GENERAL SYNTHESIS OF 2-AMINO-BENZHYDROL ANALOGS AS INTERMEDIATES (ROUTE C)

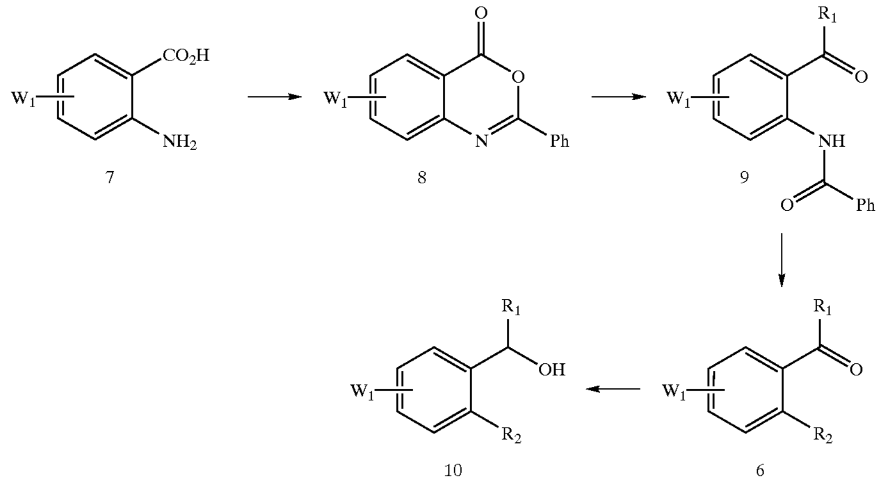

10x ($W_1$=5-Cl, $R_1$=phenyl, $R_2$=$NH_2$)
10y ($W_1$=6-$CH_3$, $R_1$=2-amino-3-pyridinyl, $R_2$=H)
10ab ($W_1$=5-$CH_3$, $R_1$=2-methylphenyl, $R_2$=H)
10ac ($W_1$=H, $R_1$=2-methylphenyl, $R_2$=methoxy)
10ad ($W_1$=5-$CH_3$, $R_1$=2-methylphenyl, $R_2$=OH)

Synthesis of 10z ($W_1$=5-Cl, $R_1$=t-butyl, $R_2$=$NH_2$)

Step 1: To a solution of 4-bromo-3,5-dimethylpyrazole (700 mg, 0.93 mmol) in THF (10 ml) under an atmosphere of nitrogen cooled to −78° C. was added t-butyllithiium (10.6 ml, 1.3M solution in pentane, 13.8 mmol). The reaction was left for 15 min then 2-amino-5-chloro-N-methoxy-N-methyl-benzamide (200 mg, 0.93 mmol) dissolved in THF (2 ml) was added. The reaction was left for 1 hr; then it was quenched with 1 M HCl (10 ml). The solution was diluted with brine (50 ml) and was extracted with ethyl acetate (3x50 ml). The combined organic phase was dried over sodium sulfate, filtered and the solvent removed in vacuum. The isolated product was the t-butyl ketone 6z ($W_1$=5-Cl, $R_1$=t-butyl, $R_2$=$NH_2$) rather than the desired pyrazole derivative. The residue was purified on silica gel (100 g) using petroleum spirit/ethyl acetate 10:1 as eluent. t-Butyl ketone 6z was isolated as a yellow solid (175.5 mg, 89% yield). clogP=2.64; HPLC (214 nm) $t_R$=7.78 (99%) min; $^1$H NMR (400 MHz, $CDCl_3$) δ 1.37 (s, 9H), 5.32 (brs, 2H), 6.62 (dd, J=3.2, 8.7 Hz, 1H), 7.14 (dd, J=2.4, 8.7 Hz, 1H), 7.70 (d, J=2.4 Hz, 1H); 13C NMR (100 MHz, $CDCl_3$) δ 28.6, 44.8, 119.0, 119.6, 119.8, 129.5, 132.3, 147.8, 208.7; $[M+H]^+$; LC/MS $t_R$=8.77 (212.2 $[M+H]^+$) min.

Step 2: To ketone 6z (250 mg, 0.96 mmol) dissolved in THF (5 ml) under an atmosphere of nitrogen cooled to 0° C. was added lithium aluminum hydride (0.5 ml, 1.0M solution in diethyl ether). Analysis by TLC indicated the reaction was complete, saturated sodium bicarbonate (20 ml) was care- Synthesis of 8a ($W_1$=5-methyl).

A mixture of 2-amino-5-methylbenzoic acid (7a) (2.0 g, 0.013 mol) and AR grade THF (21 ml) was cooled to 0° C. With vigorous stirring, anhydrous sodium carbonate (2.2 g, 0.021 mol, 1.6 eq.) was added followed by benzoyl chloride (3.02 ml, 0.026 mol, 2 eq.) dropwise. The mixture was left to stand at 0° C. for an additional 30 min, after which the cold bath was removed and the mixture stirred at rt overnight. Water (15 ml) was added. The reaction mixture was evaporated under reduced pressure (to remove the THF), extracted with $CH_2Cl_2$ (×2). The combined $CH_2Cl_2$ fractions were dried ($Na_2SO_4$) and evaporated under reduced pressure to give 8a as a cream colored solid (2.55 g, 82% yield). LC/MS $t_R$=8.16 (256.1, acyclic amide), 9.47 (237.9 $[M+H]^+$) min. The crude material was used in the next step.

Synthesis of 9a ($W_1$=5-methyl, $R_1$=2-methylphenyl).

A solution of the crude material 8a from the previous step (0.5 g, 2 mmol) in $CH_2Cl_2$ (15 ml) was cooled to −78° C. o-Tolyl magnesium bromide (2 M in diethyl ether, 2.3 ml, 5 mmol, 2.5 eq.) was added dropwise. The reaction was monitored by TLC and was allowed to proceed at −78° C. for a total of 55 min. The reaction was briefly warmed to rt, whence saturated $NH_4C$ solution (2 ml) was added. The reaction mixture was then partitioned with $CH_2Cl_2$ (×2). The combined $CH_2Cl_2$ fractions were back-extracted with brine (×2), then evaporated under reduced pressure to give crude 9a ($W_1$=5-methyl, 2-methylphenyl) as a yellow oil (0.58 g). LC/MS $t_R$=5.59 (no identifiable ion); 8.41 (195.1, unidentified); 9.45 (237.9, (8a)); 10.73 (329.9 (9a)) min. $R_f$ (ethyl acetate:petroleum 40–60 (1:20))=0.19 (target compound), 0.27 (starting material (8a)). Silica gel column chromatography was attempted using this solvent system, however co-elution of the two bands was observed. The crude material was therefore taken to the next step. The yield of product after purification by chromatography was 0.44 g.

Synthesis of 6b ($W_1$=5-methyl, $R_1$=2-methylphenyl, R═$NH_2$).

The crude product 9a from the above reaction (0.44 g), MeOH (5 ml), $H_2O$ (4 ml) and sodium hydroxide pellets (3.2 g, 0.08 mol, 100 eq.) were stirred and heated to reflux for 4 hrs, then cooled to rt and water (30 ml) added. The mixture was partitioned with $CH_2Cl_2$ (×4) and the combined $CH_2Cl_2$ fractions back-extracted with brine (×2). The combined $CH_2Cl_2$ fractions were then dried ($Na_2SO_4$) and evaporated under reduced pressure to give 6b as a dark yellow oil which was dried under vacuum overnight (0.153 g). LC/MS $t_R$ 8.34 (195.0, unidentified), 8.60 (226.1, $[M+H]^+$), 8.79 (no identifiable ion) min.

Synthesis of 10p ($W_1$=5-methyl, R=2-methylphenyl, $R_2$═$NH_2$).

The crude reaction product of 6b from above step (0.13 g) was dissolved in THF (5 ml) then cooled to ice/water temperature. Lithium aluminum hydride (nominal 1 M solution in diethyl ether) was added (1 ml) under a stream of nitrogen via syringe. The reaction was monitored using TLC. Additional aliquots of 0.5 ml of $LiAlH_4/Et_2O$ solution were added to the reaction solution at the 35 min and 2 hr 10 min marks. The reaction was allowed to proceed for 3 hr in total. Saturated $NaHCO_3$ solution was added. The mixture was partitioned between EtOAc and water. After several extractions, the combined EtOAc fractions were dried ($Na_2SO_4$) then evaporated under reduced pressure to yield LOT as a yellow oil. The crude reaction product was carried through to the next step.

Using similar procedures as outlined above, the following benzhydrol derivatives are prepared:

10g ($W_1$=H, $R_1$=2-methylphenyl, $R_2$=$NH_2$)

10r ($W_1$=H, $R_1$=2-chlorophenyl, $R_2$=$NH_2$)

10x ($W_1$=5-Cl, $R_1$=phenyl, $R_2$=$NH_2$)

10aa ($W_1$=5-Cl, $R_1$=2-methylphenyl, $R_2$=$NH_2$):

Using commercially available benzophenones, the following benzhydrol derivatives were prepared using the procedure outlined in the synthesis of 10d.

10s ($W_1$=5-Cl, $R_1$=2-chlorophenyl, $R_2$=$NH_2$).

10t ($W_1$=5-nitrol, $R_2$=phenyl, $R_2$=$NH_2$).

10ae ($W_1$=H, $R_1$=5-amino-2-chlorophenyl, $R_2$=H) using $LiBH_4$ in chlorophenyl THF.

10af ($W_1$=H, $R_1$=3-amino-4-chlorophenyl, $R_2$=H) was obtained from 4-chloro-3-nitrobenzophenone by reduction using activated iron in acetic acid/water at 90° C., followed by reduction using $LiBH_4$ in THF.

10ag ($W_1$=5-Cl, $R_1$=2-chlorophenyl, $R_2$=OH).

p-Chlorophenol (2 g, 15 mmol), methyl iodide (1.36 ml, 21.8 mmol) and potassium carbonate (2.07 g, 15.6 mmol) in dry acetone (15 ml) were taken in a 50 ml flask. After refluxing for 3 hrs at 60° C., acetone was removed using a rotary evaporator. Water was added and the product was extracted with $CH_2Cl_2$ to afford 2.2 g of crude product, which was purified by column chromatography using hexane as eluent to yield p-chloroanisole in 75% yield (1.59 g).

p-Chloroanisole (400 mg, 2.8 mmol) and $AlCl_3$ (410 mg, 3 mmol) in dry $CS_2$ (10 ml) were taken in 2-neck 25 ml rb flask. After refluxing for 15 min at 50° C. 2-chloro benzoyl chloride (420 μL, 3.36 mmol) was added via syringe and the mixture was refluxed for 4 hrs. The reaction was quenched by adding 5 ml of 1M HCl, extracted with DCM, washed with water, dried over $Na_2SO_4$ and concentrated to afford 1 g of the crude product. The product was purified by column chromatography using 20% $CHCl_3$/pet ether to yield 700 mg (72%) of compound 6ag ($W_1$=5-Cl, $R_1$=2-chlorophenyl, $R_2$=$OCH_3$). m.p. 104.5–108.1° C. $^1H$ NMR (300 MHz, $CDCl_3$) δ 11.88 (s, 1H), 7.52–7.33 (m, 5H), 7.2 (d, J=2.7 Hz, 1H), 7.03 (d, J=9 Hz, 1H).

Compound 6ag (100 mg, 0.3 mmol) in dry THF (2 ml) was taken in a 10 ml rb flask and cooled to 0° C. To the cold stirred solution LAH (28 mg, 0.6 mmol) was added and stirred for 8 hrs. A saturated solution of sodium potassium tartarate (5 ml) was added into the reaction mixture and stirring was continued for 30 min. After the separation of organic and aqueous layers, the reaction mixture was extracted with DCM, washed with water and dried over $Na_2SO_4$ to afford 78 mg (75%) of compound 10ag.

10ah ($W_1$=5-Cl, $R_1$=phenyl, $R_2$=—$OCH_3$).

5-Chloro-2-hydroxybenzophenone (500 mg, 2.5 mmol), methyl iodide (0.22 ml, 3.5 mmol) and potassium carbonate (0.37 g, 2.7 mmol) in dry acetone (15 ml) were taken in a 25 ml flask. After refluxing for 3 hrs, acetone was removed on a rotavap, water was added and the product was extracted with $CH_2Cl_2$ to afford 0.620 g of compound 4. The product was purified by column chromatography hexane as eluent to yield 0.413 g (78%) of 5-chloro-2-methoxybenzophenone.

5-chloro-2-methoxybenzophenone (200 mg, 0.94 mmol) in dry THF (5 ml) was cooled to 0° C. To the cold stirred solution LAH (115 mg, 3 mmol) was added and stirring was continued for 8 hrs. A saturated solution of sodium potassium tartarate (5 ml) was added into the reaction mixture and stirring was continued for 30 min. After the separation of organic and aqueous layers, the reaction mixture was extracted with DCM, washed with water and dried over $Na_2SO_4$ and concentrated to afford 168 mg (83%) of analytically pure 10ah.

Synthesis of 10ai ($W_1$=5-Cl, $R_1$=phenyl, $R_2$=OH).

To a solution of 5-chloro-2-hydroxybenzophenone (100 mg, 0.429 mmol) in dry THF (0.5 ml) at 0° C. under argon atmosphere was added LAH (35 mg, 0.92 mmol). The mixture was stirred for 8 hrs. The reaction mixture was added to 6 M HCl (2 ml) 0° C., neutralized with satd. $NaHCO_3$. The product was extracted with DCM (3×10 ml) dried over anhydrous $Na_2SO_4$ and concentrated to afford analytically pure 10ai (2 g, 78%).

Synthesis of 10ai ($W_1$=5-Cl, $R_1$=2-chlorophenyl, $R_2$=H).

To a solution of pentyl nitrite (2.5 mL, 19.2 mol) in THF (25 mL) at 65° C. was added a solution of compound 2-amino-2',5-dichlorobenzophenone (2 g, 7.5 mmol) in THF (10 mL) over a period of 1 hr. The reaction mixture was refluxed for 3 hrs and THF was removed on a rotary evaporator. The residue was extracted with benzene, washed with 16% $H_2SO_4$ (20 mL), dried over anhyd. $Na_2SO_4$ and concentrated to afford 3.6 g of the crude product which was purified by column chromatography using 5% ethyl acetate/petroleum ether to yield 6a ($W_1$=5-Cl, $R_1$=2-chlorophenyl, $R_2$═H) (1.8 g, 62%). $^1H$ NMR (300 MHz, $CDCl_3$) δ 7.79 (s, 1H), 7.66 (d, J=7.8 Hz, 1H), 7.56 (dd, J=8.1 Hz, J=1.2 Hz, 1H), 7.48–7.38 (m, 5H).

To a solution of compound 6a (30 mg, 0.12 mmol) in THF (0.2 mL) was added $NaBH_4$ (12 mg, 0.32 mmol) in THF (0.4 mL) followed by 1 mL of water. The reaction mixture was allowed to stir at room temperature for 48 hrs. THF was removed on a rotary evaporator, the residue was extracted with chloroform, washed with water and dried over anhyd. $Na_2SO_4$ to afford 10aj (16 mg, 52%), which was used in the next step with out further purification.

EXAMPLE 4

SCHEME 4
GENERAL SYNTHESIS OF 2-AMINO-BENZHYDROL ANALOGS AS INTERMEDIATES (ROUTE D)

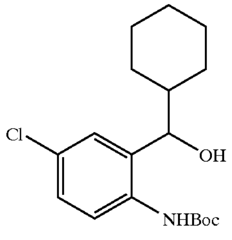

10ak

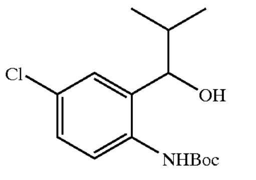

10al

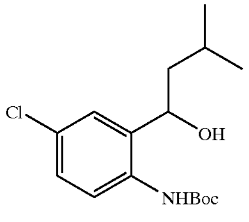

10am

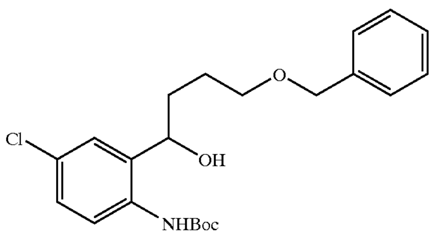

10an

10ak, 10al, 10am and 10an were prepared using a slightly modified version of the procedure set forth in Haider et al., *J. Heterocyclic Chem.*, 27:1645 (1990) and Ubeda et al., *Synthesis*, 1176 (1998).

EXAMPLE 5

SCHEME 5
SYNTHESIS OF BENZHYDROL THIOETHER-ESTERS AND -AMIDES

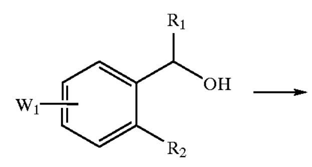

10

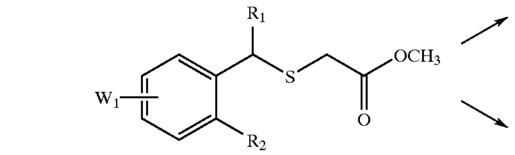

11

-continued

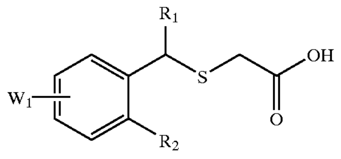

12

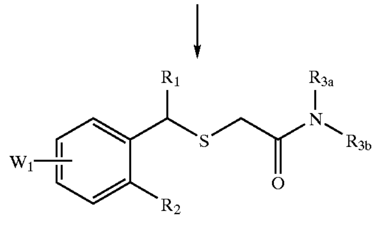

13

Synthesis of Thioether Ester 11a ($W_1$=5-Cl, $R_1$=4-pyridyl, $R_2$=$NH_2$).

A solution of 10a in methyl thioglycolate (0.5 ml) and TFA (2 ml) was stirred at room temperature for 18 hrs. After this time the solvent was removed in vacuum and the residue was diluted with dichloromethane (70 ml) and washed with 1 M NaOH (20 ml) and then with brine (20 ml). The combined aqueous phases were back extracted with dichloromethane (20 ml). The combined organic phase was dried over sodium sulfate, filtered and the solvent removed in vacuum. An attempt at purification by flash chromatography on silica gel (25 g) using ethyl acetate, then ethyl acetate/methanol 9:1 as eluent, failed to give a pure sample of the desired compound. Preparative HPLC conditions seemed to decompose most of the compound, only a small sample was obtained from the HPLC purification. 11a: brown oil (4.1 mg, 3% yield); clogP=2.20; $R_f$ (ethyl acetate)=0.49; HPLC (214 nm) $t_R$=5.98 (76.80%) min; $^1$H NMR (400 MHz, $CDCl_3$) δ 3.24 (d, J=16.3 Hz, 1H), 3.33 (d, J=16.3 Hz, 1H), 3.65 (s, 1H), 5.53 (s, 1H), 6.77 (d, J=8.6 Hz, 1H), 6.80 (d, J=2.4 Hz, 1H), 7.09 (dd, J=2.4, 8.4 Hz, 1H), 8.00 (d, J=5.0 Hz, 2H), 8.71 (d, J=5.0 Hz, 2H); ESMS m/z 323.3 $[M+H]^+$; LC/MS $t_R$=5.68 (323.0 $[M+H]^+$, 645.0 $[2M+H]^+$) min.

Synthesis of Thioether Ester 11b ($W_1$=5-Cl, $R_1$=2,6-dimethylphenyl, $R_2$=$NH_2$)and 11ba ($W_1$=5-Cl, $R_1$=2,6-dimethylphenyl, $R_2$=—NHC(—O)$CF_3$).

A solution of the amine 10b from above in methyl thioglycolate (0.5 ml) and TFA (2 ml) was stirred at room temperature for 18 hrs. After this time analysis by LCMS showed a mixture of the desired product plus starting material. The reaction was then heated to 60° C. for 15 hrs. The solvent was removed under a stream of nitrogen. The residue was diluted with dichloromethane (80 ml) and wash with brine (1×20 ml), then with 1M NaOH (1×40 ml) and then finally with brine (1×20 ml). The combined organic phase was dried over sodium sulfate, filtered and the solvent removed in vacuum. Analysis by LCMS showed a mixture of two compounds. The two compounds were separated by flash chromatography on silica gel (50 g) using petroleum spirit/ethyl acetate, 10:1 then 5:1 as eluent. The first compound to elute off the column was trilluoroanilide of 1 ba, isolated as a slightly colored oil (46.5 mg, 20% yield); clogP=5.37; $R_f$ (petroleum spirit/ethyl acetate, 5:1)=0.60; HPLC (214 nm) $t_R$=9.53 (97%) min; $^1$H NMR (400 MHz, $CDCl_3$) δ 2.26 (s, 6H), 3.19 (d, J=15.5 Hz, 1H), 3.27 (d, J=15.5 Hz, 1H), 3.71 (s, 3H), 5.85 (s, 1H), 7.08 (d, J=7.5 Hz, 2H), 7.17 (apparent t, J=7.5 Hz, 1H), 7.34 (dd, J=2.3, 8.6 Hz, 1H), 7.58 (d, J=2.3 Hz, 1H), 7.90 (d, J=8.6 Hz, 1H), 8.56 (s, 1H); $^{13}$C NMR (100 MHz, $CDCl_3$) δ 21.4, 33.1, 45.9, 52.6, 118.5 (q, J=288.9 Hz), 125.4, 128.4, 128.7, 129.9, 130.3, 131.5, 132.1, 132.2, 132.6, 137.9, 155.1 (q, J=37.4 Hz), 170.4; LC/MS $t_R$=9.81 (340.0 $[M-C_3H_5O_2S]^+$, 462.9 $[M+H_2O]^+$, 890.9 $[2M+H]^+$, 908.4 $[2M+H_2O]^+$) min.

The second compound to elute off the column was 11b, isolated as a slightly colored oil (28.2 mg, 15% yield); clogP=4.51; $R_f$ (petroleum spirit/ethyl acetate, 5:1)=0.37; HPLC (214 nm) $t_R$=9.39 (94%) min; $^1$H NMR (400 MHz, $CDCl_3$) δ 2.33 (s, 6H), 3.16 (d, J=15.5 Hz, 1H), 3.25 (d, J=15.5 Hz, 1H), 3.71 (s, 3H), 4.00 (brs, 2H), 5.64 (s, 1H), 6.59 (d, J=8.4 Hz, 1H), 7.02–7.06 (m, 3H), 7.11 (m, 1H), 7.30 (d, J=1.8 Hz, 1H); $^{13}$C NMR (100 MHz, $CDCl_3$) δ 21.7, 33.4, 46.5, 52.5, 117.8, 123.0, 123.8, 127.9, 128.0, 129.3, 129.9, 133.9, 138.0, 144.0, 171.1; LC/MS $t_R$=9.79 (244.1 $[M-C_3H_5O_2S]^+$, 350.0 $[M+H]^+$, 701.0 $[2M+H]^+$) min.

Synthesis of Thioether Ester 11c ($W_1$=5-Cl, $R_1$=3-methyl-2-pyrrolyl, $R_2$=_$NH_2$).

Alcohol 10c from above was dissolved in dichloromethane (5 ml), methyl thioglycolate (50 μL) was added followed by TFA (50 EL). After 15 min, TLC indicated the consumption of starting material along with the formation of a number of other products. The solvent was removed in vacuum and the residue was purified on silica gel (50 g) using gradient elution starting with petroleum spirit/ethyl acetate 10:1 to 2:1. The third major fraction off the column was found to be the desired compound tic, isolated as brown oil (18.5 mg, 12.2% yield); clogP=4.01; $R_f$ (petroleum spirit/ethyl acetate, 4:1)=0.21; HPLC (214 nm) $t_R$=11.41 (85.89%) min; $^1$H NMR (400 MHz, $CDCl_3$) δ 2.01 (s, 3H), 3.28 (d, J=16.5 Hz, 1H), 3.37 (d, J=16.5 Hz, 1H), 3.69 (brs, 2H), 3.75 (s, 3H), 5.56 (s, 1H), 6.65 (d, J=8.4 Hz, 1H), 6.87 (d, J=5.1 Hz, 1H), 6.96 (d, J=2.4 Hz, 1H), 7.03 (dd, J=2.4, 8.4 Hz, 1H), 7.21 (d, J=5.1 Hz, 1H); $^{13}$C NMR (100 MHz, $CDCl_3$) δ 13.7, 33.9, 42.8, 52.6, 117.7, 123.4, 124.1, 125.6, 128.2, 128.6, 131.0, 135.8, 136.9, 143.2, 171.5; ESMS m/z 341.9 $[M+H]^+$, 383.2 $[M+NH_4]^+$; LC/MS $t_R$=9.24 (342.1 $[M+H]^+$, 683.2 $[2M+H]^+$) min.

Synthesis of Thioether Ester of 11a ($W_1$=5-Cl, $R_1$=3,5-dimethylphenyl, $R_2$=$NH_2$).

(i) To the alcohol 10d from above was added methyl thioglycolate (500 μL, 5.6 mmol) followed by TFA (2 ml). The reaction was heated at 85° C. overnight. The next morning, the black solution was diluted with dichloromethane (80 ml) and washed with 1M sodium hydroxide (20 ml) followed by brine (20 ml). The organic phase was dried over sodium sulfate, filtered and the solvent removed in vacuum to yield a creamy amorphous solid (300 mg). Analysis of the solid by LCMS indicated a mixture of three compounds whose analytical data was consistent with the benzothiazepine, the thioether methyl ester 11d, as well as the thioether carboxylic acid (this acid was probably formed during the workup procedure whereby some of the methyl ester 11d was hydrolyzed by the basic wash solution). The mixture was treated with WSC, step (ii) below, in order to convert the acid to the cyclized benzothiazepine and simplify the purification of the reaction mixture.

(ii) To a solution of the mixture above in tetrahydrofuran (50 ml) was added diusopropylethylamine (125 μL, 0.72 mmol), followed by EDC (WSC.HCl) (136 mg, 0.71 mmol) and finally dimethylaminopyridine (10.6 mg, 0.09 mmol). The reaction was left to stir overnight at room temperature. Next morning TLC indicated complete consumption of the carboxylic acid resulting in a mixture of two products; assumed to be the desired thio ether methyl ester 11d, as well as the cyclized benzothiazepine. The solvent was removed in vacuum and the residues was taken up into ethyl acetate (70 ml) and washed with 10% citric acid (1×30 ml), saturated sodium bicarbonate (1×30 ml) and finally with brine (1×30 ml). The organic phase was dried over magnesium sulfate, filtered and the solvent removed in vacuum. The residue was purified by flash chromatography on silica gel (25 g) using petroleum ether:ethyl acetate 2:1 as eluent. The first compound to elute from the column was lid isolated as an off white solid (41.4 mg, 12.1% yield over three steps); clogP=4.51; $R_f$ (petroleum ether:ethyl acetate (2:1)=0.57; HPLC (214 nm) $t_R$=9.65 (88.0%) min; $^1$H NMR (400 MHz, $CDCl_3$) δ 2.32 (s, 6H), 3.13 (d, J=16.0 Hz, 1H), 3.18 (d, J=16.0 Hz, 1H), 3.72 (s, 3H), 6.62 (d, J=8.4 Hz, 1H), 6.93 (s, 1H), 6.96 (d, J=2.5 Hz, 1H), 7.02 (dd, J=2.5, 8.4 Hz, 1H), 7.07 (s, 2H); $^{13}$C NMR (100 MHz, $CDCl_3$) δ 21.32, 33.04, 49.7, 52.5, 117.6, 123.0, 126.1, 126.8, 128.2, 128.9, 129.6, 137.7, 138.4, 143.6, 171.2; ESMS m/z 244.0 $[M-C_3H_4O_2S]^+$, 350.2 $[M+H]^+$; LC/MS $t_R$=9.89 (244.0 $[M-C_3H_4O_2S]^+$, 350.1 $[M+H]^+$, 699.3 $[2M+H]^+$) min.

Synthesis of Thioether Ester 11e ($W_1$=5-C, $R_1$=1-methyl-2-imidazolyl, $R_2$=$NH_2$).

A sample of 10e (50 mg, 0.21 mmol) from above was mixed with methyl thioglycolate (500 μL) followed by TFA (2 ml). The reaction was left to stir at room temperature for 24 h. After this time the reaction was diluted with dichloromethane (100 ml) and was washed once with a 1:1 mixture of brine/1M NaOH (50 ml). The aqueous phase was extracted with dichloromethane (2×20 ml). The combined organic phase was washed with brine (1×50 ml), dried over sodium sulfate, filtered and the solvent removed in vacuum to yield a greenish solid (55 mg). Analysis of the reaction showed a very messy reaction but the main peak by LCMS had a MS consistent with the desired product. The compound was dissolved in dichloromethane (1 ml) and was carefully loaded onto two preparative TLC plates. The plates were developed using a mixture consisting of 40 ml ethyl acetate and 2 ml concentrated ammonia solution. The main UV active band was cut from the plate and the desired product was eluted from the plate by washing with ethyl acetate (250 ml). The solvent was removed in vacuum to yield a white solid (>100 mg probably silica gel). The solid was taken up into chloroform (2 ml) and the crystalline solid was removed by filtration to yield lie as a brown oil (20 mg, 29% yield); clogP=1.73; $R_f$ (ethyl acetate/5% $NH_4OH$)=0.59–0.70); HPLC (214 nm) $t_R$=5.81 (75.92%) min; $^1$H NMR (400 MHz, $CDCl_3$) δ 3.16 (d, J=15.8 Hz, 1H), 3.28 (d, J=15.8 Hz, 1H), 3.48 (s, 3H), 3.72 (s, 3H), 4.50 (brs, 2H), 5.50 (s, 1H), 6.89 (dd, J=2.0, 9.1 Hz, 1H), 6.83 (d, J=1.1 Hz, 1H), 7.01 (d, J=1.1 Hz, 1H), 7.03–7.05 (m, 2H); ESMS m/z 326.1 $[M+H]^+$; LC/MS $t_R$=5.21 (325.9 $[M+H]^+$) min.

11f ($W_1$=Cl, $R_1$=2-benzothiazolyl, $R_2$=NH))

Using a similar procedure as for the synthesis of 11e, 11f was prepared and isolated as a yellow oil (21.9 mg, 20.6% yield); clogP=4.41; $R_f$ (petroleum ether:ethyl acetate (2:1)=0.41; HPLC (214 nm) $t_R$=8.84 (76.8%) min; $^1$H NMR (400 MHz, $CDCl_3$) δ 3.32 (d, J=16.1 Hz, 1H), 3.42 (d, J=16.1 Hz, H), 3.72 (s, 3H), 5.80 (s, 1H), 6.64 (d, J=8.6 Hz, 1H), 7.07 (dd, J=2.4, 8.6 Hz, 1H), 7.14 (d, J=2.4 Hz, 1H), 7.40 (m, 1H), 7.49 (m, 1H), 7.87 (d, J=7.9 Hz, 1H), 8.02 (d, J=8.1 Hz, 1H); ESMS m/z 379.3 $[M+H]^+$; LC/MS $t_R$=9.11 (379.0 $[M+H]^+$) min.

11g ($W_1$=5-Cl, $R_1$=2-pyrrolyl, $R_2$=$NH_2$).

Using a similar procedure as for the synthesis of 11c, 11g was prepared and isolated as a yellow oil (21.9 mg, 20.6% yield); clogP=4.41; $R_f$ (petroleum ether:ethyl acetate (2:1)=0.41; HPLC (214 nm) $t_R$=8.84 (76.8%) min; $^1$H NMR (400 MHz, $CDCl_3$) δ 3.32 (d, J=16.1 Hz, 1H), 3.42 (d, J=16.1 Hz, H), 3.72 (s, 3H), 5.80 (s, 1H), 6.64 (d, J=8.6 Hz, 1H), 7.07

(dd, J=2.4, 8.6 Hz, 1H), 7.14 (d, J=2.4 Hz, 1H), 7.40 (m, 1H), 7.49 (m, 1H), 7.87 (d, J=7.9 Hz, 1H), 8.02 (d, J=8.1 Hz, 1H); ESMS m/z 379.3 $[M+H]^+$; LC/MS $t_R$=9.11 (379.0 $[M+H]^+$) min.

11h ($W_1$=5-Cl, $R_1$=1-methyl-2-pyrrolyl, $R_2$=$NH_2$).

Using a similar procedure as for the synthesis of 11ec, compound 11h was prepared and isolated as a creamy amorphous solid (55 mg); clogP=2.32; $R_f$ (petroleum ether: ethyl acetate (2:1)=0.56; HPLC (214 nm) $t_R$=8.75 (96.47%) min; $^1$H NMR (400 MHz, $CDCl_3$) δ 3.18 (d, J=16.3 Hz, 1H), 3.32 (s, 3H), 3.53 (d, J=16.3 Hz, 1H), 3.70 (s, 3H), 4.32 (brs, 1H), 5.32 (s, 1H), 6.09 (t, J=3.1 Hz, 1H), 6.36 (m, 1H), 6.59–6.61 (m, 2H), 6.84 (d, J=2.5 Hz, 1H), 7.00 (dd, J=2.5, 8.6 Hz, 1H); $^{13}$C NMR (100 MHz, $CDCl_3$) δ 29.6, 33.3, 33.6, 41.9, 52.5, 107.0, 109.8, 117.7, 123.3, 123.6, 124.7, 128.5, 128.6, 143.5, 171.6; ESMS m/z 219.3 $[M-C_3H_4O_2S]^+$, 325.1 $[M+H]^+$; LC/MS $t_R$=8.88 (325.0 $[M+H]^+$, 649.3 $[2M+H]^+$) min.

Synthesis of Thioether Ester 11i-m.

(i) To the alcohol 10i from step 6 was added methyl thioglycolate (500 mL, 5.6 mmol) followed by TFA (2 ml). The reaction was sealed with a stopper and heated at 60° C. 16 hrs. The solution was diluted with dichloromethane (80 ml) and washed with 1 M sodium hydroxide (20 ml) followed by brine (20 ml). The organic phase was dried over sodium sulfate, filtered and the solvent removed in vacuum to yield a creamy amorphous solid. Analysis of the solid by LMS indicated that only the thioether methyl ester was present along with a small amount of the acid formed by hydrolysis of the methyl ester during workup. The resulting reaction mixture above was diluted with 6 ml of methanol and 2 ml was removed for (ii) below.

(ii) To the methanol solution above (2 ml) was added 1 M sodium hydroxide solution (1 ml). The reaction was left to stir at room temperature for 1 hr. After this time the reaction was diluted with brine (30 ml) and neutralized with 10% HCl solution. The aqueous layer was extracted with ethyl acetate (3×50 ml). The combined organic phase was dried over sodium sulphate, filtered and the residue combined with the remaining material from (i) above and used in (iii) below.

(iii) To a solution of the mixture above in tetrahydrofuran (20 ml) was added diusopropylethylamine (67 μL, 0.39 mmol), followed by EDC (74 mg, 0.39 mmol) and dimethylaminopyridine (4.0 mg, 0.03 mmol). The reaction was left to stir overnight at room temperature. TLC indicated complete consumption of the carboxylic acid. The resulting mixture contained two products: the desired thio ether methyl ester 11i and the cyclized corresponding benzothiazepine. The solvent was removed in vacuum and the residues were taken up into ethyl acetate (70 ml) and washed with 10% citric acid (1×30 ml), saturated sodium bicarbonate (1×30 ml) and finally with brine (1×30 ml). The organic phase was dried over sodium sulfate, filtered and the solvent removed in vacuum. The residue was purified by flash chromatography on silica gel (25 g) using petroleum ether-:ethyl acetate 2:1 as eluent. 11i ($W_1$=5-Cl, $R_1$=3-methylphenyl, $R_2$=$NH_2$): isolated as a brown oil (52.2 mg, 38.2% yield); clogP=4.03; $R_f$ (petroleum ether:ethyl acetate (2:1)=0.65; HPLC (214 nm) $t_R$=8.80 (94.95) min; $^1$H NMR (400 MHz, $CDCl_3$) δ 2.28 (s, 3H), 3.06 (d, J=16.1 Hz, 1H), 3.11 (d, J=16.1 Hz, 1H), 3.60 (brs, 2H), 3.64 (s, 3H), 5.27 (s, 1H), 6.55 (d, J=8.4 Hz, 1H), 6.86 (d, J=2.4 Hz, 1H), 6.94 (dd, J=2.4, 8.4 Hz, 1H), 7.04 (d, J=7.5 Hz, 1H), 7.17–7.24 (m, 3H); $^{13}$C NMR (100 MHz, $CDCl_3$) δ 21.4, 33.3, 49.7, 52.5, 117.7, 123.1, 126.1, 128.3, 128.7, 128.9, 129.7, 137.7, 138.5, 143.5, 171.2; ESMS m/z 230.3 $[M-C_3H_4O_2S]^+$, 336.3 $[M+H]^+]^+$, 671.2 $[2M+H]^+$; LC/MS $t_R$=9.43 (229.9 $[M-C_3H_4O_2S]^+$, 336.1 $[M+H]^+$, 671.1 $[2M+H]^+$) min.

Using similar procedure as (i), (ii) and (iii) 11j-m were also prepared.

11j ($W_1$=5-Cl, $R_1$=4-methylphenyl, $R_2$=$NH_2$): isolated as a brown oil (40.0 mg, 29.3% yield); clogP=4.03; $R_f$ (petroleum ether:ethyl acetate (2:1)=0.65; HPLC (214 nm) $t_R$=8.90 (94.39) min; $^1$H NMR (400 MHz, $CDCl_3$) δ 2.28 (s, 3H), 3.03 (d, J=16.0 Hz, 1H), 3.10 (d, J=16.0 Hz, 1H), 3.64 (s, 2H), 4.23 (brs, 3H), 5.26 (s, 1H), 6.71 (d, J=8.5 Hz, 1H), 6.86 (d, J=2.4 Hz, 1H), 6.94 (dd, J=2.4, 8.5 Hz, 1H), 7.11 (d, J=8.0 Hz, 1H), 7.29 (d, J=8.0 Hz, 1H); $^{13}$C NMR (100 MHz, $CDCl_3$) δ 21.1, 33.3, 49.6, 52.5, 117.6, 123.0, 126.0, 128.3, 128.8, 128.9 (double intensity), 129.5 (double intensity), 134.7, 137.6, 143.5, 171.2; ESMS m/z 230.3 $[M-C_3H_4O_2S]^+$, 336.3 $[M+H]^+$, 671.2 $[2M+H]^+$; LC/MS $t_R$=9.51 (230.3 $[M-C_3H_4O_2S]^+$, 336.1 $[M+H]^+$, 671.1 $[2M+H]^+$) min.

11k ($W_1$=5-Cl, $R_1$=2,3-dimethylphenyl, $R_2$=$NH_2$): isolated as a brown oil (60.0 mg, 44.5% yield); clogP=4.51; $R_f$ (petroleum ether:ethyl acetate (2:1)=0.65; HPLC (214 nm) $t_R$=9.82 (88.81) min; $^1$H NMR (400 MHz, $CDCl_3$) δ 1.97 (s, 3H), 2.20 (s, 3H), 3.05 (d, J=16.2 Hz, 1H), 3.11 (d, J=16.2 Hz, 1H), 3.63 (s, 3H), 4.05 (brs, 2H), 5.53 (s, 1H), 6.56 (d, J=8.4 Hz, 1H), 6.72 (d, J=2.4 Hz, 1H), 6.96 (dd, J=2.4, 8.4 Hz, 1H), 7.05 (d, J=7.1 Hz, 1H), 7.10 (apparent t, J=7.5 Hz, 1H), 7.61 (d, J=7.5 Hz, 1H); $^{13}$C NMR (100 MHz, $CDCl_3$) δ 14.4, 20.7, 33.4, 46.6, 52.4, 117.5, 123.1, 125.7, 125.9, 126.2, 128.2, 128.5, 129.5, 135.4, 135.6, 137.5, 143.5, 171.4; ESMS m/z 244.3 $[M-C_3H_4O_2S]^+$, 350.2 $[M+H]^+$; LC/MS $t_R$=9.88 (244.0 $[M-C_3H_4O_2S]^+$, 350.0 $[M+H]^+$, 699.1 $[2M+H]^+$) min.

111 ($W_1$=5-Cl, $R_1$=3,4-dimethylphenyl, $R_2$=$NH_2$): isolated as a brown oil (56.0 mg, 41.6% yield); clogP=4.51; $R_f$ (petroleum ether:ethyl acetate (2:1)=0.65; HPLC (214 nm) $t_R$=9.71 (85.37) min; $^1$H NMR (400 MHz, $CDCl_3$) δ 2.18 (s, 6H), 3.04 (d, J=16.1 Hz, 1H), 3.09 (d, J=16.1 Hz, 1H), 3.64 (s, 3H), 4.05 (brs, 2H), 5.23 (s, 1H), 6.53 (d, J=8.3 Hz, 1H), 6.89 (d, J=2.4 Hz, 1H), 6.93 (dd, J=2.4, 8.3 Hz, 1H), 7.05 (d, J=7.5 Hz, 1H), 7.12–7.17 (m, 2H); $^{13}$C NMR (100 MHz, $CDCl_3$) δ 19.4, 19.8, 33.4, 49.5, 52.5, 117.6, 123.0, 126.1, 126.3, 128.2, 128.8, 130.0, 130.2, 135.1, 136.3, 137.0, 143.5, 171.2; ESMS m/z 244.2 $[M-C_3H_4O_2S]^+$, 350.3 $[M+H]^+$; LC/MS $t_R$=9.76 (244.1 $[M-C_3H_4O_2S]^+$, 350.0 $[M+H]^+$, 699.2 $[2M+H]^+$) min.

11m ($W_1$=5-Cl, $R_1$=2,5-dimethylphenyl, $R_2$=$NH_2$): isolated as a brown oil (51.0 mg, 37.9% yield); clogP=4.51; $R_f$ (petroleum ether:ethyl acetate (2:1)=0.65; HPLC (214 min) $t_R$=9.79 (76.77) min; $^1$H NMR (400 MHz, $CDCl_3$) δ 2.04 (s, 3H), 2.30 (s, 3H), 3.06 (d, J=16.0 Hz, 1H), 3.11 (d, J=16.0 Hz, 1H), 3.63 (s, 3H), 4.05 (brs, 2H), 5.44 (s, 1H), 6.55 (d, J=8.4 Hz, 1H), 6.76 (d, J=2.2 Hz, 1H), 6.92–6.99 (m, 3H), 7.51 (s, 1H); $^{13}$C NMR (100 MHz, $CDCl_3$) δ 18.5, 21.2, 33.4, 46.2, 52.4, 117.5, 123.1, 125.6, 128.2, 128.4 (double intensity), 128.8, 130.8, 134.0, 135.3, 135.8, 143.7, 171.4; ESMS m/z 244.2 $[M-C_3H_4O_2S]^+$, 350.3 $[M+H]^+$; LC/MS $t_R$=9.87 (244.0 $[M\ C_3H_4O_2S]^+$, 350.1 $[M+H]^+$, 699.2 $[2M+H]^+$) min.

11n ($W_1$=3,5-dichloro, $R_1$=2-methylphenyl, $R_2$=$NH_2$)

Using a similar procedure as for the synthesis of 11b, 11n was prepared as a light yellow solid (9 mg). HPLC (214 nm) $t_R$=9.62 min. $^1$H NMR (400 MHz, $CDCl_3$) δ 2.10 (s, 3H), 3.14 (dd, J=28.4, 16.4 Hz, 2H), 3.71 (s, 3H), 4.86 (bs, 2H, $NH_2$), 5.54 (s, 1H), 6.66 (d, J=2.4 Hz, 1H), 7.15–7.30 (m, 4H), 7.80 (d, J=7.2 Hz, 1H). LCMS $t_R$=10.67 min (369.9 $[M+H]^+$).

11o ($W_1$=3,5-dibromo, $R_1$=2-methylphenyl, $R_2$=$NH_2$)

Using a similar procedure as for the synthesis of 11b, 11o was prepared as an orange-yellow oil which solidified upon standing (35 mg). HPLC (214 nm) $t_R$=9.97 min. $^1$H NMR (400 MHz, $CDCl_3$) δ 2.11 (s, 3H), 3.13 (dd, J=29.2, 16.4 Hz, 2H), 3.71 (s, 3H), 4.95 (bs, 2H, $NH_2$), 5.53 (s, 1H), 6.82 (d, J=2.4 Hz, 1H), 7.15–7.30 (m, 3H), 7.45 (d, J=2.4 Hz, 1H), 7.80 (d, J=7.2 Hz, 1H). LCMS $t_R$=10.96 min (459.9 $[M+H]^+$).

11p ($W_1$=5-methyl, $R_1$=2-methylphenyl, $R_2$=$NH_2$)

Using a similar procedure as for the synthesis of 1b, 11p was prepared and isolated as an off-white solid (0.046 g after freeze-drying). $R_f$ (EtOAc:petrol (1:10))=0.13. HPLC (214 nm) $t_R$=7.82 (88.2%) min; $^1$H NMR (400 MHz, $CDCl_3$) δ 2.11 (s, 3H), 2.19 (s, 3H), 3.15 (dd, J=24, 16 Hz, 2H), 3.71 (s, 3H), 4.11 (bs, 2H), 5.61 (s, 1H), 6.62–6.66 (m, 2H), 6.87 (dd, J=8, 1.6 Hz, 1H), 7.15–7.30 (m, 3H), 7.82 (d, J=7.6 Hz, 1H); LC/MS $t_R$=7.72 (316.1 $[M+H]^+$) min.

11r ($W_1$=H, $R_1$=2-chlorophenyl, $R_2$=$NH_2$)

Using a similar procedure as for the synthesis of 11b, 11r was obtained as a yellow powder (360 mg, 1.11 mmol, 41% yield for three steps): $R_f$ (petroleum ether:ethyl acetate (2:1)=0.60). HPLC (214 nm) $t_R$=8.51 (80.0%) min. $^1$H NMR (400 MHz, $CDCl_3$) δ 3.11 (d, J=16.0 Hz, 1H), 3.18 (d, J=16.0 Hz, 1H), 3.68 (s, 3H), 5.82 (s, 1H), 6.63 (ddd, J=7.6, 7.6, 0.8 Hz, 1H), 6.73 (dd, J=8.0, 0.8 Hz, 1H), 6.83 (dd, J=7.6, 1.2 Hz, 1H), 7.05 (ddd, J=7.6, 7.6, 1.2 Hz, 1H), 7.22 (ddd, J=7.6, 7.6, 1.2 Hz, 1H), 7.30–7.39 (m, 2H), 7.90 (dd, J=7.6, 1.6 Hz, 1H). $^{13}$C NMR (400 MHz, $CDCl_3$) δ 6.33.6, 46.4, 52.5, 116.7, 118.6, 123.2, 127.0, 128.3, 128.6, 128.8, 129.9, 130.5, 134.6, 136.3, 144.6, 170.9. ESMS m/z 142.2, 322.4 $[M+H]^+$. LC/MS $t_R$=8.85 (216.1 $[M-HSCH_2CO_2CH_3+H]^+$, 322.1 $[M+H]^+$) min.

11s ($W_1$=5-Cl, $R_1$=2-chlorophenyl, $R_2$=$NH_2$).

Using a similar procedure as for the synthesis of 11b, 11s was prepared and isolated as a white solid (1.84 g, 5.18 mmol, 70% yield). $R_f$ (silica, 40–60 petroleum ether:ethyl acetate (2:1))=0.30. HPLC (214 nm) $t_R$=9.07 (91.4%) min. $^1$H NMR (400 MHz, $CDCl_3$) δ 3.13 (d, J=16 Hz, 1H), 3.21 (d, J=16 Hz, 1H), 3.73 (s, 3H), 4.39 (brs, 2H), 5.79 (s, 1H), 6.66 (d, J=8.4 Hz, 1H), 6.81 (d, J=2.8 Hz, 1H), 7.04 (dd, J=8.4, 2.8 Hz, 1H), 7.26–7.32 (m, 1H), 7.37–7.43 (m, 2H), 7.89–7.93 (m, 1H). $^{13}$C NMR (400 MHz, $CDCl_3$) δ 33.6, 46.1, 52.6, 118.1, 123.8, 125.2, 127.2, 128.1, 128.5, 129.2, 130.1, 130.3, 134.7, 135.4, 142.6, 170.9. ESMS m/z 250.2 $[M-HSCH_2CO_2CH_3+H]^+$, 356.3 $[M+H]^+$. LC/MS $t_R$=9.41 (250.2 $[M-HSCH_2CO_2CH_3+H]^+$, 356.0 $[M+H]^+$).

11t ($W_1$=5-nitro, $R_1$=phenyl, $R_2$=$NH_2$).

Using a similar-procedure as for the synthesis of 11b, 11t (486 mg, 1.46 mmol, 67% overall yield for two steps) was obtained as a yellow oil: $R_f$ (petroleum ether:ethyl acetate (2:1)=0.29). HPLC (214 nm) $t_R$=8.37 (96.4%) min. $^1$H NMR (400 MHz, $CDCl_3$) δ 3.15 (d, J=17.2 Hz, 1H), 3.23 (d, J=17.2 Hz, 1H), 3.74 (s, 3H), 5.35 (s, 1H), 5.38 (br s, 1H), 6.68 (d, J=8.8 Hz, 1H), 7.33–7.46 (m, 3H), 7.51–7.55 (m, 2H), 7.81 (d, J=2.4 Hz), 7.98 (dd, J=8.8, 2.4 Hz, 1H). $^{13}$C NMR (400 MHz, $CDCl_3$) δ 33.1, 49.5, 52.6, 114.9, 122.9, 125.0, 125.9, 128.2, 129.0, 129.1, 136.9, 138.6, 151.2, 171.5. ESMS m/z 227.2 $[(M-HSCH_2CO_2CH_3+H)]^+$, 333.3 $[(M+H)]^+$. LC/MS $t_R$ 9.25 (227.2 $[(M-HSCH_2CO_2CH_3+H)]^+$, 333.1 $[(M+H)]^+$, 665.4 $[2M+H]^+$) min.

11u ($W_1$=5-Cl, $R_1$=2-thiazolyl, $R_2$=$NH_2$)

Using a similar procedure as 11b, compound 11u was prepared and isolated as a brown gum (62 mg, 18.4%), clogP=2.93; $R_f$ (petroleum ether:ethyl acetate (1:1))=0.35; HPLC (214 nm) $t_R$=7.58 (81%) min; $^1$H NMR (400 m Hz, $CDCl_3$) δ 3.27 (d, J=16.0 Hz, 1H), 3.35 (d, J=16.0 Hz, 1H), 3.72 (s, 3H), 5.73 (s, 1H), 6.63 (d, J=8.8 Hz, 1H), 7.04–7.06 (m, 2H), 7.34 (d, J=3.3 Hz, 1H), 7.77 (d, J=3.3 Hz, 1H). $^{13}$C NMR (100 MHz, $CDCl_3$) δ 33.4, 47.3, 52.6, 118.0, 120.4, 123.0, 123.6, 128.5, 129.1, 143.0, 143.8, 169.8, 170.6; ESMS m/z 329.4 $[M+H]^+$.

11v ($W_1$=H, $R_1$=2,4-dimethylphenyl, $R_2$ $NH_2$)

Using a similar procedure as for the synthesis of 11c, 11v was prepared and isolated as an off white solid (56 mg, 66% yield); clogP=3.96; $R_f$ (petroleum ether:ethyl acetate (4:1)=0.70; HPLC (214 nm) $t_R$=9.17 (95%) min; $^1$H NMR (400 MHz, $CDCl_3$) δ 2.14 (s, 3H), 2.32 (s, 3H), 3.13 (d, J=15.9 Hz, 1H), 3.18 (d, J=15.9 Hz, 1H), 3.70 (s, 3H), 4.05 (br s, 2H), 5.58 (s, 1H), 6.62–6.66 (m, 1H), 6.73 (dd, J=1.1, 7.9 Hz, 1H), 6.86 (dd, J=1.4, 7.9 Hz, 1H), 6.98 (s, 1H), 7.04 (dd, J=1.4, 7.5 Hz, 1H), 7.08 (d, J=7.5 Hz, 1H), 7.69 (d, J=7.9 Hz, 1H); $^{13}$C NMR (100 MHz, $CDCl_3$) δ 18.9, 20.9, 33.5, 46.3, 52.4, 116.6, 118.8, 124.2, 126.8, 128.3, 128.5, 128.8, 131.6, 133.3, 137.1, 144.7, 171.5; ESMS m/z 210.2 $[M-C_3H_4O_2S]^+$, 316.4 $[M+H]^+$; LC/MS $t_R$=9.54 (210.1 $[M-C_3H_5O_2S]^+$, 316.1 $[M+H]^+$, desired product 95%) min.

11w ($W_1$=5-Cl, $R_1$=2,4-dimethylphenyl, $R_2$=$NH_2$)

Using a similar procedure as for the synthesis of 11c, 11w was prepared and isolated as an off white solid (89 mg, 84% yield); clogP=4.51; $R_f$ (petroleum ether:ethyl acetate (4:1)=0.69; HPLC (214 nm) $t_R$=9.90 (97%) min; $^1$H NMR (400 MHz, $CDCl_3$) δ 2.13 (s, 3H), 2.33 (s, 3H), 3.12 (d, J=16.1 Hz, 1H), 3.18 (d, J=16.1 Hz, 1H), 3.71 (s, 3H), 4.29 (br s, 2H), 5.52 (s, 1H), 6.63 (d, J=8.4 Hz, 1H), 6.83 (d, J=2.5 Hz, 1H), 6.99–7.02 (m, 2H), 7.09 (d, J=7.5 Hz, 1H), 7.65 (d, J=7.9 Hz, 1H); $^{13}$C NMR (100 MHz, $CDCl_3$) δ 18.9, 20.9, 33.4, 46.0, 52.5, 117.5, 123.2, 125.7, 127.1, 128.2, 128.3, 128.5, 131.8, 132.6, 137.0, 137.4, 143.7, 171.4; ESMS m/z 244.3 $[M-C_3H_4O_2S]^+$, 350.3 $[M+H]^+$; LC/MS $t_R$=11.01 (244.0 $[M-C_3H_4O_2S]^+$, 350.0 $[M+H]^+$, desired product 95%) min.

11x ($W_1$=5-Cl, $R_1$=phenyl, $R_2$=$NH_2$)

Using a similar procedure as for the synthesis of 11c, 11x (1.18 g, 3.67 mmol, 86% overall yield) as a yellow oil ($R_f$ (40–60 petroleum ether:ethyl acetate (2:1))=0.30). HPLC (214 nm) $t_R$=8.95 (94.4%) min. $^1$H NMR (400 MHz, $CDCl_3$) δ 3.13 (d, J=1.6 Hz, 1H), 3.20 (d, J=1.6 Hz, 1H), 3.73 (s, 3H), 5.40 (s, 1H), 6.64 (d, J=8.4 Hz, 1H), 6.93 (d, J=2.8 Hz, 1H), 7.04 (dd, J=8.4, 2.8 Hz, 1H), 7.30–7.35 (m, 1H), 7.37–7.43 (m, 3H), 7.50 (d, J=7.6 Hz, 2H). $^{13}$C NMR (400 MHz, $CDCl_3$) δ 33.3, 49.7, 52.5, 117.6, 123.0, 125.7, 127.8, 128.3, 128.8, 128.9, 129.0, 137.8, 143.5, 171. ESMS m/z 216.2 $[(M-HSCH_2CO_2CH_3+H)]^+$, 322.1 $[(M+H)]^+$. LC/MS $t_R$=9.10 (216.3 $[(M-HSCH_2CO_2CH_3+H)]^+$, 322.1 $[(M+H)]^+$, 643.1 $[(2M+H)]^+$) min.

11y ($W_1$=2-$CH_3$, $R_1$=2-amino-3-pyridinyl, $R_2$=H)

Using a similar procedure as for the synthesis of 11b, 11y was prepared and isolated as pale yellow crystals. HPLC (214 nm) $t_R$=6.08 min (92.1%). $^1$H NMR ($CDCl_3$, 400 MHz) δ 2.15 (s, 3H), 3.17 (dd, J=26.0,16.0 Hz), 3.73 (s, 3H), 5.27 (bs, $NH_2$, 2H), 5.49 (s, 1H), 6.54 (dd, J=7.6, 4.8 Hz, 1H), 7.04 (dd, J=7.6, 1.6 Hz, 1H), 7.17–7.32 (m, 3H), 7.83 (d, J=7.2 Hz, 1H), 7.98 (dd, J=4.8, 1.6 Hz, 1H). LCMS $t_R$=6.18 min (303, $[M+H]^+$).

11aa ($W_1$=5-Cl, $R_1$=2-methylphenyl, $R_2$=$NH_2$)

From 10aa, isolated as a yellow powder (254 mg, 0.756 mol, 74% yield). $R_f$ (petroleum ether:ethyl acetate (2:1)=0.60; MS=335.07 ($M^+$), $(2M+1)^+$=671.4 (MS=335.07 ($M^+$), 671.4 [2M+1]); $^1$H NMR (400 MHz) 7.80 (1H, d, J=8.0 Hz), 7.07–7.32 (3H, m), 7.05 (1H, dd, J=2.4, 8.4 Hz), 6.93 (1H, d, J=8.4 Hz), 6.76 (1H, d, J=8.4 Hz), 5.56 (1H, s), 3.69 (3H, s), 3.14–3.18 (2H, m), 2.15 (3H, s); $^{13}$C NMR (400 MHz) 171.42, 142.97, 137.29, 135.53, 130.97, 128.49, 128.36, 127.80, 126.43, 125.99, 123.78, 117.97, 52.56, 46.22, 33.40, 19.01.

11ab ($W_1$=5-$CH_3$, $R_1$=2-methylphenyl, $R_2$=H)

From 10ab, isolated as a yellow oil (0.11 g, 71%). HPLC (214 nm) $t_R$=9.05 min (95.1%). $^1$H NMR (400 MHz, $CDCl_3$) δ 2.30 (s, 3H), 2.36 (s, 3H), 3.08 (s, 2H, $NH_2$), 3.65 (s, 3H), 5.58 (s, 1H), 7.02 (dd, J=6.4, 1.6 Hz, 1H), 7.11–7.22 (m, 6H), 7.54 (d, J=7.2 Hz, 1H). LCMS $t_R$=9.87 min (318.1 $[M+NH_4]^+$, 618.5 $[2M+NH_4]^+$).

11ac ($W_1$=H, $R_1$=2-methylphenyl, $R_2$=methoxy) was obtained from 10ac as an off-white solid (0.013 g, 32% yield). $R_f$ (diethyl ether:petrol (1:4))=0.24. HPLC (214 nm) $t_R$=10.29 min (97.7%). $^1$H NMR ($CDCl_3$, 400 MHz) δ 2.36 (s, 3H), 3.12 (s, 2H), 3.62 (s, 3H), 3.78 (s, 3H), 5.99 (s, 1H), 6.82 (d, J=8.4 Hz, 1H), 6.90–6.94 (m, 1H), 7.09–7.14 (m, 3H), 7.17–7.21 (m, 1H), 7.47 (d, J=6.8 Hz, 1H), 7.52 (dd, J=7.6, 1.6 Hz, 1H). LCMS (214 nm) $t_R$=9.36 min (334.3 $[M+NH_4]^+$, 376.3, 394.7, 527.3 (not identified), 650.2 $[2M+NH_4]^+$).

11ad ($W_1$=5-$CH_3$, $R_1$=2-methylphenyl, $R_2$=OH) was obtained from 10ad as a colorless oil (0.033 g, 100% yield). $R_f$ (diethyl ether:petrol (1:2))=0.27. HPLC (214 nm) $t_R$=9.26 min (98.9%). $^1$H NMR ($CDCl_3$, 400 MHz) δ 2.21 (s, 3H), 3.20 (s, 2H), 3.76 (s, 3H), 5.72 (s, 1H), 6.75–6.79 (m, 1H), 6.83 (dd, J=7.6, 1.6 Hz, 1H), 6.95 (dd, J=16, 0.8 Hz, 1H), 7.13–7.29 (m, 5H), 7.79 (d, J=7.6 Hz, 1H). LCMS (214 nm) $t_R$=8.98 min (320.2 $[M+NH_4]^+$, 499.0 (not identified), 622.2 $[2M+NH_4]^+$).

11ae ($W_1$=H, $R_1$=5-amino-2-chlorophenyl, $R_2$=H) was obtained from 10ae as yellow oil (158 mg, 72%). $^1$H NMR ($CDCl_3$, 500 MHz) δ 3.14 (d, J=14.5 Hz, 1H), 3.18 (d, J=14.5 Hz, 1H), 3.67 (s, 3H), 5.80 (s, 1H), 6.51 (dd, J=2.8, 8.7 Hz), 7.00 (d, J=2.8 Hz, 1H), 7.10 (d, J=9.7, 1H), 7.24 (m, 1H), 7.31 (m, 2H), 7.42 (m, 2H).

11af ($W_1$=H, $R_1$=3-amino-4-chlorophenyl, $R_2$=H) was obtained as yellow oil (142 mg, 88.5%). $^1$H NMR ($CDCl_3$, 500 MHz) δ 3.09 (s, 2H), 3.68 (s, 3H), 5.28 (s, 1H), 6.76 (dd, J=2.0, 8.2 Hz, 1H), 6.84 (d, J=2.0 Hz, 1H), 7.17 (d, J=8.2 Hz, 1H), 7.25 (m, 1H), 7.31 (m, 2H), 7.40 (m, 2H).

11ag ($W_1$=5-Cl, $R_1$=2-chlorophenyl, $R_2$=—OH)

Compound 10ag (50 mg, 0.18 mmol) in dry $CH_2Cl_2$ (1 ml) was cooled to 10° C. To the cold stirred solution anhyd. $ZnCl_2$ (73 mg, 0.54 mmol) and methyl thioglycolate (32 ml, 0.36 mmol) were added and stirring was continued overnight. The reaction mixture was quenched by adding water (4 ml), extracted with $CH_2Cl_2$, washed with water, dried over anhyd. sodium sulfate and concentrated to afford 60 mg of crude product. The product was purified by column using 10% ethyl acetate in petroleum ether to yield 48 mg (62%) of compound 11ac. m.p: 160.3–162.7° C. $^1$H NMR (300 MHz, $CDCl_3$) δ 7.90 (d, J=8.4 Hz, 1H), 7.49 (s, phenolic-OH), 7.39–7.26 (m, 2H), 7.13 (dd, J=2.1 Hz, 8.4 Hz, 2H), 6.92 (d, J=8.7 Hz, 1H), 6.7 (d, J=2.1 Hz, 1H), 5.87 (s, 1H), 3.78 (s, 3H), 3.25 (d, J=16.8 Hz, 1H), 3.18 (d, J=16.8, 1H). GC-MS calcd. for $C_{16}H_{14}Cl_2O_3S$: 356.00; found: 356/358 ($M^+$), 251/253, 215/217, 181, 152.

11ah ($W_1$=5-Cl, $R_1$=phenyl, $R_2$=—$OCH_3$)

Compound 10ah (25 mg, 0.116 mmol) in dry DCM (1 ml) was cooled to 0° C. To this cold stirred solution $SnCl_4$ (27 μl, 0.23 mmol) followed by methyl thioglycolate (20 μL, 0.23 mmol) were added and stirring was continued overnight. The reaction was quenched by adding 1M HCl (2 ml) extracted with DCM (10 ml), washed with 1M HCl (2×10 ml) dried over sodium sulfate and concentrated. The crude product was purified by 10% EtOAc/PE to yield 24 mg (68%) of the product. $^1$H NMR (300 MHz, $CDCl_3$) δ 7.55 (d, J=1.5 Hz, 1H), 7.44 (d, J=7.5 Hz, 1H), 7.15–7.33 (m, 5H), 6.76 (d, J=9 Hz, 1H), 5.77 (s, 1H), 3.79 (s, 3H), 3.65 (s, 3H), 3.13 (s, 2H).

11ai ($W_1$=5-Cl, $R_1$=phenyl, $R_2$=—OH)

Compound 10ai (200 mg, 0.83 mmol) in dry DCM (2 ml) was cooled to 0° C. To the cooled stirred solution anhydrous $ZnCl_2$ (681 mg, 5 mmol) and methyl thioglycolate (223 μl, 2.5 mmol) were added and stirring was continued overnight. The reaction mixture was quenched by adding water (5 ml), extracted with DCM and washed with water. Dried over $Na_2SO_4$ and concentrated to afford 224 mg (81%) of compound 11ai. m.p: 123–125.3° C. $^1$H NMR (300 MHz, $CDCl_3$) δ 7.39 (d, J=7.2 Hz, 1H), 7.32–7.20 (m, 4H), 7.038 (dd, J=8.4 Hz, 2.6 Hz, 1H), 6.84 (d, J=2.1 Hz, 1H), 6.79 (d, J=8.4 Hz, 1H), 5.45 (s, 1H), 3.67 (s, 3H), 3.12 (s, 2H).

Synthesis of 11aj ($W_1$=5-Cl, $R_1$=2-chlorophenyl, $R_2$=H)

To a mixture of alcohol 10aj (500 mg, 1.98 mmol) in 1 mL of TFA was added methyl thioglycolate (550 mg, 5.18 mmol). The reaction mixture was stirred at room temperature for 3 days TFA was removed under high vacuum, the residue diluted with DCM, washed with $NaHCO_3$, dried over anhyd. $Na_2SO_4$ and concentrated to afford 11aj (600 mg). $^1$H NMR (300 MHz, $CDCl_3$) δ 7.65 (dd, J=7.5 Hz, J=1.5 Hz, 1H), 7.42 (s, 1H), 7.21–7.38 (m, 6H), 5.86 (s, 1H), 3.67 (s, 3H), 3.17 (d, J=15 Hz, 1H), 3.12 (d, J=15 Hz, 1H).

Synthesis of 11ak ($W_1$=5-Cl, $R_1$=cyclohexyl, $R_2$=$NH_2$)

Alcohol 10ak (0.25 g, 0.735 mmol) was mixed with methyl thioglycolate (0.656 mL, 7.35 mmol, 10 equivalents) and TFA (1.13 mL, 14.7 mmol, 20 equivalents). The mixture was stirred for 12 hrs. The TFA was then evaporated under vacuum and the resulting solution diluted with $CH_2Cl_2$ (20 mL), washed with a saturated solution of $NaHCO_3$ (2×10 mL), water (10 mL) and brine (20 mL). The organic layer was dried over sodium sulfate, filtered and concentrated under vacuum. The crude product was purified by flash chromatography on a silica gel column using a mixture of petroleum ether and ethyl acetate as eluent to give 11ak as colorless oil (0.19 g, 80% yield); LC/MS calcd. for $C_{16}H_{22}ClNO_2S$ 327 $[M-C_3H_5O_2S]^+$, found: 222.

Synthesis of 11al ($W_1$=5-Cl, $R_1$=iso-propyl, R=$NH_2$)

Using a similar procedure as for the synthesis of 11ak, 11al was prepared from 10al as a colorless oil (88% yield); LC/MS calcd. for $C_{13}H_{18}ClNO_2S$: 287 $[M-C_3H_5O_2S]^+$, found: 182.

Synthesis of 11am ($W_1$=5Cl, $R_1$=tert-butyl, $R_1$=$NH_2$)

Using a similar procedure as for the synthesis of 11ak, 11am was prepared from 10am as a colorless oil (86% yield); LC/MS calcd. for $C_{14}H_{20}ClNO_2S$: 301 $[M-C_3H_5O_2S]^+$, found: 196.

Synthesis of 11an ($W_1$=5-Cl, $R_1$=—$(CH_3)_3OCH_2(C_6H_5)$, $R_2$=$NH_2$)

Using a similar procedure as for the synthesis of 11ak, 11an was prepared from 10am as a colorless oil (78% yield); LC/MS calcd. for $C_{20}H_{24}ClNO_3S$: 393 $[M-C_3H_5O_2S]^+$, found: 288.

Synthesis of Thioether Carboxylic Acid 12

12t ($W_1$=5-nitro, $R_1$=phenyl, $R_2$=$NH_2$)

To a stirred solution of methyl ester 11t (39.3 mg, 0.118 mmol) in THF (2.4 ml) and methanol (2.4 ml) at rt was added sodium hydroxide solution (1.0 M ×2.4 ml, 20 eq). After stirring for 30 min. the reaction mixture was partitioned between brine and dichloromethane. The aqueous phase was titrated to exactly pH 7.0 with concentrated hydrochloric acid, and extracted twice with dichloromethane. The combined organic phase was dried with brine and sodium sulfate, then filtered and evaporated to give carboxylic acid 12t (38.0 mg, 0.119 mmol, 100% yield) as a yellow gum, which is analytically pure. $R_f$ (silica, dichloromethane: methanol (9:1))=0.25. HPLC (214 nm) $t_R$=7.62 (91.4%) min. $^1$H NMR (400 MHz, $CDCl_3$) δ 3.19

(d, J=16.8 Hz, 1H), 3.27 (d, J=16.8 Hz, 1H), 5.37 (s, 1H), 6.60–7.10 (br s, 3H), 6.68 (d, J=8.8 Hz, 1H), 7.36 (d, J=7.2 Hz, 1H), 7.43 (dd, J=7.2, 7.2 Hz, 1H), 7.52 (d, J=7.2 Hz, 1H), 7.91 (d, J=2.4 Hz, 1H), 8.00 (dd, J=8.8, 2.4 Hz, 1H). $^{13}C$ NMR (100 MHz, $CDCl_3$) δ 33.1, 49.7, 115.2, 122.6, 125.2, 126.1, 128.4, 128.9, 129.1, 136.6, 138.7, 151.0, 176.2. ESMS m/z 227.2 $[(M-HSCH_2CO_2H+H)]^+$, 319.4 $[(M+H)]^+$. LC/MS $t_R$ 7.94 (227.0 $[(M-HSCH_2CO_2H+H)]^+$, 318.9 $[(M+H)]^+$, 637.1 $[(2M+H)]^+$, 955.3 $[3M+H]^+$) min.

Using a similar procedure, the following thioether carboxylic acids were prepared from corresponding methyl esters.

12s ($W_1$=5-Cl, $R_1$=2-chlorophenyl, $R_2$=$NH_2$): white solid (657 mg, 1.92 mmol, 100% yield). $R_f$ (silica, dichloromethane:methanol (9:1))=0.25. HPLC (214 nm) $t_R$=8.27 (94.2%) min. $^1H$ NMR (400 MHz, $CDCl_3$) δ 3.20 (d, J=16 Hz, 1H), 3.22 (d, J=16 Hz, 1H), 6.02 (s, 1H), 7.07 (d, J=2.4 Hz, 1H), 7.31–7.37 (m, 2H), 7.40–7.47 (m, 2H), 7.80–7.89 (m, 2H), 9.02 (s, 1H). $^{13}C$ NMR (400 MHz, $CDCl_3$) δ 32.8, 45.0, 126.1, 127.6, 129.0, 129.8, 129.9, 130.5, 131.7, 132.6, 132.7, 133.9, 134.6, 175.0. ESMS m/z 250.2 $[M-HSCH_2CO_2H+H]^+$, 342.1 $[M+H]^+$. LC/MS $t_R$ 8.66 (346.0 $[M-HSCH_2CO_2H+CF_3CO+H]^+$, 438.1 $[M+CF_3CO+H]^+$, 874.8 $[2(M+CF_3CO)+H]^+$.

12x ($W_1$=5-Cl, $R_1$=phenyl, $R_2$=$NH_2$) (46.0 mg, 0.149 mmol, 77% yield) as a tan solid. $R_f$ (silica, dichloromethane:methanol (9:1))=0.25. HPLC (214 nm) $t_R$=7.61 (90.3%) min. $^1H$ NMR (400 MHz, $CDCl_3$) δ 2.79–3.14 (m, 2H), 5.27 (s, 1H), 5.90–6.30 (br s, 3H), 6.48 (d, J=8.0 Hz, 1H), 6.85 (s, 1H), 6.95 (d, J=8.0 Hz, 1H), 7.25–7.35 (m, 2H), 7.35–7.45 (m, 2H). $^3C$ NMR (100 MHz, $CDCl_3$) δ 34.8, 49.4, 118.7, 124.6, 127.4, 128.0, 128.3, 128.7, 128.8, 129.0, 137.4, 141.8, 176.4. ESMS m/z 308.2 $[M+H]^+$, 349.2 $[M+CH_3CN+H]^+$, 615.1 [2M+H]. LC/MS $t_R$ 7.89 (216.0 $[M-HSCH_2CO_2H+H]^+$, 308.2 $[M+H]^+$, 615.1 $[2M+H]^+$, 921.9 $[3M+H]^+$) min.

12r ($W_1$=H, $R_1$=2-chlorophenyl, $R_2$=$NH_2$)

From 11r, 12r was obtained as a white powder. HPLC (214 nm) $t_R$=7.33 (85.8%) min. $^1H$ NMR (400 MHz, $CDCl_3$) δ 3.16 (d, J=16.0 Hz, 1H), 3.23 (d, J=16.0 Hz), 5.87 (s, 1H), 6.14 (br s, 1H), 6.71 (dd, J=3.2, 3.2 Hz, 1H), 6.78 (d, J=7.6 Hz, 1H), 6.84 (d, J=7.6 Hz, 1H), 7.10 (ddd, J=8.0, 8.0, 1.2 Hz, 1H), 7.25–7.31 (m, 1H), 7.34–7.42 (m, 1H), 7.97 (d, J=7.6 Hz, 1H). ESMS m/z 308.5 $[(M+H)]^+$. LC/MS $t_R$ 7.06 (308.1 $[(M+H)]^+$) min.

Synthesis of Thioether Carboxamides 13

13a ($W_1$=5-Cl, $R_1$=2-chlorophenyl, $R_2$=$NH_2$, $R_{3a}$=$CH_3$, $R_{3b}$=H)

To carboxylic acid 12s (115 mg, 0.337 mmol) under a nitrogen atmosphere at rt was added methylamine (2 mol/L in THF, 1.68 ml, 3.37 mmol, 10 eq), EDC (129 mg, 0.673 mmol, 2 eq) and DMAP (4.1 mg, 0.033 mmol, 0.1 eq) and the resulting solution was stirred for 18 hrs. The reaction mixture was evaporated and the residue partitioned between brine and dichloromethane. The aqueous phase was extracted with further dichloromethane and the combined organic extracts were dried with brine and sodium sulfate, then filtered and evaporated to give the crude amide (149 mg) as a yellow oil. The crude material was purified by flash chromatography on silica (5 g) with 40–60 petroleum ether: ethyl acetate (1:1 then 2:1) to give amide 13a (74.0 mg, 0.208 mmol, 62%) as a white solid. $R_f$ (silica, petroleum ether:ethyl acetate (1:1))=0.15. HPLC (214 nm) $t_R$=8.54 (96.4%) min. $^1H$ NMR (400 MHz, $CDCl_3$) δ 2.81 (d, J=4.8 Hz, 3H), 3.04–3.16 (m, 2H), 4.17 (br s, 2H), 5.64 (s, 1H), 6.40 (br s, 1H), 6.62 (d, J=8.0 Hz, 1H), 7.01–7.07 (m, 2H), 7.26 (ddd, J=5.6, 1.6, 1.6 Hz, 1H), 7.33 (ddd, J=7.6, 1.6, 1.6 Hz, 1H), 7.39 (dd, J=7.6, 1.6, Hz, 1H), 7.72 (dd, J=7.6, 1.6 Hz, 1H). $^{13}C$ NMR (100 MHz, $CDCl_3$) δ 26.5, 35.6, 46.1, 117.7, 123.1, 124.6, 127.4, 128.0, 128.4, 129.1, 129.9, 130.2, 134.0, 136.0, 143.5, 168.9. ESMS m/z 355.1 $[M+H]^+$. LC/MS $t_R$=7.80 (250.1 $[M-HSCH_2CONHMe+H]^+$, 355.0 $[M+H]^+$, 709.0 $[2M+H]^+$) min.

13b ($W_1$=5-Cl, $R_1$=2-chlorophenyl, $R_2$=$NH_2$, $R_{3a}$=$CH_3$, $R_{3b}$=$CH_3$)

Using a similar procedure as for the synthesis of 13a, 13b was prepared from 12s and dimethylamine, and obtained as a white solid (123 mg, 0.333 mmol, 99%). $R_f$ (silica, petroleum ether:ethyl acetate (1:1))=0.20. HPLC (214 nm) $t_R$=9.10 (100%) min. $^1H$ NMR (400 MHz, $CDCl_3$) δ 2.91 (s, 3H), 2.95 (s, 3H), 3.15–3.27 (m, 2H), 4.69 (br s, 2H), 5.76 (s, 1H), 6.62 (d, J=8.4 Hz, 1H), 6.75 (d, J=2.4 Hz, 1H), 6.99 (dd, J=8.4, 2.4 Hz, 1H), 7.21–7.29 (m, 1H), 7.34–7.40 (m, 2H), 7.93–7.98 (m, 1H). $^{13}C$ NMR (100 MHz, $CDCl_3$) δ 33.3, 36.0, 37.4, 46.0, 117.2, 122.2, 124.7, 127.0, 127.9, 128.2, 128.9, 129.9, 130.4, 134.7, 136.2, 144.2, 168.7. ESMS m/z 369.2 $[(M+H)]^+$. LC/MS $t_R$=8.28 (368.9 $[(M+H)]^+$, 737.1 $[(2M+H)]^+$) min.

13c ($W_1$=5-C, $R_1$=2-chlorophenyl, $R_2$=$NH_2$, $R_3$=2-phenylethyl, $R_{3b}$=H)

To a solution of 11s (52 mg, 0.15 mmole) in methanol (0.5 ml) was added phenethylamine (0.19 ml, 1.5 mmole). The mixture was heated at 70° C. for 16 hrs. TLC indicated complete consumption of 11s. The solvent was removed under vacuum. The residue was dissolved in DCM (10 ml), washed with 10% citric acid (3×10 ml) and dried over anhydrous sodium sulfate. The crude product was purified on a silica gel column using 20% ethyl acetate in hexane as eluent to give 13c as white solid (60.4 mg, 90% yield). $^1H$ NMR (500 MHz, $CDCl_3$) δ 2.83 (t, J=7.0 Hz, 2H), 3.05 (d, J=16 Hz, 1H), 3.10 (d, J=16 Hz, 1H), 3.61–3.48 (m, 2H), 4.10 (br, s, 2H), 5.60 (s, 1H), 6.29 (br, s, 1H), 6.61 (d, J=8.4 Hz, 1H), 6.99 (d, J=2.2 Hz, 1H), 7.03 (dd, J=8.3, 2.0 Hz, 1H), 7.18 (d, J=7.0 Hz, 1H), 7.32–7.21 (m, 6H), 7.38 (d, J=7.0 Hz, 1H), 7.72 (d, J=7.5 Hz, 1H). LC-MS: calcd. For $C_{23}H_{22}Cl_2N_2OS$: 444.1; found: 444.8 $[M+H]^+$.

Using a similar procedure as for the synthesis of 13c, the following thioether amide was prepared.

13d ($W_1$=5-Cl, $R_1$=2-chlorophenyl, $R_2$=$NH_{23}R_3$, $R_{3b}$=—$(CH_2)_5$—)

$^1H$ NMR (500 MHz, $CDCl_3$) δ 1.65–1.50 (m, 6H), 3.19 (d, J=15 Hz, 1H), 3.25 (d, J=15 Hz, 1H), 3.30–3.27 (m, 2H), 3.60–3.50 (m, 2H), 4.69 (br, s, 2H), 5.74 (s, 1H), 6.63 (d, J=9.0 Hz, 1H), 6.76 (d, J=2.7 Hz, 1H), 7.00 (dd, J=8.3, 2.1 Hz, 1H), 7.28 (dd, J=8.9, 1.8 Hz, 1H), 7.38 (t, J=7.6 Hz, 2H), 7.95 (d, J=7.5 Hz, 1H). LC-MS: calcd. For $C_{20}H_{22}Cl_2N_2OS$: 408.1; found: 408.9 $[M+H]^+$.

13e ($W_1$=5-Cl, $R_1$=2-chlorophenyl, $R_2$=$NH_2$, $R_3$=2-hydroxyethyl, $R_{3b}$=H)

$^1H$ NMR (500 MHz, $CDCl_3$) δ 3.12 (d, J=16 Hz, 1H), 3.17 (d, J=16 Hz, 1H), 3.44–3.36 (m, 1H), 3.55–3.48 (m, 1H), 3.82–3.72 (m, 2H), 4.10 (br, s, 2H), 5.66 (s, 1H), 6.65 (d, J=9.0 Hz, 1H), 6.80 (br, s, 1H), 7.06–7.03 (m, 2H), 7.28 (d, J=7.1 Hz, 1H), 7.35 (t, J=8.1 Hz, 1H), 7.40 (d, J=8.3 Hz, 1H), 7.75 (d, J=8.2 Hz, 1H). LC-MS: calcd. For $C_{17}H_{18}C_2N_2O_2S$: 384.0; found: 384.8 $[M+H]^+$.

13f ($W_1$=5Cl, $R_1$=2-chlorophenyl, $R_1$=$NH_2$, $R_{3a}$=benzyl, $R_{3b}$=H)

$^1H$ NMR (500 MHz, $CDCl_3$) δ 3.14 (d, J=16 Hz, 1H), 3.18 (d, J=16 Hz, 1H), 4.45–4.38 (m, 1H), 4.55–4.48 (m, 1H), 4.10 (br, s, 2H), 5.60 (s, 1H), 6.60 (d, J=8.7 Hz, 1H), 6.72 (br, s, 1H), 7.03 (d, J=9.1 Hz, 2H), 7.37–7.23 (m, 8H), 7.71 (d, J=9.0 Hz, 1H). LC-MS: calcd. For $C_{22}H_{20}Cl_2N_2OS$: 430.1; found: 430.8 $[M+H]^+$.

13p ($W_1$=5-Cl, $R_1$=2-chlorophenyl, $R_2$=(2-acetamido) ethyl, $R_{3b}$=H)

$^1$H NMR (500 MHz, $CDCl_3$) δ 1.95 (s, 3H), 3.07 (d, J=16 Hz, 1H), 3.14 (d, J=16 Hz, 1H), 3.44–3.35 (m, 4H), 4.10 (br, s, 2H), 6.18 (br, s, 1H), 6.64 (d, J=8.3 Hz, 1H), 6.93 (br, s, 1H), 6.97 (d, J=2.0 Hz, 1H), 7.04 (dd, J=8.3, 2.0 Hz, 1H), 7.28 (d, J=7.3 Hz, 1H), 7.36 (t, J=7.2 Hz, 1H), 7.39 (d, J=8.3 Hz, 1H), 7.78 (d, J=8.1 Hz, 1H). LC-MS: calcd. For $C_{19}H_{21}Cl_2N_3O_2S$: 425.07; found: 425.9 $[M+H]^+$.

13h ($W_1$=5-Cl, $R_1$=2-chlorophenyl, $R_2$=$NH_2$, $R_{3b}$= cyclohexyl, $R_3$=H)

$^1$H NMR (500 MHz, $CDCl_3$) δ 1.98–1.12 (m, 10H), 3.06 (d, J=16 Hz, 1H), 3.11 (d, J=16 Hz, 1H), 3.84–3.75 (m, 1H), 4.10 (br, s, 2H), 5.63 (s, 1H), 6.16 (br, d, J=7.9 Hz, 1H), 6.64 (d, J=9.1 Hz, 1H), 7.05–7.02 (br, m, 2H), 7.27 (d, J=7.3 Hz, 1H), 7.34 (t, J=7.3 Hz, 1H), 7.40 (d, J=7.9 Hz, 1H), 7.73 (d, J=7.9 Hz, 1H). LC-MS: calcd. For $C_{21}H_{24}Cl_2N_2OS$: 422.1; found: 422.9 $[M+H]^+$.

13i ($W_1$=5-Cl, $R_1$=2-chlorophenyl, $R_2$=$NH_2$, $R_{3a}$=2,2-diphenylethyl, $R_{3b}$=H)

$^1$H NMR (500 MHz, $CDCl_3$) δ 3.00 (d, J=16 Hz, 1H), 3.04 (d, J=16 Hz, 1H), 3.90–3.85 (m, 1H), 3.98–3.94 (m, 1H), 4.08 (br, s, 1H), 4.10 (br, s, 2H), 5.55 (s, 1H), 6.21 (br, s, 1H), 6.60 (d, J=8.4 Hz, 1H), 6.91 (d, J=2.1 Hz, 1H), 7.02 (dd, J=8.4, 2.2 Hz, 1H), 7.34–7.20 (m, 12H), 7.38 (d, J=8.1 Hz, 1H), 7.71 (d, J=8.4 Hz, 1H). LC-MS: calcd. For $C_{29}H_{26}Cl_2N_2OS$: 520.1; found: 520.9 $[M+H]^+$.

13j ($W_1$=5-Cl, $R_1$=2-chlorophenyl, $R_2$=$NH_2$, $R_{3a}$, $R_{3b}$=—$(CH_2)_2$—N(Ph)—$(CH_2)_2$—)

$^1$H NMR (500 MHz, $CDCl_3$) δ 3.18–3.10 (m, 4H), 3.25 (d, J=16 Hz, 1H), 3.30 (d, J=16 Hz, 1H), 3.56–3.52 (br, m, 2H), 3.82–3.78 (br, m, 2H), 4.56 (br, s, 2H), 5.76 (s, 1H), 6.64 (d, J=8.6 Hz, 1H), 6.85 (d, J=2.0 Hz, 1H), 6.95–6.90 (m, 3H), 7.02 (dd, J=8.0, 2.0 Hz, 1H), 7.32–7.25 (m, 3H), 7.37 (t, J=7.7 Hz, 2H), 7.90 (d, J=7.7 Hz, 1H). LC-MS: calcd. For $C_{25}H_{25}Cl_2N_3OS$: 485.1; found: 485.9 $[M+H]^+$.

13k ($W_1$=5-Cl, $R_2$=chlorophenyl, $R_2$=$NH_2$, $R_3$=n-propyl, $R_{3b}$=H)

$^1$H NMR (500 MHz, $CDCl_3$) δ 0.93 (t, J=7.4 Hz, 3H), 1.58–1.50 (m, 2H), 3.10 (d, J=16 Hz, 1H), 3.15 (d, J=16 Hz, 1H), 3.28–3.20 (m, 2H), 4.20 (br, s, 2H), 5.63 (s, 1H), 6.33 (br, s, 1H), 6.63 (d, J=8.5 Hz, 1H), 7.06–7.02 (m, 2H), 7.30–7.25 (m, 1H), 7.33 (t, J=7.2 Hz, 1H), 7.40 (d, J=7.5 Hz, 1H), 7.71 (d, J=8.0 Hz, 1H). LC-MS: calcd. For $C_{18}H_{20}Cl_2N_2OS$: 382.1; found: 382.8 $[M+H]^+$.

13l ($W_1$=5-Cl, $R_1$=2-chlorophenol, $R_2$=$NH_2$, $R_{3a}$=n-hexyl, $R_{3b}$=H)

$^1$H NMR (500 MHz, $CDCl_3$) δ 0.88 (t, J=5.8 Hz, 3H), 1.36–1.26 (br, m, 6H), 1.55–1.46 (m, 2H), 3.10 (d, J=16 Hz, 1H), 3.14 (d, J=16 Hz, 1H), 3.29–3.22 (m, 2H), 4.20 (br, s, 2H), 5.63 (s, 1H), 6.30 (br, s, 1H), 6.64 (d, J=8.5 Hz, 1H), 7.06–7.02 (m, 2H), 7.30–7.25 (m, 1H), 7.33 (t, J=7.2 Hz, 1H), 7.40 (d, J=7.5 Hz, 1H), 7.71 (d, J=8.0 Hz, 1H). LC-MS: calcd. For $C_{21}H_{26}Cl_2N_2OS$: 424.1; found: 424.9 $[M+H]^+$.

13m ($W_1$=5Cl, $R_1$=2-chlorophenyl, $R_2$=$NH_2$, $R_{3a}$=3-ethoxypropyl, $R_{3b}$=H)

LC-MS: calcd. For $C_{20}H_{24}Cl_2N_2O_2S$: 426.1; found: 426.9 $[M+H]^+$.

13n ($W_1$=5-Cl, $R_2$=2-chlorophenyl, $R_2$=$NH_2$, $R_{3a}$= cyclohexylmethyl, $R_{3b}$=H)

LC-MS: calcd. For $C_{22}H_{26}Cl_2N_2OS$: 436.1; found: 437.0 $[M+H]^+$.

13o ($W_1$=5-Cl, $R_1$=2-chlorophenyl, $R_2$=$NH_2$, $R_{3a}$= propargyl, $R_{3b}$=H)

LC-MS: calcd. For $C_{18}H_{16}Cl_2N_2OS$: 378.0; found: 378.8 $[M+H]^+$.

13p ($W_1$=5-Cl, $R_1$=2-chlorophenyl, $R_2$=$NH_2$, $R_{3a}$=3-(1-imidazolyl)propyl, $R_{3b}$=H)

$^1$H NMR (500 MHz, $CDCl_3$) δ 2.05–1.98 (m, 2H), 3.10 (d, J=16 Hz, 1H), 3.15 (d, J=16 Hz, 1H), 3.34–3.24 (m, 2H), 3.99 (t, J=6.8 Hz, 2H), 4.20 (br, s, 2H), 5.61 (s, 1H), 6.42 (br, s, 1H), 6.63 (d, J=8.5 Hz, 1H), 6.93 (s, 1H), 7.08–7.03 (m, 2H), 7.11 (d, J=2.7 Hz, 1H), 7.28 (d, J=7.5 Hz, 1H), 7.34 (t, J=6.9 Hz, 1H), 7.40 (d, J=8.1 Hz, 1H), 7.49 (s, 1H), 7.66 (d, J=8.9 Hz, 1H). LC-MS: calcd. For $C_{21}H_{22}Cl_2N_4OS$: 448.1; found: 449.0 $[M+H]^+$.

13q ($W_1$=5-Cl, $R_1$=2-chlorophenyl, $R_2$=NH—, $R_3$=3-(N,N-dimethylamino)propyl, $R_{3b}$=H)

LC-MS: calcd. For $C_{20}H_{25}Cl_2N_3OS$: 425.1; found: 426.1 $[M+H]^+$.

13r ($W_1$=5-Cl, $R_1$=2-chlorophenyl, $R_2$=$NH_2$, $R_{3a}$= cyclopropyl, $R_{3b}$=H)

LC-MS: calcd. For $C_{18}H_{18}Cl_2N_3OS$: 380.0; found: 380.9 $[M+H]^+$.

13s ($W_1$=5-Cl, $R_1$=2-chlorophenyl, $R_2$=$NH_2$, $R_{3a}$=2-(4-hydroxyphenyl)ethyl, $R_{3b}$=H)

LC-MS: calcd. For $C_{23}H_{22}Cl_2N_2O_2S$: 460.08; found: 460.9.

Synthesis of 13t ($W_1$=5-Cl, $R_1$=2-chlorophenyl, $R_2$=$NH_2$, $R_{3a}$=2-(3-iodo-4-hydroxyphenyl)ethyl, $R_{3b}$=H) and 13u ($W_1$=5-Cl, $R_1$=2-chlorophenyl, $R_2$=$NH_2$, $R_{3a}$=2-(3,5-diiodo-4-hydroxyphenyl)ethyl, $R_{3b}$=H).

13s (23 mg, 50 mmole) was dissolved in ethanol (50 ml). De-ionized water (200 ml) was added and the solution became slightly cloudy. NaI (20 mg, 200 μmole), 30% hydrogen peroxide (1.0 ml) and lactoperoxidase (LPO) (100μl×1 unit/μl) were added. The mixture was shaken gently continuously at room temperature on a shaker. The progress of the reaction was monitored using LC-MS. After 3 hrs, the reaction mixture became very cloudy. LC-MS indicated about 15% conversion. The reaction mixture was diluted with 20% aqueous ethanol (250 ml) upon which the reaction mixture became clear. LPO (250 μl×1 unit/μl) was added and the mixture was shaken over night. LC-MS showed about 50% conversion and the formation of small amount of di-iodo-product. The ethanol was removed under vacuum. The aqueous residue was extracted with dichloromethane (50 ml×4). The combined organic layer was dried over anhydrous sodium sulfate. The crude product was dissolved in methanol (3 ml) and purified on reverse phase preparative HPLC. 13t: white solid (10.6 mg). LC-MS: calcd. For $C_{23}H_{21}Cl_{21}N_2O_2S$: 585.97; found: 586.8. 13u: white solid (3.1 mg). LC-MS: calcd. For $C_{23}H_{20}Cl_{212}N_2O_2S$: 711.87; found: 712.7.

13v ($W_1$=5-Cl, $R_1$=2-chlorophenyl, $R_2$=$NH_2$, $R_{3a}$=—$(CH)_2O(CH_2)_2O(CH_2)_2NH_2$, $R_{3b}$=H)

Yellow viscous oil (0.505 g, quantitative). LC-MS: calcd. For $C_{23}H_{27}Cl_2N_3O_3S$: 471.12; found: 472.1.

13ag ($W_1$=5-Cl, $R_1$=2-chlorophenyl, $R_2$OH, $R_{3a}$ & $R_{3b}$=—$(CH_2)_5$—)

m.p.=219.2–221.2° C. $^1$H NMR (300 MHz, $CDCl_3$) δ 9.7 (s, phenolic-OH), 8.01 (d, J=7.2 Hz, 1H), 7.37–7.44 (m, 2H), 7.31 (d, J=6.6 Hz, 1H), 7.09 (dd, J=2.7 Hz, 9 Hz, 1H), 6.94 (dd, J=8.7 Hz, 1H), 6.6 (d, J=2.4 Hz, 1H), 5.84 (s, 1H), 3.64 (s, 2H), 3.35–3.36 (m, 2H), 3.26 (d, J=15.9 Hz, 1H), 3.18 (d, J=15.9 Hz, 1H), 1.55–1.59 (m, 6H).

GC-MS: calcd. for $C_{20}H_{21}Cl_2NO_2S$: 409.07; found: 410 ($MH^+$), 215/217, 152, 126/127, 112.

13ai ($W_1$=5-Cl, $R_1$=phenyl, $R_2$=OH, $R_{3a}$ & $R_{3b}$=—$(CH_2)_5$—)

m.p.=192° C. $^1$H NMR (300 MHz, $CDCl_3$) δ 9.58 (s, 1H), 7.48 (d, J=7.8 Hz, 1H), 7.415–7.30 (m, 3H), 7.1–7.06 (dd, J=8.4 Hz, 3 Hz, 2H), 6.92 (d, J=9 Hz, 1H), 6.76 (d, J=2.1 Hz, 1H), 5.48 (s, 1H), 3.72–3.53 (m, 4H), 3.16 (d, J=16.2 Hz, 1H), 3.27 (d, J=16.2 Hz, 1H), 1.64–1.61 (m, 6H).

13aj ($W_1$=5-Cl, $R_1$=2-chlorophenyl, $R_2$=H, $R_3$=cyclohexylmethyl, $R_{3b}$=H)

Compound 13aj was obtained from 11aj and cyclohexylmethylamine as a white solid. LC-MS: calcd. for $C_{22}H_{25}Cl_2NOS$: 421.10, found: 421.9 $(M+H)^+$.

EXAMPLE 6

SCHEME 6
SYNTHESIS OF THIOETHER OXADIAZOLE 14
(ROUTE 1)

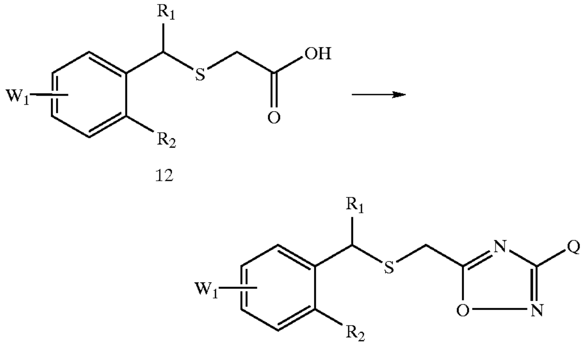

12

14

14a ($W_1$=5-Cl, $R_1$=2-chlorophenyl, $R_2$=$NH_2$, Q=4-fluorophenyl)

To the solution of 12s (0.342 g, 1 mmol) in diglyme (3 ml) was added 4-fluorobenzamidoxime (from Aldrich, 0.154 g, 1 mmol) and EDC (0.38 g, 2 mmol). The mixture was stirred at 50° C. for 16 hrs followed by at 110° C. for 3 hrs. The crude product was purified on a silica gel column using 30% ethyl acetate in hexane to give 14a as a white solid (0.116 g, 25%): $^1H$ NMR (400 MHz, $CDCl_3$) δ 3.78 (d, 1H), 3.86 (d, 1H), 6.00 (s, 1H), 6.64 (d, 1H), 6.93 (d, 1H), 7.03 (dd, 1H), 7.19 (m, 2H), 7.27 (m, 2H), 7.36 (m, 2H), 7.86 (d, 1H), 8.08 (m, 1H). LC-MS: calcd. for $C_{22}H_{16}Cl_2FN_3OS$: 459.04; found: 459.8.

14b ($W_1$=5-Cl, $R_1$=2-chlorophenyl, $R_2$=$NH_2$, Q=methyl)

Using a similar procedure as for 14a, 14b was obtained from 12s and acetamidoxime as a white solid. $^1H$ NMR (400 MHz, $CDCl_3$) δ 2.39 (s, 3H), 3.71 (d, J=15.8 Hz, 1H), 3.77 (d, J=15.8 Hz, 1H), 5.80 (s, 1H), 6.64 (d, J=8.4 Hz, 1H), 6.92 (d, J=2.4 Hz, 1H), 7.04 (dd, J=2.4, 8.4 Hz, 1H), 7.28 (dd, J=7.8, 7.9 Hz, 1H), 7.38 (m, 2H), 7.81 (d, J=7.9 Hz, 1H).

EXAMPLE 7

SCHEME 7
SYNTHESIS OF THIOETHER OXADIAZOLE 14
(ROUTE 2)

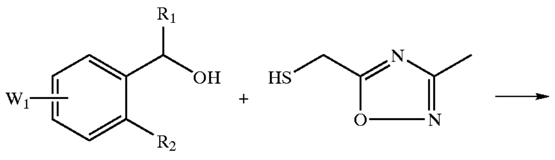

10

-continued

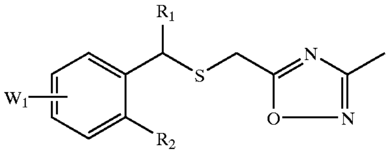

14

General Procedures for the Synthesis of 14 from 10 and 3-methyl-(5-mercatptomethyl)-1,2,4-oxadiazole.

Compound 10 was converted to 14 using one of the three alternative methods listed below. The experimental detail for each compound was noted along with its spectral data.

(a) Compound 10 was dissolved in anhydrous dichloromethane (1 ml). The 1-methyl-5-(mercaptomethyl)-1,2,4-oxadiazole (synthesized in five steps following a procedure from Broughton et al. published PCT WO98/04559) (1 equivalent) was added followed by TFA (1 equivalent). The reactions were monitored by TLC. After 1 hr the reaction mixture was diluted with dichloromethane (20 ml) and washed with 1:1 brine/1 M NaOH (10 ml). The aqueous layer was extracted with dichloromethane (1×10 ml). The combined organic phase was dried over sodium sulfate, filtered and the solvent removed in vacuo. The crude material was purified by flash chromatography on silica gel (25 g) using petroleum spirit/ethyl acetate as eluent. The desired compound from the flash column was taken up into 4 ml of 90% aqueous acetonitrile and was lyophilised to yield the desired products.

(b) The procedure was essentially the same as (a) except a large excess of TFA (200 μL) was added to each reaction and the reactions were left overnight.

(c) The procedure was essentially the same as (a) except neat TFA (1 ml) was used instead of the dichloromethane and the reaction was heated at 60° C. over the weekend.

14d ($W_1$=5-Cl, $R_1$=3,5-dimethylphenyl, $R_2$=$NH_2$)

Compound 14d was synthesized using procedure (b) and obtained as a golden colored oil (55 mg, 66% yield); clogP=6.00; $R_f$ (petroleum spirit/ethyl acetate, 2.5:1)=0.35; HPLC (214 nm) $t_R$=10.22 (96.79%) min; $^1H$ NMR (400 MHz, $CDCl_3$) δ 2.31 (s, 6H), 2.40 (s, 3H), 3.68 (d, J=15.9 Hz, 1H), 3.73 (d, J=15.9 Hz, 1H), 4.13 (brs, 2H), 5.35 (s, 1H), 6.61 (d, J=8.2 Hz, 1H), 6.93 (s, 1H), 7.02–7.07 (m, 4H); $^{13}C$ NMR (100 MHz, $CDCl_3$) δ 11.6, 21.3, 26.1, 49.8, 117.8, 123.3, 125.5, 126.6, 128.5, 129.0, 129.8, 137.3, 138.5, 143.4, 167.4, 176.9; LC/MS $t_R$=9.40 (374.3 $[M+H]^+$) min.

14 g ($W_1$=5-Cl, $R_2$-thiophenyl, $R_2$=$NH_2$).

Compound 14g was using procedure (a) and obtained as a golden colored oil (31 mg, 34% yield); clogP=5.01; $R_f$ (petroleum spirit/ethyl acetate, 2:1)=0.3; HPLC (214 nm) $t_R$=9.27 (90.20%) min; $^1H$ NMR (400 MHz, $CDCl_3$) δ 2.40 (s, 3H), 3.77 (d, J=16.1 Hz, 1H), 3.83 (d, J=16.1 Hz, 1H), 4.22 (brs, 2H), 5.66 (s, 1H), 6.62 (d, J=8.5 Hz, 1H), 7.00 (dd, J=3.5, 5.1 Hz, 1H), 7.05 (dd, J=2.4, 8.5 Hz, 1H), 7.10 (brd, J=3.5 Hz, 1H), 7.12 (d, J=2.4 Hz, 1H), 7.30 (dd, J=1.1, 5.1 Hz, 1H); $^{13}C$ NMR (100 MHz, $CDCl_3$) δ 11.5, 26.2, 45.1, 118.0, 123.3, 125.0, 126.1, 127.1, 127.3, 128.8, 128.9, 141.9, 143.2, 167.4, 176.7; ESMS m/z 352.0 $[M+H]^+$, 393.2 $[M+CH_3CN+H]^+$; LC/MS $t_R$=8.55 (351.9 $[M+H]^+$) min.

14h ($W_1$=5-Cl, $R_1$=1-methyl-2-pyrrolyl, $R_2$=$NH_2$).

Compound 14h was synthesized using procedure (a) and obtained as a dark green solid (19 mg, 42% yield); clogP=3.81; $R_f$ (petroleum spirit/ethyl acetate, 1:1)=0.70; HPLC (214 nm) $t_R$=9.06 (78.26%) min; $^1H$ NMR (400 MHz, $CDCl_3$) δ 2.40 (s, 3H), 3.35 (s, 3H), 3.75 (d, J=16.1 Hz, 1H), 3.90 (d, J=16.1 Hz, 1H), 4.05 (brs, 2H), 5.42 (s, 1H), 6.12

(t, J=3.2 Hz, 1H), 6.38–6.40 (m, 1H), 6.60–6.62 (m, 2H), 7.00 (d, J=2.4 Hz, 1H), 7.03 (dd, J=2.4, 8.4 Hz, 1H); $^{13}$C NMR (100 MHz, $CDCl_3$) δ 11.6, 26.4, 33.7, 42.1, 107.2, 110.0, 117.9, 123.5, 123.8, 124.3, 128.0, 128.7, 128.9, 143.3, 167.3, 177.2; ESMS m/z 349.2 $[M+H]^+$; LC/MS $t_R$=8.32 (349.3 $[M+H]^+$) min.

14i ($W_1$=5-Cl, $R_1$=3-methylphenyl, R=$NH_2$).

Compound 14i was synthesized using procedure (b) and obtained as a golden colored oil (40 mg, 66% yield); clogP=5.50; $R_f$ (petroleum spirit/ethyl acetate, 2:1)=0.35; HPLC (214 nm) $t_R$=9.79 (92.66%) min; $^1$H NMR (400 MHz, $CDCl_3$) δ 2.35 (s, 3H), 2.40 (s, 3H), 3.67 (d, J=15.9 Hz, 1H), 3.73 (d, J=15.9 Hz, 1H), 4.15 (brs, 2H), 5.38 (s, 1H), 6.61 (d, J=7.8 Hz, 1H), 7.01–7.04 (m, 2H), 7.12 (d, J=5.8 Hz, 1H), 7.24–727 (m, 3H); $^{13}$C NMR (100 MHz, $CDCl_3$) δ 11.6, 21.4, 26.1, 49.8, 117.9, 123.3, 125.4, 126.0, 128.5, 128.8, 128.9, 129.0, 129.6, 137.3, 138.7, 143.4, 167.4, 176.9; ESMS m/z 360.1 $[M+H]^+$, 401.3 $[M+CH_3CN+H]^+$; LC/MS $t_R$=9.02 (360.0 $[M+H]^+$) min.

14j ($W_1$=5-Cl, $R_1$=4-methylphenyl, R__=$NH_2$).

Compound 14j was synthesized using procedure (b) and obtained as a golden colored oil (69 mg, 64% yield); clogP=5.50; $R_f$ (petroleum spirit/ethyl acetate, 2:1)=0.41; HPLC (214 nm) $t_R$=9.90 (92.77%) min; $^1$H NMR (400 MHz, $CDCl_3$) δ 2.35 (s, 3H), 2.39 (s, 3H), 3.65 (d, J=15.9 Hz, 1H), 3.72 (d, J=15.9 Hz, 1H), 3.78 (brs, 2H), 5.38 (s, 1H), 6.60 (d, J=8.2 Hz, 1H), 7.01–7.05 (m, 2H), 7.17 (d, J=7.9 Hz, 2H), 7.34 (d, J=7.9 Hz, 2H); $^{13}$C NMR (100 MHz, $CDCl_3$) δ 11.5, 21.0, 26.0, 49.6, 117.9, 123.3, 125.4, 128.5, 128.8, 128.9, 129.6, 134.3, 137.9, 143.4, 167.4, 176.8; ESMS m/z 360.1 $[M+H]^+$, 401.2 $[M+CH_3CN+H]^+$; LC/MS $t_R$=9.06 (360.0 $[M+H]^+$) min.

14k ($W_1$=5-Cl, $R_1$=2,3-dimethylphenyl, $R_2$=$R_2$=$NH_2$).

Compound 14k was synthesized using procedure (b) and obtained as a golden colored oil (20.7 mg, 30.3% yield); clogP=6.00; $R_f$ (petroleum spirit/ethyl acetate, 3:1)=0.35; HPLC (214 nm) $t_R$=10.48 (95.19%) min; $^1$H NMR (400 MHz, $CDCl_3$) δ 2.03 (s, 3H), 2.28 (s, 3H), 2.40 (s, 3H), 3.68 (d, J=15.9 Hz, 1H), 3.74 (d, J=15.9 Hz, 1H), 4.17 (brs, 2H), 5.63 (s, 1H), 6.63 (d, J=8.4 Hz, 1H), 6.91 (d, J=2.4 Hz, 1H), 7.02 (dd, J=2.4, 8.4 Hz, 1H), 7.12–7.20 (m, 2H), 7.64 (d, J=7.5 Hz, 1H); $^{13}$C NMR (100 MHz, $CDCl_3$) δ 11.5, 14.4, 20.7, 26.2, 46.7, 117.7, 123.5, 125.5, 125.9, 126.1, 128.4, 128.8, 129.8, 135.0, 135.6, 137.6, 143.4, 167.3, 177.0; ESMS m/z 374.2 $[M+H]^+$, 367.3 $[M+CH_3CN+H]$; LC/MS $t_R$=9.58 (244.1 $[M-C_4H_5N_2OS]^+$, 374.2 $[M+H]^+$) min.

14l ($W_1$=5-Cl, $R_1$=3,4-dimethylphenyl, R=$NH_2$) and 14la ($W_1$=5-Cl, $R_1$=3,4-dimethylphenyl, $R_2$=—NHC(=O)$CF_3$)

Compound 14l and corresponding trifluoroacetamide 14la were synthesized using procedure (b). Compound 14la was obtained as a golden colored oil (48.5 mg, 55.4% yield); clogP=6.86; $R_f$ (petroleum spirit/ethyl acetate, 3:1)=0.92; HPLC (214 nm) $t_R$=10.69 (96.50%) min; $^1$H NMR (400 MHz, $CDCl_3$) δ 2.24 (s, 6H), 2.40 (s, 3H), 3.55 (d, J=15.5 Hz, 1H), 3.71 (d, J=15.5 Hz, 1H), 5.59 (s, 1H), 7.07–7.14 (m, 3H), 7.32 (dd, J=1.5, 8.6 Hz, 1H), 7.46 (d, J=1.5 Hz, 1H), 7.70 (d, J=8.6 Hz, 1H), 9.16 (s, 1H); $^{13}$C NMR (100 MHz, $CDCl_3$) δ 11.3, 19.3, 19.8, 25.2, 48.3, 115.8 (q, J=288 Hz, $CF_3$), 125.6, 126.7, 128.9, 129.4, 129.7, 130.4, 131.5, 133.1, 133.5, 134.5, 137.2, 137.7, 155.5 (q, J=37 Hz, $COCF_3$), 167.4, 176.1; ESMS m/z 470.2 $[M+H]^+$; LC/MS $t_R$=9.83 (469.9 $[M+H]^+$) min. 14l was obtained as a golden colored oil (17.0 mg, 24.4% yield); clogP=6.00; $R_f$ is petroleum spirit/ethyl acetate, 3:1)=0.34; HPLC (214 nm) $t_R$=10.75 (95.51%) min; $^1$H NMR (400 MHz, $CDCl_3$) δ 2.25 (s, 6H), 2.39 (s, 3H), 3.67 (d, J=15.9 Hz, 1H), 3.72 (d, J=15.9 Hz, 1H), 4.13 (brs, 2H), 5.35 (s, 1H), 6.61 (d, J=8.4 Hz, 1H), 7.03 (dd, J=2.3, 8.5 Hz, 1H), 7.07 (d, J=2.3 Hz, 1H), 7.13 (d, J=7.5 Hz, 1H), 7.18–7.21 (m, 2H); $^{13}$C NMR (100 MHz, $CDCl_3$) δ 11.6, 19.4, 19.8, 26.1, 49.6, 117.8, 123.3, 125.6, 126.2, 128.4, 129.0, 130.1, 130.1, 134.7, 136.5, 137.2, 143.4, 167.4, 176.9; ESMS m/z 374.3 $[M+H]^+$, 415.3 $[M+CH_3CN+H]^+$; LC/MS $t_R$=9.40 (244.1 $[M-C_4H_5N_2OS]^+$, 374.1 $[M+H]^+$) min.

14m ($W_1$=5-Cl, $R_1$=2,5-dimethylphenyl, $R_2$=$NH_2$) and 14ma ($W_1$=5-Cl, $R_1$=2,5-dimethylphenyl, $R_2$=—NHC(=O)$CF_3$)

Compound 14m and 14ma were synthesized from 10m using procedure (b). 14ma was obtained as a golden colored oil (19.1 mg, 40.8% yield); clogP=6.86; $R_f$ (petroleum spirit/ethyl acetate, 3:1)=0.57; HPLC (214 nm) $t_R$=10.72 (90.00%) min; $^1$H NMR (400 MHz, $CDCl_3$) δ 2.12 (s, 3H), 2.35 (s, 3H), 2.39 (s, 3H), 3.60 (d, J=15.6 Hz, 1H), 3.75 (d, J=15.6 Hz, 1H), 5.79 (s, 1H), 7.04–7.10 (m, 2H), 7.33–7.35 (m, 2H), 7.41 (d, J=2.1 Hz, 1H), 7.74 (d, J=8.6 Hz, 1H), 8.99 (s, 1H); $^{13}$C NMR (100 MHz, $CDCl_3$) δ 11.3, 18.5, 21.1, 25.5, 45.1, 118.7 (q, J=289 Hz, $CF_3$), 126.5, 128.5, 128.9, 129.4, 129.8, 131.4, 131.6, 133.1, 133.5, 133.7, 136.5, 155.5 (q, J=37 Hz, $COCF_3$), 167.4, 176.1; ESMS m/z 324.3, 470.0 $[M+H]^+$; LC/MS $t_R$=9.70 (470.1 $[M+H]^+$) min.

14m was obtained as a golden colored oil (5.0 mg, 13.4% yield); clogP=6.00; $R_f$ (petroleum spirit/ethyl acetate, 3:1)=0.24; HPLC (214 nm) $t_R$=10.27 (87.59%) min; $^1$H NMR (400 MHz, $CDCl_3$) δ 2.10 (s, 3H), 2.37 (s, 3H), 2.39 (s, 3H), 3.70 (d, J=15.8 Hz, 1H), 3.75 (d, J=15.8 Hz, 1H), 4.13 (brs, 2H), 5.54 (s, 1H), 6.63 (d, J=8.6 Hz, 1H), 6.93 (s, 1H), 7.02–7.07 (m, 3H), 7.52 (s, 1H); $^{13}$C NMR (100 MHz, $CDCl_3$) δ 11.5, 18.4, 21.2, 26.3, 46.3, 117.7, 123.5, 125.2, 128.5, 128.7, 131.0, 134.0, 134.9, 136.0, 143.5, 167.3, 177.0; ESMS m/z 374.2 $[M+H]^+$, 415.4 $[M+CH_3CN+H]^+$; LC/MS $t_R$=9.60 (374.1 $[M+H]^+$) min.

14o ($W_1$=3,5-dibromo, $R_1$=2-methylphenyl, $R_2$=$NH_2$)

Compound 14o was synthesized from 10o using procedure (b), isolated as a clear oil. $R_f$ (EtOAc:petrol (1:10))=0.09. HPLC (214 nm) $t_R$=11.72 min (98.7%). $^1$H NMR ($CDCl_3$, 400 MHz) δ 2.11 (s, 3H), 2.42 (s, 3H), 3.71 (dd, J=29, 16 Hz, 2H), 4.81 (bs, 2H), 5.61 (s, 1H), 6.95 (d, J=2 Hz, 1H), 7.18 (d, J=7.2 Hz, 1H), 7.23–7.27 (m, 1H), 7.29–7.33 (m, 1H), 7.49 (d, J=2 Hz, 1H), 7.78 (d, J=7.6 Hz, 1H). ESMS m/z 482.0, 484.0, 486.0 $[M+H]^+$, correct isotope pattern observed.

14p ($W_1$=5-methyl, $R_1$=2-methylphenyl, $R_2$=$NH_2$).

Compound 14p was synthesized from 10p using procedure (b), isolated as a pale yellow oil (0.016 g, 28% yield). $R_f$ (EtOAc:petrol (1:2))=0.4. HPLC (214 nm) $t_R$=8.27 min (97.1%). $^1$H NMR ($CDCl_3$, 400 MHz) δ 2.13 (s, 3H), 2.17 (s, 3H), 2.39 (s, 3H), 3.71 (dd, J=23.6, 15.6 Hz, 2H), 5.62 (s, 1H), 6.61 (d, J=8 Hz, 1H), 6.75 (s, 1H), 6.87 (d, J=8 Hz, 1H), 7.15–7.30 (m, 3H), 7.79 (d, J=7.2 Hz, 1H). ESMS m/z 340.4 $[M+H]^+$, 381.4 $[M+H+CH_3CN]^+$. LCMS (214 nm) $t_R$=7.84 min (340.0 $[M+H]^+$).

14q ($W_1$=H, $R_1$=2-methylphenyl, $R_2$=$NH_2$).

Compound 14o from 10q, was isolated as an orange oil. $R_f$ (EtOAc:petrol (1:5))=0.09. HPLC (214 nm) $t_R$=8.06 min (5.7%), 8.81 (89.9). $^1$H NMR ($CDCl_3$, 400 MHz) δ 2.12 (s, 3H), 2.37 (s, 3H), 3.70 (dd, J=23,16 Hz, 2H), 5.62 (s, 1H), 6.62–6.68 (m, 2H), 6.90 (dd, J=7.6, 0.8 Hz, 1H), 7.02–7.06 (m, 1H), 7.14 (d, J=7.2 Hz, 1H), 7.18–7.21 (m, 1H), 7.24–7.28 (m, 1H), 7.79 (d, 7.6 Hz, 1H). ESMS m/z 326.0 $[M+H]^+$, 367.4 $[M+H+CH_3CN]^+$.

14t ($W_1$=5-nitro, $R_1$=phenyl, $R_2$=$NH_2$).

Compound 14d was synthesized using procedure (b) and obtained as a bright yellow gum (230 mg, 0.645 mmol, 83% yield). $R_f$ (silica, dichloromethane:methanol (9:1)=0.20.

HPLC (214 nm) $t_R$=8.95 (93.1%) min. $^1$H NMR (400 MHz, $CDCl_3$) δ 2.40 (s, 3H), 3.67 (d, J=16.4 Hz, 1H), 3.75 (d, J=16.4 Hz, 1H), 5.27 (br s, 2H), 5.45 (s, 1H), 6.67 (d, J=8.8 Hz, 1H), 7.32–7.43 (m, 3H), 7.48–7.52 (m, 2H), 7.92 (d, J=2.4 Hz, 1H), 7.97 (dd, J=8.8, 2.4 Hz, 1H). $^{13}$C NMR (100 MHz, $CDCl_3$) δ 11.4, 25.9, 49.5, 115.1, 122.2, 125.1, 126.0, 128.4, 128.8, 129.1, 136.5, 138.7, 151.1, 167.2, 176.8. ESMS-m/z 357.4 $[(M+H)]^+$, 713.4 $[(2M+H)]^{30}$ . LC/MS $t_R$=8.23 (356.9 $[(M+H)]^+$, 713.1 $[(2M+H)]^+$) min.

14w ($W_1$=5-Cl, $R_1$=2,4-dimethylphenyl, $R_2$=NH,) and 14wa ($W_1$=5-Cl, $R_1$=2,4-dimethylphenyl, $R_2$=—NHC(=O)$CF_3$)

Compound 14w and 14wa were synthesized using procedure (b) above. 14wa was obtained as a golden colored oil (45.7 mg, 40.8% yield); clogP-6.86; $R_f$ (petroleum spirit/ethyl acetate, 3:1)=0.75; HPLC (214 nm) $t_R$=10.41 (94.58%) min; $^1$H NMR (400 MHz, $CDCl_3$) δ 2.14 (s, 3H), 2.31 (s, 3H), 2.39 (s, 3H), 3.58 (d, J=15.6 Hz, 1H), 3.73 (d, J=15.6 Hz, 1H), 5.80 (s, 1H), 7.01 (s, 1H), 7.08 (d, J=8.0 Hz, 1H), 7.33 (dd, J=2.5, 8.6 Hz, 1H), 7.40 (d, J=2.5 Hz, 1H), 7.43 (d, J=8.0 Hz, 1H), 7.73 (d, J=8.6 Hz, 1H), 9.02 (s, 1H); $^{13}$C NMR (100 MHz, $CDCl_3$) δ 11.3, 18.8, 20.9, 25.5, 44.7, 126.5, 127.6, 127.9, 128.9, 129.8, 130.8, 131.6, 132.3, 133.1, 133.7, 136.6, 138.5, 167.4, 176.1, Both the carbon signals for the $COCF_3$ group were not observed with the number of scans used; ESMS m/z 470.2 $[M+H]^+$; LC/MS $t_R$=9.85 (470.0 $[M+H]^+$) min. Compound 14w was obtained compound as a golden colored oil (18.3 mg, 20.0% yield); clogP=6.00; $R_f$ (petroleum spirit/ethyl acetate, 3:1)=0.45; HPLC (214 nm) $t_R$=10.60 (83.38%) min; $^1$H NMR (400 MHz, $CDCl_3$) δ 2.11 (s, 3H), 2.32 (s, 3H), 2.39 (s, 3H), 3.68 (d, J=15.8 Hz, 1H), 3.73 (d, J=15.8 Hz, 1H), 4.14 (brs, 2H), 5.53 (s, 1H), 6.62 (d, J=8.5 Hz, 1H), 6.94 (d, J=2.4 Hz, 1H), 6.99 (s, 1H), 7.02 (dd, J=2.4, 8.5 Hz, 1H), 7.08 (d, J=7.9 Hz, 1H), 7.60 (d, J=7.9 Hz, 1H); $^{13}$C NMR (100 MHz, $CDCl_3$) δ 11.5, 18.8, 20.9, 26.2, 46.0, 117.7, 123.5, 125.3, 127.2, 128.2, 128.4, 128.7, 131.9, 132.1, 136.9, 137.6, 143.5, 167.4, 177.0; ESMS m/z 374.3 $[M+H]^+$, 415.3 $[M+CH_3CN+H]^+$; LC/MS $t_R$=9.74 (374.2 $[M+H]^+$) min.

14y ($W_1$=6-$CH_3$, $R_1$=2-amino-3-pyridinyl, $R_2$=H) was synthesized from 10y using procedure (b), isolated as a yellow oil, which crystallised upon standing was obtained (0.026 g, 32% yield). $R_f$ (EtOAc:petrol (1:1))=0.2. HPLC (214 nm) $t_R$=6.84 min (95.9%). $^1$H NMR ($CDCl_3$, 400 MHz) δ 2.14 (s, 3H), 2.41 (s, 3H), 3.72 (dd, J=26.4, 16 Hz, 2H), 5.08 (bs, 2H), 5.54 (s, 1H), 6.57 (dd, J=7.6, 4.8 Hz, 1H), 7.14–7.19 (m, 2H), 7.22–7.31 (m, 2H), 7.78 (d, J=7.2 Hz, 1H), 8.00 (dd, J=5.2, 1.6 Hz, 1H). ESMS m/z 327.4 $[M+H]^+$, 368.3 $[M+H+CH_3CN]^+$.

14z ($W_1$=5-Cl, $R_1$=t-butyl, $R_2$—$NH_2$) was synthesized using procedure (c) and obtained as a golden colored oil (19 mg, 14.8% yield); clogP=5.06; $R_f$ (petroleum spirit/ethyl acetate, 2:1)=0.52; HPLC (214 nm) $t_R$=9.41 (82.21%) min; $^1$H NMR (400 MHz, $CDCl_3$) δ 1.03 (s, 9H), 2.38 (s, 3H), 3.34 (d, J=15.1 Hz, 1H), 3.63 (d, J=15.1 Hz, 1H), 4.19 (s, 1H), 6.60 (d, J=8.4 Hz, 1H), 7.00 (dd, J=2.4, 8.4 Hz, 1H), 7.50 (d, J=2.4 Hz, 1H); ESMS m/z 326.2 $[M+H]^+$, 367.3 $[M+CH_3CN+H]^+$; LC/MS $t_R$=8.52 (326.2 $[M+H]^+$) min.

14ac ($W_1$=H, $R_1$=2-methylphenyl, $R_2$=methoxy) was synthesized from 10ac using procedure (b) and obtained as a clear oil which crystallised upon standing (0.029 g, 65% yield). $R_f$ (EtOAc:petrol (1:10))=0.18. HPLC (214 nm) $t_R$=10.37 min (99.7%). $^1$H NMR ($CDCl_3$, 400 MHz) δ 2.31 (s, 3H), 2.34 (s, 3H), 3.72 (s, 2H), 3.33 (s, 3H), 5.98 (s, 1H), 6.83 (d, J=8.4 Hz, 1H), 6.90–6.94 (m, 1H), 7.11–7.25 (m, 4H), 7.48 (d, J=7.6 Hz, 1H), 7.52 (d, J=7.6 Hz, 1H). ESMS m/z 341.3 $[M+H]^+$, 681.3 $[2M+H]^+$.

14ad ($W_1$=5-$CH_3$, $R_1$=2-methylphenyl, $R_2$=OH) was synthesized from 10ad using procedure (b) and obtained as a white solid (0.022 g, 40% yield). $R_f$ (EtOAc:petrol (1:5))=0.15. HPLC (214 nm) $t_R$=9.30 min (99.5%). $^1$H NMR ($CDCl_3$, 400 MHz) δ 2.20 (s, 3H), 2.42 (s, 3H), 3.74 (s, 2H), 5.89 (s, 1H), 6.79–6.82 (m, 1H), 6.88 (d, J=8 Hz, 1H), 7.08 (dd, J=7.6, 1.2 Hz, 1H), 7.11–7.26 (m, 4H), 7.43 (bs, 1H), 7.75 (d, J=7.6 Hz, 1H). ESMS m/z 327.1 $[M+H]^+$, 482.0 (unidentified).

EXAMPLE 8

SCHEME 8
SYNTHESIS OF THIOETHER DERIVATIVES

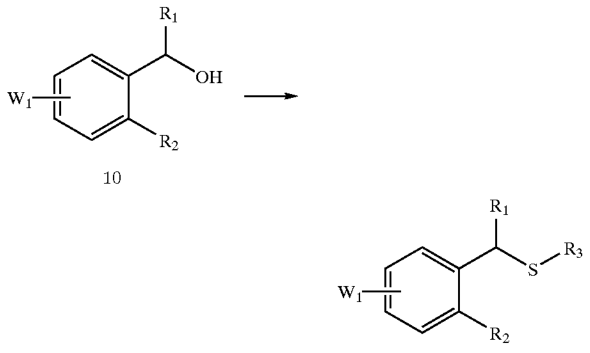

10

15

15a ($W_1$=5-Cl, $R_1$=2-chlorophenyl, $R_2$=$NH_2$, $R_3$=2-aminoethyl)

To a stirred solution of 10s (250 mg, 0.932 mmol) in TFA (5.0 ml) under a nitrogen atmosphere at rt was added 2-aminoethanethiol hydrochloride (530 mg, 4.66 mmol, 5 eq). After stirring for 96 hrs the reaction mixture was partitioned between dichloromethane and aqueous NaOH (1 mol/L). The aqueous phase was back extracted twice with dichloromethane and the combined organic phase was dried with brine and sodium sulfate, then filtered and evaporated to give the crude thiol ether (339 mg) as a brown oil. The crude material was purified by flash chromatography on silica (15 g) by eluting with dichloromethane:methanol (10:1) to give thiol ether 15a (222 mg, 0.678 mmol, 73% yield) as a white solid. $R_f$ (silica, dichloromethane:methanol (10:1))=0.25. HPLC (214 nm) $t_R$=7.06 (96.1%) min. $^1$H NMR (400 MHz, $CDCl_3$) δ 1.00–1.70 (br s, 2H), 2.50–2.60 (m, 2H), 2.80–3.00 (m, 2H), 3.85–4.40 (br s, 2H), 5.62 (s, 1H), 6.61 (d, J=8.4 Hz, 1H), 7.03 (dd, J=8.4, 2.4 Hz, 1H), 7.11 (d, J=2.4 Hz, 1H), 7.23 (ddd, J=7.6, 7.6, 1.6 Hz, 1H), 7.31 (ddd, J=7.6, 7.6, 1.2 Hz, 1H), 7.38 (dd, J=7.6 Hz, 1.2 Hz, 1H), 7.73 (dd, J=7.6, 1.6 Hz, 1H). $^{13}$C NMR (100 MHz, $CDCl_3$) δ 36.0, 41.1, 45.4, 117.5, 123.2, 125.7, 127.2, 128.1, 128.2, 128.8, 129.7, 130.5, 133.8, 136.8, 143.2. ESMS m/z 250.2 $[M-HS(CH_2)_2NH_2+H]^+$, 327.3 $[(M+H)]^+$. LC/MS $t_R$ 6.81 (250.0 $[M-HS(CH_2)_2NH_2+H]^+$, 327.2 $[M+H]^+$, 653.3 $[2M+H]^+$) min.

15b ($W_1$=5-Cl, $R_1$=2-chlorophenyl, $R_2$=$NH_2$, $R_3$=2-carboxylethyl)

Using a similar procedure as for the preparation of 15a, 15b (($R_1$=5-C, $R_2$=2-chlorophenyl, $R_3$=2-carboxylethyl) was prepared from 10s and 3-mercaptopropionic acid, obtained as a yellow gum obtained (311 mg, 0.873 mmol, 47% yield). $R_f$ (silica, 40:60 petroleum ether:ethyl acetate (1:1)=0.42. HPLC (214 nm) $t_R$=8.28 (86.7%) min. $^1$H NMR (400 MHz, $CDCl_3$) δ 2.64–2.76 (m, 4H), 5.66 (s, 1H), 6.63 (d, J=8.4 Hz, 1H), 6.83 (s, 3H), 7.03–7.08 (m, 2H), 7.25 (ddd, J=7.6, 7.6, 1.2 Hz, 1H), 7.30–7.36 (m, 1H), 7.38–7.40 (m, 1H), 7.74 (dd, J=8.0, 1.2 Hz, 1H). $^{13}$C NMR (100 MHz, $CDCl_3$) δ 27.1, 34.0, 45.7, 118.1, 123.8, 125.8, 127.3, 128.30, 128.34, 128.9, 129.8, 130.4, 133.9, 136.2, 142.7, 177.4. ESMS m/z 250.0 $[(M-HS(CH_2)_2CO_2H+H)]^+$, 356.1 $[(M+H)^+$. LC/MS $t_R$8.43 (250.0 $[(M-HS(CH_2)_2CO_2H+H)]^+$, 355.9 $[(M+H)]^+$, 710.9 $[(2M+H)]^+$) min.

15c ($W_1$=5-Cl, $R_1$=2-chlorophenyl, $R_2$ $NH_2R_3$=ethyl)

Using a similar procedure as for the preparation of 15a, 15c was prepared from 10s and ethanethiol, obtained as a pale brown oil (135 mg, 0.432 mmol, 47% yield). $R_f$ (silica, 40–60 petroleum ether:ethyl acetate (10:1)=0.20. HPLC (214 nm) $t_R$=9.97 (97.8%) min. $^1$H NMR (400 MHz, $CDCl_3$) δ 1.28 (t, J=7.2 Hz, 3H), 2.50 (m, 2H), 4.01 (br s, 2H), 5.62 (s, 1H), 6.63 (d, J=8.4 Hz, 1H), 7.05 (dd, J=8.4, 2.4 Hz, 1H), 7.12 (d, J=2.4 Hz, 1H), 7.25 (ddd, J=8.0, 8.0, 1.6 Hz, 1H), 7.32 (ddd, J=7.6, 7.7, 1.2 Hz, 1H), 7.40 (dd, J=7.6, 1.2 Hz, 1H), 7.73 (dd, J=8.0, 1.6 Hz, 1H). $^{13}$C NMR (100 MHz, $CDCl_3$) δ 14.2, 26.4, 45.2, 117.7, 123.5, 126.1, 127.2, 128.0, 128.4, 128.7, 129.7, 130.5, 133.8, 136.8, 143.0. ESMS m/z 250.3 $[M-HSCH_2CH_3+H]^+$, 312.3 $[M+H]^+$. LC/MS $t_R$=10.26 (250.0 $[M-HSCH_2CH_3+H]^+$, 312.0 $[M+H]^+$, 622.9 $[2M+H]^+$) min.

15d ($W_1$=5-Cl, $R_1$=2-chlorophenyl, $R_2$=$NH_2$, $R_3$=2-hydroxlethyl)

Using a similar procedure as for the preparation of 15a, 15d was prepared from 10s and 2-mercaptoethanol, obtained as a yellow gum (142 mg, 0.432 mmol, 46% yield). $R_f$ (silica, 40–60 petroleum ether:ethyl acetate (2:1)=0.60. HPLC (214 nm) $t_R$=7.98 (82.3%) min. $^1$H NMR (400 MHz, $CDCl_3$) δ 2.61–2.78 (m, 2H), 2.63 (t, J=5.6 Hz, 1H), 3.20–3.60 (br s, 2H), 3.78 (ddd, J=5.6, 5.6, 2.8 Hz, 2H), 5.66 (s, 1H), 6.62 (d, J=8.4 Hz, 1H), 7.04 (dd, J=8.4, 2.4 Hz, 1H), 7.12 (d, J=2.4 Hz, 1H), 7.22–7.28 (m, 1H), 7.30–7.36 (m, 1H), 7.39 (dd, J=8.0, 1.2 Hz, 1H), 7.72 (dd, J=8.0, 1.6 Hz, 1H). $^{13}$C NMR (100 MHz, $CDCl_3$) δ 35.0, 45.1, 60.7, 117.7, 123.4, 125.7, 127.3, 128.2, 128.3, 128.9, 129.7, 130.3, 133.8, 136.5, 143.0. ESMS m/z 328.1 $[M+H]^+$, 369.3 $[M+CH_3CN+H]^+$. LC/MS $t_R$=8.19 (249.9 $[M-HSCH_2OH+H]^+$, 328.1 $[M+H]^+$, 655.2 $[2M+1]^+$) min.

15e ($W_1$=5Cl, $R_1$=2-chlorophenyl, $R_2$=NH, $R_3$=(2-methoxycarbonyl)ethyl)

Using a similar procedure as for the preparation of 15a, 15e was prepared from 10s and methyl 3-mercaptopropionate, obtained as a white solid (193 mg, 0.719 mmol, 38%). $R_f$ (silica, 40–60 petroleum ether:ethyl acetate (3:1)=0.42. HPLC (214 nm) $t_R$=9.13 (94.3%) min. $^1$H NMR (400 MHz, $CDCl_3$) δ 2.80–2.97 (m, 2H), 3.90 (s, 3H), 4.25 (br s, 2H), 5.84 (s, 1H), 6.83 (d, J=8.4 Hz, 1H), 7.22–7.29 (m, 2H), 7.43–7.49 (m, 1H), 7.54 (dd, J=7.2, 7.2 Hz, 1H), 7.60 (d, J=7.2 Hz, 1H), 7.92–7.97 (m, 1H). $^{13}$C NMR (100 MHz, $CDCl_3$) δ 27.4, 33.9, 45.6, 51.8, 117.7, 123.3, 125.4, 127.2, 128.2, 128.3, 128.9, 129.7, 130.3, 133.8, 136.2, 143.1, 172.1. ESMS m/z 370.3 $[(M+H)]^+$, 411.2 $[(M+CH_3CN+H)]^+$. LC/MS $t_R$ 9.51 (250.0 $[(M-HS(CH_2)_2CO_2CH_3+H)]^+$, 370.0 $[(M+H)]^+$, 739.0 $[(2M+H)]^+$) min.

15ea ($W_1$=5-Cl, $R_1$=2-chlorophenyl, $R_2$=—NHC(═O)$CF_3$, $R_3$=(2-methoxycarbonyl)ethyl)

To a stirred solution of alcohol 10s (500 mg, 1.86 mmol) in TFA (10.0 ml) under a nitrogen atmosphere at rt was added methyl 3-mercaptopropionate (1.03 ml, 9.32 mmol, 5 eq). After stirring for 48 hrs the TFA was evaporated and the residue was partitioned between dichloromethane and saturated aqueous sodium bicarbonate solution. The aqueous phase was back extracted twice with further dicloromethane then the combined organic phase was dried with sodium sulfate, filtered and evaporated to give the crude thiol ether (1.157 g) as a brown oil. The crude material was purified by flash chromatography on silica (50 g) by eluting with 40–60 petroleum ether:ethyl acetate (10:1 then 5:1) to give thiol ether 15ea (510 mg, 1.09 mmol, 59% yield) as a white solid. $R_f$ (silica, 40–60 petroleum ether:ethyl acetate (5:1)=0.33. HPLC (214 nm) $t_R$=9.39 (91.5%) min. $^1$H NMR (400 MHz, $CDCl_3$) δ 2.58–2.72 (m, 2H), 3.66 (s, 3H), 5.73 (s, 1H), 7.20–7.30 (m, 2H), 7.32 (ddd, J=7.6, 7.6, 1.2 Hz, 1H), 7.37 (dd, J=7.6, 1.2 Hz, 1H), 7.65 (dd, J=7.6, 1.6 Hz, 1H), 7.68 (d, J=8.8 Hz), 8.97 (br s, 1H). $^{13}$C NMR (100 MHz, $CDCl_3$) δ 27.3, 30.0, 45.9, 52.0, 115.8 (q, J=287 Hz), 126.4, 127.5, 128.6, 129.2, 129.5, 130.0, 130.1, 131.3, 132.7, 133.9, 135.0, 155.4 (q, J=37.2 Hz), 172.2. ESMS m/z 322.9 $[(unknown)]^+$, 466.3 $[(M+H)]^+$, 483.1 $[(M+NH_4)]^+$. LC/MS $t_R$ 9.65 (345.9 $[(M-HS(CH_2)_2CO_2Me+H)]^+$, 466.0 $[(M+H)]^+$, 931.0 $[(2M+H)]^+$, 948.2 $[(2M+NH_4)]^+$) min.

15f ($W_1$=5-Cl, $R_{1s=2}$-chlorophenyl, $R_2$=—$NH_2$, $R_3$=2-pyridyl)

Using a similar procedure as for the preparation of 15a, 15f was prepared from 10s and 2-mercaptopyridne, as a white solid (105 mg, 0.291 mmol, 31% yield). $R_f$ (silica, 40–60 petroleum ether:ethyl acetate (10:1)=0.25. HPLC (214 nm) $t_R$=12.03 (72.9%) min. $^1$H NMR (400 MHz, $CDCl_3$) δ 4.31 (br s, 2H), 6.65 (d, J=8.4 Hz, 1H), 8.68 (s, 1H), 6.97–7.05 (m, 2H), 7.15 (d, J=8.0 Hz, 1H), 7.24 (ddd, J=9.2, 9.2, 1.6 Hz, 1H), 7.31 (ddd, J=9.6, 9.6, 1.6 Hz, 1H), 7.38 (dd, J=8.8, 1.2 Hz, 1H), 7.47 (ddd, J=9.9, 9.6, 1.6 Hz, 1H), 7.85 (dd, J=9.2, 1.6 Hz, 1H), 8.40–8.44 (m, 1H). $^{13}$C NMR (100 MHz, $CDCl_3$) δ 45.7, 117.3, 120.3, 122.3, 122.9, 125.7, 126.9, 128.2, 128.3, 128.8, 129.8, 130.5, 134.0, 136.4, 137.2, 143.2, 149.7, 157.5. ESMS m/z 361.2 $[M+H]^+$. LC/MS $t_R$ 9.49 (360.9 $[M+H]^+$) min.

15g ($W_1$=5-Cl, $R_1$=2-chlorophenyl, $R_2$=$NH_2$, $R_3$=4-methoxybenzyl)

Using a similar procedure as for the preparation of 15a, 15 g was prepared from 10s and 4-methoxybenzyl, obtained as a yellow oil (98 mg, 0.242 mmol, 26% yield). $R_f$ (silica, 40–60 petroleum ether:ethyl acetate (10:1)=0.40. HPLC (214 nm) $t_R$=9.75 (81.5%) min. $^1$H NMR (400 MHz, $CDCl_3$) δ 3.46 (d, J=13.5 Hz, 1H), 3.59 (d, J=13.5 Hz, 1H), 3.63 (br s, 2H), 3.77 (s, 3H), 5.20 (s, 1H), 6.52 (d, J=8.4 Hz, 1H), 6.80–6.83 (m, 2H), 6.90 (d, J=2.0 Hz, 1H), 6.97 (dd, J=8.4, 2.4 Hz, 1H), 7.05–7.10 (m, 2H), 7.21–7.27 (m, 1H), 7.31–7.38 (m, 2H), 7.86 (dd, J=7.6, 1.6 Hz, 1H). $^{13}$C NMR (100 MHz, $CDCl_3$) δ 36.1, 44.4, 55.2, 110.3, 114.0, 17.4, 123.2, 125.4, 127.2, 128.0, 128.4, 128.8, 129.3, 129.8, 129.9, 130.7, 134.2, 136.2, 142.9, 158.8. ESMS m/z 404.2 $[M+H]^+$, 445.1 $[M+CH_3CN+H]^+$. LC/MS $t_R$ 10.69 (404.0 $[M+H]^+$) min.

15h ($W_1$=5-Cl, $R_1$=2-chlorophenyl, $R_2$=$NH_2$, $R_3$=n-butyl)

Using a similar procedure as for the preparation of 15a, 15h was prepared from 10s and 1-butanethiol, obtained as a pale yellow oil (76 mg, 0.223 mmol, 24% yield). $R_f$ (silica, 40–60 petroleum ether:ethyl acetate (10:1)=0.20. HPLC (214 nm) $t_R$=13.30 (95.2%) min. $^1$H NMR (400 MHz, $CDCl_3$) δ 0.89 (t, J=8.8 Hz, 3H), 1.35–1.46 (m, 2H), 1.54–1.64 (m, 2H), 2.41–2.54 (m, 2H), 4.00 (br s, 2H), 5.58 (s, 1H), 6.63 (d, J=8.4 Hz, 1H), 7.05 (dd, J=8.4, 2.4 Hz, 1H), 7.12 (d, J=2.4 Hz, 1H), 7.25 (ddd, J=7.6, 7.6, 1.6 Hz, 1H), 7.33 (ddd, J=7.6, 7.6, 1.2 Hz, 1H), 7.40 (dd, J=7.6, 1.2 Hz, 1H), 7.72 (dd, J=7.6, 1.6 Hz, 1H). $^{13}$C NMR (100 MHz, $CDCl_3$) δ 13.5, 21.9, 31.1, 32.2, 45.7, 117.7, 123.6, 126.2, 127.2, 128.0, 128.4, 128.7, 129.7, 130.5, 133.9, 136.9, 143.1. ESMS m/z 340.2 $[M+H]^+$, 381.2 $[M+CH_3CN+H]^+$. LC/MS $t_R$ 10.98 (249.8 $[M-HS(CH_2)_3CH_3+H]^+$, 340.0 $[M+H]^+$) min.

15i ($W_1$=5-Cl, $R_1$=2-chlorophenyl, $R_2$=$NH_2$, $R_3$=2,2,2-trifluoroethyl)

Using a similar procedure as for the preparation of 15a, 15i was prepared from 10s and 2,2,2-trifluoroethanthiol, obtained as a pale yellow oil (132 mg, 0.360 mmol, 39%). $R_f$ (silica, 40–60 petroleum ether:ethyl acetate (15:1)=0.33. HPLC (214 nm) $t_R$=12.13 (90.1%) min. $^1$H NMR (400 MHz, $CDCl_3$) δ 2.89–3.10 (m, 4H), 3.98 (br s, 2H), 5.85 (s, 1H), 6.67 (d, J=8.4 Hz, 1H), 7.03 (d, J=2.4 Hz, 1H), 7.08 (dd, J=8.4, 2.4 Hz, 1H), 7.30 (ddd, J=7.6, 7.6, 1.6 Hz, 1H), 7.34–7.40 (m, 1H), 7.44 (dd, J=7.6, 1.2 Hz, 1H), 7.75 (dd, J=7.6, 1.6 Hz, 1H). $^{13}$C NMR (100 MHz, $CDCl_3$) δ 34.1 (q, J=33.4 Hz), 46.0, 118.0, 123.6, 124.2, 127.4, 128.3, 128.8, 129.4, 130.1, 134.4, 135.1, 143.3. ESMS m/z 407.1 [(M+$CH_3CN$+H)]$^+$, LC/MS $t_R$ 8.86 (365.9 [(M+H)]$^+$) min.

15j ($W_1$=5-Cl, $R_1$=2-chlorophenyl, $R_2$=$NH_2$, $R_3$=2-(N,N-dimethylamino)ethyl)

Using a similar procedure as for the preparation of 15a, 15j was prepapred from 10s and 2-(dimethylamino) ethanethiol, obtained as a white solid (183 mg, 0.515 mmol, 55%). $R_f$ (silica, 40–60 petroleum ether:ethyl acetate (2:1)= 0.10. HPLC (214 nm) $t_R$=7.42 (97.7%) min. $^1$H NMR (400 MHz, $CDCl_3$) δ 2.25 (s, 6H), 2.47–2.55 (m, 4H), 4.71 (br s, 2H), 5.66 (s, 1H), 6.60 (8.4 Hz, 1H), 6.67 (d, J=2.4 Hz, 1H), 6.97 (dd, J=8.4, 2.4 Hz, 1H), 7.22–7.28 (m, 1H), 7.36–7.41 (m, 2H), 8.03 (d, J=8.0 Hz). $^{13}$C NMR (100 MHz, $CDCl_3$) δ 29.1, 45.0, 45.3, 58.4, 117.0, 122.3, 125.5, 127.0, 127.7, 127.9, 128.7, 129.7, 130.8, 134.2, 136.7, 143.8. ESMS m/z 355.1 [(M+H)]$^+$, LC/MS $t_R$ 6.86 (354.9 [(M+H)]$^+$) min.

15k ($W_1$=5-Cl, $R_1$=2-chlorophenyl, $R_2$=$NH_2$, $R_3$=3-hydroxypropyl)

To a stirred solution of ester 15e (74.0 mg, 0.199 mmol) in THF (2.5 ml) under a nitrogen atmosphere at 0° C. was added $LiAlH_4$ (15.1 mg, 0.400 mmol, 2 eq). The reaction mixture was warmed to rt and then stirred for 30 min. The reaction mixture was partitioned between dichloromethane (10 ml) and potassium sodium tartrate (1 mol/L, 5 ml) and stirring carried out for 1 hr at rt. Brine was added and the aqueous layer was extracted thrice with dichloromethane. The combined organic extracts were dried with sodium sulfate, filtered and evaporated to give the crude alcohol (80.0 mg) as a brown oil. The crude material was purified by flash chromatography on silica (5 g) by eluting with 40–60 petroleum ether:ethyl acetate (1:1) to give alcohol 15k (67.0 mg, 0.195 mmol, 98% yield) as a white solid. $R_f$ (silica, 40–60 petroleum ether:ethyl acetate (1:1))=0.40. HPLC (214 nm) $t_R$=10.56 (94.4%) min. $^1$H NMR (400 MHz, $CDCl_3$) δ 1.69 (br s, 1H), 1.78–1.87 (m, 2H), 2.49–2.63 (m, 2H), 3.69 (t, J=6.0 Hz, 2H), 3.95 (br s, 2H), 5.57 (s, 1H), 6.61 (d, J=8.8 Hz, 1H), 7.03 (dd, J=8.8, 2.4 Hz, 1H), 7.14 (d, J=2.4 Hz, 1H), 7.19–7.26 (m, 1H), 7.27–7.33 (m, 1H), 7.37 (dd, J=8.0, 1.2 Hz, 1H), 7.66 (dd, J=7.6, 1.6 Hz, 1H). $^{13}$C NMR (100 MHz, $CDCl_3$) δ 29.1, 31.7, 45.6, 61.4, 117.8, 123.6, 126.0, 127.3, 128.2, 128.5, 128.8, 129.7, 130.4, 133.8, 136.7, 143.0. ESMS m/z 342.2 [M+H]$^+$, 383.2 [M+$CH_3CN$+H]$^+$. LC/MS $t_R$=8.34 (249.8 [M-HS$(CH_2)_3$OH+H]$^+$, 341.9 [M+H]$^+$, 682.9 [2M+H]$^+$) min.

151 ($W_1$=5-Cl, $R_1$=cyclohexyl, $R_2$=NHBoc, $R_3$=2-aminoethyl

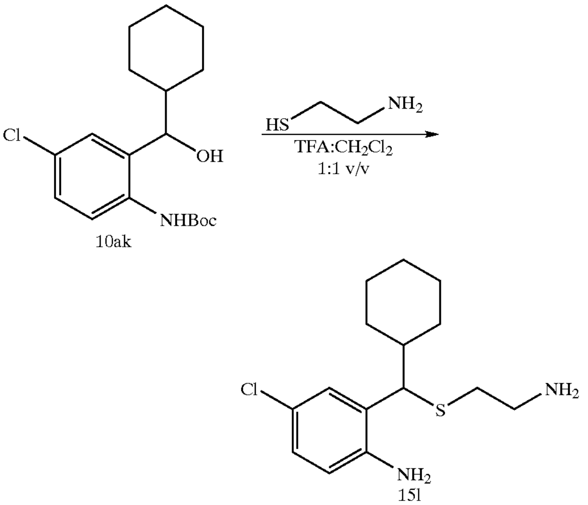

10ak

151

EXAMPLE 9

SCHEME 9

SYNTHESIS OF THIOETHER AMIDE

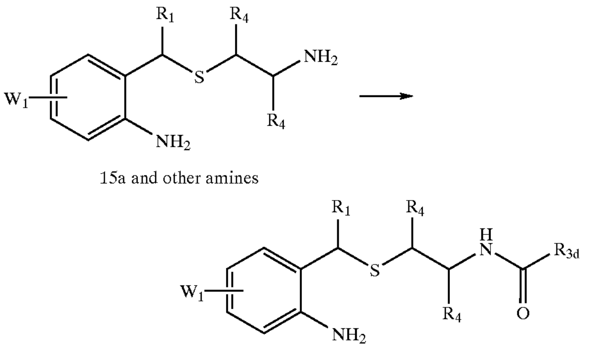

15a and other amines

16

Synthesis of 16a ($W_1$=5-Cl, $R_1$=2-chlorophenyl, $R_4$/$R_4$=H, $R_{3d}$=phenyl).

To a stirred solution of primary amine 15a (100 mg, 0.305 mmol) in THF (2.5 ml) under a nitrogen atmosphere at rt was added benzoic acid (37.3 mg, 0.305 mmol, 1 eq), EDC (70.3 mg, 0.367 mmol, 1.2 eq) and DMAP (3.7 mg, 0.030 mmol, 0.1 eq.). After stirring for 18 hrs the reaction mixture was partitioned between dichloromethane and brine. The aqueous phase was back extracted twice with dichloromethane and the combined organic phase was dried with sodium sulfate, then filtered and evaporated to give the crude amide (167 mg) as a brown oil. The crude material was purified by flash chromatography first on silica (5 g) by eluting with 40–60 petroleum ether:ethyl acetate (2:1) to give amide 16a (108 mg, 0.250 mmol, 82% yield) as a white solid. $R_f$ (silica, 40–60 petroleum ether:ethyl acetate (2:1))= 0.20. HPLC (214 nm) $t_R$=9.93 (99.1%) min. $^1$H NMR (400 MHz, $CDCl_3$) δ 2.65–2.74 (m, 2H), 3.46–3.59 (m, 1H), 3.64–3.75 (m, 1H), 3.96 (br s, 2H), 5.62 (s, 1H), 6.58 (d, J=8.4 Hz, 1H), 6.76 (dd, J=5.2 Hz, 1H), 7.02 (dd, J=8.4, 2.4 Hz, 1H), 7.18–7.29 (m, 3H), 7.34–7.42 (m, 3H), 7.44–7.50 (m, 1H), 7.60 (dd, J=7.6, 1.6 Hz, 1H), 7.39–7.77 (m, 2H).

$^{13}C$ NMR (100 MHz, $CDCl_3$) δ 32.5, 38.2, 44.8, 117.8, 123.3, 125.2, 126.8, 127.3, 128.2, 128.4, 128.5, 128.9, 129.7, 130.1, 131.4, 133.7, 134.1, 136.3, 143.0, 167.5. ESMS m/z 247.3 $[unknown]^+$, 430.9 $[(M+H)]^+$. LC/MS $t_R$=9.11 (431.1 $[(M+H)]^+$) min.

Using a similar procedure as for the synthesis of 16a, except the solvent was changed from THF to DCM, the following amides were prepared.

16b ($W_1$=5-Cl, $R_1$=2-chlorophenyl, $R_4/R_4$=H, $R_3$=3,4-dimethoxybenzyl).

Form 15a and (3,4-dimethoxyphenyl)acetic acid, compound 16b was obtained as a white solid (110 mg, 0.217 mmol, 89% yield). $R_f$ (silica, dichloromethane:methanol (40:1))=0.20. HPLC (214 nm) $t_R$=9.33 (97.9%) min. $^1H$ NMR (400 MHz, $CDCl_3$) δ 2.48–2.62 (m, 2H), 3.21–3.31 (m, 1H), 3.46–3.57 (m, 3H), 3.80 (s, 3H), 3.86 (s, 3H), 4.06 (br s, 2H), 5.54 (s, 1H), 5.91 (t, J=1.6 Hz, 1H), 6.59 (d, J=8.4 Hz, 1H), 6.76 (m, 3H), 7.02 (dd, J=8.4, 4.2 Hz, 1H), 7.13 (d, J=1.6 Hz, 1H), 7.19–7.30 (m, 2H), 7.36 (dd, J=8.4, 1.6 Hz, 1H), 7.58 (dd, J=7.6, 1.6 Hz, 1H). $^{13}C$ NMR (100 MHz, $CDCl_3$) δ 32.3, 37.7, 43.1, 44.5, 55.7, 55.8, 111.3, 112.3, 117.7, 121.6, 123.2, 125.1, 126.9, 127.3, 128.2, 128.3, 128.9, 129.7, 130.1, 133.7, 136.2, 143.1, 148.1, 149.1, 171.4. ESMS m/z 505.3 $[(M+H)]^+$. LC/MS $t_R$=8.64 (505.2 $[(M+H)]^+$) min.

16e ($W_1$=5-Cl, $R_1$=2-chlorophenyl, $R_4/R_4$=H, $R_{3d}$=2,4-dichlorophenyl).

From 15a and 2,4-dichlorobenzoic acid, compound 16c was obtained as a white solid (89.0 mg, 0.177 mmol, 83% yield). $R_f$ (silica, dichloromethane:methanol (100:1))=0.20. HPLC (214 nm) $t_R$=10.65 (96.1%) min. $^1H$ NMR (400 MHz, $CDCl_3$) δ 2.64–2.79 (m, 2H), 3.48–3.58 (m, 1H), 3.65–3.83 (m, 3H), 5.62 (s, 1H), 6.59 (d, J=8.4 Hz, 1H), 6.64–6.72 (m, 1H), 7.19–7.30 (m, 4H), 7.34–7.40 (m, 2H), 7.55 (d, J=8.4 Hz, 1H), 7.60 (dd, J=7.6, 1.6 Hz, 1H). $^{13}C$ NMR (100 MHz, $CDCl_3$) δ 32.4, 38.6, 45.1, 117.9, 123.5, 125.4, 127.4, 128.3, 128.5, 129.0, 129.8, 129.9, 130.2, 131.1, 131.5, 133.1, 133.7, 136.4, 136.7, 143.0, 165.5. ESMS m/z 499.2 $[(M+H)]^+$. LC/MS $t_R$=9.83 (498.8 $[(M+H)]^+$) min.

16d ($W_1$=5-Cl, $R_1$=2-chlorophenyl, $R_4/R_4$=H, $R_{3d}$=3,4-dimethoxyphenyl)

From 15a and 3,4-dimethoxybenzoic acid, compound 16d was obtained as a white solid (70.0 mg, 0.142 mmol, 66% yield). $R_f$ (silica, dichloromethane:methanol (40:1))=0.20. HPLC (214 nm) $t_R$=9.54 (99.5%) min. $^1H$ NMR (400 MHz, $CDCl_3$) δ 2.68–2.79 (m, 2H), 3.49–3.59 (m, 1H), 3.65–3.75 (m, 1H), 3.89 (s, 3H), 3.90 (s, 3H), 3.85–4.05 (br s obs, 2H), 5.63 (s, 1H), 6.57–6.63 (m, 2H), 6.82–6.87 (m, 1H), 7.01–7.06 (m, 1H), 7.19–7.32 (m, 4H), 7.35–7.43 (m, 2H), 7.57–7.61 (m, 1H). $^{13}C$ NMR (100 MHz, $CDCl_3$) δ 32.6, 38.3, 44.9, 55.9, 110.3, 110.6, 117.9, 119.4, 123.5, 125.4, 126.9, 127.4, 128.3, 128.5, 129.0, 129.8, 130.2, 133.7, 136.5, 143.1, 148.9, 151.8, 167.0. ESMS m/z 491.2 $[(M+H)]^+$. LC/MS $t_R$=8.86 (491.0 $[(M+H)]^+$, 980.9 $[(2M+H)]^+$) min.

16e ($W_1$=5-Cl, $R_1$=2-chlorophenyl, $R_4/R_4$=H, $R_{3d}$=3-bromophenyl)

From 15a and 3-bromobenzoic acid, compound 16e was obtained as a white solid (93.0 mg, 0.182 mmol, 85% yield). $R_f$ (silica, dichloromethane:methanol (40:1))=0.20. HPLC (214 nm) $t_R$=10.64 (96.1%) min. $^1H$ NMR (400 MHz, $CDCl_3$) δ 2.65–2.79 (m, 2H), 3.49–3.59 (m, 1H), 3.63–3.73 (m, 1H), 3.86 (br s, 2H), 5.61 (s, 1H), 6.59 (d, J=8.4 Hz, 1H), 6.61–6.70 (m, 1H), 7.03 (dd, J=8.4, 3.6 Hz, 1H), 7.19–7.30 (m, 4H), 7.37 (dd, J=7.6, 1.2 Hz, 1H), 7.56–7.62 (m, 2H), 7.65 (dd, J=7.6, 1.6 Hz, 1H), 7.89 (d, J=1.6 Hz, 1H). $^{13}C$ NMR (100 MHz, $CDCl_3$) δ 32.5, 38.5, 45.0, 117.9, 122.7, 123.6, 125.4, 127.4, 128.4, 128.5, 129.0, 129.8, 130.0, 130.2, 133.7, 134.4, 136.2, 136.4, 143.0, 166.1. ESMS m/z 509.1 $[(M+H)]^+$. LC/MS $t_R$=9.79 (509.1 $[(M+H)]^+$) min.

16f ($W_1$=5-Cl, $R_1$=2-chlorophenyl, $R_4/R_4$=H, $R_{3d}$=4-methoxycyclohexyl).

From 15a and 4-methoxycyclohexanecarboxylic acid, compound 16f was obtained as a yellow oil (89.0 mg, 0.190 mmol, 89% yield). $R_f$ (silica, dichloromethane:methanol (100:1))=0.20. HPLC (214 nm) $t_R$=9.29 (42.6%) and 9.46 (56.6%) min. (This compound is a mixture of cis and trans isomers due to the nature of the reagent used. The total purity of this mixture is 99.2%.) $^1H$ NMR (400 MHz, $CDCl_3$) δ 1.12–1.27 (m, 1H), 1.37–1.56 (m, 2H), 1.60–1.67 (m, 1H), 1.70–1.82 (m, 1H), 1.86–2.05 (m, 2H), 2.08–2.17 (m, 1H), 2.52–2.66 (m, 2H), 3.08–3.16 (m, 1H), 3.29 (s, 3H), 3.30 (s obs, 0.5H), 3.33 (s, 3H), 3.40–3.45 (m, 0.5H), 3.46–3.57 (m, 1H), 4.10 (br s, 2H), 5.59 (s, 1H), 5.95–6.00 (m, 1H), 6.60 (d, J=8.4 Hz, 1H), 7.00–7.04 (m, 1H), 7.17 (d, J=2.4 Hz, 1H), 7.20–7.32 (m, 3H), 7.38 (d, J=8.0 Hz, 1H), 7.59 (d, J=8.0 Hz, 0.5H), 7.63 (d, J=7.6 Hz, 0.5 Hz). $^{13}C$ NMR (100 MHz, $CDCl_3$) δ 23.8, 27.7, 28.6, 30.9, 32.7, 37.5, 37.6, 44.3, 44.5, 44.8, 55.4, 55.5, 74.1, 78.3, 117.8, 123.2, 125.3, 127.3, 128.2, 128.4, 128.9, 129.8, 130.2, 133.8, 136.5, 143.1, 175.5, 175.6. ESMS m/z 467.1 $[(M+H)]^+$. LC/MS $t_R$=8.55 (467.0 $[(M+H)]^+$, 933.3 $[(2M+H)]^+$) and 8.73 (467.0 $[(M+H)]^+$, 933.0 $[(2M+H)]^+$) min.

16g ($W_1$=5-Cl, $R_1$=2-chlorophenyl, $R_4$/R4=H, $R_{3d}$=4-nitrophenyl).

From 15a and 4-nitrobenzoic acid, compound 16g was obtained as a yellow gum (100 mg, 0.209 mmol, 98% yield). $R_f$ (silica, dichloromethane:methanol (100:1))=0.20. HPLC (214 nm) $t_R$=10.19 (94.1%) min. $^1H$ NMR (400 MHz, $CDCl_3$) δ 2.75–2.80 (m, 2H), 3.50 (br s, 2H), 3.52–3.68 (m, 1H), 3.68–3.81 (m, 1H), 5.62 (s, 1H), 6.62 (d, J=8.4 Hz, 1H), 6.69 (br s, 1H), 7.06 (dd, J=8.4, 2.4 Hz, 1H), 7.21–7.31 (m, 2H), 7.35–7.41 (m, 1H), 7.50–7.55 (m, 1H), 7.92 (d, J=8.8 Hz, 2H), 8.28 (d, J=8.8 Hz, 2H). $^{13}C$ NMR (100 MHz, $CDCl_3$) δ 32.5, 38.6, 44.9, 118.1, 123.8, 125.5, 127.6, 127.8, 128.1, 128.6, 129.2, 129.9, 130.1, 133.6, 136.4, 139.8, 142.8, 149.6, 165.5. ESMS m/z 476.2 $[(M+H)]^+$. LC/MS $t_R$=9.40 (475.9 $[(M+H)]^+$) min.

16h ($W_1$=5-Cl, $R_1$=2-chlorophenyl, $R_4/R_4$=H, $R_{3d}$=cyclobutyl).

From 15a and cyclobutanecarboxylic acid, compound 16h was obtained as a white solid (75.0 mg, 0.183 mmol, 85% yield). $R_f$ (silica, dichloromethane:methanol (40:1))=0.20. HPLC (214 nm) $t_R$=9.50 (99.1%) min. $^1H$ NMR (400 MHz, $CDCl_3$) δ 1.80–2.00 (m, 2H), 2.08–2.18 (m, 2H), 2.20–2.30 (m, 2H), 2.53–2.67 (m, 2H), 2.92–3.02 (m, 1H), 3.29–3.38 (m, 1H), 3.47–3.57 (m, 1H), 3.90 (br s, 2H), 5.59 (s, 1H), 5.76 (br s, 1H), 5.61 (d, J=8.4 Hz, 1H), 7.03 (dd, J=8.4, 2.0 Hz, 1H), 7.19–7.32 (m, 3H), 7.39 (dd, J=7.6, 1.6 Hz, 1H), 7.60 (dd, J=7.6, 1.6 Hz, 1H). $^{13}C$ NMR (100 MHz, $CDCl_3$) δ 18.1, 25.3, 32.7, 37.7, 39.8, 44.9, 117.8, 123.4, 125.4, 127.4, 128.3, 128.5, 129.0, 129.8, 130.2, 133.8, 136.5, 143.1, 175.0. ESMS m/z 409.2 $[(M+H)]^+$. LC/MS $t_R$=8.77 (409.2 $[(M+H)]^+$, 817.2 $[(M+H)]^+$) min.

16i ($W_1$=5-Cl, $R_1$=2-chlorophenyl, $R_4/R_4$=H, $R_{3d}$=cyclohexyl).

From 15a and cyclohexanecarboxylic acid, compound 16i was obtained as a white solid (94.0 mg, 0.214 mmol, 100% yield). $R_f$ (silica, dichloromethane:methanol (100:1))=0.20. HPLC (214 nm) $t_R$=10.23 (95.7%) min. $^1H$ NMR (400 MHz, $CDCl_3$) δ 1.16–1.34 (m, 3H), 1.34–1.48 (m, 2H), 1.62–1.71 (m, 1H), 1.71–1.98 (m, 3H), 2.00–2.12 (m, 1H), 2.54–2.68 (m, 2H), 3.28–3.38 (m, 1H), 3.47–3.58 (m, 1H), 3.97 (br s, 2H), 5.94 (s, 1H), 5.84 (br s, 1H), 6.61 (d, J=8.4 Hz, 1H), 7.03 (dd, J=8.4, 2.4 Hz), 7.20–7.32 (m, 3H), 7.37–7.42 (m, 1H), 7.58–7.62 (m, 1H). $^{13}$C NMR (100 MHz, $CDCl_3$) δ 25.6, 28.8, 29.6, 32.8, 37.6, 44.9, 45.4, 117.9, 123.5, 125.4, 127.4, 128.3, 128.5, 129.0, 129.8, 130.2, 133.8, 136.6, 143.1, 17.2. ESMS m/z 137.1 $[(M+H)]^+$. LC/MS $t_R$=9.42 (437.1 $[(M+H)]^+$, 873.1 $[(2M+H)]^+$) min.

16j ($W_1$=5Cl, $R_1$=2-chlorophenyl, $R_4/R_4$=H, $R_{3d}$= isopropyl).

From 15a and isobutyric acid, compound 16 was obtained as a colourless gum (74.0 mg, 0.186 mmol, 87% yield). $R_f$ (silica, dichloromethane:methanol (40:1))=0.20. HPLC (214 nm) $t_R$=9.30 (98.8%) min. $^1$H NMR (400 MHz, $CDCl_3$) δ 1.14 (d, J=6.8 Hz, 6H), 2.34 (septet, J=6.8 Hz, 1H), 2.54–2.68 (m, 2H), 3.28–3.38 (m, 1H), 3.47–3.57 (m, 1H), 4.05 (br s, 2H), 5.60 (s, 1H), 5.91 (br s, 1H), 6.61 (d, J=8.4 Hz, 1H), 7.03 (dd, J=8.4, 1.6 Hz, 1H), 7.19–7.32 (m, 3H), 7.38 (d, J=7.6 Hz, 1H), 7.61 (d, J=7.6 Hz, 1H). $^{13}$C NMR (100 MHz, $CDCl_3$) δ 19.5, 32.7, 35.5, 37.6, 44.9, 117.8, 123.4, 125.3, 127.3, 128.3, 128.5, 128.9, 129.8, 130.2, 133.8, 136.5, 143.1, 177.1. ESMS m/z 397.3 $[(M+H)]^+$. LC/MS $t_R$=8.57 (397.0 $[(M+H)]^+$, 792.9 $[(2M+H)]^+$) min.

16k ($W_1$=5-Cl, $R_1$=2-chlorophenyl, $R_4/R_4$=H, $R_{3d}$=3-pyridyl).

From 15a and nicotinic acid, compound 16k was obtained as a white solid (77.0 mg, 0.178 mmol, 83% yield). $R_f$ (silica, dichloromethane:methanol (40:1))=0.10. HPLC (214 nm) $t_R$=7.80 (98.4%) min. $^1$H NMR (400 MHz, $CDCl_3$) δ 2.72–2.79 (m, 2H), 3.2–4.0 (m, 4H), 5.62 (s, 1H), 6.60 (d, J=8.4 Hz, 1H), 6.77–6.88 (m, 1H), 7.03 (dd, J=8.4, 2.4 Hz, 1H), 7.19–7.30 (m, 3H), 7.30–7.40 (m, 2H), 7.57 (dd, J=7.6, 1.6 Hz, 1H), 8.07–8.11 (m, 1H), 8.70 (br s, 1H), 8.97 (br s, 1H). $^3$C NMR (100 MHz, $CDCl_3$) δ 32.5, 38.5, 45.0, 118.0, 123.4, 123.6, 125.4, 127.5, 128.4, 128.5, 129.1, 129.8, 130.2, 133.7, 135.0, 136.4, 143.0, 147.9, 152.2, 165.6. ESMS m/z 432.1 $[(M+H)]^+$, 473.3 $[(M+CH_3CN+H)]^+$. LC/MS $t_R$=7.17 (432.1 $[(M+H)]^+$, 863.0 $[(2M+1)]^+$) min.

16l ($W_1$=5-Cl, $R_1$=2-chlorophenyl, $R_4/R_4$=H, $R_{3d}$= phenoxymethyl).

From 15a and phenoxyacetic acid, compound 16l was obtained as a pale brown gum (101 mg, 0.218 μmol, 102% yield). $R_f$ (silica, dichloromethane:methanol (100:1))=0.20. HPLC (214 nm) $t_R$=10.26 (98.4%) min. $^1$H NMR (400 MHz, $CDCl_3$) δ 2.66 (br s, 2H), 3.41–3.48 (m, 1H), 3.61–3.68 (m, 1H), 4.05 (br s, 2H), 4.50 (s, 2H), 5.65 (br s, 1H), 6.59 (br s, 1H), 6.90–7.09 (m, 5H), 7.15–7.20 (m, 1H), 7.20–7.36 (m, 4H), 7.39 (dd, J=7.6, 1.2 Hz, 1H), 7.64 (dd, J=7.6, 1.2 Hz, 1H). $^{13}$C NMR (100 MHz, $CDCl_3$) δ 32.3, 37.6, 45.0, 67.3, 114.7, 118.2, 122.2, 123.9, 125.6, 127.4, 128.3, 129.0, 129.8, 129.9, 130.3, 133.9, 136.4, 157.1, 168.6. ESMS m/z 461.1 $[(M+H)]^+$. LC/MS $t_R$=9.49 (461.0 $[(M+H)]^+$) min.

16m ($W_1$=5-Cl, $R_1$=2-chlorophenyl, $R_4H/R_4$=H, $R_{3d}$=2-pyridyl).

From 15a and picolinic acid, compound 16m was obtained as a white solid (70.0 mg, 0.162 mmol, 75% yield). $R_f$ (silica, dichloromethane:methanol (100:1))=0.20. HPLC (214 nm) $t_R$=9.73 (96.7%) min. $^1$H NMR (400 MHz, $CDCl_3$) δ 2.70–2.77 (m, 2H), 3.56–3.63 (m, 3H), 3.72–3.78 (m, 1H), 5.69 (s, 1H), 6.60 (d, J=8.4 Hz, 1H), 7.11 (d, J=2.8 Hz, 1H), 7.20–7.33 (m, 2H), 7.35–7.45 (m, 2H), 7.72 (dd, J=7.6, 1.6 Hz, 1H), 7.84 (ddd, J=7.6, 1.6, 1.6 Hz, 1H), 8.17 (d, J=7.6 Hz, 1H), 8.28–8.39 (m, 1H), 8.54–8.57 (m, 1H). $^{13}$C NMR (100 MHz, $CDCl_3$) δ 32.5, 38.2, 45.2, 117.8, 122.2, 123.4, 125.5, 126.2, 127.3, 128.3, 128.5, 128.9, 129.8, 130.4, 134.0, 136.5, 137.3, 143.2, 148.1, 149.6, 164.4. ESMS m/z 432.0 $[(M+H)]^+$. LC/MS $t_R$=8.93 (432.1 $[(M+H)]^+$, 863.1 $[(2M+H)]^+$) min.

Synthesis of 16n ($W_1$=5-Cl, $R_1$=cyclohexyl, $R_4R_4$=H, $R_3$ =3,4-dimethoxyphenyl)

To a stirred solution of compound 151 (0.48 g, 1.34 mmol) in dry $CH_2Cl_2$ (10 mL), 3,4-dimethoxybenzoic acid (0.25 g, 1.34 mmol), EDC (0.31 g, 1.6 mmol) and DMAP (3 mg, 0.27 mmol) were added and the solution was stirred at room temperature for 24 hrs. The reaction was diluted with additional $CH_2Cl_2$ (20 mL) and washed with a saturated solution of $NaHCO_3$ (2×10 mL), water (10 mL) and brine (20 mL). The organic layer was dried over sodium sulfate, filtered and concentrated under vacuum. The crude product was purified by flash chromatography on a silica gel column using a mixture of petroleum ether and ethyl acetate as eluent to give 16n as semi-transparent solid (0.5 g, 83%): LC/MS calcd for $C_{24}H_{31}ClN_2O_3S$: 462 $[M+Na]^+$, found: 486.

16o ($W_1$=5-Cl, $R_1$=cyclohexyl, $R_4R_4$=H, $R_{3d}$=3,4,5-trimethoxyphenyl)

Using a similar procedure as for the synthesis of 16n, 16o was prepared from 151 and 3,4,5-trimethoxybenzoic acid as a semi-transparent solid (90% yield): LC/MS calcd for $C_{25}H_{33}ClN_2O_4S$: 492 $[M+Na^+]$, found: 515.

16p ($W^1{}_{=5}$-Cl, $R_1$=cyclohexyl, $R_4/R_4$=H, $R_1$=3,5-dimethoxy-4-hydroxyphenyl)

Using a similar procedure as for the synthesis of 16n, 16p was prepared from 151 and 3,5-dimethoxy-4-hydroxybenzoic acid as a semi-transparent solid (88% yield): LC/MS calcd for $C_{24}H_{31}ClN_2O_4S$: 478 $[M+Na^+]$, found: 501.

16q ($W_1$=5-Cl, $R_1$=cyclohexyl, $R_4/R_4$=H, $R_{3d}$=2-methoxyphenyl)

Using a similar procedure as for the synthesis of 16n, 16 was prepared from 151 and o-Anisic acid as a semi-transparent solid (77% yield): LC/MS calcd for $C_{23}H_{29}ClN_2O_2S$: 432 $[M+Na^+]$, found: 455).

16r ($W_1$=5-Cl, $R_1$=cyclohexyl, $R_4/R_4$=H, $R_{3d}$=3-methoxyphenyl)

Using a similar procedure as for the synthesis of 16n, 16r was prepared from 151 and m-Anisic acid as a semi-transparent solid (83% yield): LC/MS calcd for $C_{23}H_{29}ClN_2O_2S$: 432 $[M+Na^+]$, found: 455.

16s ($W_1$=5-Cl, $R_1$=cyclohexyl, $R_4/R_4$=H, $R_{3d}$=4-methoxyphenyl)

Using a similar procedure as for the synthesis of 16n, 16s was prepared from 151 and p-Anisic acid as a semi-transparent solid (86% yield): LC/MS calcd for $C_{23}H_{29}ClN_2O_2S$: 432 $[M+Na^+]$, found: 455.

16t ($W_1$=5-Cl, $R_1$=cyclohexyl, $R_4/R_4$=H, $R_{3d}$=3-pyridyl)

Using a similar procedure as for the synthesis of 16n, 16t was prepared from 151 and nicotinic acid as a semi-transparent solid (75% yield): LC/MS calcd for $C_{21}H_{26}ClN_3OS$: 403 $[M+Na^+]$, found: 425.

16u ($W_1$=5-Cl, $R_1$=cyclohexyl, $R_4/R_4$=H, $R_{3d}$=4-pyridyl)

Using a similar procedure as for the synthesis of 16n, 16u was prepared from 151 and isonicotinic acid as a semi-transparent solid (83% yield): LC/MS calcd for $C_{21}H_{26}ClN_3OS$: 403 $[M-C_8H_9N_2OS)]$, found: 222.

16v ($W_1$=5-Cl, $R_1$=cyclohexyl, $R_4/R_4$=4-pyrazolyl)

Using a similar procedure as for the synthesis of 16n, 16v was prepared from 151 and 4-pyrazolcarboxylic acid as a semi-transparent solid (86% yield): LC/MS calcd for $C_{19}H_{25}ClN_4OS$: 392 $[M+Na^+]$, found: 415.

16w ($W_1$=5-Cl, $R_1$=cyclohexyl, $R_4/R_4$=H, $R_{3d}$=piperonyl)

Using a similar procedure as for the synthesis of 16n, 16w was prepared from 151 and piperonylic acid as a semi-transparent solid (88% yield): LC/MS calcd for $C_{23}H_{27}ClN_2O_3S$: 446 $[M+Na^+]$, found: 469.

16x ($W_1$=5-Cl, $R_1$=cyclohexyl, $R_4/R_4$=H, $R_{3d}$=4-(methylsulfonyl)phenyl)

Using a similar procedure as for the synthesis of 16n, 16x was prepared from 15l and 4-(methylsulfonyl) benzoic acid as a semi-transparent solid (76% yield): LC/MS calcd for $C_{23}H_{29}ClN_2O_3S_2$: 480 [M+Na+], found: 503.

16y ($W_1$=5-Cl, $R_1$=cyclohexyl, $R_4/R_4$=H, $R_{3d}$=—($C_6H_5$) $SO_2NH_2$)

Using a similar procedure as for the synthesis of 16n, 16y was prepared from 15l and 4-carboxybenzene sulfonamide as a semi-transparent solid (84% yield): LC/MS calcd for $C_{22}H_{28}ClN_3O_3S_2$: 481 [M+Na+], found: 504.

16z ($W_1$=5-Cl, $R_1$=iso-propyl, $R_4/R_4$=H, $R_{3d}$=3,4-dimethoxyphenyl)

Using a similar procedure as for the synthesis of 16n, 16z was prepared from an analog of 15l and 3,4-dimethoxybenzoic acid as a semi-transparent solid (90% yield): LC/MS calcd for $C_{21}H_{27}ClN_2O_3S$: 422 [M+Na+], found: 445.

16aa ($W_1$=5-Cl, $R_1$=tert-butyl, $R_4/R_4$=H, $R_{3d}$=3,4-dimethoxyphenyl)

Using a similar procedure as for the synthesis of 16n, 16aa was prepared from an analog of 15l and 3,4-dimethoxybenzoic acid as a semi-transparent solid (85% yield): LC/MS calcd for $C_{22}H_{29}ClN_2O_3S$: 436 [M+Na+], found: 459.

16ab ($W_1$=5-Cl, $R_1$=iso-propyl, $R_4/R_4$H=3,4,5-trimethoxyphenyl)

Using a similar procedure as for the synthesis of 16n, 16ab was prepared from an analog of 15l and 3,4,5-trimethoxybenzoic acid as a semi-transparent solid.(85% yield): LC/MS calcd for $C_{22}H_{29}ClN_2O_4S$: 452 [M+Na+], found: 475.

16ac ($W_1$=5-Cl, $R_1$=tert-butyl, $R_4$=H, $R_{3d}$=3,4,5-trimethoxyphenyl)

Using a similar procedure as for the synthesis of 16n, 16ac was prepared from an analog of 15l and 3,4,5-trimethoxybenzoic acid as a semi-transparent solid (80% yield): LC/MS calcd for $C_{23}H_{31}ClN_2O_4S$: 466 [M+Na+], found: 489.

Alternate synthesis of 16n ($W_1$=5-Cl, $R_1$=cyclohexyl, $R_4/R_4$=H, $R_{3d}$=3,4-dimethoxyphenyl)

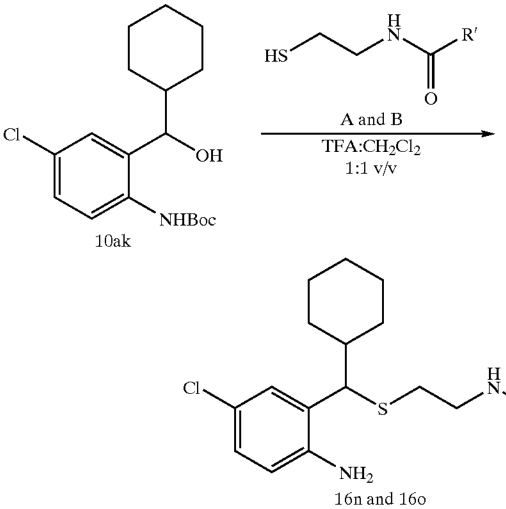

10ak 16n and 16o

Where A: R' = 3,4 dimethoxyl benzoyl
B: R' = 3,4,5 trimethoxy benzoyl

To a solution of 10ak (0.46 g, 1.36 mmol) in dry $CH_2Cl_2$ (5 mL), A (0.4 g, 1.63 mmol) and TFA (5 mL) were added and stirred for 12 hrs. The TFA was pumped off and the residue was dissolved in $CH_2Cl_2$ (30 mL) and washed with saturated solution of $NaHCO_3$ (2x10 mL), water (10 mL) and brine (20 mL). The organic layer was dried over sodium sulfate, filtered and concentrated under vacuum. The crude product was purified by flash chromatography on a silica gel column using a mixture of petroleum ether and ethyl acetate as eluent to give 16n as a semi-transparent solid (0.58 g, 92% yield): LC/MS calcd for $C_{24}H_{31}ClN_2O_3S$: 462 [M+Na+], found: 486.

Alternate Synthesis of 16o ($W_1$=5Cl, $R_1$=cyclohexyl, $R_4/R_4$=H, $R_{3d}$=3,4,5-trimethoxyphenyl)

Using a similar procedure as for the alternate synthesis of 16n, 16o was prepared from 10ak and B as a semi-transparent solid (91% yield): LC/MS calcd for $C_{25}H_{33}ClN_2O_4S$: 492 [M+Na+], found: 515.

EXAMPLE 10

SCHEME 10

SYNTHESIS OF THIOETHER UREAS 17 AND ANALOGS

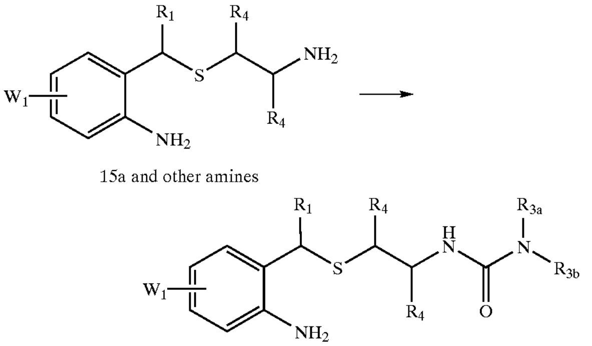

15a and other amines

17

17a ($W_1$=5-Cl, $R_1$=2-chlorophenyl, $R_4/R_4$=H, $R_{3d}$=3-fluorophenyl).

Amine 15a (10 mg, 0.031 mmol) was dissolved in dichloromethane (0.5 ml) and 3-fluorophenylisocyanate (3 μL, 0.031 mmol, 11 eq) was added. After standing for 20 hrs at rt, the solvent was removed. The crude material was purified by filtration through a plug of silica (EtOAc/LP 1:1, v/v) and evaporated to dryness to yield 17a as a white solid (11 mg, 0.023 mmol, 77%). $R_f$(silica, EtOAc/LP (1:2))=0.21. HPLC (214 nm) $t_R$=10.16 (>98%) min. $^1$H NMR (400 MHz, $CDCl_3$) δ 2.55–2.65 (m, 2H), 2.70–3.30 (br s, 2H), 3.30–3.40 (m, 1H), 3.45–3.55 (m, 1H), 5.30–5.40 (m, 1H), 5.60 (s, 1H), 6.59 (d, J=8.4 Hz, 1H), 6.70–6.76 (m, 1H), 6.88 (s, 1H), 6.92–7.00 (m, 1H), 7.03 (dd, J=8.4, 2.4 Hz, 1H), 7.14–7.32 (m, 4H), 7.36 (dd, J=7.8, 1.2 Hz, 1H), 7.59 (dd, J=7.6, 1.6 Hz, 1H). ESMS m/z 464.0 $[(M+H)]^+$. LC/MS $t_R$ 9.93 (464.0 $[(M+H)]^+$) min.

Using similar procedure as for the synthesis of 17a, the following thioether ureas were synthesized.

17b ($W_1$=5-Cl, $R_1$=2-chlorophenyl, $R_4$=H, $R_3$=2-trifluoromethoxyphenyl, $R_{3b}$=H From 15a and 2-trifluoromethoxyphenyl isocyanate, compound 17b was obtained as a white solid (58.9 mg, 73% yield). LC-MS: calcd. for $C_{23}H_{20}Cl_2F_3N_3O_2S$: 529.06; found: 551.9 $[M+Na]^+$.

17c ($W_1$=5-Cl, $R_1$=2-chlorophenyl, $R_4/R_4$=H, $R_{3a}$=3,5-dichlorophenyl, $R_b$=H).

From 15a and 3,5-dichlorophenyl isocyanate, compound 17c was obtained as a white solid (59.5 mg, 76% yield). LC-MS: calcd. for $C_{22}H_{19}C]_4N_3OS$: 513.00; found: 513.8 $[M+H]^+$.

17d ($W_1$=5-Cl, $R_1$=2-chlorophenyl, $R_4r_4$=H, $R_{3a}$=2,5-difluorophenyl, $R_{3b}$=H).

From 15a and 2,5-difluorophenyl isocyanate, compound 17d was obtained as a white solid (53.9 mg, 74% yield). LC-MS: calcd. for $C_{22}H_{19}Cl_2F_2N_3OS$: 481.06; found: 481.8 $[M+H]^+$.

17e ($W_1$=5-Cl, $R_1$=2-chlorophenyl, $R_4/R_4$=H, $R_{3a}$=2,3-dichlorophenyl, $R_{3b}$=H).

From 15a and 2,3-dichlorophenyl isocyanate, compound 17e was obtained as a white solid (53.9 mg, 74% yield). LC-MS: calcd. for $C_{22}H_{19}Cl_4N_3OS$: 513.00; found: 513.8 $[M+H]^+$.

17f ($W_1$=5-Cl, $R_1$=2-chlorophenyl, $R_4/R_4$=H, $R_{3a}$=2,4-dimethoxyphenyl, $R_{3b}$=H).

From 15a and 2,4-dimethoxyphenyl isocyanate, compound 17f was obtained as a colorless gum (41.9 mg, 74% yield). LC-MS: calcd. for $C_{24}H_{25}Cl_2N_3O_3S$: 505.10 found: 528.0 $[M+Na]^+$.

Synthesis of 17g ($W_1$=5-Cl, $R_1$=cyclohexyl, $R_4/R_4$=H, $R_{3a}$=2,4-dimethoxyphenyl, $R_{3b}$=H)

To a solution of 151 (0.070 g, 0.23 mmol) in dry $CH_2Cl_2$ (5 mL), 2,4-dimethoxyphenyl isocyanate (0.046 g, 2.6 mmol) in $CH_2Cl_2$ (2 mL) was added over a period of 8 hrs and stirred additionally for 16 hrs at room temperature. The reaction was diluted with additional $CH_2Cl_2$ (20 mL) and washed with a saturated solution of $NaHCO_3$ (2×10 mL), water (10 mL) and brine (20 mL). The organic layer was dried over sodium sulfate, filtered and concentrated under vacuum. The crude product was purified by flash chromatography on a silica gel column using a mixture of petroleum ether and ethyl acetate as eluent to give 17 g as a semi-transparent solid (0.08 g, 73% yield): LC/MS calcd for $C_{24}H_{32}ClN_3O_3S$: 477 $[M+Na^+]$, found: 500.

17h ($W_1$=5-Cl, $R_1$=cyclohexyl, $R_4/R_4$=H, $R_{3a}$=3,4,5-trimethoxyphenyl, $R_{3b}$=H)

Using a similar procedure as for the synthesis of 17 g, 17 h was prepared from 151 and 3,4,5-trimethoxyphenyl isocyanate as a semi-transparent solid (88% yield): LC/MS calcd for $C_{25}H_{34}ClN_3O_4S$: 507 $[M+Na^+]$, found: 530.

Synthesis of 17i

17i

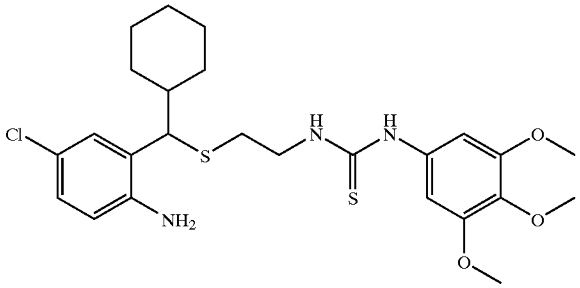

Using a similar procedure as for the synthesis of 17g, 17i was prepared from 151 and 3,4,5-trimethoxyphenyl isothiocyanate as a semi-transparent solid (62% yield): LC/MS calcd for $C_{25}H_{34}ClN_3O_3S_2$: 523 $[M+Na^+]$, found: 546.

17j ($W_1$=5-Cl, $R_1$=cyclohexyl, $R_4/R_4$=H, $R_{3a}$=3,4-dimethoxyphenyl, $R_{3b}$=H)

Using a similar procedure as for the synthesis of 17g, 171 was prepared from 151 and 3,4-dimethoxyphenyl isocyanate as a semi-transparent solid (83% yield): LC/MS calcd for $C_{24}H_{32}ClN_3O_3S$: 477 $[M+Na^+]$, found: 500.

Synthesis of 17k

17k

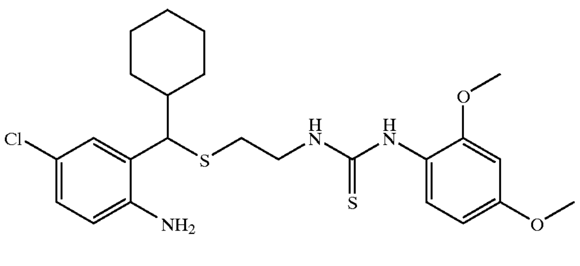

Using a similar procedure as for the synthesis of 17g, 17k was prepared from 151 and 2,4-dimethoxyphenyl isothiocyanate as a semi-transparent solid (70% yield): LC/MS ($C_{24}H_{32}ClN_3O_2S_2$: 493 $[M+Na^+]$, found: 516.

EXAMPLE 11

SCHEME 11

SYNTHESIS OF THIOETHER SULFONAMIDES 18

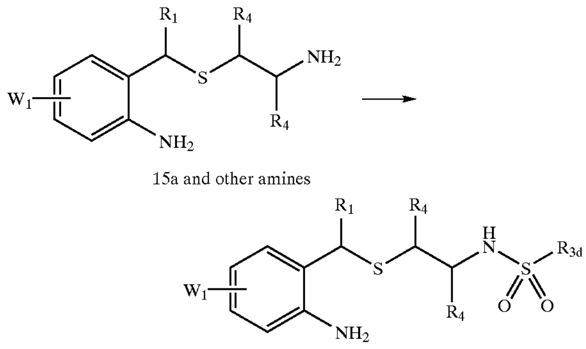

18

18a ($W_1$=5-Cl, $R_1$=2-chlorophenyl, $R_4/R_4$=H, $R_{3d}$=3-trifluoromethylphenyl)

Amine 15a (10 mg, 0.031 mmol) was dissolved in dichloromethane (0.5 ml) and 3-trifluorobenzenesulfonyl chloride (5 μL, 0.031 mmol, 1 eq) and DIEA (11 μL, 0.062 mmol, 2 eq) were added. After standing for 20 hrs at rt, the solvent was removed. The crude material was purified by filtration through a plug of silica (EtOAc/LP 1:1, v/v) and evaporated to dryness to yield 18a (12 mg, 0.022 mmol, 73%) as a white solid. $R_f$ (silica, EtOAc/LP (1:2))=0.40. HPLC (214 nm) $t_R$=10.84 (92.7%) min. $^1H$ NMR (400 MHz, $CDCl_3$) δ 2.55–2.67 (m, 2H), 2.75–3.09 (br s, 2H), 3.09–3.25 (m, 2H), 5.21 (t, J=5.8 Hz, 1H), 5.50 (s, 1H), 6.62 (d, J=8.4 Hz, 1H), 7.04 (dd, J=8.4, 2.4 Hz, 1H), 7.21–7.29 (m, 3H), 7.37 (dd, J=7.6, 1.6 Hz, 1H), 7.51 (dd, J=7.6, 2.0 Hz, 1H), 7.65 (t, J=7.8 Hz, 1H), 7.83 (d, J=7.6 Hz, 1H), 8.02 (d, J=8.0 Hz, 1H), 8.11 (s, 1H). ESMS m/z 535.1 $[(M+H)]^+$, 576.2 $[(M+CH_3CN+H)]^+$. LC/MS $t_R$ 10.65 (315.1 $[(unknown)]^+$, 535.0 $[(M+H)]^+$) min.

Using similar procedure as for the synthesis of 18a, the following thioether sulfonamides were synthesized.

18b ($W_1$=5-Cl, $R_1$=2-chlorophenyl, $R_4/R_4$=H, $R_{3d}$=phenyl).

From 15a and benzenesulfonyl chloride, compound 18b was obtained as a white solid (50.7 mg, 71%). LC-MS: calcd. for $C_{21}H_{20}Cl_2N_2O_2S_2$: 466.03 found: 466.8 $[M+H]^+$.

18c ($W_1$=5-Cl, $R_1$=2-chlorophenyl, $R_4/R_4$=H, $R_{3d}$=2-nitrophenyl).

From 15a and 2-nitrobenzenesulfonyl chloride, compound 18c was obtained as a white solid. LC-MS: calcd. for $C_{21}H_{19}Cl_2N_3O_4S_2$: 511.02 found: 533.9 $[M+H]^+$.

18d ($W_1$=5-Cl, $R_1$=2-chlorophenyl, $R_4/R_4$=H, $R_{3d}$=4-trifluoromethoxyphenyl).

From 15a and 4-trifluoromethoxybenzenesulfonyl chloride, compound 18d was obtained as a white solid. LC-MS: calcd. for $C_{22}H_{19}Cl_2F_3N_2O_3S_2$: 550.02 found: 550.8 $[M+H]^+$.

18e ($W_1$=5-Cl, $R_1$=2-chlorophenyl, $R_4/R_4$=H, $R_3$=dimethyl).

From 15a and methanesulfonyl chloride, compound 18e was obtained as a white solid. LC-MS: calcd. for $C_{16}H_{18}Cl_2N_2O_2S_2$: 404.02 found: 404.7 $[M+H]^+$.

18f ($W_1$=5-Cl, $R_1$=cyclohexyl, $R_4/R_4$=H, $R_3$=3,4-dimethoxyphenyl)

To a solution of 151 (0.3 g, 1 mmol) in dry $CH_2Cl_2$ (5 mL), DIPEA (0.15 mL, 1.11 μmol) was added and stirred at 0° C. A solution of 3,4-dimethoxy benzenesulfonyl chloride (0.26 g, 1.11 mmol) in dry $CH_2Cl_2$ (3 mL) was added over a period of 8 hrs and stirred for additional for 5 hrs at room temperature. The reaction was diluted with $CH_2Cl_2$ (20 mL) and washed with saturated solution of $NaHCO_3$ (2x10 mL), water (10 mL) and brine (20 mL). The organic layer was dried over sodium sulfate, filtered and concentrated under vacuum. The crude product was purified by flash chromatography on a silica gel column using a mixture of petroleum ether and ethyl acetate as eluent to give 18f as semi transparent solid (0.5 g, 90% yield): LC/MS calcd for $C_{23}H_{31}ClN_2O_4S_2$: 498 $[M+Na^+]$, found: 521.

EXAMPLE 12 dropwise. The reaction mixture was then stirred at room temperature under argon overnight. The reaction mixture was quenched with $H_2O$ and was extracted twice with EtOAc. The combined organic layers were washed with saturated $NaHCO_3$, brine, dried over $Na_2SO_4$, filtered, concentrated, and the residue was purified by column chromatography on silica gel.

Following the general procedure, 19a ($W_1$=5-Cl, $R_1$=2-chlorophenyl) was obtained as slightly orange oil (1.95 g, 73%) after chromatography (EtOAc/Hexane: 10/90). $^1H$ NMR (500 MHz, $CDCl_3$) δ 3.66 (b, 2H), 5.61 (s, 1H), 5.87 (s, 1H), 6.57 (d, J=8.4 Hz, 1H), 7.06 (m, 2H), 7.17–7.23 (m, 3H), 7.26–7.31 (m, 1H); MS calcd for $C_{14}H_{12}Cl_2N$ $(MH^+)$ 264.04, found 264.0.

Following the general procedure, 19b ($W_1$=5-Cl, $R_1$=2-fluorophenyl) was obtained as colorless oil (5.93 g, 80%) after chromatography (EtOAc/Hexane: 10/90). $^1H$ NMR (500 MHz, $CDCl_3$) δ 3.67 (b, 2H), 5.61 (s, 1H), 5.86 (s, 1H), 6.62 (d, J=8.3 Hz, 1H), 7.04–7.10 (m, 3H), 7.16–7.19 (m, 1H), 7.25–7.35 (m, 2H);

Following the general procedure, 19c ($W_1$=5-Br, $R_1$=2-fluorophenyl) was obtained as colorless oil (7.20 g, 73%) after chromatography (EtOAc/Hexane: 10/90). $^1H$ NMR (500 MHz, $CDCl_3$) δ 3.65 (b, 2H), 5.61 (s, 1H), 5.87 (s, 1H), 6.57 (d, J=8.3 Hz, 1H), 7.06 (m, 2H), 7.16–7.22 (m, 3H), 7.25–7.30 (m, 1H);

Following the general procedure, 19d ($W_1$=5-Cl, $R_1$=phenyl) was as colorless oil (4.26 g, 61%) after chromatography (EtOAc/Hexane: 10/90). $^1H$ NMR (500 MHz, $CDCl_3$) δ 3.55 (b, 2H), 5.36 (s, 1H), 5.81 (s, 1H), 6.62 (d, J=9.1 Hz, 1H), 7.11 (s, 1H), 7.11–7.13 (m, 1H), 7.31–7.37 (m, 4H);

SCHEME 12

SYNTHESIS OF HOMOLOGS 11, 2 AND 13

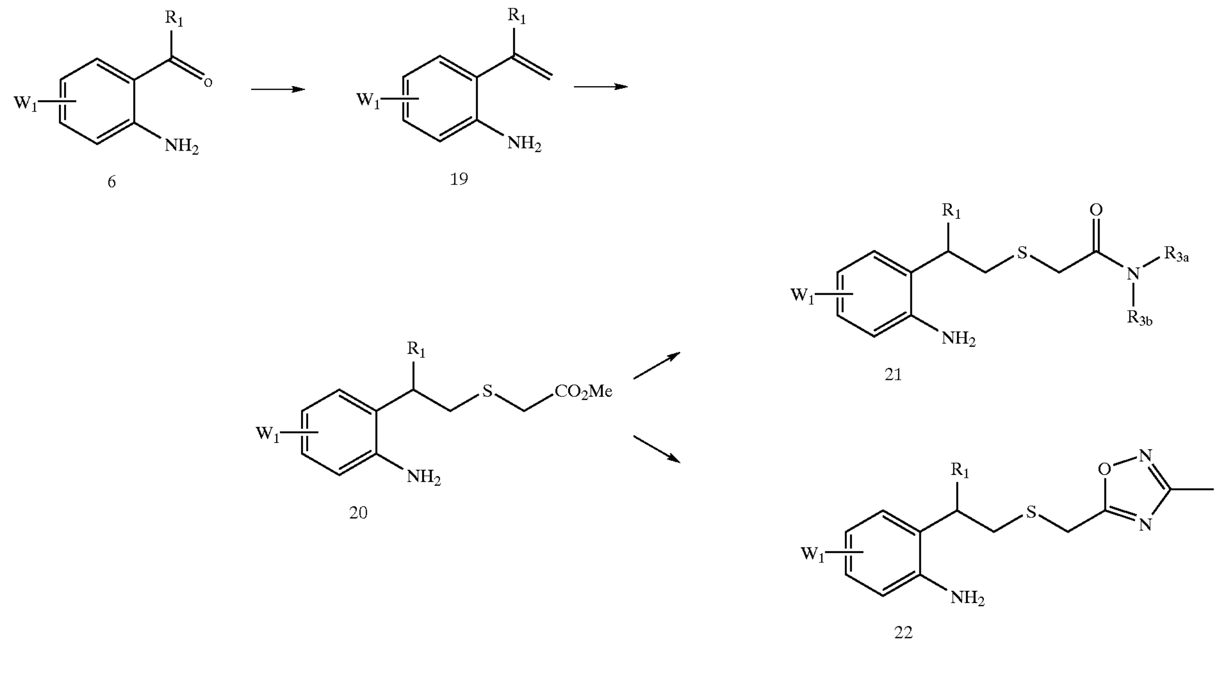

6 19 20 21 22

General procedure for the preparation of 19: To a solution of $Ph_3PMeBr$ (1.5 equiv.) in dry THF was added t-$C_5H_{11}OK$ (1.5 equiv.) in portions under argon. After the mixture was stirred at room temperature for 0.5 h, a solution of the corresponding benzophenone derivative 6 in THF was added General procedure for the preparation of 20: To a solution of the corresponding styrene derivative 19 and $HSCH_2CO_2Me$ (3.0 equiv.) in 1,4-dioxane was added 1,1'-azobis (cyclohexanecarbonitrile) (0.1 equiv.). The reaction mixture was then warmed to 80° C. under argon and stirred at that temperature overnight. Additional 1,1'-azobis (cyclohexanecarbonitrile) (0.05–0.1 equiv.) was added to the reaction mixture and it was stirred at 80° C. until TLC analysis indicated disappearance of 19. The reaction mixture was diluted with EtOAc and was washed with saturated $NaHCO_3$, brine, dried over $Na_2SO_4$, filtered, concentrated, and the residue was purified by column chromatography on silica gel.

Following the general procedure, 20a ($W_1$=5-Cl, $R_1$=2-chlorophenyl) was obtained as colorless oil (3.15 g, 84%) after chromatography (EtOAc/Hexane: 15/85). $^1$H NMR (500 MHz, $CDCl_3$) δ 3.10–3.30 (m, 2H), 3.18 and 3.23 (AB q, J=14.79 Hz, 2H), 3.74 (s, 3H), 4.68 (t, J=7.7 Hz, 1H), 6.60 (d, J=8.9 Hz, 1H), 7.02 (t, J=2.0 Hz, 1H), 7.03 (s, 1H), 7.16–7.26 (m, 3H), 7.40 (d, J=8.5 Hz, 1H); MS calcd for $C_{17}H_{18}Cl_2NO_2S$ ($MH^+$) 370.05, found 370.1.

Following the general procedure, 20b ($W_1$=5-Cl, $R_1$=2-fluorophenyl) was obtained as colorless oil (2.05 g, 82%) after chromatography (EtOAc/Hexane: 20/80). $^1$H NMR (500 MHz, $CDCl_3$) δ 3.18 and 3.23 (AB q, J=15.2 Hz, 2H), 3.22–3.34 (m, 2H), 3.74 (s, 3H), 3.77 (b, 2H), 4.54 (t, J=7.8 Hz, 1H), 6.59 (d, J=8.7 Hz, 1H), 7.00–7.26 (m, 6H).

Following the general procedure, 20c ($W_1$=5-Br, $R_1$=2-fluorophenyl) was obtained as pale orange oil (5.11 g, 79%) after chromatography (EtOAc/Hexane: 20/80). $^1$H NMR (500 MHz, $CDCl_3$) δ 3.18 and 3.23 (AB q, J=14.6 Hz, 2H), 3.21–3.34 (m, 2H), 3.74 (s, 3H), 4.53 (t, J=7.8 Hz, 1H), 6.55 (d, J=8.3 Hz, 1H), 7.04–7.26 (m, 6H).

Following the general procedure, 20d ($W_1$=5-Cl, $R_1$=phenyl) was obtained as colorless oil (3.60 g, 75%) after chromatography (EtOAc/Hexane: 20/80). $^1$H NMR (500 MHz, $CDCl_3$) δ 3.12 and 3.17 (AB q, J=14.5 Hz, 2H), 3.21–3.34 (m, 2H), 3.74 (s, 3H), 4.19 (t, J=7.7 Hz, 1H), 6.58 (d, J=8.5 Hz, 1H), 7.03 (dd, J=8.3 Hz, 2.7 Hz, 1H), 7.13 (d, J=2.6 Hz, 1H), 7.23–7.26 (m, 3H), 7.31–7.34 (m, 2H).

General procedure for the preparation of amide 21: A solution of the corresponding ester 20 and ammonia (saturated solution in $H_2O$, 30 equiv.) or $MeNH_2$ (1.0 M solution in MeOH, 10 equiv.) in MeOH was stirred at room temperature until TLC analysis indicated the complete disappearance of 20. The reaction mixture was concentrated under reduced pressure, and the residue was purified by column chromatography on silica gel.

Following the general procedure, 21a ($W_1$=5-Cl, $R_2$4=2-chlorophenyl, $R_{3a}$=H, $R_b$=H) was obtained as white solid (55 mg, 96%) after chromatography (MeOH/$CH_2Cl_2$: 2.5/97.5). $^1$H NMR (500 MHz, $CDCl_3$) δ 3.16 and 3.27 (AB q, J=16.5 Hz, 2H), 3.66 and 3.71 (AB q, J=13.5 Hz, 2H), 5.86 (s, 1H), 6.52–6.54 (m, 1H), 6.57 (b, 1H), 7.03–7.04 (m, 2H), 7.26–7.29 (m, 1H), 7.32–7.35 (m, 2H), 7.78–7.80 (m, 1H).

Following the general procedure, 21b ($W_1$=5-Cl, $R_1$=2-fluorophenyl. $R_{3a}$=H, $R_{3b}$=H) was obtained as white solid (90 mg, 96%) after chromatography (MeOH/$CH_2Cl_2$: 2.5/97.5). $^1$H NMR (500 MHz, $CDCl_3$) δ 3.14–3.29 (m, 4H), 3.73 (b, 2H), 4.51 (t, J=7.8 Hz, 1H), 5.58 (s, 1H), 6.45 (s, 1H), 6.50 (d, J=8.3 Hz, 1H), 7.02–7.17 (m, 5H), 7.24–7.27 (m, 1H).

Following the general procedure, 21c ($W_1$=5-Br, $R_1$=2-fluorophenyl, $R_{3a}$=H, $R_{3b}$=H) was obtained as white solid (117 mg, 93%) after chromatography (MeOH/$CH_2Cl_2$: 2.5/97.5). $^1$H NMR (500 MHz, $CDCl_3$) δ 3.14–3.29 (m, 4H), 3.60–3.80 (b, 2H), 4.49 (t, J=7.8 Hz, 1H), 5.66 (s, 1H), 6.46 (s, 1H), 6.55 (d, J=8.4 Hz, 1H), 7.05–7.17 (m, 4H), 7.21–7.26 (m, 2H).

Following the general procedure, 21d ($W_1$=5-Cl, $R_1$=phenyl, $R_{3a}$=H, $R_{3b}$=H) was obtained as white solid (102 mg, 97%) after chromatography (MeOH/$CH_2Cl_2$: 2.5/97.5). $^1$H NMR (500 MHz, $CDCl_3$) δ 3.10–3.31 (m, 4H), 4.15 (t, J=7.9 Hz, 1H), 5.60 (s, 1H), 6.43 (s, 1H), 6.58 (d, J=8.3 Hz, 1H), 7.04 (dd, J=8.3 Hz, 2.8 Hz, 1H), 7.12 (d, J=2.3 Hz, 1H), 7.22–7.27 (m, 3H), 7.31–7.34 (m, 2H).

Following the general procedure, 21e ($W_1$=5-Cl, $R_1$=2-chlorophenyl, $R_{3a}$=$CH_3$, $R_{3b}$=H) was obtained as white solid (102 mg, 91%) after chromatography (MeOH/$CH_2Cl_2$: 2.5/97.5). $^1$H NMR (500 MHz, $CDCl_3$) δ 2.78 (d, J=4.9 Hz, 3H), 3.04–3.19 (m, 2H), 3.24 (s, 2H), 3.6–3.8 (b, 2H), 4.59 (t, J=7.7 Hz, 1H), 6.58 (m, 1H), 6.60 (d, J=9.2 Hz, 1H), 7.04 (s, 1H), 7.05 (m, 1H), 7.11 (dd, J=7.1 Hz, 2.7 Hz, 1H), 7.20–7.26 (m, 2H), 7.40 (dd, J=7.0 Hz, 1.5 Hz, 1H).

Following the general procedure, 21f ($W_1$=5-Cl, $R_1$=2-fluorophenyl $R_{3a}$=$CH_3$, $R_{3b}$=H), was obtained as white solid (91 mg, 96%) after chromatography (MeOH/$CH_2Cl_2$: 2/98). $^1$H NMR (500 MHz, $CDCl_3$) δ 2.80 (d, J=5.0 Hz, 3H), 3.09–3.25 (m, 4H), 3.75 (s, 2H), 4.46 (t, J=7.8 Hz, 1H), 6.56 (m, 1H), 6.60 (d, J=8.3 Hz, 1H), 7.02–7.14 (m, 5H), 7.25–7.26 (m, 1H).

Following the general procedure, 21 g ($W_1$=5-Br, $R_1$=2-fluorophenyl, $R_{3a}$=$CH_3$, $R_{3b}$=H) was obtained as white solid (116 mg, 96%) after chromatography (MeOH/$CH_2Cl_2$: 2/98). $^1$H NMR (500 MHz, $CDCl_3$) δ 2.80 (d, J=5.0 Hz, 3H), 3.09–3.25 (m, 4H), 3.76 (b, 2H), 4.45 (t, J=7.8 Hz, 1H), 6.55 (d, J=8.5 Hz, 1H), 7.05–7.26 (m, 6H).

Following the general procedure, 21h ($W_1$=5-Cl, $R_1$=phenyl, $R_3$=$CH_3$, $R_{3b}$=H) was obtained as white solid (86 mg, 96%) after chromatography (MeOH/$CH_2Cl_2$: 2/98). $^1$H NMR (500 MHz, $CDCl_3$) δ 2.78 (d, J=5.1 Hz, 3H), 3.06–3.28 (m, 4H), 4.11 (t, J=7.9 Hz, 1H), 6.51 (m, 1H), 6.58 (d, J=8.3 Hz, 1H), 7.04 (dd, J=8.4 Hz, 2.9 Hz, 1H), 7.11 (d, J=2.1 Hz, 1H), 7.21–7.22 (m, 2H), 7.25–7.28 (m, 1H), 7.31–7.34 (m, 2H).

Following the general procedure, 21i ($W_1$=5-Br, $R_1$=2-fluorophenyl, $R_{3a}$/$R_{3b}$=—$(CH_2)_2O(CH_2)_2$—) was obtained as white solid (55 mg, 95%). MS calcd for $C_{20}H_{23}BrFN_2O_2S$ ($MH^+$) 453.07, found 453.0.

Preparation of 21j ($W_1$=5-Br, $R_1$=2-fluorophenyl, $R_{3a}$=, OH, $R_{3b}$=H). To a solution of the corresponding ester 20c (228 mg, 0.57 mmol), $NH_2OHHCl$ (0.80 g, 11.5 mmol) in dry MeOH was added MeONa (25% wt. in MeOH, 4.0 ml). NaCl precipitated from the solution immediately. The reaction mixture was then refluxed overnight. After it was cooled down to room temperature, the solution was neutralized with 1.0 N HCl to pH around 8.0, and extracted twice with $CH_2Cl_2$. The combined organic layers were washed with saturated $NaHCO_3$, brine, dried over $Na_2SO_4$, filtered, concentrated, and the residue was purified by column chromatography on silica gel (MeOH/$CH_9Cl_2$: 10/90) to give 2j (82 mg, 36%) as pale yellow solid. $^1$H NMR (500 MHz, $CDCl_3$) δ 3.11–3.29 (m, 4H), 4.50 (m, 1H), 6.60 (d, J=7.5 Hz, 1H), 7.06 (t, J=8.9 Hz, 1H), 7.08–7.26 (m, 5H); MS calcd for $C_{16}H_{27}BrFN_2O_2S$ ($MH^+$) 399.02, found 398.9.

General procedure for the preparation of 22: To a solution of the corresponding ester 20 and acetimidoxime hydrochloride salt (5.0 equiv.) in dry THF/MeOH (1:1) was added dropwise a solution of MeONa (25% wt. solution in MeOH, 12.0 equiv.) under argon at room temperature. NaCl precipitated immediately from the reaction mixture. The suspension was then stirred at room temperature overnight. After TLC analysis indicated the completion of the reaction, the reaction mixture was quenched with $H_2O$ and was extracted twice with EtOAc. The combined organic layers were washed with brine, dried over $Na_2SO_4$, filtered, concentrated, and the residue was purified by column chromatography on silica gel.

Following the general procedure, 22a ($W_1$=5-Cl, $R_1$=2-chlorophenyl) was obtained as colorless oil (175 mg, 56%)

after chromatography (EtOAc/Hexane: 20/80). $^1$H NMR (500 MHz, $CDCl_3$) δ 2.41 (s, 3H), 3.19–3.33 (m, 2H), 3.65–3.85 (b, 2H), 3.79 and 3.83 (AB q, J=15.4 Hz, 2H), 4.69 (t, J=7.7 Hz, 1H), 6.60 (d, J=8.3 Hz, 1H), 7.01–7.04 (m, 2H), 7.15–7.16 (m, 1H), 7.21–7.26 (m, 2H), 7.39 (d, J=8.6 Hz, 1H).

Following the general procedure 22b ($W_1$=5-Cl, $R_1$=2-fluorophenyl) as colorless oil (101 mg, 42%) after chromatography (EtOAc/Hexane: 20/80). $^1$H NMR (500 MHz, $CDCl_3$) δ 2.41 (s, 3H), 3.23–3.37 (m, 2H), 3.76 and 3.82 (AB q, J=15.5 Hz, 2H), 4.54 (t, 7.8 Hz, 1H), 6.60 (d, J=8.5 Hz, 1H), 7.01–7.27 (m, 6H).

Following the general procedure, 22c ($W_1$=5-Br, $R_1$=2-fluorophenyl) as colorless oil (137 mg, 45%) after chromatography (EtOAc/Hexane: 20/80). $^1$H NMR (500 MHz, $CDCl_3$) δ 2.41 (s, 3H), 3.23–3.37 (m, 2H), 3.76 and 3.81 (AB q, J=15.4 Hz, 2H), 4.53 (t, 7.8 Hz, 1H), 6.55 (d, J=8.4 Hz, 1H), 7.04–7.27 (m, 6H).

Following the general procedure, 22d ($W_1$=5-Cl, $R_1$=phenyl) as colorless oil (146 mg, 51%) after chromatography (EtOAc/Hexane: 30/70). $^1$H NMR (500 MHz, $CDCl_3$) δ 2.41 (s, 3H), 3.23–3.37 (m, 2H), 3.66 and 3.73 (AB q, J=14.9 Hz, 2H), 4.16 (t, 7.7 Hz, 1H), 6.58 (d, J=8.3 Hz, 1H), 7.04 (dd, J=8.3 Hz, 2.5 Hz, 1H), 7.14 (d, J=2.5 Hz, 1H), 7.22–7.27 (m, 3H), 7.31–7.34 (m, 2H).

EXAMPLE 13

SCHEME 13
SYNTHESIS OF SYNTHESIS OF NITROGEN AND NITROGEN CYCLIC ANALOGS OF 20 AND 21

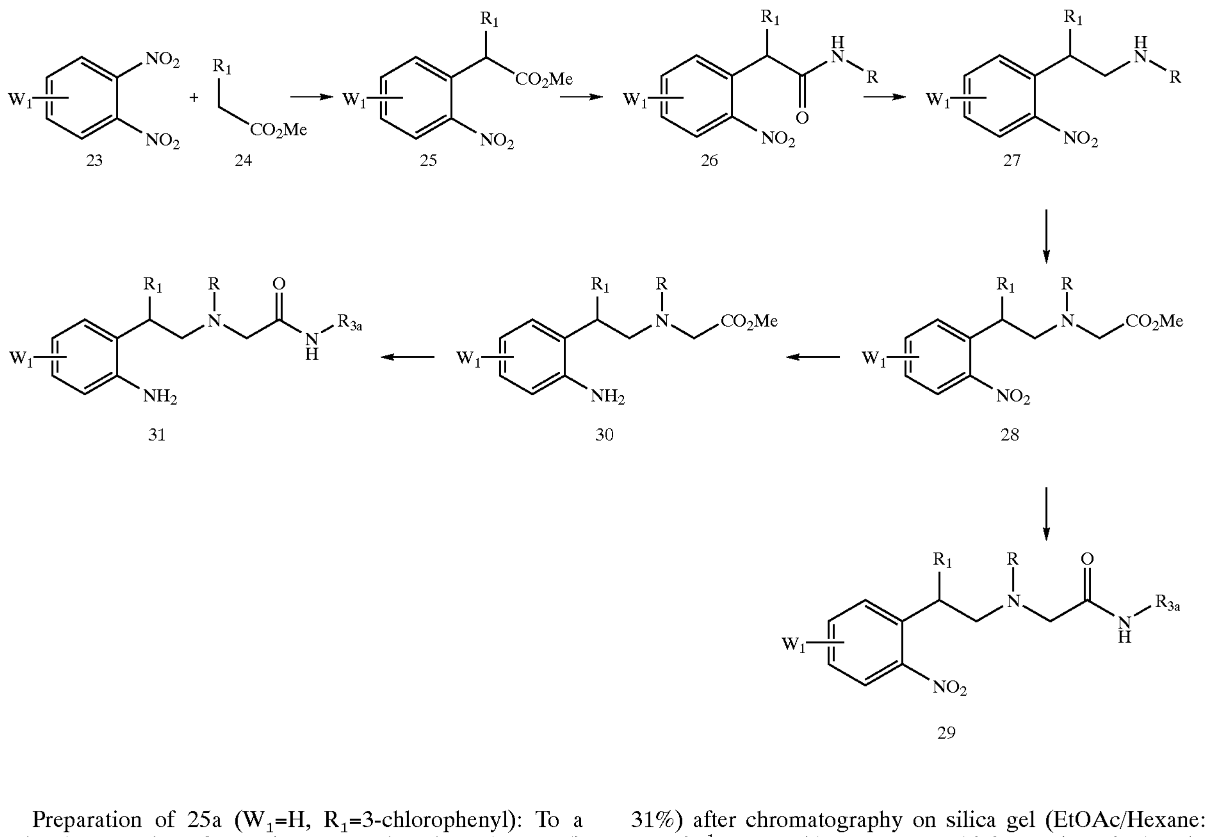

Preparation of 25a ($W_1$=H, $R_1$=3-chlorophenyl): To a stirred suspension of NaH (0.60 g, 60% purity, 15.0 mmol) in dry DMF was added dropwise methyl 3-chlorophenylacetate (24a, $R_1$=3-chlorophenyl) (2.22 g, 12.0 mmol) via syringe at 0° C. under argon. After the solution was stirred at 0° C. for 0.5 hrs, 1,2-dinitrobenzene (23a, $R_1$=H)(1.68 g, 10.0 mmol) was added in small portions. The reaction mixture was then stirred at 0° C. and allowed to warm to rt overnight. The reaction was quenched with saturated aqueous $NH_4Cl$ solution and was extracted twice with EtOAc. The combined organic layers were washed with brine, dried over $Na_9SO_4$, filtered, concentrated, and the residue was purified by column chromatography on silica gel (EtOAc/Hexane: 10/90) to give 25a, which was further purified by recrystallization from EtOAc/Hexane, as a yellow solid (1.28 g, 42%). $^1$H NMR (500 MHz, $CDCl_3$) δ 3.79 (s, 3H), 5.08 (s, 1H), 7.19–7.21 (m, 1H), 7.30–7.31 (m, 3H), 7.52 (t, J=7.9 Hz, 1H), 7.66 (d, J=7.5 Hz, 1H), 8.16 (d, J=8.4 Hz, 1H), 8.18 (s, 1H); MS calcd for $C_{15}H_{13}ClNO_4$ ($MH^+$) 306.06, found 306.0.

25b ($W_1$=H, $R_2$-methylphenyl)

Using a similar procedure as for 25a, 25b was obtained from ethyl 1-methylphenylacetate (6.72 g, 40.0 mmol) and 1,2-dinitrobenzene (10.70 g, 60.0 mmol) as a yellow solid (2.63 g, 22%). $^1$H NMR (500 MHz, $CDCl_3$) δ 1.27 (t, J=7.1 Hz, 3H), 2.28 (s, 3H), 4.26 (q, J=7.1 Hz, 2H), 5.30 (s, 1H), 7.23–7.28 (m, 5H), 7.60 (dd, J=8.2 Hz, 1.7 Hz, 1H), 7.78 (d, J=1.7 Hz, 1H), 7.87 (d, J=8.3 Hz, 1H).

25c ($W_1$=H, $R_1$=phenyl)

Using a similar procedure as for 25a, 25c was obtained from methyl phenylacetate (2.68 g, 17.8 mmol), and 1,2-dinitrobenzene (2.50 g, 14.9 mmol) as yellow solid (1.26 g, 31%) after chromatography on silica gel (EtOAc/Hexane: 10/90). $^1$H NMR (500 MHz, $CDCl_3$) δ 3.70 (s, 3H), 5.04 (s, 1H), 7.18–7.32 (m, 3H), 7.40–7.49 (m, 2H), 7.58 (t, J=7.6 Hz, 1H), 7.72 (d, J=7.8 Hz, 1H), 8.07 (t, J=7.8 Hz, 1H).

25d ($W_1$=H, $R_1$=1-naphthyl)

Using a similar procedure as for 25a, 25d was obtained from methyl 1-naphthalenylacetate (6.01 g, 30.0 mmol) and 1,2-dinitrobenzene (3.36 g, 20.0 mmol) as a yellow solid (1.63 g, 25%). $^1$H NMR (500 MHz, $CDCl_3$) δ 3.81 (s, 3H), 5.89 (s, 1H), 7.42–7.45 (m, 1H), 7.51–7.55 (m, 3H), 7.66 (dd, J=8.3 Hz, 1.9 Hz, 1H), 7.80–7.93 (m, 6H).

General procedure for the preparation of 26: A solution of 25 and ammonia (saturated solution in $H_2O$, 30 equiv.) or MeNH (1.0 M solution in MeOH, 10 equiv.) in MeOH, or $PhCH_2CH_2NH_2$ (neat, 10 equiv.) was stirred at indicated temperature until TLC analysis indicated the complete disappearance of 25. The reaction mixture was concentrated under reduced pressure, and the residue was purified by column chromatography on silica gel Following the general procedure, 26a ($W_1$=H, $R_1$=3-chlorophenyl, R=$CH_3$) was obtained from 25a (120 mg, 0.39 mmol), and $MeNH_2$ (1.0 M solution in MeOH, 3.9 ml, 3.9 mmol) as pale yellow solid (112 mg, 94%) after chromatography (EtOAc/Hexane: 40/60). $^1$H NMR (500 MHz, $CDCl_3$) δ 2.88 (d, J=4.9 Hz, 3H), 4.90 (s, 1H), 5.72 (b, 1H), 7.18–7.20 (m, 1H), 7.26–7.31 (m, 3H), 7.52 (t, J=8.0 Hz, 1H), 7.66 (d, J=8.1 Hz, 1H), 8.14 (s, 1H), 8.15 (d, J=7.3 Hz, 1H); MS calcd for $C_{15}H_{14}ClN_2O_3$ ($MH^+$) 305.07, found 305.1.

Following the general procedure, 26b ($W_1$=H, $R_1$=3-chlorophenyl, R=2-phenylethyl) was obtained from 25a (270 mg, 0.88 mmol), and $PhCH_2CH_2NH_2$ (1.07 g, 8.8 mmol) as pale yellow oil (310 mg, 89%) after chromatography (EtOAc/Hexane: 30/70). $^1$H NMR (500 MHz, $CDCl_3$) δ 2.81 (t, J=6.7 Hz, 2H), 3.54–3.64 (m, 2H), 4.82 (s, 1H), 5.62 (m, 1H), 7.05–7.09 (m, 3H), 7.20–7.30 (m, 6H), 7.48 (t, J=7.8 Hz, 1H), 7.55 (d, J=7.5 Hz, 1H), 8.08 (s, 1H), 8.13 (d, J=8.2 Hz, 1H); MS calcd for $C_{22}H_2ClN_2O_3$ ($MH^+$) 395.12, found 395.1.

Following the general procedure, 26c ($W_1$=H, $R_1$=3-chlorophenyl, R=H) was obtained from 25a (225 mg, 0.74 mmol), and $NH_4OH$ (~14.8 N in $H_2O$, 1.5 ml, ~22.2 mmol) as pale yellow solid (194 mg, 91%) after chromatography ($MeOH/CH_2Cl_2$: 2.5/97.5). $^1$H NMR (500 MHz, $CDCl_3$) δ 4.97 (s, 1H), 5.65 (s, 1H), 5.86 (s, 1H), 7.20–7.22 (m, 1H), 7.30–7.32 (m, 3H), 7.53 (t, J=8.2 Hz, 1H), 7.66 (d, J=7.7 Hz, 1H), 8.15–8.16 (m, 1H), 8.17 (s, 1H);

General procedure for the preparation of 27: To a solution of the corresponding amide derivative 26 in dry THF was added dropwise a solution of $BH_3$.THF complex in THF (1.0 M, 2–3 equiv.) at 0° C. under argon. The reaction mixture was then stirred at 0° C. and allowed to warm to rt overnight. After the reaction was complete indicated by TLC analysis, the reaction mixture was carefully quenched with MeOH at 0° C., and then diluted with EtOAc. The organic layer was washed with saturated $NaHCO_3$, brine, dried over $Na_2SO_4$, filtered, concentrated, and the residue was purified by column chromatography on silica gel.

Following the general procedure, 27a ($W_1$=H, $R_1$=3-chlorophenyl, R=$CH_3$) was obtained from 26a (129 mg, 0.42 mmol), and $BH_3$.THF complex in THF (1.0 M, 1.26 ml, 1.26 mmol) as pale yellow solid (110 mg, 89%) after chromatography (EtOAc/Hexane: 20/80). $^1$H NMR (500 MHz, $CDCl_3$) δ 2.64 (dd, J=6.0 Hz, 2.0 Hz, 3H), 3.24–3.51 (m, 2H), 4.71 (t, J=7.4 Hz, 1H), 4.83–4.86 (m, 1H), 7.15–7.37 (m, 3H), 7.53–7.65 (m, 3H), 8.07–8.16 (m, 2H); MS calcd for $C_{15}H_{16}ClN_2O_2$ ($MH^+$) 291.09, found 291.1.

Following the general procedure, 27b ($W_1$=H, $R_1$=3-chlorophenyl, R=2-phenylethyl) was obtained from 26b (196 mg, 0.50 mmol), and $BH_3$.THF complex in THF (1.0 M, 1.99 ml, 1.99 mmol) as pale yellow oil (147 mg, 88%) after chromatography (EtOAc/Hexane: 10/90). MS calcd for $C_{22}H_{22}ClN_2O_2$ ($MH^+$) 381.04, found 381.2.

General procedure for the preparation of 28: To a solution of the corresponding amine derivative 27 and DI EA (2.0–5.0 equiv.) in dry THF was added dropwise $BrCH_2CO_2Me$ (1.2–2.5 equiv.) at 0° C. under argon. The reaction mixture was then stirred at 0° C. and allowed to warm to rt overnight. The reaction mixture was quenched with saturated $NaHCO_3$ and was extracted twice with EtOAc. The combined organic layers were washed with saturated $NaHCO_3$ brine, dried over $Na_2SO_4$, filtered, concentrated, and the residue was purified by column chromatography on silica gel.

Following the general procedure, 28a ($W_1$=H, $R_1$=3-chlorophenyl, R=$CH_3$) was obtained from 27a (110 mg, 0.38 mmol), $BrCH_2CO_2Me$ (116 mg, 0.76 mmol), and DIEA (245 mg, 1.90 mmol) as colorless oil (104 mg, 76%) after chromatography (EtOAc/Hexane: 20/80). $^1$H NMR (500 MHz, $CDCl_3$) δ 2.43 (s, 3H), 3.17–3.22 (m, 2H), 3.28 and 3.32 (AB q, J=15.5 Hz, 2H), 3.70 (s, 3H), 4.26 (t, J=7.2 Hz, 1H), 7.12 (d, J=6.6 Hz, 1H), 7.21–7.26 (m, 3H), 7.48 (t, J=7.7 Hz, 1H), 7.60 (d, J=7.7 Hz, 1H), 8.09 (d, J=7.7 Hz, 1H), 8.14 (s, 1H); MS calcd for $C_{18}H_{20}ClN_2O_4$ ($MH^+$) 363.11, found 363.1.

Following the general procedure, 28b ($W_1$=H, $R_1$=3-chlorophenyl, R=2-phenylethyl) was obtained from 27b (70 mg, 0.18 mmol), $BrCH_2CO_2Me$ (56 mg, 0.37 mmol), and DIEA (119 mg, 0.92 mmol) as colorless oil (81 mg, 97%) after chromatography (EtOAc/Hexane: 10/90). $^1$H NMR (500 MHz, $CDCl_3$) δ 2.61–2.65 (m, 2H), 2.94 (t, J=7.5 Hz, 2H), 3.31–3.33 (m, 2H), 3.36 (s, 2H), 3.69 (s, 3H), 4.16 (t, J=7.8 Hz, 1H), 7.04–7.07 (m, 3H), 7.15–7.26 (m, 6H), 7.43 (t, J=8.1 Hz, 1H), 7.48 (d, J=7.3 Hz, 1H), 8.06–8.07 (m, 2H); MS calcd for $C_{25}H_{26}ClN_2O_4$ ($MH^+$) 453.16, found 453.3.

Following the general procedure, 28c ($W_1$=H, R=3-chlorophenyl, R=H) was obtained from 27c (35 mg, 0.13 mmol), $BrCH_2CO_2Me$ (77 mg, 0.50 mmol), and DIEA (163 mg, 1.26 mmol) as colorless oil (50 mg, 94%) after chromatography (EtOAc/Hexane: 30/70). MS calcd for $C_{20}H_{22}ClN_2O_6$ ($MH^+$) 421.12, found 421.1.

General procedure for the preparation of 30: A suspension of the corresponding 4 and Pd/C (10% on the charcoal, 0.05 equiv.) in EtOAc was stirred under an atmospheric of hydrogen at atmospheric pressure for 2 h. The Pd/C was filtered off. The filtration was concentrated, and the residue was purified by column chromatography on silica gel.

Following the general procedure, 30a ($W_1$=H, $R_1$=3-chlorophenyl, R=$CH_3$) was obtained from 28a (15 mg, 0.04 mmol) and Pd/C as colorless oil (13 mg, 94%) after chromatography (EtOAc/Hexane: 50/50). $^1$H NMR (500 MHz, $CDCl_3$) δ 2.42 (s, 3H), 3.09–3.16 (m, 2H), 3.27 and 3.31 (AB q, J=15.5 Hz, 2H), 3.61 (b, 2H), 3.69 (s, 3H), 4.04 (t, J=7.7 Hz, 1H), 6.52–6.53 (m, 2H), 6.63 (d, J=8.1 Hz, 1H), 7.07 (t, J=7.9 Hz, 1H), 7.15–7.26 (m, 4H); MS calcd for $C_{18}H_{22}ClN_2O_2$ ($MH^+$) 333.14, found 333.1.

Following the general procedure, 30b ($W_1$=H, $R_1$=3-chlorophenyl, R=2-phenylethyl) was obtained from 28b (32 mg, 0.07 mmol) and Pd/C as colorless oil (27 mg, 90%) after chromatography (EtOAc/Hexane: 30/70). $^1$H NMR (500 MHz, $CDCl_3$) δ 2.63–2.67 (m, 2H), 2.91 (t, J=7.6 Hz, 2H), 3.24–3.32 (m, 2H), 3.34 (s, 2H), 3.59 (b, 2H), 3.66 (s, 3H), 3.98 (t, J=7.6 Hz, 1H), 6.49 (d, J=1.7 Hz, 1H), 6.52 (dd, J=8.0 Hz, 1.8 Hz, 1H), 6.60 (d, J=7.4 Hz, 1H), 7.05–7.14 (m, 4H), 7.16–7.20 (m, 3H), 7.22–7.26 (m, 3H); MS calcd for $C_{25}H_{28}ClN_2O_2$ ($MH^+$) 423.19, found 423.1.

General procedure for the preparation of 29 and 31: A solution of the corresponding ester derivative 28 (or 30) in cyclohexylamine was stirred at 120° C. overnight. Cyclohexylamine was then removed under reduced pressure, and the residue was purified by column chromatography on silica gel.

Following the general procedure, 29a ($W_1$=H, $R_1$=3-chlorophenyl, R=$CH_3$, $R_4$=cyclohexyl) was obtained from 28a (11 mg, 0.03 mmol) as pale brown oil (12.9 mg, 99%) after chromatography (EtOAc/Hexane: 50/50). $^1$H NMR (500 MHz, $CDCl_3$) δ 0.77–0.82 (min, 2H), 1.07 (m, 1H), 1.24–1.31 (m, 3H), 1.53–1.55 (m, 2H), 1.64–1.67 (m, 2H), 2.33 (s, 3H), 3.07 (s, 2H), 3.11 (d, J=8.1 Hz, 2H), 3.59–3.61 (m, 1H), 4.22 (t, J=8.1 Hz, 1H), 6.37 (bd, J=8.0 Hz, 1H), 7.11 (d, J=7.5 Hz, 1H), 7.20 (s, 1H), 7.24–7.31 (m, 2H), 7.49–7.55 (m, 2H), 8.10–8.13 (m, 2H); MS calcd for $C_{23}H_{29}ClN_3O_3$ ($MH^+$) 430.19, found 430.1.

29b ($W_1$=H, R=3-chlorophenyl, R=2-phenylethyl, $R_{3a}$=cyclohexyl): Following the general procedure, 28b (4.0 mg, 0.0088 mmol) was employed to give 29b (4.4 mg, 95%) as pale yellow oil after chromatography (EtOAc/Hexane: 40/60). MS calcd for $C_{30}H_{35}ClN_3O_3$ ($MH^+$) 520.24, found 520.2.

31a ($W_1$=H, $R_1$=3-chlorophenyl, R=$CH_3$, $R_{3a}$=cyclohexyl): Following the general procedure, 30a (5.0 mg, 0.015 mmol) was employed to give 31a (5.5 mg, 92%) as pale yellow oil after chromatography (EtOAc/Hexane: 60/40). LC-MS calcd for $C_{23}H_{31}ClN_3O$ ($MH^+$) 400.22, found 400.2.

EXAMPLE 14

Further Synthesis of Representative Compounds

34

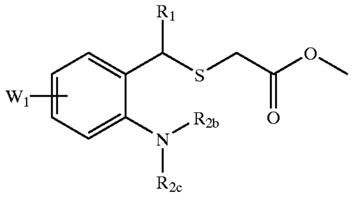

34a ($W_1$=5-Cl, $R_1$=2-chlorophenyl, $R_{2b}$/$R_{2b}$=$CH_3$).

To a stirred solution of 11s (100 mg, 0.280 mmol) in THF (2.0 ml) under a nitrogen atmosphere at rt was added acetic acid (20 μL, to give a 1% solution in THF) and paraformaldehyde (100 mg) and the reaction mixture was heated to 60° C. for 24 hrs. Further acetic acid (20 μL) and paraformaldehyde (100 mg) were added and stirring was continued for 48 hrs at 60° C. Sodium cyanoborohydride (35.2 mg, 0.56 mmol, 2 eq) was added and stirring was continued at 60° C. for a further 24 hrs. The reaction mixture was partitioned between dichloromethane and brine, the aqueous phase was back extracted, then the combined organic phase was dried with brine and sodium sulfate, then filtered and evaporated to give the crude N,N-dimethylamine (130 mg) as a yellow oil. The crude material was purified by flash chromatography on silica (10 g) with petroleum ether:ethyl acetate (10:1 then 5:1) to give 34a as a yellow oil (53.0 mg, 0.138 mmol, 64% yield). $R_f$ (silica, petroleum ether:ethyl acetate (5:1))=0.72. HPLC (214 nm) $t_R$=10.13 (92.0%) min. $^1$H NMR (400 MHz, $CDCl_3$) δ 2.58 (s, 6H), 3.17 (d, J=1.2 Hz, 2H), 3.64 (s, 3H), 6.42 (s, 1H), 7.12–7.28 (m, 4H), 7.37 (dd, J=8.0, 1.2 Hz, 1H), 7.57 (d, J=2.8 Hz, 1H), 7.60 (dd, J=8.4, 1.6 Hz, 1H). $^{13}$C NMR (400 MHz, $CDCl_3$) δ .34.5, 45.1, 45.2, 52.1, 123.0, 126.9, 128.4, 128.5, 129.5, 129.6, 129.9, 134.6, 137.0, 137.8, 152.0, 170.0. ESMS m/z 384.3 $[(M+H)]^+$. LC/MS $t_R$ 9.31 (383.9 $[M+H]^+$) min.

34b ($W_1$=5-Cl, $R_1$=2-chlorophenyl, $R_{2b}$=$CH_3CO$, $R_2$ =H).

To a stirred solution of 11s (50 mg, 0.140 mmol) in THF (5.0 ml) under a nitrogen atmosphere at rt was added acetic anhydride (26.5 μL, 0.280 mmol, 2 eq), DIEA (90.6 μL, 0.702 mmol, 5 eq) and DMAP (1.7 mg, 0.014 mmol, 0.1 eq) and stirring was continued for 1 hr. Acetyl chloride (20 μL, 0.28 mmol, 2 eq) was added and was stirring continued for 1 hr. Further acetyl chloride (20 μL, 0.28 mmol, 2 eq) was added and stirring was continued for 24 hrs. The reaction mixture was partitioned between dichloromethane and water, the aqueous phase was back extracted twice with dichloromethane, then the combined organic phases were dried with brine and sodium sulfate, then filtered and evaporated to give the crude amide (120 mg) as a yellow oil. The crude material was purified by flash chromatography on silica (5 g) with petroleum ether:ethyl acetate (2:1) to give 34b as a white solid (34.0 mg, 0.853 mmol, 61% yield). $R_f$ (silica, petroleum ether:ethyl acetate (2:1))=0.20. HPLC (214 nm) $t_R$=8.82 (87.7%) min. $^1$H NMR (400 MHz, $CDCl_3$) δ 2.38 (s, 3H), 3.15 (d, J=17.2 Hz, 1H), 3.22 (d, J=17.2 Hz, 1H), 3.78 (s, 3H), 5.90 (s, 1H), 6.78 (brs, 1H), 7.24 (dd, J=8.8, 2.4 Hz, 1H), 7.29–7.37 (m, 1H), 7.39–7.47 (m, 2H), 8.01 (d, J=7.6 Hz, 1H), 8.07 (d, J=8.4 Hz, 1H), 5.38 (brs, 1H). $^{13}$C NMR (400 MHz, $CDCl_3$) δ 24.3, 33.4, 45.5, 52.9, 125.1, 127.4, 127.7, 128.4, 129.5, 130.2, 130.3, 130.6, 134.8, 134.9, 169.4, 171.6. ESMS m/z 292.3 $[(M-HSCH_2CO_2CH_3+H)]^+$, 398.1 $[(M+H)]^+$. LC/MS $t_R$ 8.73 (397.9 $[(M+H)]^+$, 794.8 $[(2M+H)]^+$) min.

34c ($W_1$=H, $R_1$=2-methylphenyl, $R_{2b}$=benzoyl, $R_{2c}$=H)

Step 1. To a solution of benzophenone 9 ($W_1$=H, $R_1$=2-methylphenyl) (287 mg, 0.9 mmol) in DMF (10 ml) at 0° C. was added sodium borohydride (35 mg, 0.9 mmol) in one portion and the mixture stirred for 2 h, keeping the temperature between 0–4° C. The mixture was then poured into water (200 ml), acidified to pH=5 with dilute HCl, then extracted with ethyl acetate (20 ml). The aqueous layer was extracted with ethyl acetate (20 ml×3) and the combined ethyl acetate layers were washed with water (60 ml x 2). The organic phase was dried ($Na_2SO_4$) and concentrated under reduced pressure to yield the crude product that is used immediately in the next step.

Step 2: To a stirred solution of the above crude product in TFA (5.0 ml) under a nitrogen atmosphere at rt was added methyl thioglycolate (0.323 ml, 3.62 mmol, 4 eq). After stirring for 18 hrs the TFA was evaporated and the residue partitioned between dichloromethane and aqueous NaOH (1 mol/L). The aqueous phase was back extracted with dichloromethane and the combined organics were dried with brine and sodium sulphate, then filtered and evaporated to give the crude product (317 mg) as a yellow solid: The crude material was purified by flash chromatography on silica (15 g) by eluting with petroleum ether:ethyl acetate (5:1 then 2:1) to give the thiol ether 34c as a yellow oil (225 mg, 0.555 mmol, 61%): $R_f$ (petroleum ether:ethyl acetate (2:1)=0.65; $EM_{calc.}$=405.1 $(M+1)^+_{obs}$=406.1; $^1$H NMR (400 MHz) 8.90 (1H, br s), 8.01 (1H, d, J=7.6 Hz), 7.88–7.96 (2H, m), 7.70 (1H, dd, J=0.8, 7.6 Hz), 7.40–759 (m, 3H), 7.01–7.36 (6H, m), 5.83 (1H, s), 3.41 (3H, s), 3.13 (2H, s), 2.11 (3H, s); $^{13}$C NMR (400 MHz) 170.79, 165.98, 137.35, 136.22, 135.46, 134.76, 133.50, 131.77, 131.11, 130.12, 129.08, 128.55, 128.49, 128.44, 127.89, 127.53, 126.46, 125.26, 124.61, 52.25, 46.41, 33.27, 19.12.

34d ($W_1$=5-Cl, $R_1$=3-methyl-2-thiophenyl, $R_{2b}$=—NHC(=O)C($CH_3$) $R_{2c}$=H)

To a solution of the alcohol 3c ($W_1$=5-Cl, $R_1$=3-methyl-2-thiophenyl) (50 mg, 0.14 mmol) in methanol (3 ml) was added 1M HCl (3 ml) dropwise. The reaction was then heated at a gentle reflux for 15 min. After this time TLC analysis indicated the formation of a new product. The reaction was worked up by diluting with brine (30 ml), raising the pH to >10 with 1M NaOH and the aqueous solution was extracted with dichloromethane (4×20 ml). The combined organic phase was dried over sodium sulfate, filtered and the solvent removed in vacuo. The residue was dissolved in dichloromethane (5 ml), methyl thioglycolate (50 $\mu$L) was added followed by TFA (50 $\mu$L). After 15 min TLC indicated the complete consumption of starting material. The solvent was removed in vacuo and the residue was purified on silica gel (50 g) using petroleum spirit/ethyl acetate 4:1 as eluent to yield 34d, isolated as white solid (50 mg, 79% yield); clogP=5.65; $R_f$ (petroleum spirit/ethyl acetate, 4:1)=0.50; HPLC (214 nm) $t_R$=10.81 (99.34%) min; $^1$H NMR (400 MHz, $CDCl_3$) δ 1.33 (s, 9H), 2.10 (s, 3H), 3.15 (d, J=15.6 Hz, 1H), 3.27 (d, J=15.6 Hz, 1H), 3.71 (s, 3H), 5.83 (s, 1H), 6.83 (d, J=5.1 Hz, 1H), 7.20 (d, J=5.1 Hz, 1H), 7.25 (dd, J=2.4, 8.8 Hz, 1H), 7.43 (d, J=2.4 Hz, 1H), 7.80 (d, J=8.8 Hz, 1H), 8.22 (s, 1H); $^{13}$C NMR (100 MHz, $CDCl_3$) δ 13.9, 27.5, 33.4, 39.7, 42.6, 52.5, 124.6, 126.6, 128.5, 128.9, 130.6, 130.8, 132.4, 134.5, 135.0, 136.2, 170.8, 177.3; ESMS m/z 426.3 $[M+H]^+$, 443.3 $[M+NH_4]^+$; LC/MS $t_R$=9.74 (426.2 $[M+H]^+$, 851.2 $[2M+3H]^+$) min.

34e ($W_1$=5-Cl, $R_1$=1-methyl-2-pyrrolyl, $R_{2b}$=—NHC(=O)$C(CH_3)_3$, $R_{2c}$=H)

Following a similar procedure of 34c, 34e was obtained from the reaction of methyl thioglycolate and the condensation product of 2a with 1-methylpyrrole-2-carboxaldehyde. Compound 34e was isolated as a brown crystaline solid (233 mg, 75% yield); clogP=3.90; $R_f$ (petroleum ether:ethyl acetate (4:1)=0.53; HPLC (214 nm) $t_R$=9.51 (90.86%) min; $^1$H NMR (400 MHz, $CDCl_3$) δ 1.27 (s, 9H), 3.10 (d, J=15.5 Hz, 1H), 3.27 (d, J=15.5 Hz, 1H), 3.50 (s, 3H), 3.70 (s, 3H), 5.54 (s, 1H), 6.07 (m, 1H), 6.14 (m, 1H), 6.62 (t, J=2.2 Hz, 1H), 7.26 (m, 1H), 7.33 (d, J=2.4 Hz, 1H), 7.82 (d, J=8.6 Hz, 1H), 8.16 (s, 1H); $^{13}$C NMR (100 MHz, $CDCl_3$) δ 27.4, 32.8, 34.0, 39.6, 42.2, 52.5, 107.3, 110.0, 124.0, 126.5, 127.3, 128.5, 129.4, 130.4, 131.5, 134.8, 170.9, 177.2; ESMS m/z 303.2 $[M SCH_2CO_2CH_3]^+$, 408.9 $[M+H]^+$; LC/MS $t_R$=9.37 (303.1 $[M-SCH_2CO_2CH_3]^+$, 408.9 $[M+H]^+$, 817.1 $[2M+H]^+$) min.

Preparation of 35f ($W_1$=5-Cl, $R_1$=2-fluorophenyl, $R_{3a}$=$CH_3$)

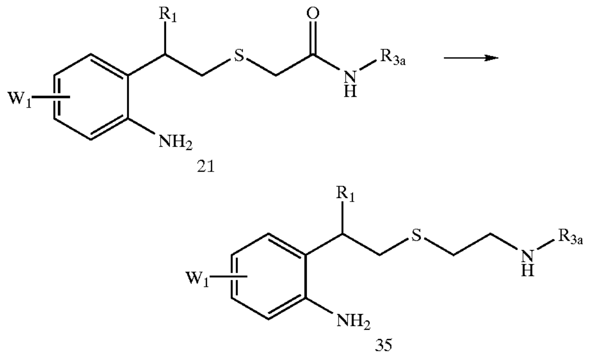

21

35

To a solution of the corresponding amide derivative 21f (178 mg, 0.48 mmol) in dry THF was added dropwise a solution of $BH_3$.THF complex in THF (1.0 M, 1.45 ml, 1.45 mmol) at 0° C. under argon. The reaction mixture was then stirred at 0° C.—rt overnight. After the reaction was complete indicated by TLC analysis, the reaction mixture was carefully quenched with MeOH at 0° C., and then diluted with EtOAc. The organic layer was washed with saturated $NaHCO_3$, brine, dried over $Na_2SO_4$, filtered, concentrated, and the residue was purified by column chromatography on silica gel (EtOAc/Hexane: 30/70) to give 35f (138 mg, 84%) as colorless oil. $^1$H NMR (500 MHz, $CDCl_3$) δ 2.50–2.52 (m, 3H), 2.67–2.80 (m, 2H), 2.94–3.00 (m, 2H), 3.11–3.26 (m, 2H), 3.63–3.68 (b, 2H), 4.05–4.08 (m, 1H), 4.42–4.47 (m, 1H), 6.60–6.63 (m, 1H), 7.03–7.27 (m, 6H); MS calcd for $C_{17}H_{21}ClFN_2S$ ($MH^+$) 339.11, found 339.1.

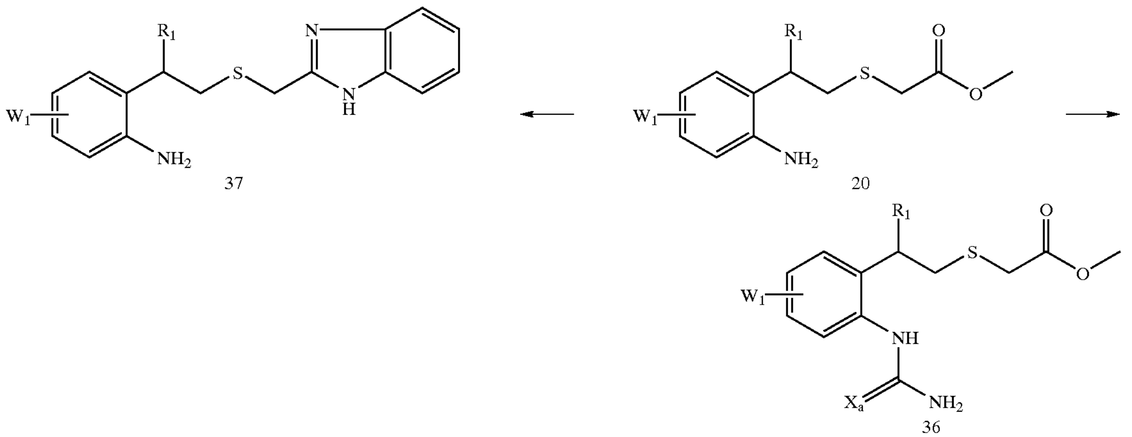

37

20

36

Preparation of 36a ($W_1$=5-Br, $R_1$=2-fluorophenyl, $X_a$=S): A solution of the corresponding ester 20c (175 mg, 0.44 mmol) and KSCN (215 mg, 2.21 mmol) in $AcOH/H_2O$ (3:1) was heated at 80° C. overnight. After it was cooled down to room temperature, the reaction mixture was then diluted with $H_2O$, and was extracted twice with EtOAc. The combined organic layers were washed with saturated $NaHCO_3$, brine, dried over $Na_2SO_4$, filtered, concentrated, and the residue was purified by column chromatography on silica gel ($MeOH/CH_2Cl_2$, 2.5/97.5) to give 36a (88 mg, 44%) as white solid. MS calcd for $C_{18}H_{19}BrFN_2O_2S_2$ ($MH^+$) 457.01, found 456.9.

Preparation of 36b ($W_1$=5-Br, $R_1$=2-fluorophenyl, $X_a$=O): A solution of the corresponding ester 20e (131 mg, 0.33 mmol) and KOCN (135 mg, 1.66 mmol) in $AcOH/H_2O$ (3:1)

was heated at 80° C. overnight. After it was cooled down to room temperature, the reaction mixture was then diluted with $H_2O$, and was extracted twice with EtOAc. The combined organic layers were washed with saturated $NaHCO_3$, brine, dried over $Na_2SO_4$, filtered, concentrated, and the residue was purified by column chromatography on silica gel ($MeOH/CH_2Cl_2$, 2.5/97.5) to give 36b (90 mg, 62%) as white solid. $^1H$ NMR (500 MHz, $CDCl_3$) δ 3.23 (d, J=7.9 Hz, 2H), 3.28 (s, 2H), 3.82 (s, 3H), 4.75 (t, J=7.9 Hz, 1H), 7.02 (t, J=9.4 Hz, 1H), 7.16–7.20 (m, 2H), 7.25–7.29 (m, 2H), 7.33 (dd, J=8.4 Hz, 1.6 Hz, 1H), 7.60 (d, J=8.4 Hz, 1H), 8.66 (b, 1H); MS calcd for $C_{18}H_{19}BrFN_2O_3S$ ($MH^+$) 441.03, found 441.0.

Preparation of 36c ($W_1$=5-Br, $R_1$=2-fluorophenyl, X=NH): A solution of the corresponding ester 20c (186 mg, 0.47 mmol), HCl (1.0 M in $Et_2O$, 1.0 ml, 1.0 mmol), and $H_2NCN$ (80 mg, 2.0 mmol) in chlorobenzene was stirred at 130° C. overnight. The reaction mixture was then concentrated under reduced pressure, and the product was precipitated from the solution. The white solid was collected by filtration, and washed with ether to give 36c (115 mg, 52%). $^1H$ NMR (500 MHz, $CDCl_3$) δ 1.88 (b, 3H), 3.24–3.35 (m, 4H), 3.67 (s, 3H), 4.78 (t, J=7.9 Hz, 1H), 6.99 (t, J=9.3 Hz, 1H), 7.10 (d, J=8.2 Hz, 1H), 7.15 (t, J=7.7 Hz, 1H), 7.22–7.26 (m, 1H), 7.33 (t, J=7.7 Hz, 1H), 7.41–7.42 (m, 1H), 7.43 (s, 1H); MS calcd for $C_{18}H_{20}BrFN_3O_2S$ ($MH^+$) 440.04, found 440.1.

Preparation of 37a ($R_1$=5-Br, R2=2-fluorophenyl): To a solution of 1,2-phenylenediamine (70 mg, 0.65 mmol) in dry THF was added dropwise a solution of n-BuLi (2.0 M, 1.0 ml, 2.0 mmol) in cyclohexane at 0° C. under argon. The solution was stirred at 0° C. for 0.5 hrs. To this mixture was then added dropwise a solution of 20c (130 mg, 0.33 mmol) in THF. The reaction mixture was stirred at 0° C. rt overnight. After the reaction was complete indicated by LC-MS analysis, the reaction mixture was carefully quenched with aqueous $NH_4Cl$ solution, and extracted twice with EtOAc. The combined organic layers were washed with saturated $NaHCO_3$, brine, dried over $Na_2SO_4$, filtered, concentrated, and the residue was purified by column chromatography on silica gel (EtOAc/Hexane: 40/60) to give 37a (106 mg, 71%) as yellow solid. $^1H$ NMR (500 MHz, $CDCl_3$) δ 3.01 (s, 2H), 3.19–3.33 (m, 2H), 4.43 (t, J=7.9 Hz, 1H), 6.50 (d, J=8.3 Hz, 1H), 7.01–7.41 (m, 9H), 7.91 (s, 1H); MS calcd for $C_{22}H_{20}BrFN_2S$ ($MH^+$) 456.06, found 456.1.

General Procedure for the Preparation of Sulfoxides and Sulphones

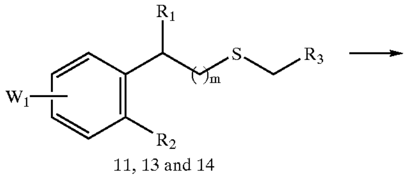

11, 13 and 14

-continued

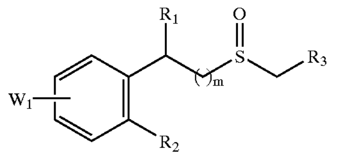

+

38

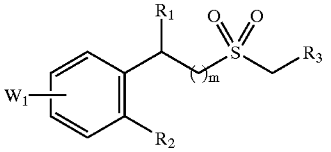

39

To a solution of the corresponding thioether in dry $CH_2Cl_2$ (5.0 ml) was added m-chloroperoxybenzoic acid (2–3 equiv.) at 0° C. under argon. The reaction mixture was then stirred at 0° C. was allowed to warm to rt overnight. The reaction mixture was diluted with $CH_2Cl_2$ and was washed with saturated $NaHCO_3$, brine, dried over $Na_2SO_4$, filtered, concentrated, and the residue was purified by column chromatography on silica gel.

38a ($W_1$=5-Cl, $R_1$=2-chlorophenyl, $R_2$=$NH_2$, $R_3$=3-methyl-1,2,4-oxadiazol-5-yl, m=1): obtained from 22a (70 mg, 0.18 mmol) as a white solid (41 mg, 56%). $^1H$ NMR (500 MHz, $CDCl_3$) δ 2.45 (s, 3H), 3.53–3.67 (m, 2H), 4.18 and 4.32 (AB q, J=14.3 Hz, 2H), 5.01 (dd, J=10.0 Hz, 5.5 Hz, 1H), 6.63 (d, J=8.9 Hz, 1H), 6.99 (d, J=8.9 Hz, 1H), 7.05 (dd, J=8.4 Hz, 2.8 Hz, 1H), 7.24–7.29 (m, 3H), 7.42 (d, J=7.9 Hz, 1H); MS calcd for $C_{18}H_{18}Cl_2N_3O_2S$ ($MH^+$) 410.05, found 409.9.

38b ($W_1$=5-Cl, $R_1$=2-chlorophenyl, $R_2$=$NH_2$, $R_3$=3-(4-fluorophenyl)-1,2,4-oxadiazol-5-yl, m=0): obtained from 14a. LC-MS: calcd. For $C_{22}H_{16}Cl_2FN_3O_2S$: 475.03; found: 497.9 $[M+Na]^+$.

38c ($W_1$=5-Cl, $R_1$=2-chlorophenyl, $R_3$=$NH_2$, $R_3$=[(2,2-diphenylethyl)amino]carbonyl, m=0): obtained from 13i. LC-MS: calcd. For $C_{29}H_{26}Cl_2N_2O_2S$: 536.1; found: 558.9 $[M+Na]^+$.

38d and 39d ($W_1$=5-Cl, $R_1$=2-chlorophenyl, $R_2$=H, $R_3$=[(cyclohexymethyl)amino]carbonyl, m=0) were obtained from 13aj. 38d: LC-MS: calcd. For $C_{22}H_{25}Cl_2NO_2S$: 437.1; found: 437.8 $[M+H]^+$. 39d: $C_{22}H_{25}C_{12}NO_3S$: 453.1, found: 453.8 $[M+H]^+$.

38e ($W_1$=5-Br, $R_1$=2-fluorophenyl, $R_2$=$NH_2$, $R_3$=(hydroxyamino)carbonyl, m=0): isolated as a side product in the synthesis of 21 (79 mg, 33%) as white solid: $^1H$ NMR (500 MHz, $CDCl_3$) δ 3.38–3.63 (m, 4sH), 4.71 (t, J=8.00 Hz, 1H), 6.52 (d, J=8.5 Hz, 1H), 6.97 (t, J=9.2 Hz, 1H), 7.04–7.13 (m, 3H), 7.23–7.27 (m, 2H); MS calcd. for $C_{16}H_{27}BrFN_2O_3S$ ($MH^+$) 415.01, found: 414.9.

Synthesis of 39

39

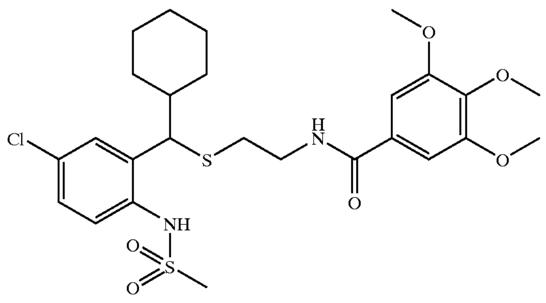

To a solution of 16o (0.035 g, 0.071 mmol) in dry $CH_2Cl_2$ (5 mL), DIPEA (0.049 mL, 0.28 mmol) was added and stirred at 0° C. A solution of MsCl (0.016 mL, 0.21 mmol) in dry $CH_2Cl_2$ (2 mL) was added dropwise slowly over 30 min and the reaction was stirred for additional 3 hrs. The reaction was diluted with $CH_2Cl_2$ (20 mL) and washed with a saturated solution of $NaHCO_3$ (2×10 mL), water (10 mL) and brine (20 mL). The organic layer was dried over sodium sulfate, filtered and concentrated under vacuum. The crude product was purified by flash chromatography on a silica gel column using a mixture of petroleum ether and ethyl acetate as eluent to give 39 as a semi-transparent solid (0.032 g, 80% yield): LC/MS calcd for $C_{26}H_{35}ClN_2O_6S_2$: 570 [$M-C_{12}H_{16}NO_4S$], found: 300.

Synthesis of 40

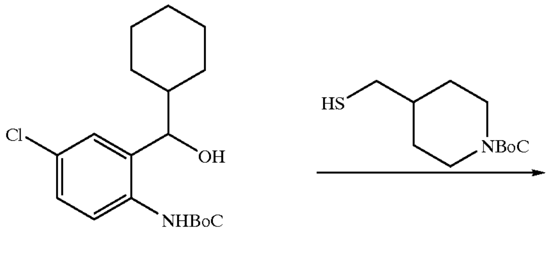

10ak

-continued

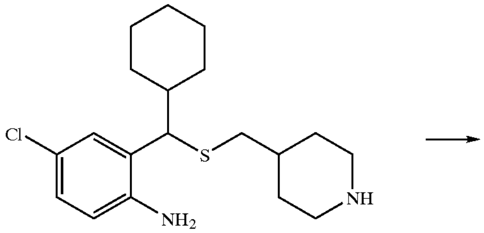

151a

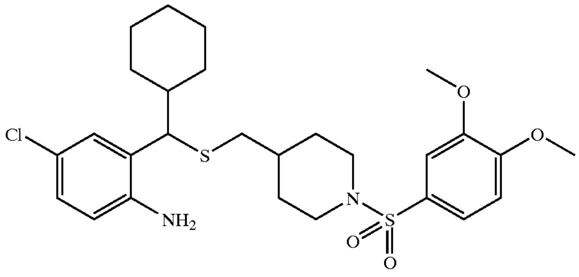

40

Using similar procedures as for 151 and 18f, 40 was obtained from 10ak and 151a (72% yield): LC/MS calcd for $C_{27}H_{37}ClN_2O_4S_2$: 552 [$M+Na^+$], found: 575.

Synthesis of 41a and 41b

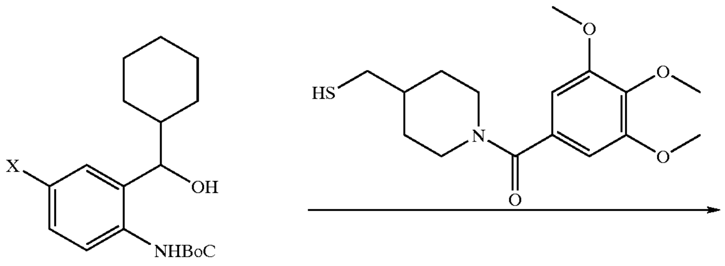

-continued

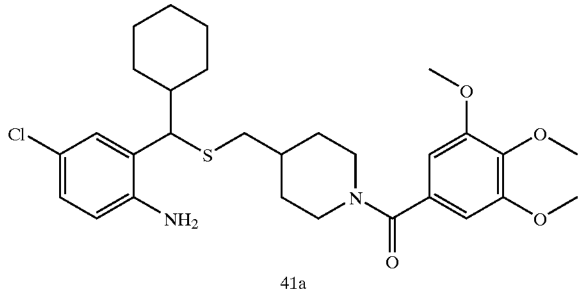

41a

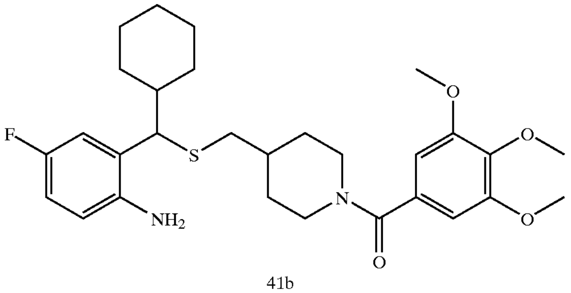

41b 41a (X=Cl)

Using a similar procedure as for 15l, 41a was obtained from 10ak (84% yield): LC/MS calcd for $C_{29}H_{39}ClN_2O_4S$: 546 [M+Na$^+$], found: 569.

41b (X=F)

Using a similar procedure as for 15l, 41b was obtained from 10ak (85% yield): LC-MS calcd for $C_{29}H_{39}FN_2O_4S$: 530 [M+Na$^+$], found: 553.

EXAMPLE 15

Representative Compounds

The compounds listed in the following Table 1 were made by the procedures disclosed in Examples 1–14 above.

TABLE 1

| Representative Compounds<br>Compound Structure & Number |
|---|
| 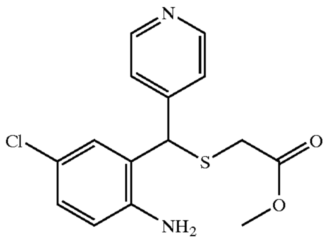<br>11a |
| 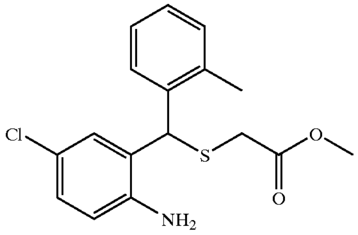<br>11aa |

TABLE 1-continued

| Representative Compounds<br>Compound Structure & Number |
|---|
| 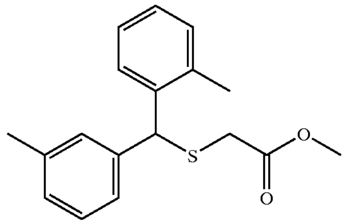<br>11ab |
| 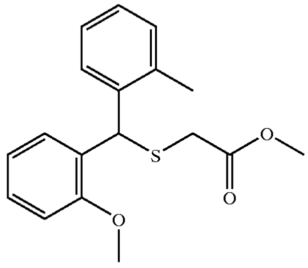<br>11ac |
| 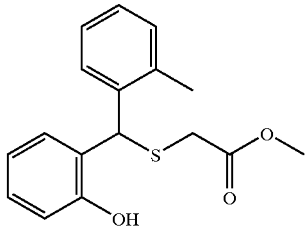<br>11ad |

TABLE 1-continued
Representative Compounds
Compound Structure & Number
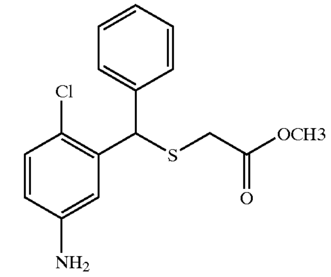
11ae
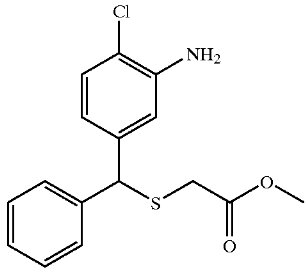
11af
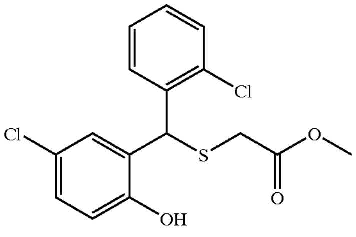
11ag
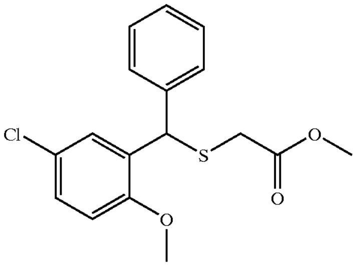
11ah
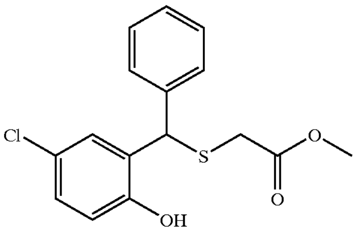
11ai
TABLE 1-continued
Representative Compounds
Compound Structure & Number
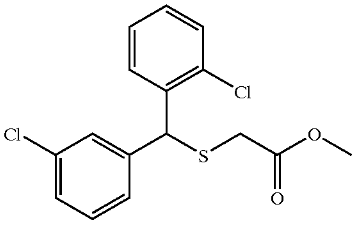
11aj
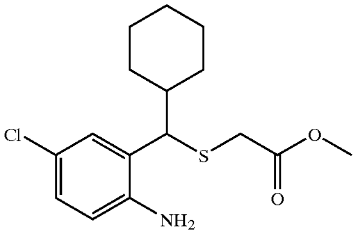
11ak
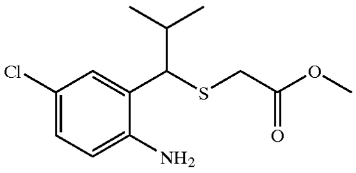
11al
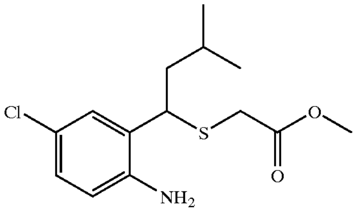
11am
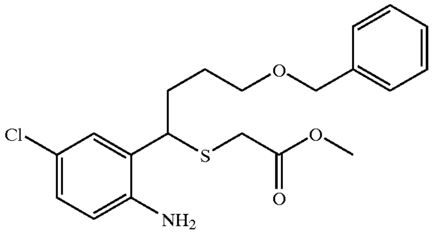
11an TABLE 1-continued
| Representative Compounds |
| --- |
| Compound Structure & Number |
| 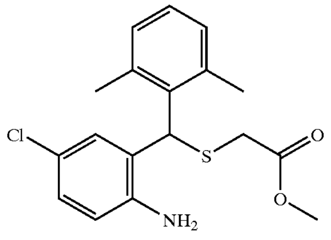 11b |
| 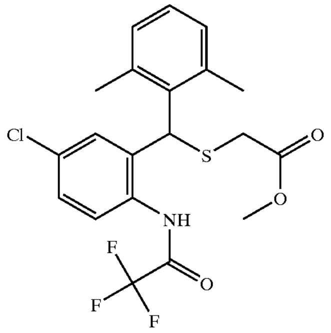 11ba |
| 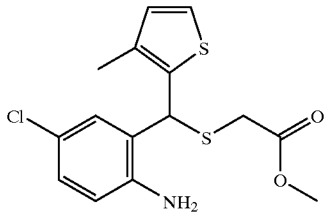 11c |
| 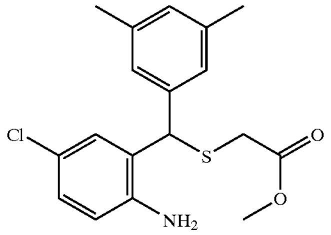 11d |
| 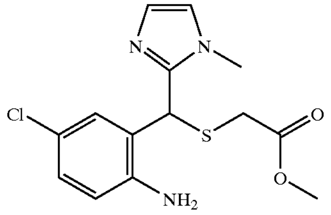 11e |
TABLE 1-continued
| Representative Compounds |
| --- |
| Compound Structure & Number |
| 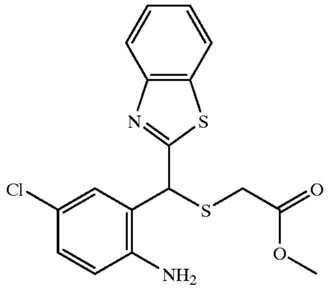 11f |
| 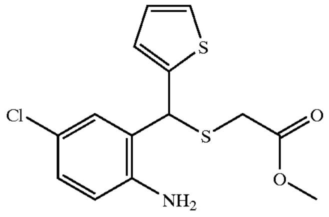 11g |
| 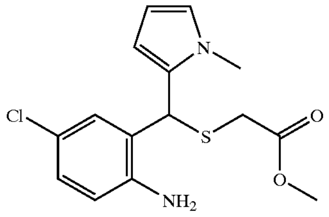 11h |
| 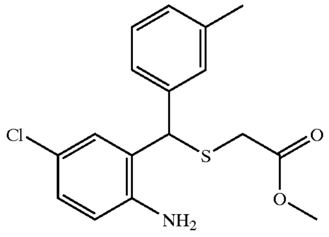 11i |
| 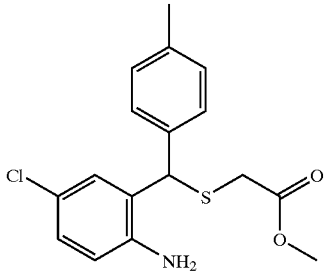 11j |

TABLE 1-continued
| Representative Compounds<br>Compound Structure & Number |
| --- |
| 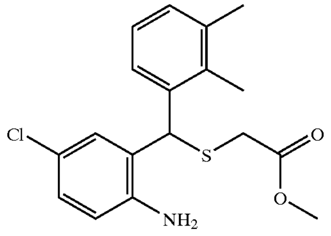<br>11k |
| 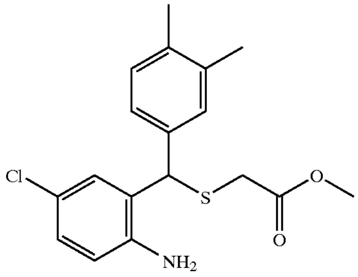<br>11l |
| 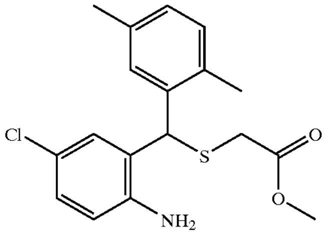<br>11m |
| 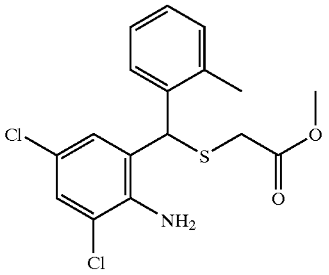<br>11n |
| 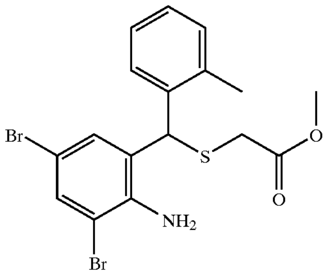<br>11o |
TABLE 1-continued
| Representative Compounds<br>Compound Structure & Number |
| --- |
| 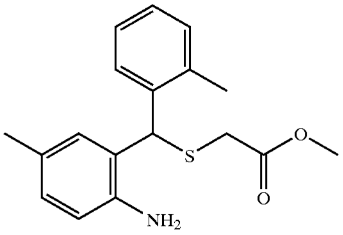<br>11p |
| 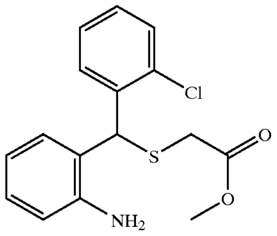<br>11r |
| 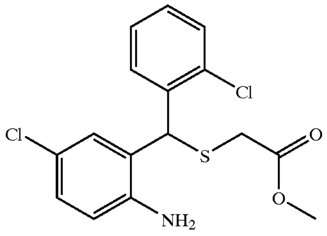<br>11s |
| 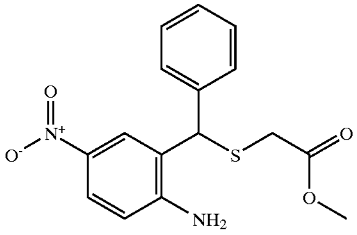<br>11t |
| 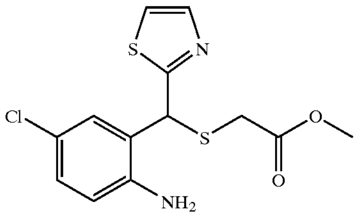<br>11u |

TABLE 1-continued
| Representative Compounds |
| --- |
| Compound Structure & Number |
| 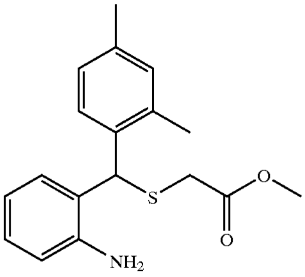 11v |
| 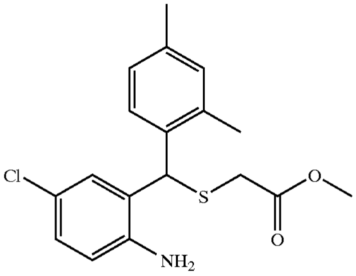 11w |
| 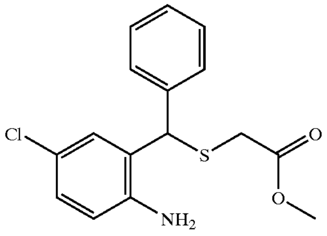 11x |
| 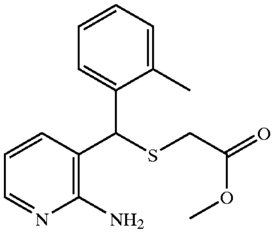 11y |
| 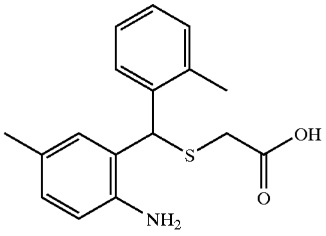 12p |
TABLE 1-continued
| Representative Compounds |
| --- |
| Compound Structure & Number |
| 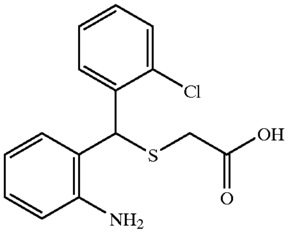 12r |
| 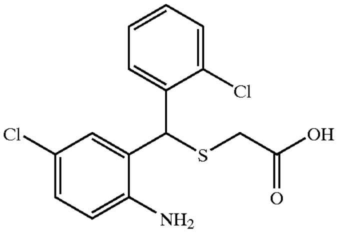 12s |
| 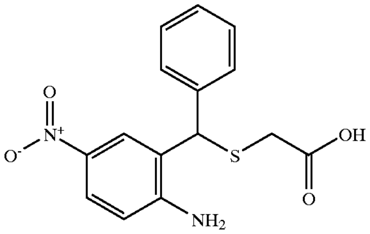 12 |
| 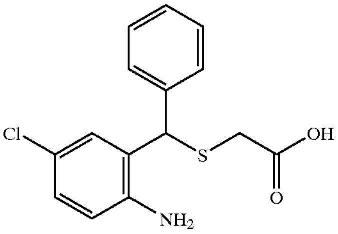 12x |
| 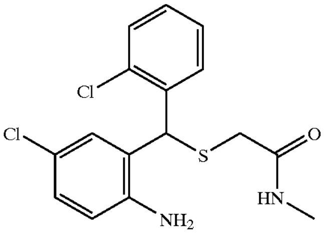 13a |

TABLE 1-continued
| Representative Compounds<br>Compound Structure & Number |
|---|
| 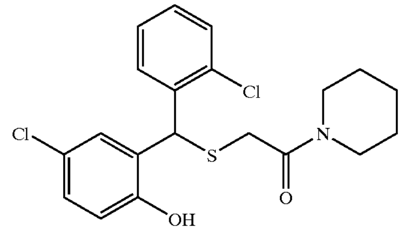<br>13ag |
| 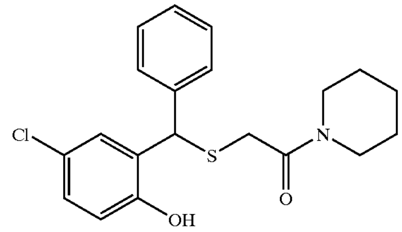<br>13ai |
| 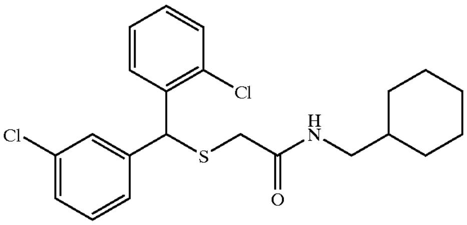<br>13aj |
| 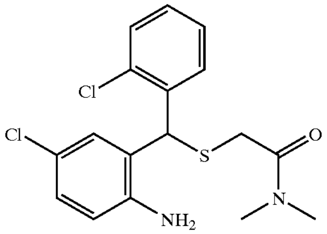<br>13b |
| 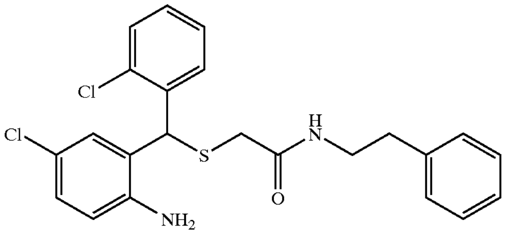<br>13c |
TABLE 1-continued
| Representative Compounds<br>Compound Structure & Number |
|---|
| 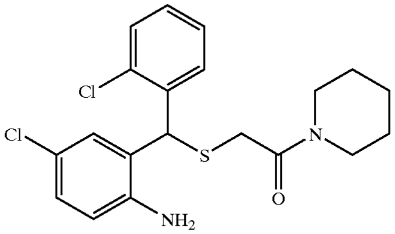<br>13d |
| 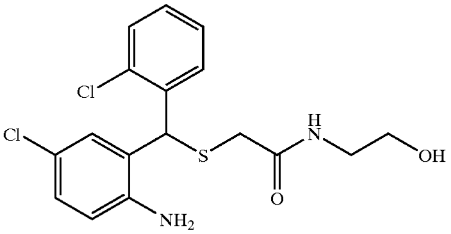<br>13e |
| 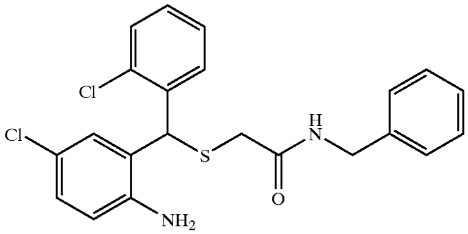<br>13f |
| 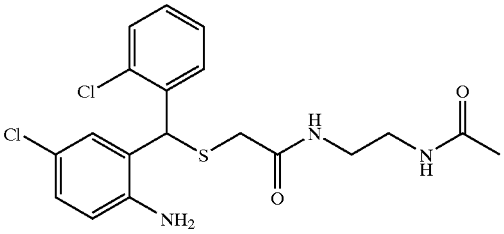<br>13g |
| 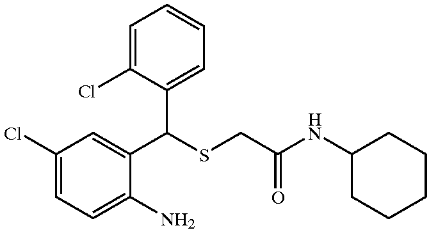<br>13h |

TABLE 1-continued
| Representative Compounds<br>Compound Structure<br>& Number |
|---|
| 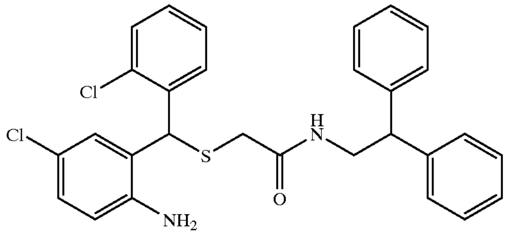<br>13i |
| 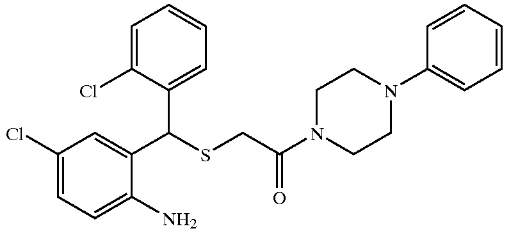<br>13j |
| 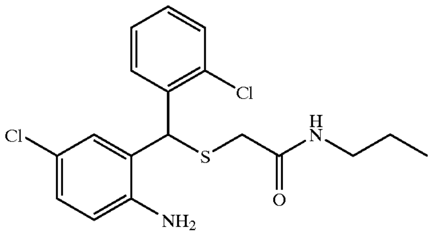<br>13k |
| 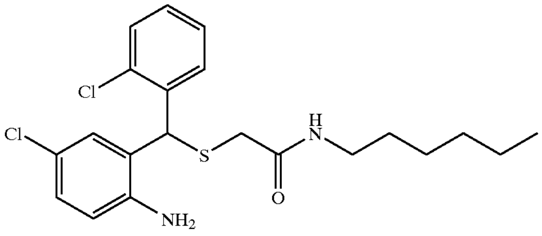<br>13l |
| 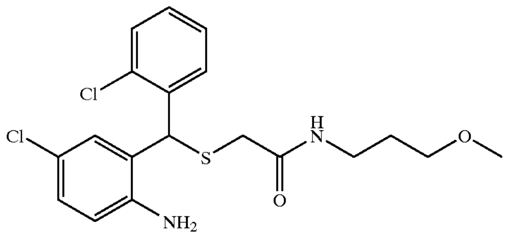<br>13m |
TABLE 1-continued
| Representative Compounds<br>Compound Structure<br>& Number |
|---|
| 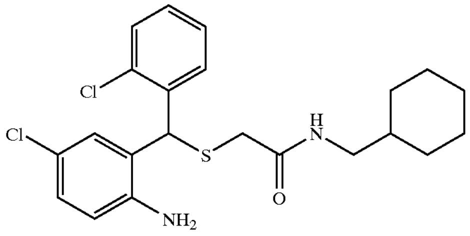<br>13n |
| 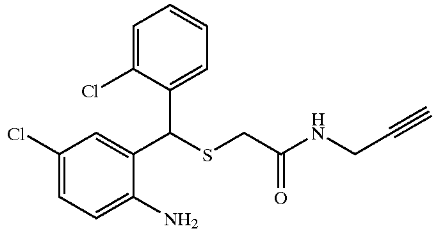<br>13o |
| 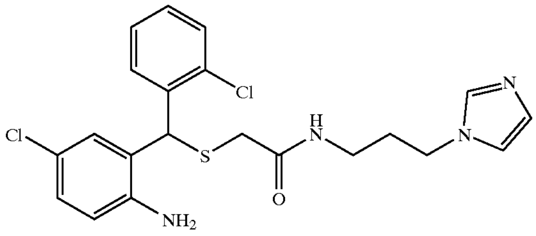<br>13p |
| 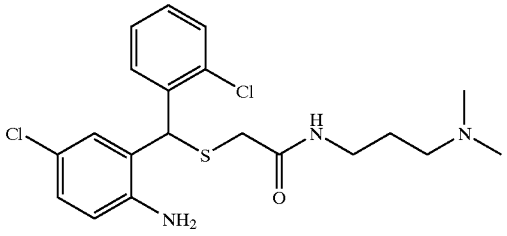<br>13q |
| 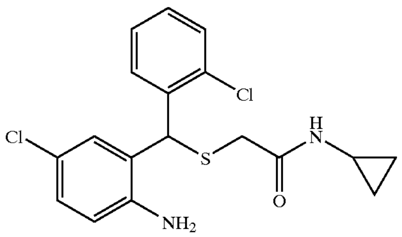<br>13r |

TABLE 1-continued
| Representative Compounds Compound Structure & Number |
|---|
| 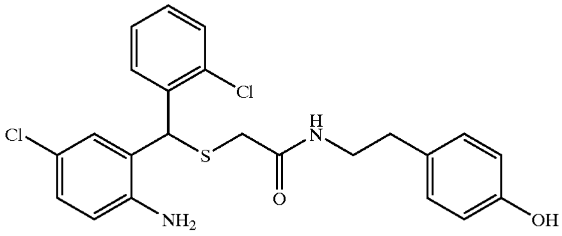 |
| 13s |
| 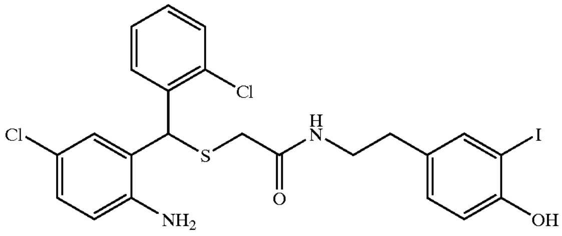 |
| 13t |
| 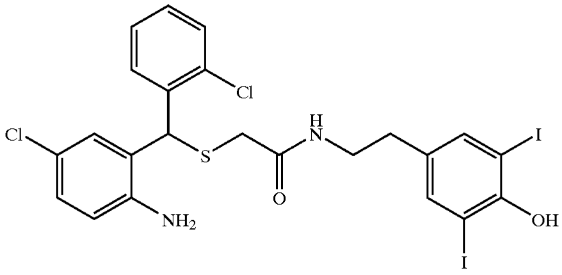 |
| 13u |
| 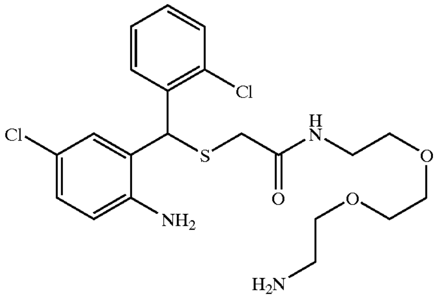 |
| 13v |
| 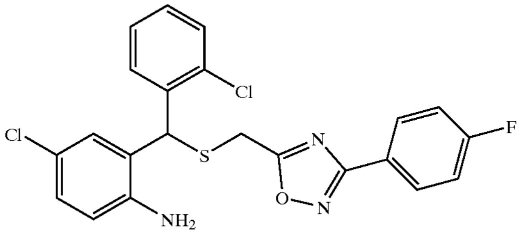 |
| 14a |
TABLE 1-continued
| Representative Compounds Compound Structure & Number |
|---|
| 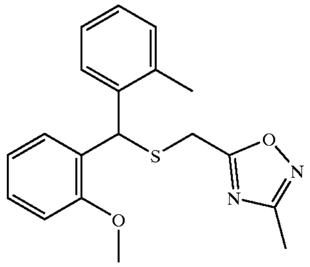 |
| 14ac |
| 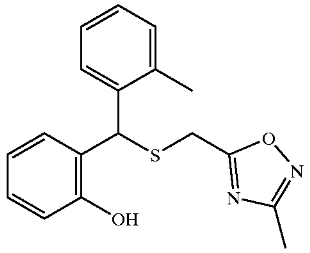 |
| 14ad |
| 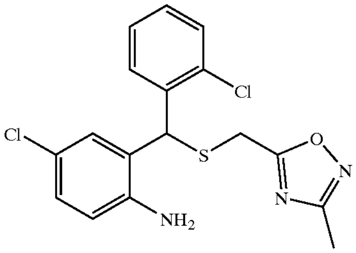 |
| 14b |
| 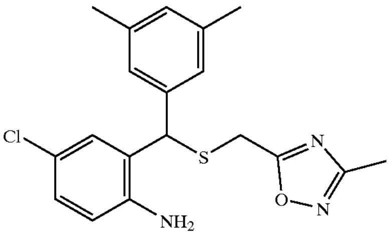 |
| 14d |
| 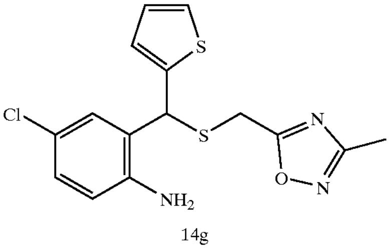 |
| 14g |

TABLE 1-continued
| Representative Compounds |
| --- |
| Compound Structure & Number |
| 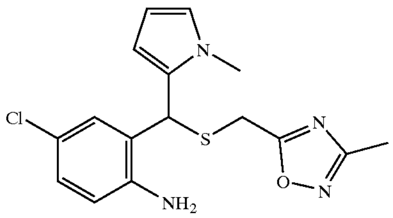 |
| 14h |
| 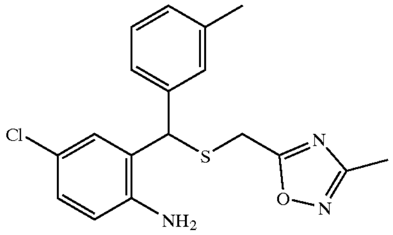 |
| 14i |
| 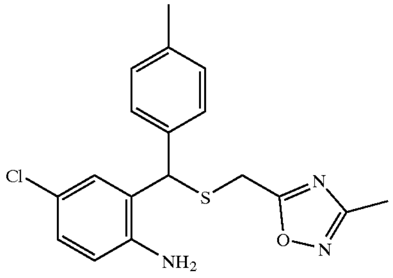 |
| 14j |
| 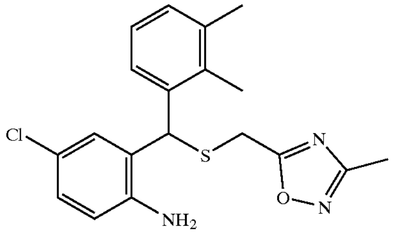 |
| 14k |
| 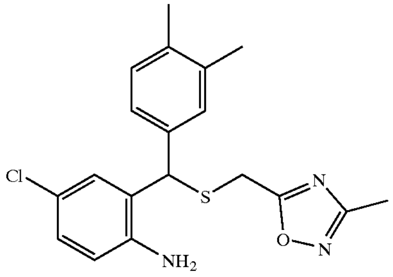 |
| 14l |
TABLE 1-continued
| Representative Compounds |
| --- |
| Compound Structure & Number |
| 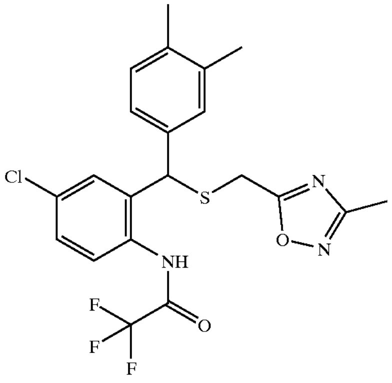 |
| 14la |
| 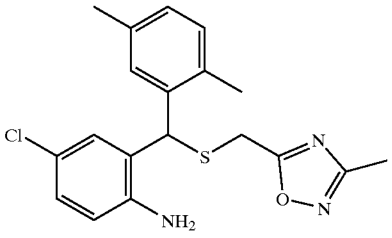 |
| 14m |
| 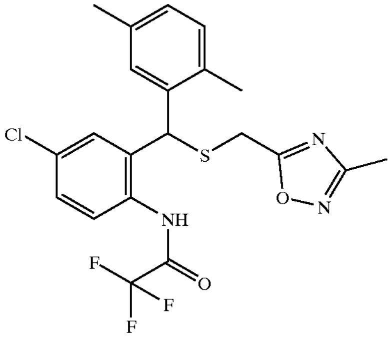 |
| 14ma |
| 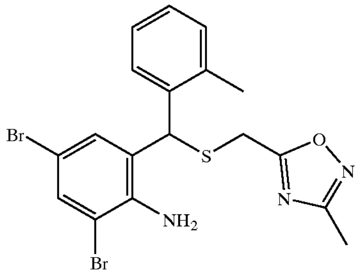 |
| 14o |

TABLE 1-continued
Representative Compounds
Compound Structure & Number
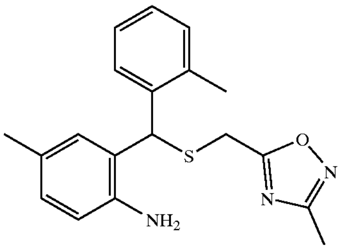
14p
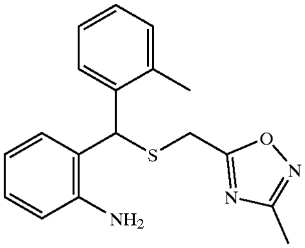
14q
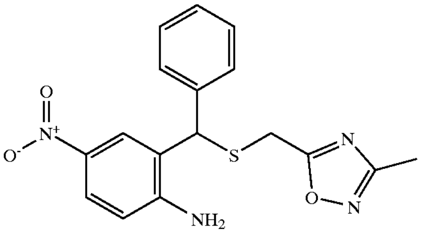
14t
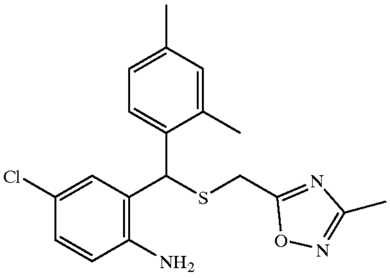
14w
TABLE 1-continued
Representative Compounds
Compound Structure & Number
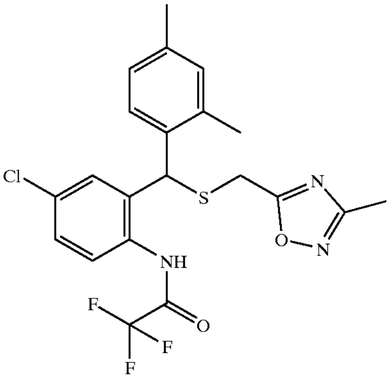
14wa
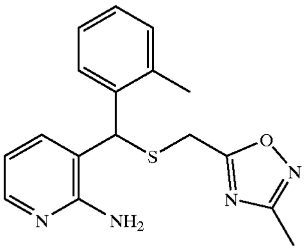
14y
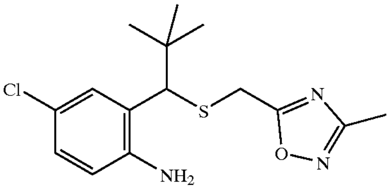
14z
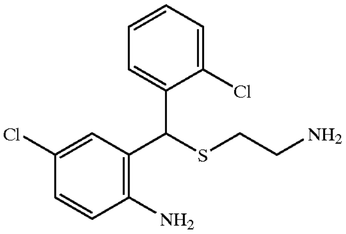
15a
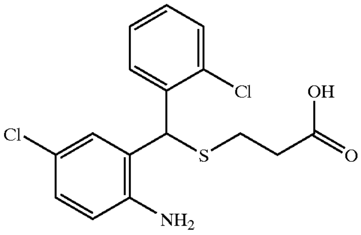
15b TABLE 1-continued
Representative Compounds
Compound Structure & Number
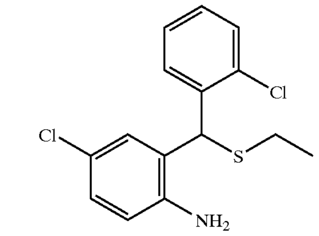
15c
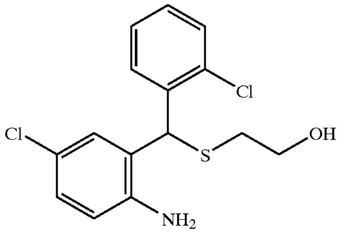
15d
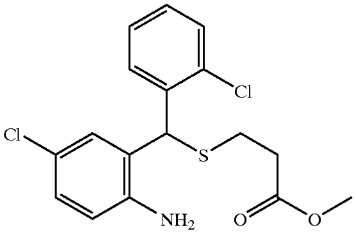
15e
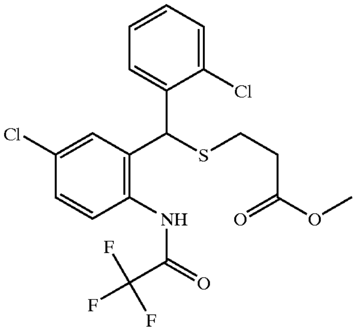
15ea
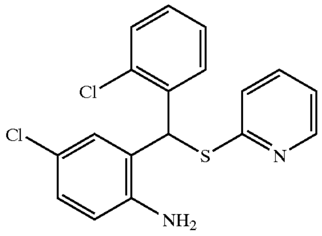
15f
TABLE 1-continued
Representative Compounds
Compound Structure & Number
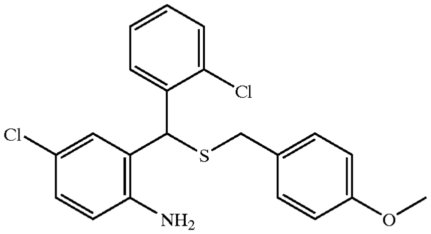
15g
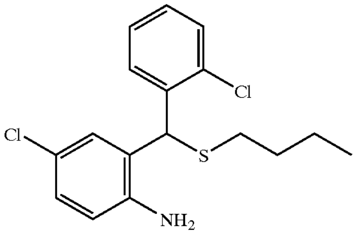
15h
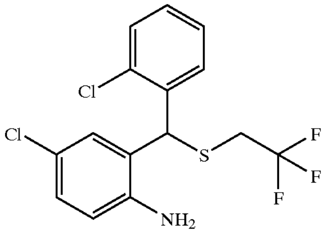
15i
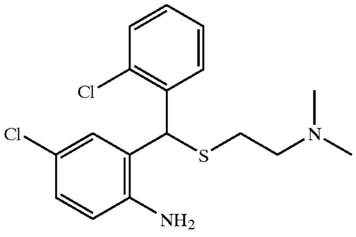
15j
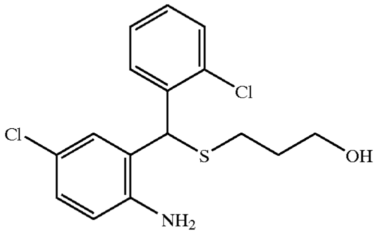
15k TABLE 1-continued
Representative Compounds
Compound Structure & Number
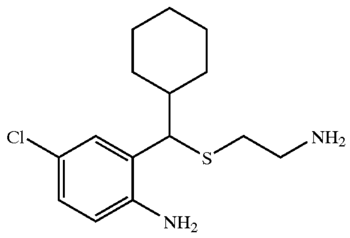
15l
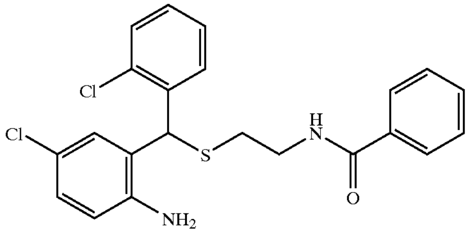
16a
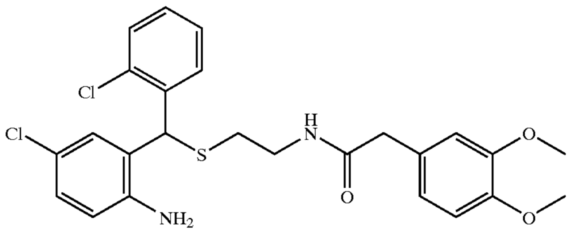
16b
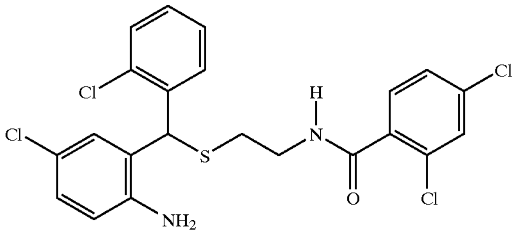
16c
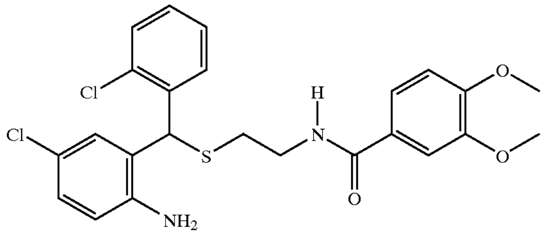
16d
TABLE 1-continued
Representative Compounds
Compound Structure & Number
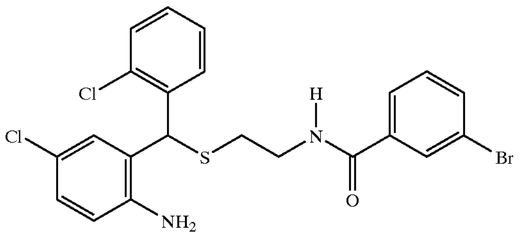
16e
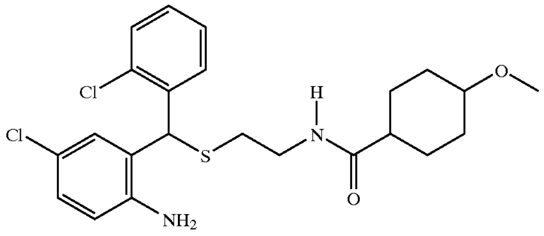
16f
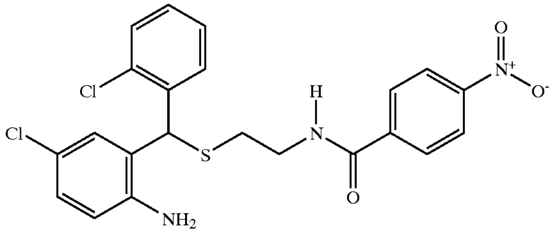
16g
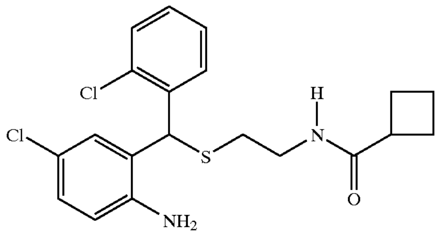
16h
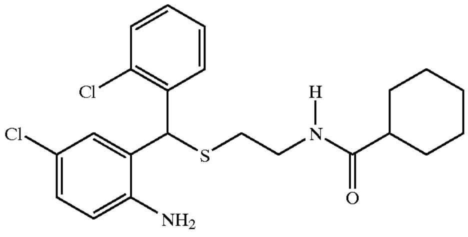
16i TABLE 1-continued
| Representative Compounds |
|---|
| Compound Structure & Number |
| 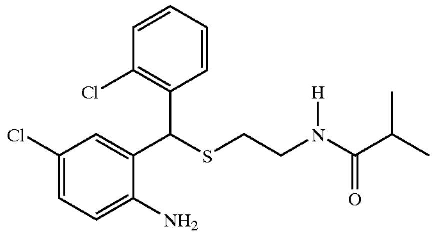 |
| 16j |
| 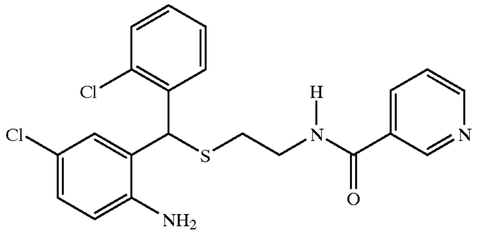 |
| 16k |
| 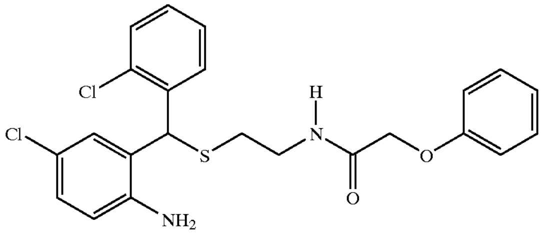 |
| 16l |
| 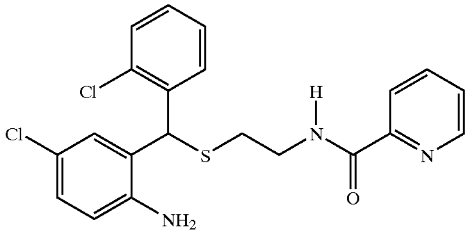 |
| 16m |
| 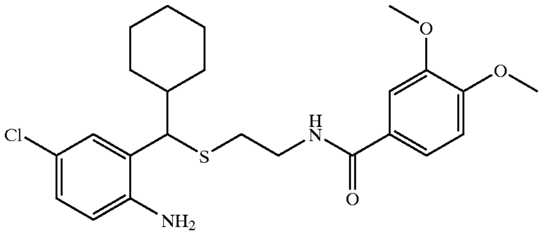 |
| 16n |
TABLE 1-continued
| Representative Compounds |
|---|
| Compound Structure & Number |
| 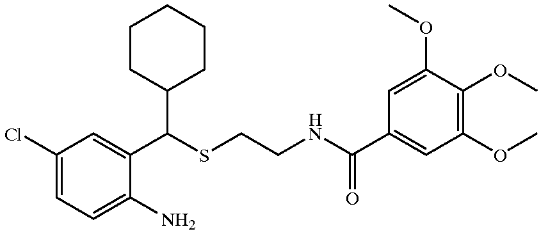 |
| 16o |
| 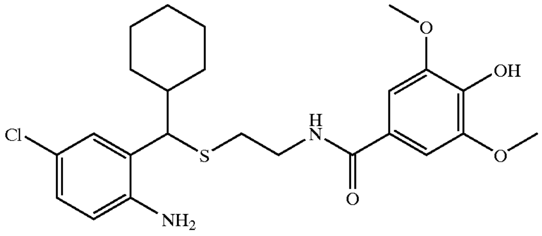 |
| 16p |
| 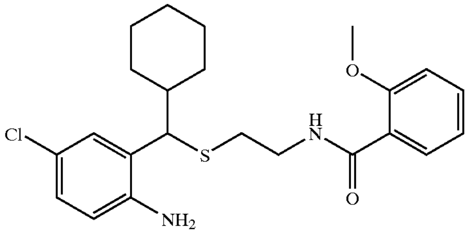 |
| 16q |
| 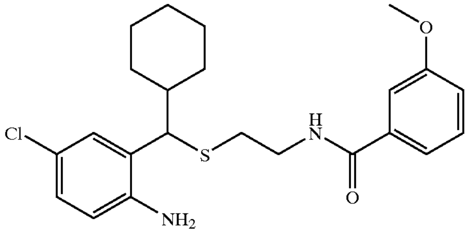 |
| 16r |
| 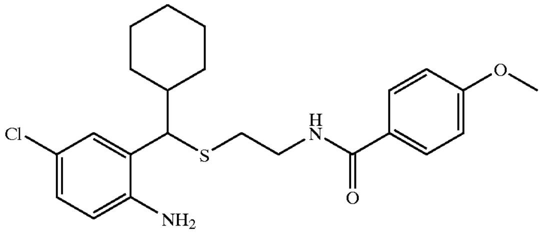 |
| 16s |

TABLE 1-continued
| Representative Compounds |
|---|
| Compound Structure & Number |
| 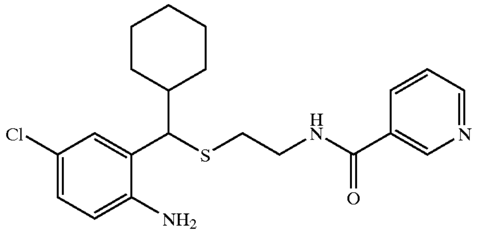 |
| 16t |
| 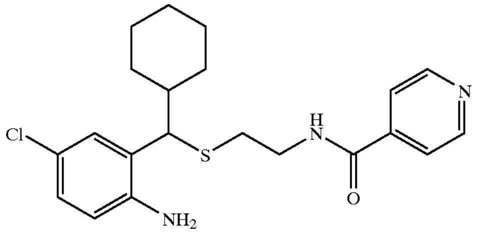 |
| 16u |
| 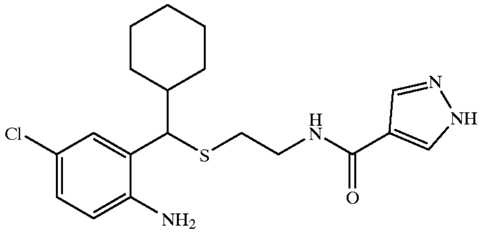 |
| 16v |
| 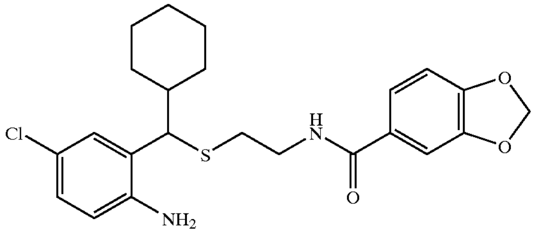 |
| 16w |
| 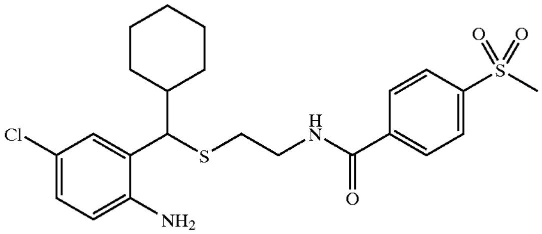 |
| 16x |
TABLE 1-continued
| Representative Compounds |
|---|
| Compound Structure & Number |
| 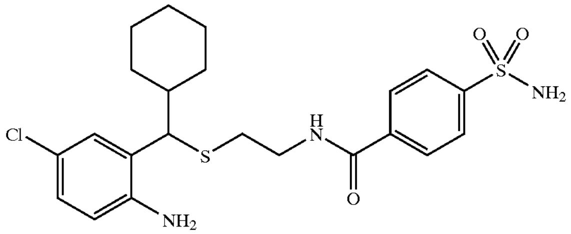 |
| 16y |
| 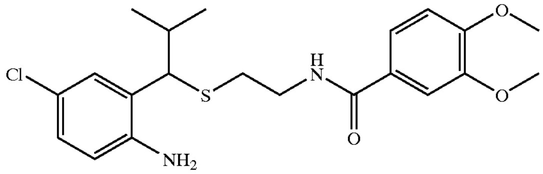 |
| 16z |
| 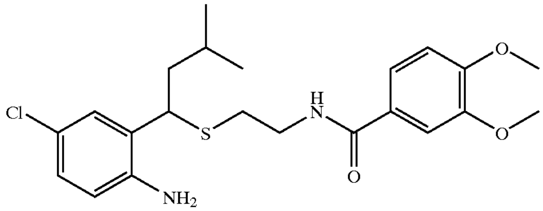 |
| 16aa |
| 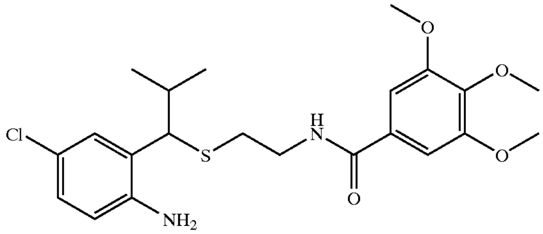 |
| 16ab |
| 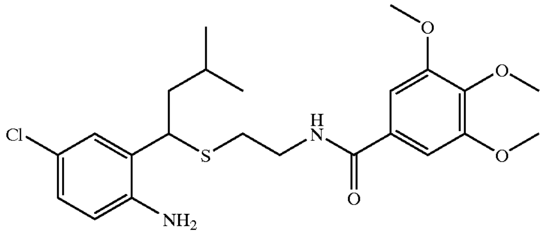 |
| 16ac |

TABLE 1-continued
Representative Compounds
Compound Structure & Number
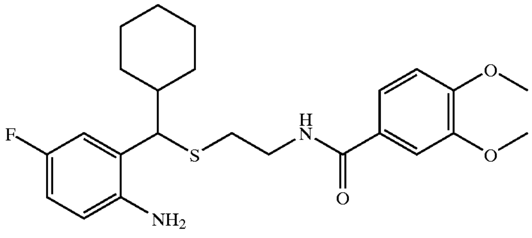
16ad
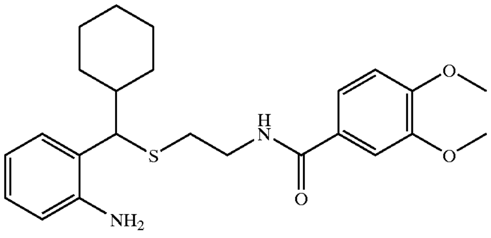
16ae
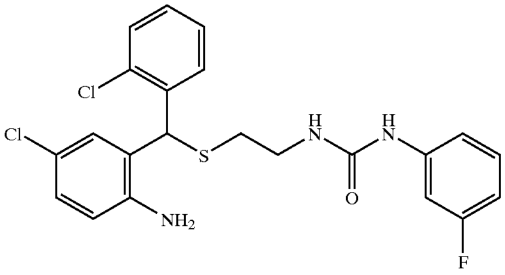
17a
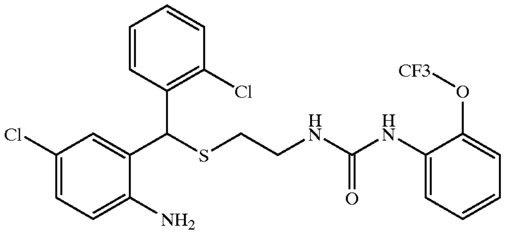
17b
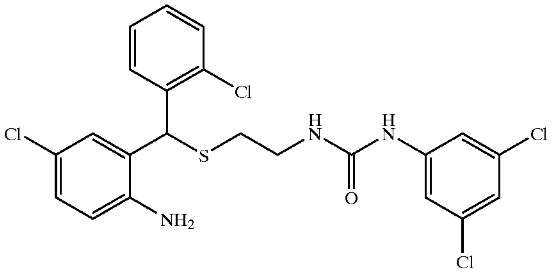
17c
TABLE 1-continued
Representative Compounds
Compound Structure & Number
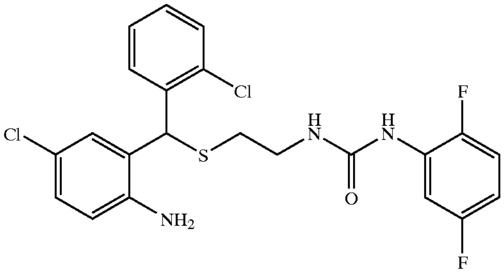
17d
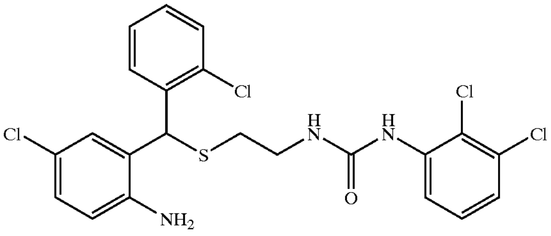
17e
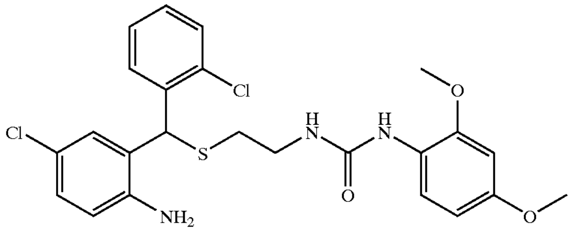
17f
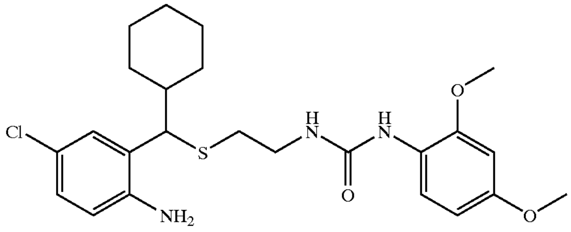
17g
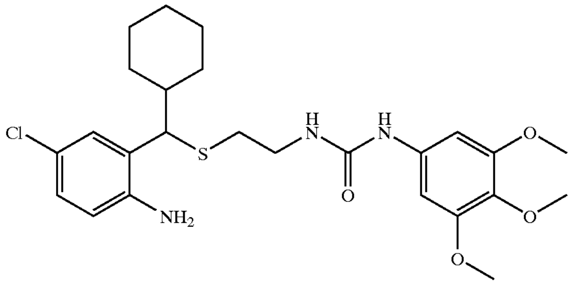
17h TABLE 1-continued
| Representative Compounds |
| --- |
| Compound Structure & Number |
| 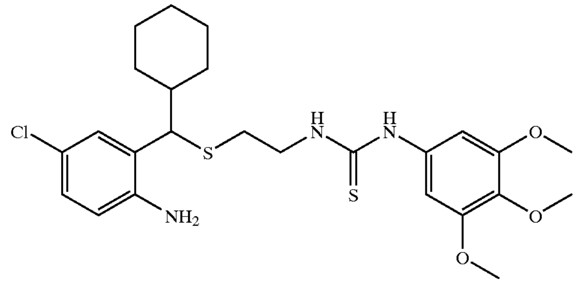 17i |
| 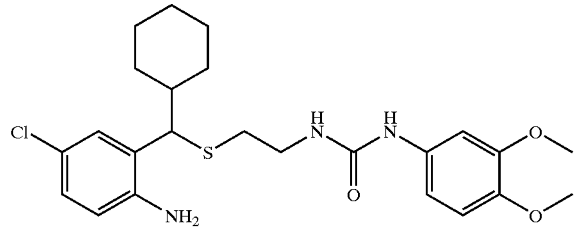 17j |
| 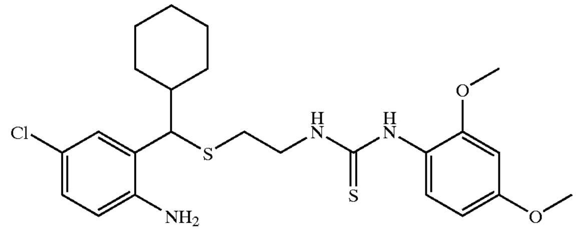 17k |
| 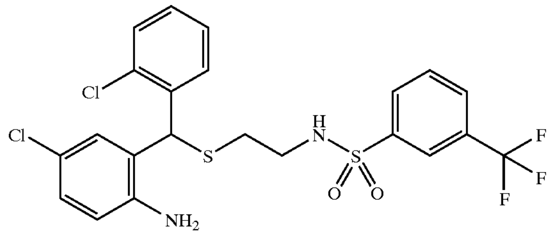 18a |
| 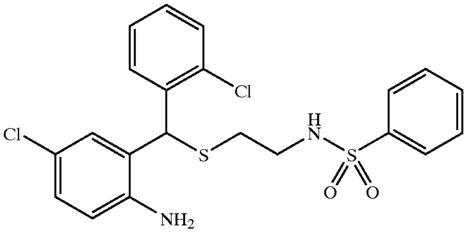 18b |
TABLE 1-continued
| Representative Compounds |
| --- |
| Compound Structure & Number |
| 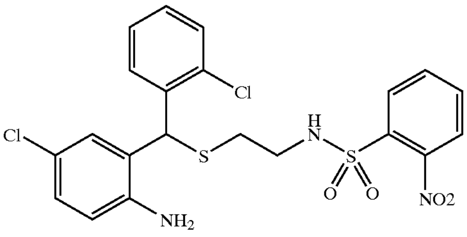 18c |
| 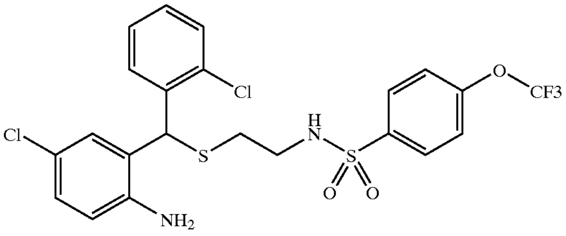 18d |
| 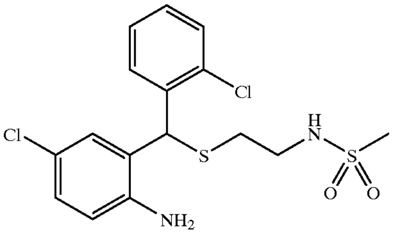 18e |
| 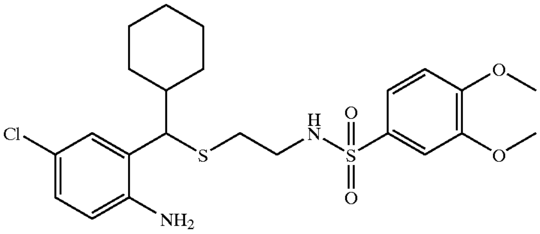 18f |
| 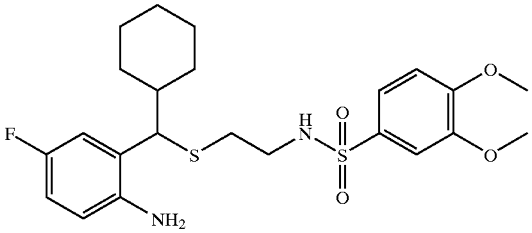 18g |

TABLE 1-continued
| Representative Compounds<br>Compound Structure & Number |
|---|
| 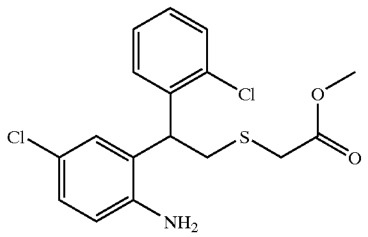<br>20a |
| 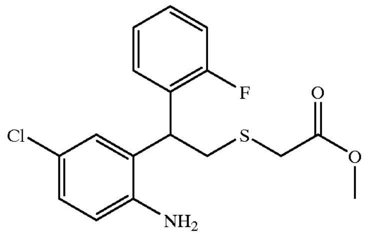<br>20b |
| 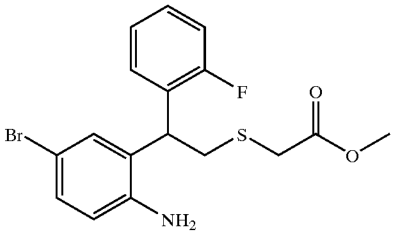<br>20c |
| 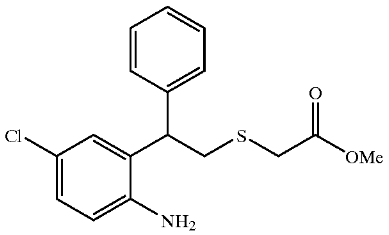<br>20d |
| 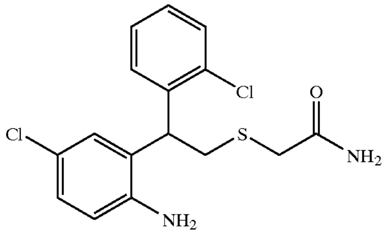<br>21a |
TABLE 1-continued
| Representative Compounds<br>Compound Structure & Number |
|---|
| 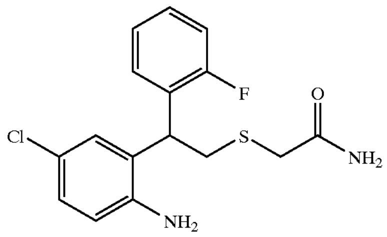<br>21b |
| 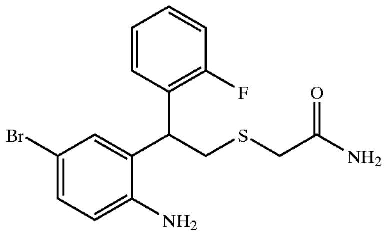<br>21c |
| 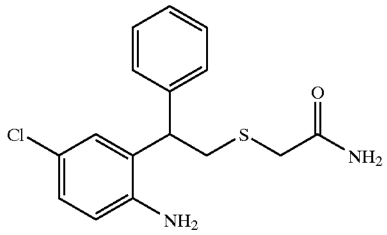<br>21d |
| 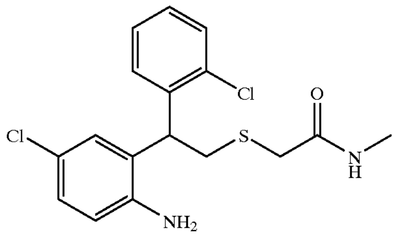<br>21e |
| 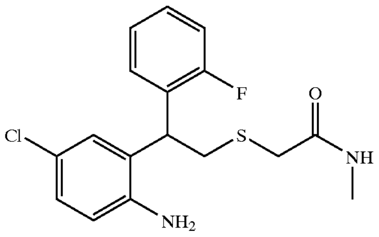<br>21f |

TABLE 1-continued
Representative Compounds
Compound Structure & Number
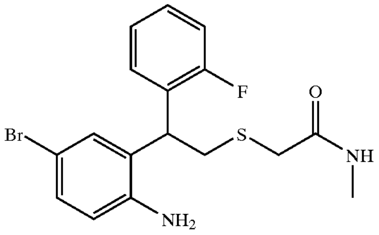
21g
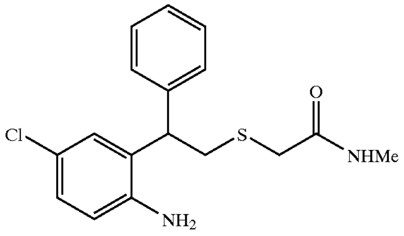
21h
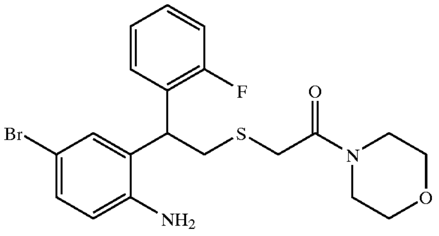
21i
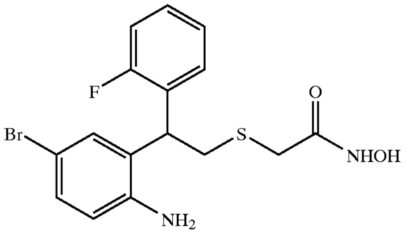
21j
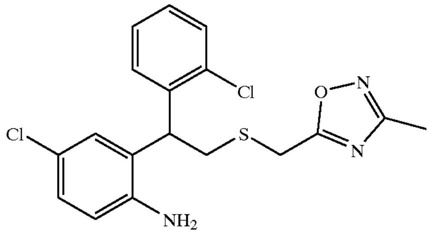
22a
TABLE 1-continued
Representative Compounds
Compound Structure & Number
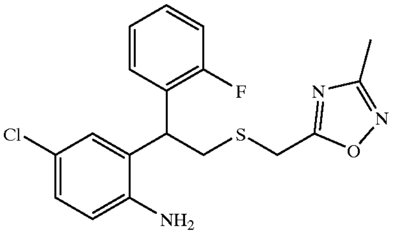
22b
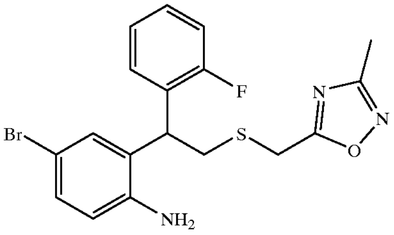
22c
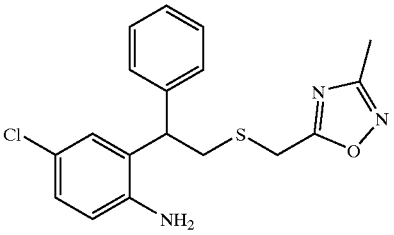
22d
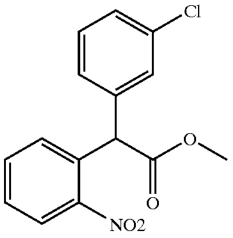
25a
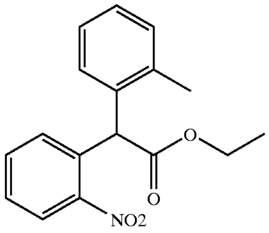
25b TABLE 1-continued
Representative Compounds
Compound Structure & Number
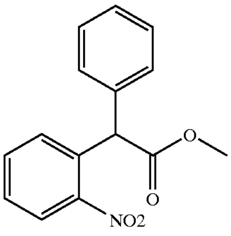
25c
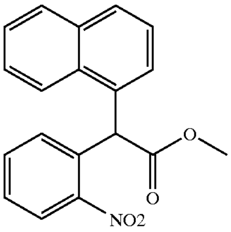
25d
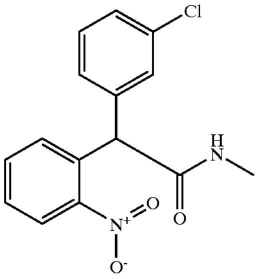
26a
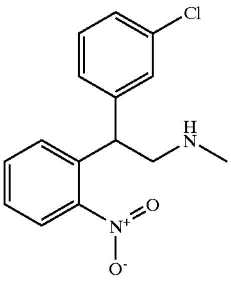
27a
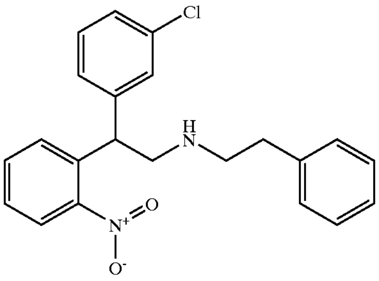
27b
TABLE 1-continued
Representative Compounds
Compound Structure & Number
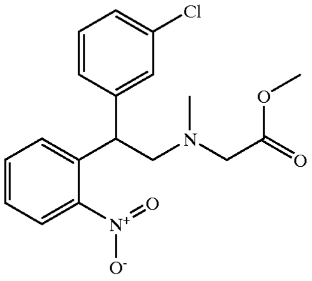
28a
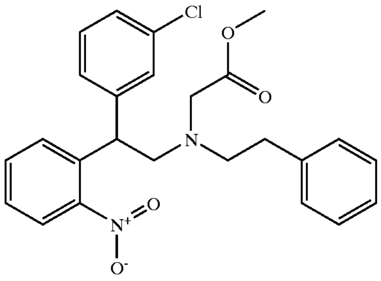
28b
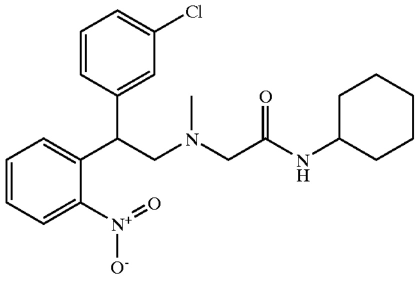
29a
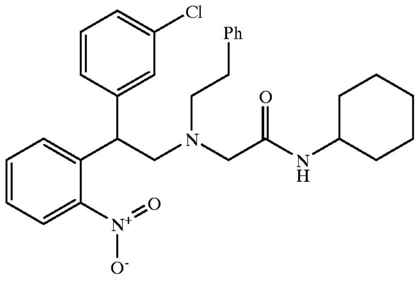
29b TABLE 1-continued
| Representative Compounds<br>Compound Structure & Number |
| --- |
| 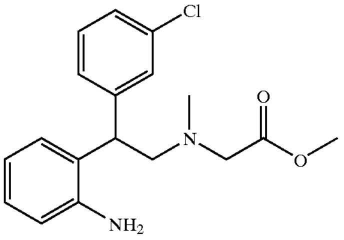 |
| 30a |
| 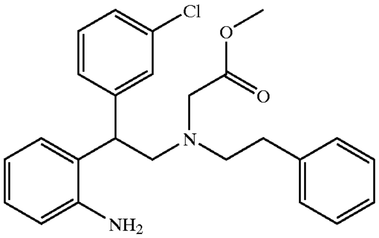 |
| 30b |
| 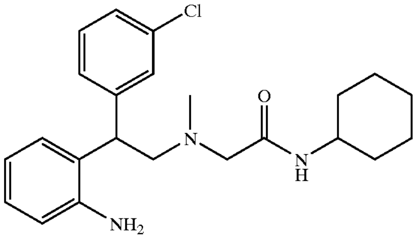 |
| 31a |
| 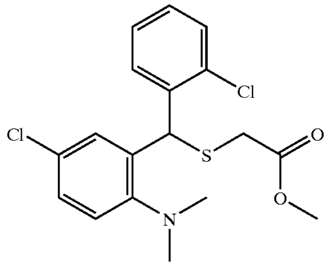 |
| 34a |
| 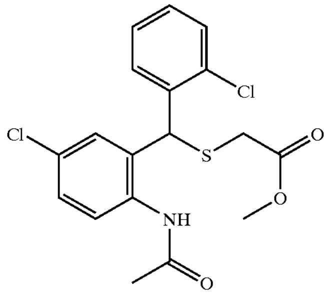 |
| 34b |
TABLE 1-continued
| Representative Compounds<br>Compound Structure & Number |
| --- |
| 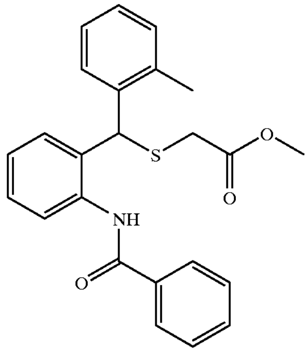 |
| 34c |
| 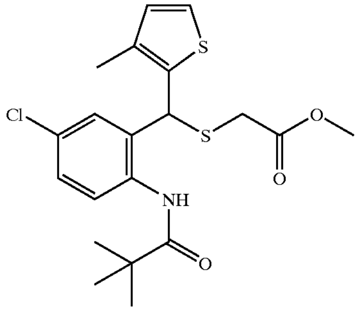 |
| 34d |
| 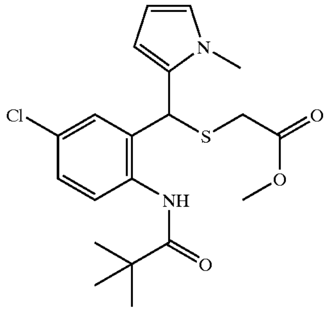 |
| 34e |
| 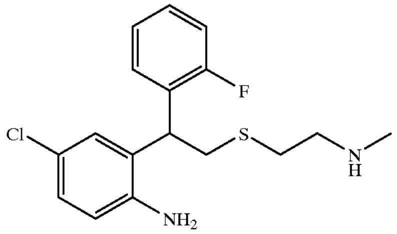 |
| 35f |

TABLE 1-continued
| Representative Compounds |
| --- |
| Compound Structure & Number |
| 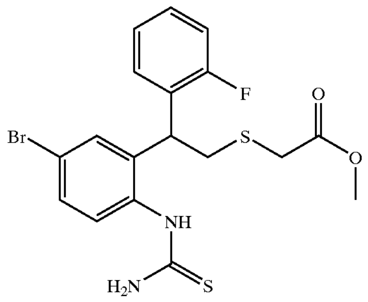 36a |
| 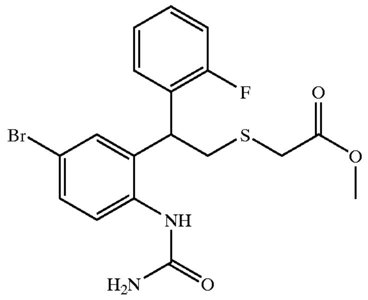 36b |
| 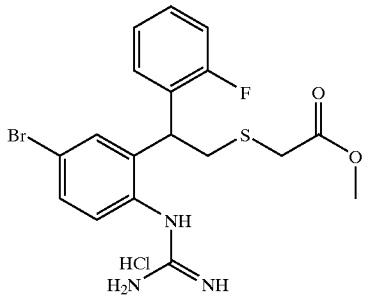 36c |
| 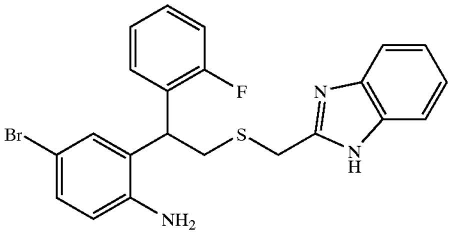 37a |
TABLE 1-continued
| Representative Compounds |
| --- |
| Compound Structure & Number |
| 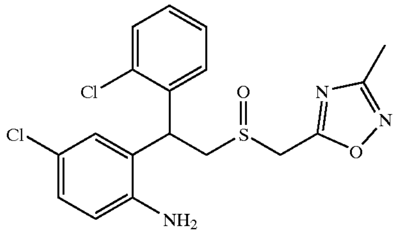 38a |
| 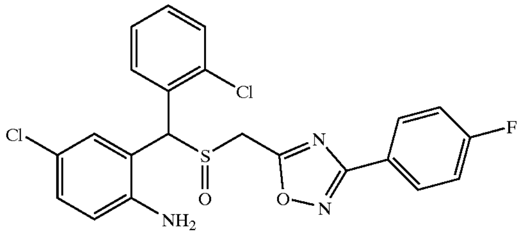 38b |
| 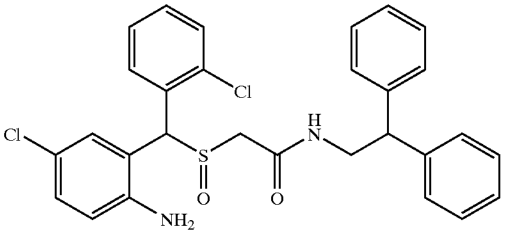 38c |
| 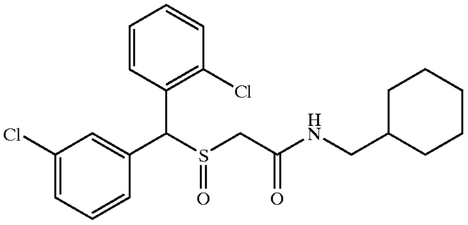 38d |
| 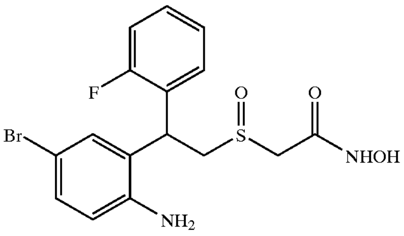 38e |

TABLE 1-continued

| Representative Compounds |
| --- |
| Compound Structure & Number |
| 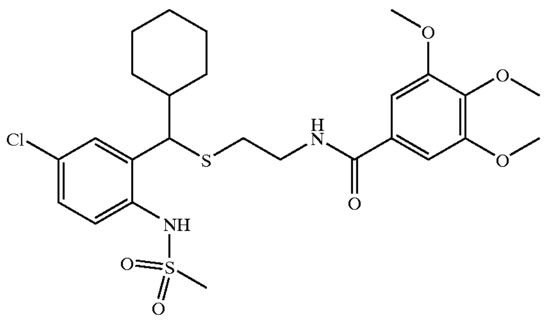 39 |
| 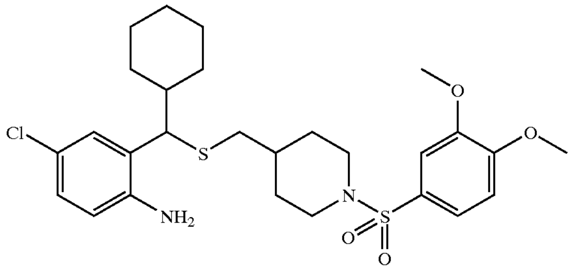 40 |
| 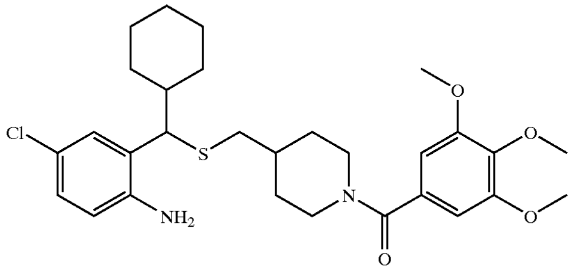 41a |
| 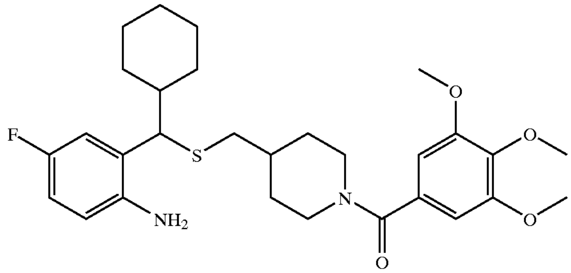 41b |

EXAMPLE 16

Mitochondrial Calcium/Sodium Antiporter Inhibitor Promotes Enhanced Insulin Secretion by Insulin-secreting Cells

COMPARATIVE EXAMPLE

INS-1 rat insulinoma cells were provided by Prof. Claes Wollheim, University Medical Centre, Geneva, Switzerland, and cultured at 37° C. in a humidified 5% $CO_2$ environment in RPMI cell culture media (Gibco BRL, Gaithersburg, Md.) supplemented with 10% fetal bovine serum (Irvine Scientific, Irvine, Calif.), 2 mM L-glutamine, 100 U/ml penicillin, 100 μg/ml streptomycin, 10 mM HEPES, 1 mM sodium pyruvate and 50 μM β-mercaptoethanol (all reagents Sigma, St. Louis, Mo., unless otherwise noted).

Figure 2:
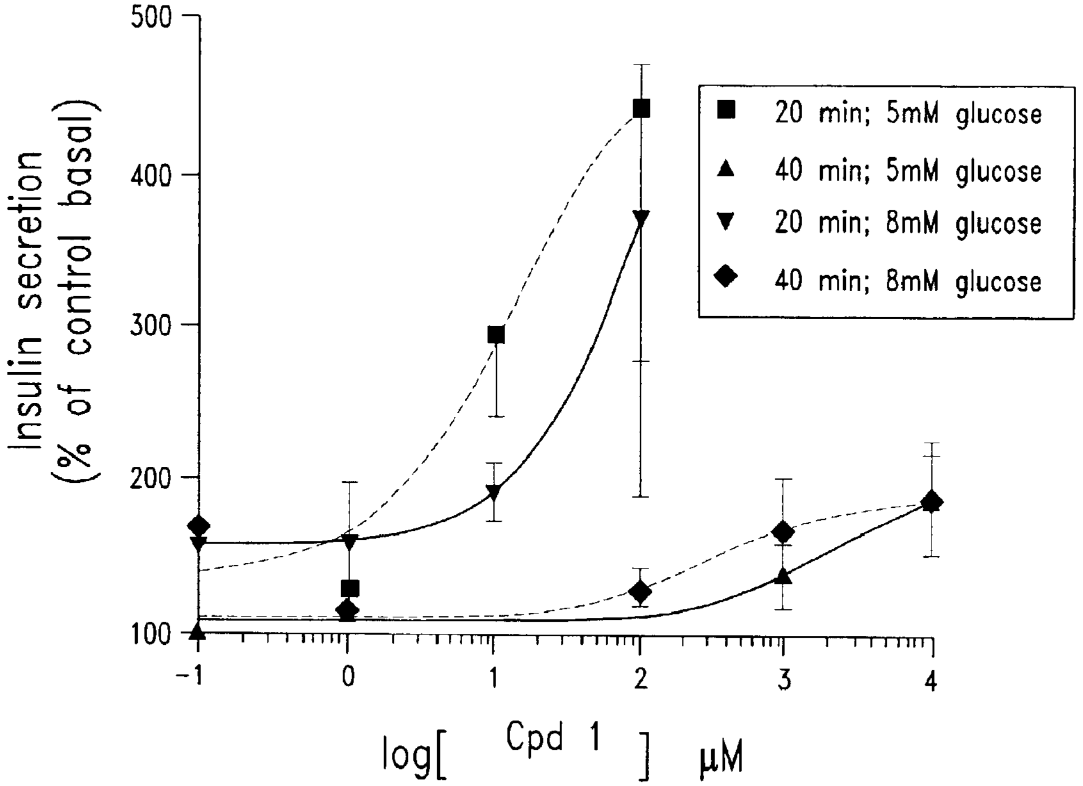

INS-1 cells were seeded into 24-well plates containing RPMI media supplemented as described at $0.5\times10^6$ cells/well and cultured at 37° C., 5% $CO_2$ for 2 days. Cells at or near confluence ($0.7\times10^6$ cells/well) were rinsed with glucose-free KRH buffer (134 mM NaCl, 4.7 mM KCl, 1.2 mM $KH_2PO4$, 1.2 mM $MgSO_4$, 1.0 mM $CaCl_2$, 10 mM HEPES-pH 7.4, 25 mM $NaHCO_3$, 0.5% BSA), then incubated in the same buffer for 1 hr at 37° C. in a humidified 5% $CO_2$/95% air atmosphere. Fresh KRH buffer was then added, either without added glucose (basal) or containing 8 mM glucose, in the absence or presence of CPG37157—a known potent inhibitor of MCA (7-Chloro-5-(2-chlorophenyl)-1,5-dihydro-4,1-benzothiazepin-2(3H)-one) (Tocris Cookson, Inc., Ballwin, Mo.); see, e.g., Cox et al., 1993 *Trends Pharmacol. Sci.* 14:408; Maechler et al. 1997 *EMBO J.* 16:3833; Cox et al 1993 *J. Cardiovasc. Pharmacol.* 21:595; White et al., 1997 *J. Physiol.* 498:31; Baron et al., 1997 *Eur. J. Pharmacol.* 340:295; for related compounds see, e.g., Chiesi et al., 1988 *Biochem. Pharmacol.* 37:4399). After an additional incubation for 15, 30 or 60 minutes at 37° C., 5% $CO_2$, the culture supernatants were collected. Insulin concentrations in the supernatants were measured and normalized to cell number using an insulin-specific radioimmunoassay kit (ICN Biochemicals, Irvine, Calif.) according to the manufacturer's instructions. The results are shown in FIG. 1, which illustrates enhanced glucose stimulated insulin secretion by INS-1 cells when exposed to CPG37157. FIG. 2 shows results that were obtained when rat pancreatic islet cells were cultured under similar conditions in the presence of "basal" (5 mM) or supraphysiological (8 mM) glucose, and in the absence or presence of various concentrations of CPG37157.

EXAMPLE 17

Inhibition of Mitochondrial Calcium/Sodium Antireporter Activity

INS-1 rat insulinoma cells (see Example 16) were harvested by trypsinization, washed and resuspended at $10\times10^6$ cells/ml in assay buffer (250 mM sucrose, 10 mM HEPES, 2.5 mM $K_2HPO_4$, 5 mM succinate, pH 7.4) containing 0.007% digitonin, 60 μM $CaCl_2$ and 0.05 μM calcium green 5N (Molecular Probes, Inc., Eugene, Oreg.). After a five-minute calcium loading incubation, ruthenium red (1 μM; Sigma, St. Louis, Mo.) was added to block further calcium uptake by mitochondria. Cell suspensions were dispensed into 96-well plates (100 μl per well, $1\times10^6$ cells per well) and candidate agents (i.e., candidate mitochondrial calcium/sodium antiporter inhibitors) were added to some sets of triplicate wells at concentrations of 1, 10 or 100 μM, while other sets of wells provided appropriate control conditions (e.g., buffer and vehicle controls). Baseline fluorescence measurements were made using a multiwell plate fluorimeter (F-MAX™, Molecular Devices Corp., Sunnyvale, Calif.; or PolarStar™, BMG Labtechnologies, Inc., Durham, N.C.) according to the manufacturer's instructions. Calcium efflux from mitochondria was then induced by adding NaCl to all wells to achieve a final concentration of 20 mM, and the rate of change in fluorescence in each well was monitored was monitored for two minutes and quantified using software included with the plate reader. Wells exhibiting significantly decreased changes in fluorescence over time relative to control wells indicated the presence of agents that were candidate MCA inhibitors, and $IC_{50}$ values were calculated for these compounds. Preferred compounds of this invention have an $IC_{50}$ value of less than 10 $\mu$M, and more preferably less than 1 $\mu$M. To that end, preferred compounds are listed in Table 2, while more preferred compounds are listed in Table 3.

TABLE 2

| $IC_{50} \leq 10\ \mu M$ Compound Number |
|---|
| 11aa |
| 11am |
| 11an |
| 11ba |
| 11c |
| 11d |
| 11f |
| 11g |
| 11h |
| 11i |
| 11k |
| 11l |
| 11m |
| 11r |
| 11s |
| 11t |
| 11u |
| 11w |
| 11x |
| 13a |
| 13ag |
| 13ai |
| 13b |
| 13c |
| 13d |
| 13e |
| 13f |
| 13g |
| 13h |
| 13i |
| 13j |
| 13k |
| 13l |
| 13m |
| 13n |
| 13o |
| 13p |
| 13q |
| 13r |
| 13s |
| 13t |
| 13u |
| 13v |
| 14a |
| 14b |
| 14d |
| 14g |
| 14h |
| 14i |
| 14k |
| 14l |
| 14m |
| 14ma |
| 14t |
| 15c |
| 15d |
| 15e |
| 15f |
| 15i |
| 15k |
| 16a |
| 16b |
| 16c |
| 16d |
| 16e |
| 16f |
| 16g |
| 16h |
| 16i |
| 16j |
| 16k |
| 16l |
| 16m |
| 16p |
| 16v |
| 16y |
| 17a |
| 17b |
| 17d |
| 17e |
| 17f |
| 18b |
| 18c |
| 18d |
| 18e |
| 20a |
| 20b |
| 20c |
| 20d |
| 21a |
| 21d |
| 21e |
| 21f |
| 21g |
| 21h |
| 22a |
| 22b |
| 22c |
| 22d |
| 25a |
| 25b |
| 25c |
| 25d |
| 26a |
| 26b |
| 27b |
| 28a |
| 34c |
| 35f |
| 37a |
| 38a |
| 38c |
| 39a |
| 41a |

TABLE 3

| $IC_{50} \leq 1\ \mu M$ Compound Number |
|---|
| 11aa |
| 11ak |
| 11ba |
| 11d |
| 11g |
| 11h |
| 11s |
| 13b |
| 13c |
| 13d |
| 13f |

TABLE 3-continued

| $IC_{50} \leqq 1\ \mu M$ Compound Number |
|---|
| 13g |
| 13h |
| 13i |
| 13j |
| 13k |
| 13l |
| 13m |
| 13n |
| 13o |
| 13p |
| 13r |
| 13s |
| 13u |
| 13v |
| 14b |
| 14g |
| 14h |
| 14k |
| 15c |
| 15d |
| 15e |
| 15f |
| 15i |
| 15k |
| 16a |
| 16b |
| 16d |
| 16e |
| 16f |
| 16g |
| 16h |
| 16i |
| 16j |
| 16k |
| 16l |
| 16m |
| 16n |
| 16o |
| 16q |
| 16r |
| 16s |
| 16t |
| 16u |
| 16w |
| 16x |
| 16z |
| 16aa |
| 16ab |
| 16ac |
| 16ad |
| 16ae |
| 17b |
| 17f |
| 17g |
| 17h |
| 17i |
| 17j |
| 17k |
| 18b |
| 18c |
| 18e |
| 18f |
| 18g |
| 20b |
| 20c |
| 20d |
| 21d |
| 21e |
| 21f |
| 21h |
| 22a |
| 22b |
| 22d |
| 25b |

TABLE 3-continued

| $IC_{50} \leqq 1\ \mu M$ Compound Number |
|---|
| 25d |
| 26b |
| 27b |
| 38c |
| 40 |
| 41b |

EXAMPLE 18

Stimulation of Glucose-stimulated Insulin Secretion

Pancreatic islets of Langerhans were isolated from adult male Sprague-Dawley rats using a standard collagenase infusion and digestion procedure as described in Example 16. Islets were cultured at 37° C. for 1–2 days in CMRL-1066 medium supplemented with 5.5 mM glucose, 10% fetal bovine serum, 100 U/ml penicillin and 100 $\mu$g/ml streptomycin, in a humidified atmosphere containing 5% $CO_2$. Islets were manually picked and washed in Krebs Ringer Bicarbonate buffer (KRB: 134 mM NaCl, 4.7 mM KCl, 1.2 mM $KH_2PO_4$, 1.2 mM $MgSO_4$, 1 mM $CaCl_2$, 10 mM $NaHCO_3$, pH 7.4) in preparation for measurement of glucose-stimulated insulin secretion (GSIS). Aliquots of washed islets were preincubated in oxygenated KRB supplemented with 16 mM HEPES, 0.01% fetal bovine serum and 5.5 mM glucose for 60 min at 37° C. Compounds to be tested (e.g., candidate mitochondrial calcium/sodium antiporter inhibitors) were added at various concentrations for 10 minutes, after which additional glucose was added to different islet cultures to achieve a final glucose concentration of 5.5, 8, 11 or 20 mM, and incubations were allowed to proceed an additional 20 min. Cell-conditioned media samples were then collected by centrifugation and their insulin content was determined using enzyme-linked immunosorbent assay (ELISA) kits (CrystalChem or ALPCO rat insulin ELISA) according to the kit supplier's instructions. Following treatment with a preferred compound, the concentration of insulin detected in the islet-conditioned medium was at least 1.5 times the insulin concentration detected in the medium conditioned by islets that were exposed to 8 mM glucose.

At a concentration of 1 $\mu$M, CGP37157 stimulated islet GSIS by 222 (±48) % relative to GSIS detected with 8 mM glucose. Preferred compounds of this invention stimulate GSIS by 150% or more at a concentration of 1 $\mu$M, and more preferably by 200% or more at a concentration of 1 $\mu$M. To that end, preferred compounds are listed in Table 4, while more preferred compounds are listed in Table 5.

TABLE 4

| Compound Number |
|---|
| 11d |
| 11g |
| 11h |
| 11k |
| 11t |
| 11x |
| 13t |
| 14a |

TABLE 4-continued

| Compound Number |
|---|
| 14b |
| 16d |
| 16d |
| 16e |
| 16f |
| 16i |
| 16k |
| 17a |
| 20a |
| 20b |
| 20c |
| 21e |
| 22a |
| 25b |
| 25c |
| 25d |
| 27b |
| 28b |

TABLE 5

| Compound Number |
|---|
| 20a |
| 11t |
| 25c |
| 25d |
| 11g |
| 11d |
| 25b |
| 11h |
| 14a |
| 11k |
| 20b |
| 20c |
| 13t |
| 16d |
| 16e |
| 16k |
| 17a |

EXAMPLE 19

Effect of Oral Administration of a Representative Compound on Glucose Tolerance in Mutant db/db Mice This Example illustrates the effects of a representative compound on glucose tolerance in an established animal model of type II diabetes mellitus, the db/db mutant mouse. As a brief background, the recessive db mutation has been localized to murine chromosome 4, and homozygous recessive (db/db) individuals are characterized by, inter alia, obesity, hyperphagia, transient increases in plasma insulin concentrations, hyperglycemia, abnormal immune and renal functions, diabetic neuropathy and myocardial disease (see, e.g., Hummel et al., 1966 *Science* 153:1127; Herberg et al., 1977 *Metabolism* 26:59; Leiter et al., 1981 *Metabolism* 30:554; Guenet et al., 1982 *Mouse News Letter* 67:30; Guenet et al., 1984 *Mouse News Letter* 70:95; Bray et al., 1971 *Physiol. Rev.* 51:598; Bailey et al., 1989 *J. Endocrinol.* 123:19–24; Bray et al., 1979 *Physiol. Rev.* 59:719; Sima et al., 1979 *Lab. Invest.* 40:627; Sima et al., 1978 *Acta Nettropathol.* 41:85; Giacomelli et al., 1979 *Lab. Invest.* 40:460).

16o (dissolved in vehicle: 10% (v/v) EtOH, 10% (v/v) polyethylene glycol-400, 30% (v/v) propylene glycol, 50% (v/v) $H_2O$) was administered orally at a dosage of 100 mg/kg body weight to eight-week old mutant C57BLKs-db/db mice (Harlan Bioproducts for Science, Inc., Indianapolis, Ind.). After one hour, a bolus of glucose dissolved in sterile normal saline solution (1 gm glucose/kg body weight) was injected intraperitoneally (time 0, FIG. 3), and blood samples were collected at 15, 30, and 90 minutes following the glucose load. Glucose concentrations in each blood sample were determined using OneTouch® glucose test strips (LifeScan, Inc., Milpitas, Calif.) according to the manufacturer's instructions. Control animals received the EtOH/PEG/propylene glycol/$H_2O$ vehicle only, containing no 16o.

Figure 3:
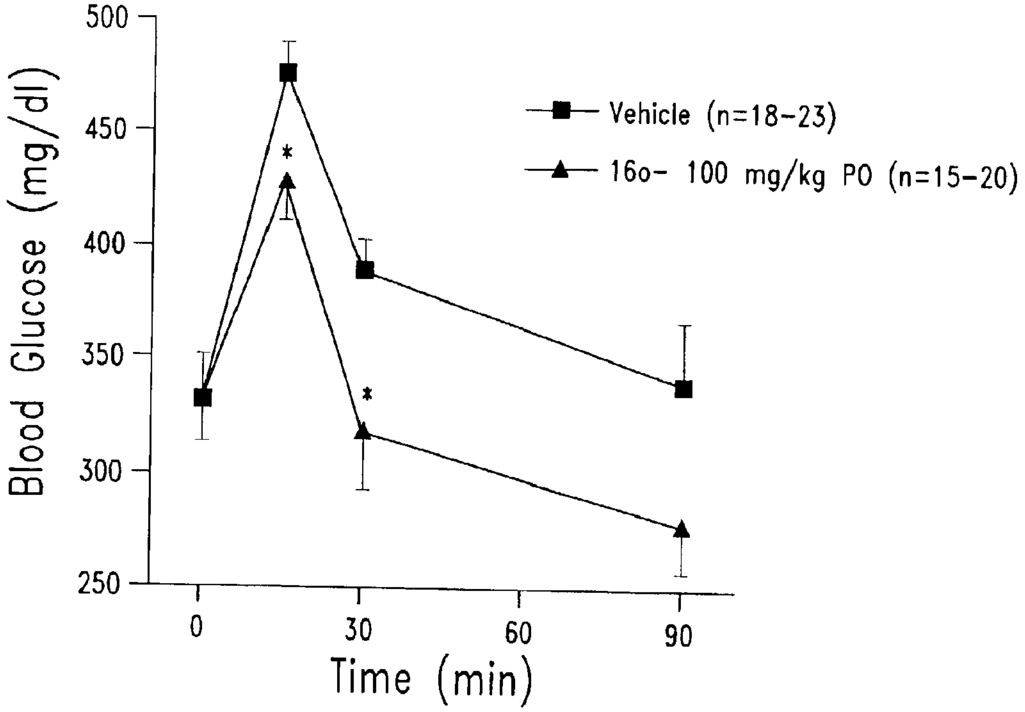
FIG. 3 shows blood glucose concentrations following a glucose load at time 0, in db/db mutant mice treated one hour prior to time 0 with compound no. 16o (▼) or with vehicle only (■); (error bars show SEM, *p<0.05).

The results are presented in FIG. 3, which shows that relative to db/db mice that received only the vehicle control, the db/db animals that received 16o exhibited lower peak blood glucose levels after the glucose bolus, and returned to a lower baseline more rapidly (*p<0.05).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the structure:

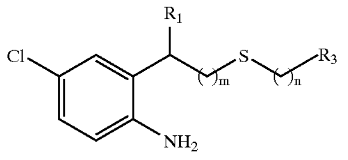

or a stereoisomer, prodrug or pharmaceutically acceptable salt thereof, wherein:

m is 0 or 1;

n is 1 or 2;

$R_1$ is alkyl, aryl, substituted aryl;

$R_3$ is substituted alkyl, substituted heterocycle, —C(=O)N($R_{3a}$)($R_{3b}$), —NHC(=O)N($R_{3a}$)($R_{3b}$), —NHC(=S)N($R_{3a}$)($R_{3b}$), —C(=O)O$R_{3c}$, or —NHC(=O)$R_{3d}$;

$R_{3a}$ and $R_{3b}$ are the same or different and independently hydrogen, alkyl, substituted alkyl, substituted aryl, arylalkyl, or $R_{3a}$ and $R_{3b}$ taken together with the nitrogen atom to which they are attached form a heterocycle;

$R_{3c}$ is alkyl; and $R_{3d}$ is alkyl or substituted aryl.

2. The compound of claim 1 wherein $R_1$ is alkyl.

3. The compound of claim 1 wherein $R_1$ is alkyl or substituted aryl.

4. The compound of claim 2 wherein $R_2$ is —NHC(=O)$R_{3d}$.

5. The compound of claim 3 wherein $R_3$ is —NHC(=O)$R_{3d}$.

6. The compound of claim 2 wherein $R_3$ is substituted heterocycle.

7. The compound of claim 3 wherein $R_3$ is substituted heterocycle.

8. The compound of claim 3 wherein $R_3$ is —C(=O)N($R_{3a}$)($R_{3b}$).

9. The compound as claimed in claim 1, selected from the group consisting of:

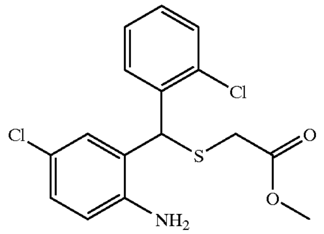
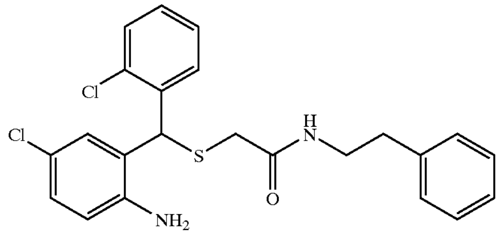
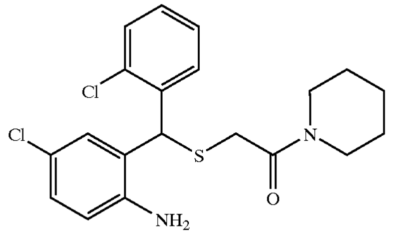
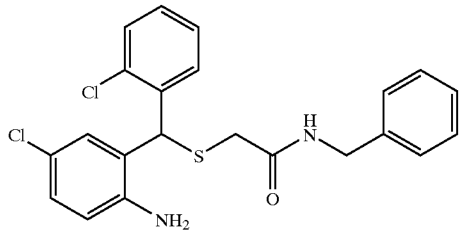
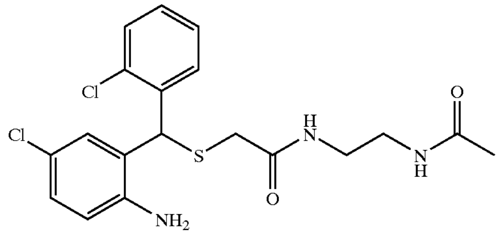
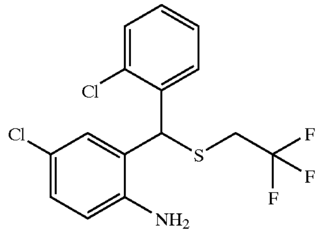
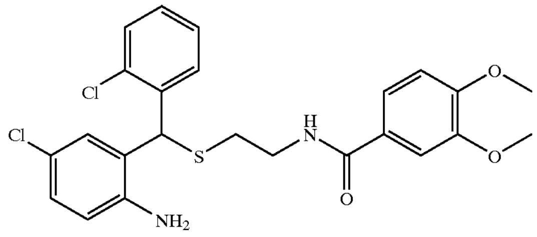
-continued
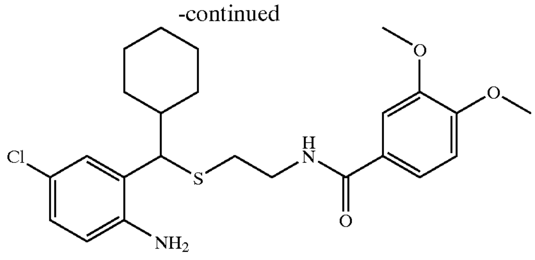
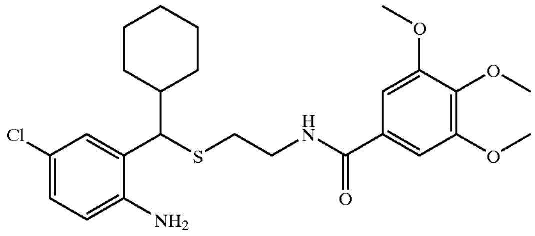
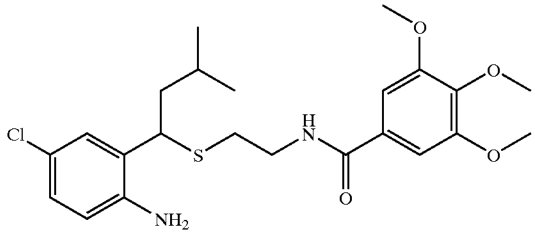
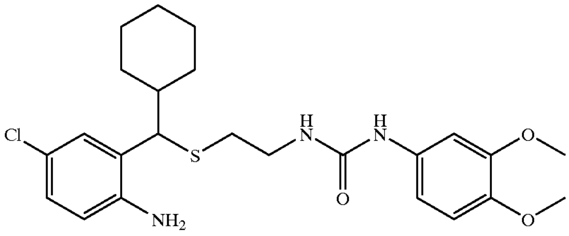
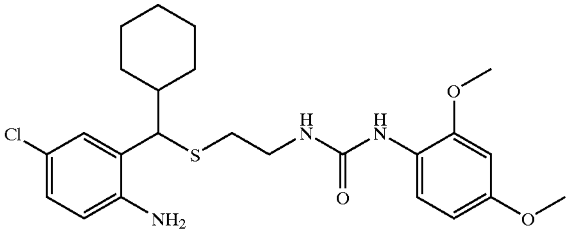
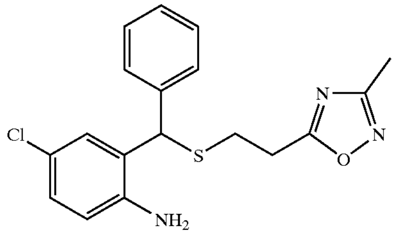
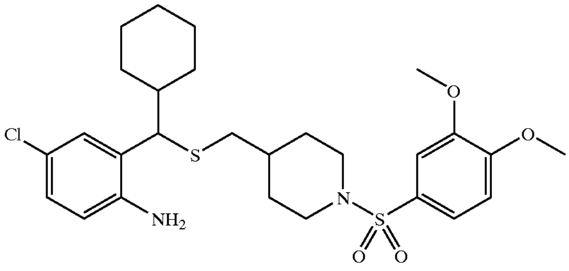

including stereoisomers, prodrugs and pharmaceutically acceptable salts thereof.

10. A method for treating diabetes mellitus, comprising administering, to a subject having or suspected of being at risk for having diabetes mellitus, a therapeutically effective amount of a pharmaceutically composition comprising a pharmaceutically acceptable canter and a compound of claim 1.

11. The method of claim 10 wherein the diabetes mellitus is type 2 diabetes mellitus.

12. The method of claim 10 wherein the diabetes mellitus is maturity onset diabetes of the young.

13. A method for enhancing insulin secretion, comprising administering to a subject in need thereof a therapeutically effective amount at a pharmaceutical composition comprising a pharmaceutically acceptable carrier and a compound of claim 1.

14. A method for inhibiting a mitochondrial calcium/sodium antiporter, comprising administering to a subject in need thereof a therapeutically effective amount of a pharmaceutical composition comprising a pharmaceutically acceptable carrier and a compound of claim 1.

15. The method of claim 10 further comprising administration to the subject one or more agents that lower circulating glucose concentration.

* * * * *